US009199979B2

(12) United States Patent
Pulici et al.

(10) Patent No.: US 9,199,979 B2
(45) Date of Patent: Dec. 1, 2015

(54) THIAZOLYLPHENYL-BENZENESULFONAMIDO DERIVATIVES AS KINASE INHIBITORS

(75) Inventors: Maurizio Pulici, Caponago (IT); Gabriella Traquandi, Milan (IT); Chiara Marchionni, Milan (IT); Alessandra Scolaro, Bresso (IT); Nicoletta Colombo, Bregnano (IT)

(73) Assignee: NERVIANO MEDICAL SCIENCES S.R.L., Nerviano (MI) (IT)

( * ) Notice: Subject to any disclaimer, the term of this patent is extended or adjusted under 35 U.S.C. 154(b) by 0 days.

(21) Appl. No.: 13/985,698

(22) PCT Filed: Feb. 21, 2012

(86) PCT No.: PCT/EP2012/052906
§ 371 (c)(1),
(2), (4) Date: Aug. 15, 2013

(87) PCT Pub. No.: WO2012/113774
PCT Pub. Date: Aug. 30, 2012

(65) Prior Publication Data
US 2013/0324551 A1    Dec. 5, 2013

(30) Foreign Application Priority Data

Feb. 24, 2011   (EP) ..................................... 11155857

(51) Int. Cl.
| | | |
|---|---|---|
| *C07D 401/00* | (2006.01) | |
| *C07D 417/00* | (2006.01) | |
| *C07D 417/04* | (2006.01) | |
| *C07D 417/14* | (2006.01) | |
| *A61K 31/44* | (2006.01) | |
| *A61K 45/06* | (2006.01) | |
| *A61K 31/4439* | (2006.01) | |
| *A61K 31/4545* | (2006.01) | |
| *A61K 31/496* | (2006.01) | |

(52) U.S. Cl.
CPC .............. *C07D 417/04* (2013.01); *A61K 31/44* (2013.01); *A61K 31/4439* (2013.01); *A61K 31/4545* (2013.01); *A61K 31/496* (2013.01); *A61K 45/06* (2013.01); *C07D 417/14* (2013.01)

(58) Field of Classification Search
USPC ................................. 546/268.1, 269.7, 270.4
See application file for complete search history.

(56) References Cited

U.S. PATENT DOCUMENTS

| | | | | |
|---|---|---|---|---|
| 2003/0105091 A1* | 6/2003 | Riedl et al. | ................. | 514/227.5 |
| 2009/0298815 A1* | 12/2009 | Adams et al. | ............. | 514/227.8 |
| 2013/0096149 A1* | 4/2013 | Madera et al. | ................. | 514/275 |

FOREIGN PATENT DOCUMENTS

| | | |
|---|---|---|
| WO | WO 2009/012283 A1 | 1/2009 |
| WO | WO 2009/137391 A2 | 11/2009 |
| WO | WO 2010/010154 A1 | 1/2010 |
| WO | WO 2011/059610 A1 | 5/2011 |
| WO | WO 2011/161216 A1 | 12/2011 |

OTHER PUBLICATIONS

Foyes Principles of Medicinal Chemistry 5th Ed. pp. 59-63. Published 2002.*
Wan et al., Cell vol. 166 pp. 855-867. Published 2004.*
Wan et al, Cell vol. 116 pp. 855-867. Published 2004.*
Williams et al., Foye's Principles of Medicinal Chemistry, pp. 37-64, 5th Edition (2002).*
Foye's Principles of Medicinal Chemistry, 5th Edition (2002).*
Wan et al (Cell vol. 116 pp. 855-867, published 2004).*
Cohen Y. et al., "BRAF Mutation in Papillary Thyroid Carcinoma", Journal of the National Cancer Institute 95 (8):625-627 (Apr. 16, 2003).
Colombo M. et al., "A Fully Automated Method for Accurate Mass Determination Using High-Performance Liquid Chromatography with a Quadrupole/Orthogonal Acceleration Time-of-Flight Mass Spectrometer", Rapid Communications in Mass Spectrometry 18:511-517 (2004).
Davies H. et al., "Mutations of the BRAF Gene in Human Cancer", Nature 417:949-954 (Jun. 27, 2002).
Hagemann C. et al., "Isotype-Specific Functions of Raf Kinases", Experimental Cell Research 253:34-46 (1999).
Hingorani S.R. et al., "Suppression of BRAFV599E in Human Melanoma Abrogates Transformation", Cancer Research 63:5198-5202 (Sep. 1, 2003).
Hoshino R. et al., "Constitutive Activation of the 41-/43-kDa Mitogen-Activated Protein Kinase Signaling Pathway in Human Tumors", Oncogene 18:813-822 (1999).
Kolch W. et al., "The Role of Raf Kinases in Malignant Transformation", Expert Reviews in Molecular Medicine (Apr. 25, 2002).
Mercer K.E. et al., "Raf Proteins and Cancer: B-Raf is Identified as a Mutational Target", Biochimica et Biophysica Acta 1653:25-40 (2003).
Peyssonnaux C. et al., "The Raf/MEK/ERK Pathway: New Concepts of Activation", Biology of the Cell 93:53-62 (2001).
Tannapfel A. et al., "Mutations of the BRAF Gene in Cholangiocarcinoma But Not in Hepatocellular Carcinoma", Gut 52:706-712 (2003).
Tsai J. et al., "Discovery of a Selective Inhibitor of Oncogenic B-Raf Kinase With Potent Antimelanoma Activity", PNAS 105(8):3041-3046 (Feb. 26, 2008).
Wellbrock C. et al., "V599EB-Raf is an Oncogene in Melanocytes", Cancer Research 64:2338-2342 (Apr. 1, 2004).
Wojnowski L. et al., "Endothelial Apoptosis in Braf-Deficient Mice", Nature Genetics 16:293-297 (Jul. 1997).
International Search Report dated May 8, 2012 received from the European Patent Office from related Application No. PCT/EP2012/052906.

* cited by examiner

*Primary Examiner* — Paul Zarek
*Assistant Examiner* — George W Kosturko
(74) *Attorney, Agent, or Firm* — Scully, Scott, Murphy & Presser, P.C.

(57) ABSTRACT

Thiazolylphenyl-benzenesulfonamido derivatives of formula (I) as defined in the specification, and pharmaceutically acceptable salts thereof, process for their preparation and pharmaceutical compositions comprising them are disclosed; the compounds of the invention may be useful, in therapy, in the treatment of diseases associated with a disregulated protein kinase activity, like cancer.

8 Claims, No Drawings

THIAZOLYLPHENYL-BENZENESULFONAMIDO DERIVATIVES AS KINASE INHIBITORS

The present invention relates to certain substituted thiazolylphenyl-benzenesulfonamido compounds, which modulate the activity of protein kinases. The compounds of this invention are therefore useful in treating diseases caused by deregulated protein kinase activity. The present invention also provides methods for preparing these compounds, pharmaceutical compositions comprising these compounds, and methods of treating diseases utilizing pharmaceutical compositions comprising these compounds.

The classical Ras, Raf, MEK (mitogen activated protein kinase/extracellular signal-regulated kinase kinase), ERK (extracellular signal-regulated kinase) pathway plays a central role in the regulation of a variety of cellular functions dependent upon cellular context, including cellular proliferation, differentiation, survival, immortalisation and angiogenesis (reviewed in Peyssonnaux and Eychene, Biology of the Cell, 2001, 93, 3-62). In this pathway, Raf family members are recruited to the plasma membrane upon binding to guanosine triphosphate (GTP) loaded Ras, resulting in the phosphorylation and activation of Raf proteins. Activated Rafs then phosphorylate and activate MEKs, which in turn phosphorylate and activate ERKs. Upon activation, ERKs translocate from the cytoplasm to the nucleus resulting in the phosphorylation and regulation of activity of transcription factors such as Elk-I and Myc. The Ras/Raf/MEK/ERK pathway has been reported to contribute to the tumorigenic phenotype by inducing immortalisation, growth factor-independent growth, insensitivity to growth-inhibitory signals, ability to invade and metastasize, by stimulating angiogenesis and by inhibiting apoptosis (reviewed in Kolch et al., Exp. Rev. Mol. Med., 2002, 25 Apr., http://www.expertreviews.org/02004386h.htm). In fact, ERK phosphorylation is enhanced in approximately 30% of all human tumours (Hoshino et al., Oncogene, 1999, 18, 813-822). This may be a result of overexpression and/or mutation of key members of the pathway.

Three Raf serine/threonine protein kinase isoforms have been reported: Raf-1/C-Raf, B-Raf and A-Raf (reviewed in Mercer and Pritchard, Biochim. Biophys. Acta, 2003, 1653, 25-40), the genes for which are thought to have arisen from gene duplication. All three Raf genes are expressed in most tissues but with differences: C-Raf is expressed ubiquitously at high levels, whereas B-Raf high-level expression is found in neuronal tissue and A-Raf in urogenital tissue. The highly homologous Raf family members have overlapping but distinct biochemical activities and biological functions (Hagemann and Rapp, Expt. Cell Res. 1999, 253, 34-46). Expression of all three Raf genes is required for normal murine development however both C-Raf and B-Raf are required to complete gestation. B-Raf−/− mice die at E12.5 due to vascular haemorrhaging caused by increased apoptosis of endothelial cells (Wojnowski et al. Nature Genet., 1997, 16, 293-297). B-Raf is reportedly the major isoform involved in cell proliferation and the primary target of oncogenic Ras. Activating somatic missense mutations have been identified exclusively for B-Raf, occurring with a frequency of 66% in malignant cutaneous melanomas (Davies et al., Nature, 2002, 417, 949-954) and also present in a wide range of human cancers, including but not limited to papillary thyroid tumours (Cohen et al., J. Natl. Cancer Inst., 2003, 95, 625-627), cholangiocarcinomas (Tannapfel et al., Gut, 2003, 52, 706-712), colon and ovarian cancers (Davies et al., Nature, 2002, 417, 949-954). The most frequent mutation in B-Raf (80%) is a glutamic acid for valine substitution at position 600. These mutations increase the basal kinase activity of B-Raf and are thought to uncouple Raf/MEK/ERK signalling from upstream proliferation drives including Ras and growth factor receptor activation resulting in constitutive activation of ERK. Mutated B-Raf proteins are transforming in NIH3T3 cells (Davies et al., Nature, 2002, 15 417, 949-954) and melanocytes (Wellbrock et al., Cancer Res., 2004, 64, 2338-2342) and have also been shown to be essential for melanoma cell viability and transformation (Hingorani et al., Cancer Res., 2003, 63, 5198-5202). As a key driver of the Raf/MEK/ERK signalling cascade, B-Raf represents a likely point of intervention in tumours dependent on this pathway.

Substituted thiazole derivatives for the treatment of protein kinase-mediated diseases such as cancer are disclosed in WO2009/137391 in the name of SKB & Co, in WO2011/059610 in the name of Glaxosmithkline LLC and in WO2011/161216 in the name of Novartis AG.

The present inventors have now discovered that compounds of formula (I), described below, are kinase inhibitors and are thus useful in therapy as antitumor agents.

Accordingly, a first object of the present invention is to provide a substituted thiazolylphenyl-benzenesulfonamido compound represented by formula (I)

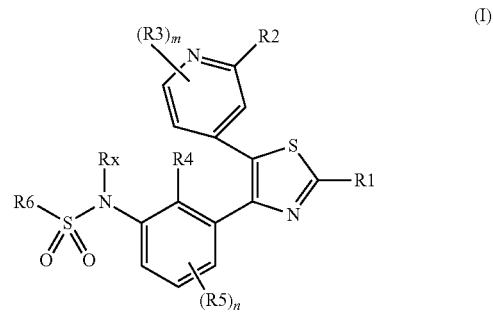

wherein:
n and m are each independently 1 or 2;
R1 is hydrogen, halogen, cyano or an optionally substituted group selected from straight or branched ($C_1$-$C_8$) alkyl, ($C_2$-$C_8$) alkenyl, ($C_2$-$C_8$) alkynyl, ($C_3$-$C_8$) cycloalkyl, ($C_3$-$C_8$) cycloalkenyl, heterocyclyl, aryl and heteroaryl; or R1 is NR7R8 or COR9,
  wherein:
    R7 and R8 are, each independently, hydrogen or an optionally substituted group selected from straight or branched ($C_1$-$C_8$) alkyl, ($C_2$-$C_8$) alkenyl, ($C_2$-$C_8$) alkynyl, ($C_3$-$C_8$) cycloalkyl, ($C_3$-$C_8$) cycloalkenyl, heterocyclyl, aryl and heteroaryl; or, taken together with the nitrogen atom to which they are bonded, R7 and R8 may form an optionally substituted 3 to 8 membered heterocyclyl, optionally containing one additional heteroatom or heteroatomic group selected from S, O, N and NH; or
    R7 is hydrogen and R8 is COR10,
  wherein:
    R10 is OR11, NR12R13 or an optionally substituted group selected from straight or branched ($C_1$-$C_8$) alkyl, ($C_2$-$C_8$) alkenyl, ($C_2$-$C_8$) alkynyl, ($C_3$-$C_8$) cycloalkyl, ($C_3$-$C_8$)
      R11 is an optionally substituted group selected from straight or branched ($C_1$-$C_8$) alkyl, ($C_2$-$C_8$) alkenyl, ($C_2$-$C_8$) alkynyl, ($C_3$-$C_8$) cycloalkyl, heterocyclyl, aryl and heteroaryl;
      R12 and R13 are, each independently, hydrogen or an optionally substituted group selected from straight or branched ($C_1$-$C_8$) alkyl, ($C_2$-$C_8$) alkenyl, ($C_2$-$C_8$) alkynyl, ($C_3$-$C_8$) cycloalkyl, heterocyclyl, aryl and heteroaryl; or, taken together with the nitrogen atom to which they are bonded, R12 and R13 may form an optionally substituted 3 to 8 membered heterocyclyl or heteroaryl, optionally containing one additional heteroatom or heteroatomic group selected from S, O, N and NH;

R9 is OR14 or NR15R16, wherein:
R14 is hydrogen or an optionally substituted group selected from straight or branched ($C_1$-$C_8$) alkyl, ($C_2$-$C_8$) alkenyl, ($C_2$-$C_8$) alkynyl, ($C_3$-$C_8$) cycloalkyl, heterocyclyl, aryl and heteroaryl;
R15 and R16 are, each independently, hydrogen or an optionally substituted group selected from straight or branched ($C_1$-$C_8$) alkyl, ($C_2$-$C_8$) alkenyl, ($C_2$-$C_8$) alkynyl, ($C_3$-$C_8$) cycloalkyl, heterocyclyl, aryl and heteroaryl; or, taken together with the nitrogen atom to which they are bonded, R15 and R16 may form an optionally substituted 3 to 8 membered heterocyclyl or heteroaryl, optionally containing one additional heteroatom or heteroatomic group selected from S, O, N and NH;

R2 and R3 are, each independently, hydrogen, halogen, cyano or an optionally substituted group selected from straight or branched ($C_1$-$C_8$) alkyl, ($C_2$-$C_8$) alkenyl, ($C_2$-$C_8$) alkynyl, ($C_3$-$C_8$) cycloalkyl, ($C_3$-$C_8$) cycloalkenyl, heterocyclyl, aryl and heteroaryl; or R2 and R3 are, each independently, NR17R18, CONR19R20, OR21, SR21 or SO$_2$R21,
wherein:
R17 and R18 are, independently, hydrogen or an optionally substituted group selected from straight or branched ($C_1$-$C_8$) alkyl, ($C_2$-$C_8$) alkenyl, ($C_2$-$C_8$) alkynyl, ($C_3$-$C_8$) cycloalkyl, heterocyclyl, aryl and heteroaryl; or, taken together with the nitrogen atom to which they are bonded, R17 and R18 may form an optionally substituted 3 to 8 membered heterocyclyl or heteroaryl, optionally containing one additional heteroatom or heteroatomic group selected from S, O, N and NH; or
R17 is hydrogen and R18 is COR22,
wherein:
R22 is OR23, NR24R25 or an optionally substituted group selected from straight or branched ($C_1$-$C_8$) alkyl, ($C_2$-$C_8$) alkenyl, ($C_2$-$C_8$) alkynyl, ($C_3$-$C_8$) cycloalkyl, ($C_3$-$C_8$)
R23 is an optionally substituted group selected from straight or branched ($C_1$-$C_8$) alkyl, ($C_2$-$C_8$) alkenyl, ($C_2$-$C_8$) alkynyl, ($C_3$-$C_8$) cycloalkyl, ($C_3$-$C_8$) cycloalkenyl, heterocyclyl, aryl and heteroaryl, and
R24 and R25 are, each independently, hydrogen or an optionally substituted group selected from straight or branched ($C_1$-$C_8$) alkyl, ($C_2$-$C_8$) alkenyl, ($C_2$-$C_8$) alkynyl, ($C_3$-$C_8$) cycloalkyl, heterocyclyl, aryl and heteroaryl: or, taken together with the nitrogen atom to which they are bonded, R24 and R25 may form an optionally substituted 3 to 8 membered heterocyclyl or heteroaryl, optionally containing one additional heteroatom or heteroatomic group selected from S, O, N and NH;
R19 and R20 are, each independently, hydrogen or an optionally substituted group selected from straight or branched ($C_1$-$C_8$) alkyl, ($C_2$-$C_8$) alkenyl, ($C_2$-$C_8$) alkynyl, ($C_3$-$C_8$) cycloalkyl, heterocyclyl, aryl and heteroaryl; or, taken together with the nitrogen atom to which they are bonded, R19 and R20 may form an optionally substituted 3 to 8 membered heterocyclyl or heteroaryl, optionally containing one additional heteroatom or heteroatomic group selected from S, O, N and NH;
R21 is hydrogen or an optionally substituted group selected from straight or branched ($C_1$-$C_8$) alkyl, ($C_2$-$C_8$) alkenyl, ($C_2$-$C_8$) alkynyl, ($C_3$-$C_8$) cycloalkyl, heterocyclyl, aryl and heteroaryl;
or, R2 and R3 taken together can be part of a heterocyclyl, aryl or heteroaryl when m is 1 and R3 is at position 3 of the pyridine nucleus;
R4 and R5 are, each independently, hydrogen, halogen, trifluoromethyl, trichloromethyl, cyano, OR26 or an optionally substituted group selected from straight or branched ($C_1$-$C_8$) alkyl, ($C_2$-$C_8$) alkenyl, ($C_2$-$C_8$) alkynyl and ($C_3$-$C_8$) cycloalkyl, wherein:
R26 is hydrogen or an optionally substituted group selected from straight or branched ($C_1$-$C_8$) alkyl, ($C_2$-$C_8$) alkenyl, ($C_2$-$C_8$) alkynyl and ($C_3$-$C_8$) cycloalkyl;
Rx is hydrogen, an optionally substituted straight or branched ($C_1$-$C_3$) alkyl, an optionally substituted ($C_2$-$C_6$) acyl group or an optionally substituted ($C_2$-$C_6$) alkoxycarbonyl group;
R6 is an optionally substituted group selected from straight or branched ($C_2$-$C_8$) alkenyl, ($C_2$-$C_8$) alkynyl, ($C_3$-$C_8$) cycloalkyl, ($C_3$-$C_8$) cycloalkenyl, heterocyclyl, aryl and heteroaryl;
or pharmaceutically acceptable salts thereof.

The present invention also provides methods of preparing the substituted thiazolylphenyl-benzenesulfonamido compounds, represented by formula (I), prepared through a process consisting of standard synthetic transformations. The present invention also provides a method for treating diseases caused by and/or associated with deregulated protein kinase activity, particularly the Raf family, ABL, ACK1, AKT1, ALK, AUR1, AUR2, BRK, BUB1, CDC7/DBF4, CDK2/CYCA, CHK1, CK2, EEF2K, EGFR1, EphA2, EphB4, ERK2, FAK, FGFR1, FLT3, GSK3beta, Haspin, IGFR1, IKK2, IR, JAK1, JAK2, JAK3, KIT, LCK, LYN, MAPKAPK2, MELK, MET, MNK2, MPS1, MST4, NEK6, NIM1, P38alpha, PAK4, PDGFR, PDK1, PERK, PIM1, PIM2, PKAalpha, PKCbeta, PLK1, RET, ROS1, SULU1, Syk, TLK2, TRKA, TYK, VEGFR2, VEGFR3, ZAP70, more particularly the Raf family, which comprises administering to a mammal, in need thereof, an effective amount of a substituted thiazolylphenyl-benzenesulfonamido compound represented by formula (I) as defined above.

A preferred method of the present invention is to treat a disease caused by and/or associated with deregulated protein kinase activity selected from the group consisting of cancer, cellular proliferation disorders, viral infections, autoimmune and neurodegenerative disorders.

Another preferred method of the present invention is to treat specific types of cancer including but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage, including leukaemia, acute lymphocitic leukaemia, acute lymphoblastic leukaemia, B-cell lymphoma, T-cell-lymphoma, Hodgkin's lymphoma, non-Hodgkin's lymphoma, hairy cell lymphoma and Burkitt's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

Another preferred method of the present invention is to treat specific cellular proliferation disorders such as, for example, benign prostate hyperplasia, familial adenomatosis, polyposis, neurofibromatosis, psoriasis, vascular smooth cell proliferation associated with atherosclerosis, pulmonary fibrosis, arthritis, glomerulonephritis and post-surgical stenosis and restenosis.

Another preferred method of the present invention is to treat viral infections, in particular the prevention of AIDS development in HIV-infected individuals.

Another preferred method of the present invention is to treat immune cell-associated diseases and disorders, such as inflammatory and autoimmune diseases, for examples multiple sclerosis, systemic lupus erythematosis, inflammatory bowel diseases (IBD), Crohn's disease, irritable bowel syndrome, pancreatitis, ulcerative colitis, diverticulosis, myasthenia gravis, vasculitis, psoriasis, scleroderma, asthma, allergy, systemic sclerosis, vitiligo, arthritis such as osteoarthritis, juvenile rheumatoid arthritis, ankylosing spondylitis.

Another preferred method of the present invention is to treat neurodegenerative disorders, such as Alzheimer's disease, Parkinson's disease and Huntington's disease.

In addition, the method of the present invention also provides tumor angiogenesis and metastasis inhibition as well as the treatment of organ transplant rejection and host versus graft disease.

In a further preferred embodiment, the method of the present invention further comprises subjecting the mammal in need thereof to a radiation therapy or chemotherapy regimen in combination with at least one cytostatic or cytotoxic agent.

Moreover the invention provides an in vitro method for inhibiting the Raf family protein activity which comprises contacting the said protein with an effective amount of a compound of formula (I).

The present invention also provides a pharmaceutical composition comprising one or more compounds of formula (I) or a pharmaceutically acceptable salt thereof and a pharmaceutically acceptable excipient, carrier or diluent.

The present invention further provides a pharmaceutical composition comprising a compound of formula (I) in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, RAS-RAF signal transduction pathway inhibitors, cell cycle inhibitors, other Cdks inhibitors, tubulin binding agents, topoisomerase I inhibitors, topoisomerase II inhibitors, and the like. Additionally, the invention provides a product or kit comprising a compound of formula (I) or a pharmaceutically acceptable salt thereof, as defined above, or pharmaceutical compositions thereof and one or more chemotherapeutic agents, as a combined preparation for simultaneous, separate or sequential use in anticancer therapy.

In yet another aspect the invention provides a compound of formula (I) or a pharmaceutically acceptable salt thereof, as defined above, for use as a medicament.

Moreover the invention provides the use of a compound of formula (I) or a pharmaceutically acceptable salt thereof, as defined above, in the manufacture of a medicament with antitumor activity.

Finally, the invention provides a compound of formula (I) or a pharmaceutically acceptable salt thereof, as defined above, for use in a method of treating cancer.

Unless otherwise specified, when referring to the compounds of formula (I) per se as well as to any pharmaceutical composition thereof or to any therapeutic treatment comprising them, the present invention includes all of the isomers, tautomers, hydrates, solvates, complexes, metabolites, prodrugs, carriers, N-oxides and pharmaceutically acceptable salts of the compounds of this invention.

A metabolite of a compound of formula (I) is any compound into which this same compound of formula (I) is converted in vivo, for instance upon administration to a mammal in need thereof. Typically, without however representing a limiting example, upon administration of a compound of formula (I), this same derivative may be converted into a variety of compounds, for instance including more soluble derivatives like hydroxylated derivatives, which are easily excreted. Hence, depending upon the metabolic pathway thus occurring, any of these hydroxylated derivatives may be regarded as a metabolite of the compounds of formula (I).

Prodrugs are any covalently bonded compounds, which release in vivo the active parent drug according to formula (I).

N-oxides are compounds of formula (I) wherein nitrogen and oxygen are tethered through a dative bond.

If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases when compounds can exist in tautomeric forms, each form is contemplated as being included within this invention whether existing in equilibrium or predominantly in one form.

In cases wherein compounds may exist in other tautomeric forms, such as keto-enol tautomers, each tautomeric form is contemplated as being included within this invention whether existing in equilibrium or predominantly in one form.

In cases when m is 1 and R3 is at position 3 of the pyridine nucleus, R2 and R3 taken together can be part of a heterocyclyl, aryl or heteroaryl, so that, in such a case, we intend a group as depicted below:

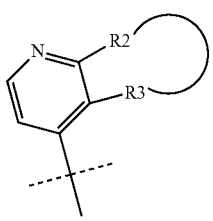

Non limiting examples of such groups are:

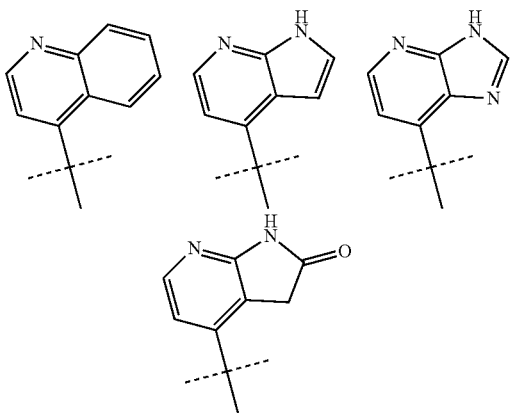

With the term "straight or branched ($C_1$-$C_8$) alkyl", we intend any of the groups such as, for instance, methyl, ethyl, n-propyl, isopropyl, n-butyl, isobutyl, tert-butyl, sec-butyl, n-pentyl, n-hexyl, n-heptyl, n-octyl and the like.

With the term "straight or branched ($C_1$-$C_6$) alkyl", we intend any of the groups such as, for instance, methyl, ethyl, n-propyl, isopropyl, n-butyl, isobutyl, tert-butyl, sec-butyl, n-pentyl, n-hexyl, and the like.

With the term "straight or branched ($C_1$-$C_3$) alkyl", we intend any of the groups such as, for instance, methyl, ethyl, n-propyl, isopropyl.

With the term "($C_3$-$C_8$) cycloalkyl" we intend, unless otherwise provided, 3- to 8-membered all-carbon monocyclic ring, which may contain one or more double bonds but does not have a completely conjugated π-electron system. Examples of cycloalkyl groups, without limitation, are cyclopropane, cyclobutane, cyclopentane, cyclopentene, cyclohexane, cyclohexene and cyclohexadiene.

With the term "heterocyclyl" we intend a 3- to 8-membered, saturated or partially unsaturated carbocyclic ring where one or more carbon atoms are replaced by heteroatoms such as nitrogen, oxygen and sulfur. Non limiting examples of heterocyclyl groups are, for instance, pyrane, pyrrolidine, pyrroline, imidazoline, imidazolidine, pyrazolidine, pyrazoline, thiazoline, thiazolidine, dihydrofuran, tetrahydrofuran (THF), 1,3-dioxolane, piperidine, piperazine, morpholine and the like.

With the term "($C_2$-$C_8$) alkenyl" we intend an aliphatic ($C_2$-$C_8$) hydrocarbon chain containing at least one carbon-carbon double bond and which can be straight or branched. Representative examples include, but are not limited to, ethenyl, 1-propenyl, 2-propenyl, 1- or 2-butenyl, and the like.

With the term "($C_2$-$C_8$) alkynyl" we intend an aliphatic ($C_2$-$C_8$) hydrocarbon chain containing at least one carbon-carbon triple bond and which can be straight or branched. Representative examples include, but are not limited to, ethynyl, 1-propynyl, 2-propynyl, 1- or 2-butynyl, and the like.

The term "aryl" refers to a mono-, bi- or poly-carbocyclic hydrocarbon with from 1 to 4 ring systems, optionally further fused or linked to each other by single bonds, wherein at least one of the carbocyclic rings is "aromatic", wherein the term "aromatic" refers to completely conjugated π-electron bond system. Non-limiting examples of such aryl groups are phenyl, α- or β-naphthyl or biphenyl groups.

The term "heteroaryl" refers to aromatic heterocyclic rings, typically 5- to 8-membered heterocycles with from 1 to 3 heteroatoms selected among N, O or S; the heteroaryl ring can be optionally further fused or linked to aromatic and non-aromatic carbocyclic and heterocyclic rings. Not limiting examples of such heteroaryl groups are, for instance, pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazolyl, pyrazolyl, thienyl, benzothienyl, isoindolinyl, benzoimidazolyl, quinolinyl, isoquinolinyl, 1,2,3-triazolyl, 1-phenyl-1,2,3-triazolyl, 2,3-dihydroindolyl, 2,3-dihydrobenzofuranyl, 2,3-dihydrobenzothiophenyl; benzopyranyl, 2,3-dihydrobenzoxazinyl, 2,3-dihydroquinoxalinyl and the like.

According to the present invention and unless otherwise provided, any of the above Rx, R1, R2, R3, R4, R5 and R6 group may be optionally substituted, in any of their free positions, by one or more groups, for instance 1 to 6 groups, independently selected from: halogen, nitro, oxo groups (=O), cyano, ($C_1$-$C_8$) alkyl, polyfluorinated alkyl, polyfluorinated alkoxy, ($C_2$-$C_8$) alkenyl, ($C_2$-$C_8$) alkynyl, hydroxyalkyl, aryl, arylalkyl, heteroaryl, heteroarylalkyl, heterocyclyl, heterocyclylalkyl, ($C_3$-$C_8$) cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclylalkyloxycarbonyl-amino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkyl aminocarbonyl, arylaminocarbonyl, heterocyclylaminocarbonyl, alkoxycarbonylamino, hydroxyaminocarbonyl alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate. In their turn, whenever appropriate, each of the above substituent may be further substituted by one or more of the aforementioned groups.

With the term "halogen" we intend a fluorine, chlorine, bromine or iodine.

With the term "cyano" we intend a —CN residue.

With the term "nitro" we intend a —$NO_2$ group.

With the term "polyfluorinated alkyl" or "polyfluorinated alkoxy" we intend any of the above straight or branched ($C_1$-$C_8$) alkyl or alkoxy groups which are substituted by more than one fluorine atom such as, for instance, trifluoromethyl, trifluoroethyl, 1,1,1,3,3,3-hexafluoropropyl, trifluoromethoxy and the like.

With the term "hydroxyalkyl" we intend any of the above ($C_1$-$C_8$) alkyl, bearing an hydroxyl group such as, for instance, hydroxymethyl, 2-hydroxyethyl, 3-hydroxypropyl and the like.

From all of the above, it is clear to the skilled person that any group which name is a composite name such as, for instance, arylamino has to be intended as conventionally construed by the parts from which it derives, e.g. by an amino group which is further substituted by aryl, wherein aryl is as above defined.

Likewise, any of the terms such as, for instance, alkylthio, alkylamino, dialkylamino, alkoxycarbonyl, alkoxycarbonylamino, heterocyclylcarbonyl, heterocyclylcarbonylamino, cycloalkyloxycarbonyl and the like, include groups wherein the alkyl, alkoxy, aryl, ($C_3$-$C_8$) cycloalkyl and heterocyclyl moieties are as above defined.

Pharmaceutically acceptable salts of the compounds of formula (I) include the acid addition salts with inorganic or organic acids, e.g., nitric, hydrochloric, hydrobromic, sulfuric, perchloric, phosphoric, acetic, trifluoroacetic, propionic, glycolic, lactic, oxalic, fumaric, malonic, malic, maleic, tartaric, citric, benzoic, cinnamic, mandelic, methanesulphonic, isethionic and salicylic acid.

Pharmaceutically acceptable salts of the compounds of formula (I) also include the salts with inorganic or organic bases, e.g., alkali or alkaline-earth metals, especially sodium, potassium, calcium, ammonium or magnesium hydroxides, carbonates or bicarbonates, acyclic or cyclic amines, preferably methylamine, ethylamine, diethylamine, triethylamine, piperidine and the like.

A preferred class of compounds of formula (I) are the compounds wherein:

R1 is NR7R8 or an optionally substituted heterocyclyl, wherein R7 and R8 are as defined above.

A more preferred class of compounds of formula (I) are the compounds wherein:

R2 is hydrogen or a NR17R18 group, wherein R17 and R18 are as defined above.

An even more preferred class of compounds of formula (I) are the compounds wherein:

R2 is a NR17R18 group, wherein R17 is hydrogen and R18 is COR22, wherein R22 is as defined above.

A most preferred class of compounds of formula (I) are the compounds wherein:

R3 is hydrogen, R4 is halogen and R5 is hydrogen or halogen.

A further most preferred class of compounds of formula (I) are the compounds wherein:

Rx is hydrogen and R6 is an optionally substituted phenyl group.

Preferred specific compounds (cmpd.) of formula (I) or a pharmaceutically acceptable salt thereof are the compounds listed below:

1) N-{3-[2-amino-5-(pyridin-4-yl)-1,3-thiazol-4-yl]-2,4-difluorophenyl}-2,5-difluorobenzenesulfonamide;
2) N-{2,4-difluoro-3-[2-(methylamino)-5-(pyridin-4-yl)-1,3-thiazol-4-yl]phenyl}-2,5-difluorobenzenesulfonamide;
3) N-{3-[2-(diethylamino)-5-(pyridin-4-yl)-1,3-thiazol-4-yl]-2,4-difluorophenyl}-2,5-difluorobenzenesulfonamide;
4) N-(2,4-difluoro-3-{2-[(2-methylpropyl)amino]-5-(pyridin-4-yl)-1,3-thiazol-4-yl}phenyl)-2,5-difluorobenzenesulfonamide;
5) N-(2,4-difluoro-3-{2-[(2-methoxyethyl)amino]-5-(pyridin-4-yl)-1,3-thiazol-4-yl}phenyl)-2,5-difluorobenzenesulfonamide;
6) N-{2,4-difluoro-3-[2-(piperidin-4-ylamino)-5-(pyridin-4-yl)-1,3-thiazol-4-yl]phenyl}-2,5-difluorobenzenesulfonamide;
7) N-(3-{2-[cyclohexyl(methyl)amino]-5-(pyridin-4-yl)-1,3-thiazol-4-yl}-2,4-difluorophenyl)-2,5-difluorobenzenesulfonamide;
8) N-{2,4-difluoro-3-[2-(4-methylpiperazin-1-yl)-5-(pyridin-4-yl)-1,3-thiazol-4-yl]phenyl}-2,5-difluorobenzenesulfonamide;
9) N-{2,4-difluoro-3-[2-(piperidin-1-yl)-5-(pyridin-4-yl)-1,3-thiazol-4-yl]phenyl}-2,5-difluorobenzenesulfonamide;
10) N-(3-{2-[4-(dimethylamino)piperidin-1-yl]-5-(pyridin-4-yl)-1,3-thiazol-4-yl}-2,4-difluorophenyl)-2,5-difluorobenzenesulfonamide;
11) N-{3-[2-(1,4-dioxa-8-azaspiro[4.5]dec-8-yl)-5-(pyridin-4-yl)-1,3-thiazol-4-yl]-2,4-difluorophenyl}-2,5-difluorobenzenesulfonamide;
12) N-{2,4-difluoro-3-[2-(4-oxopiperidin-1-yl)-5-(pyridin-4-yl)-1,3-thiazol-4-yl]phenyl}-2,5-difluorobenzenesulfonamide;
13) N-{2,4-difluoro-3-[2-(4-hydroxypiperidin-1-yl)-5-(pyridin-4-yl)-1,3-thiazol-4-yl]phenyl}-2,5-difluorobenzenesulfonamide;
14) N-{3-[2-(4,4-difluoropiperidin-1-yl)-5-(pyridin-4-yl)-1,3-thiazol-4-yl]-2,4-difluorophenyl}-2,5-difluorobenzenesulfonamide;
15) N-{2,4-difluoro-3-[2-(morpholin-4-yl)-5-(pyridin-4-yl)-1,3-thiazol-4-yl]phenyl}-2,5-difluorobenzenesulfonamide;
16) N-{3-[2-(diethylamino)-5-(pyridin-4-yl)-1,3-thiazol-4-yl]-2-fluorophenyl}-2,5-difluorobenzenesulfonamide;
17) N-{3-[2-(1,4-dioxa-8-azaspiro[4.5]dec-8-yl)-5-(pyridin-4-yl)-1,3-thiazol-4-yl]-2-fluorophenyl}-2,5-difluorobenzenesulfonamide;
18) N-{3-[2-(4,4-difluoropiperidin-1-yl)-5-(pyridin-4-yl)-1,3-thiazol-4-yl]-2-fluorophenyl}-2,5-difluorobenzenesulfonamide;
19) 2,5-difluoro-N-{2-fluoro-3-[2-(1-methylpiperidin-4-yl)-5-(pyridin-4-yl)-1,3-thiazol-4-yl]phenyl}benzenesulfonamide;
20) 2,5-difluoro-N-{2-fluoro-3-[5-(pyridin-4-yl)-2-(tetrahydro-2H-pyran-4-yl)-1,3-thiazol-4-yl]phenyl}benzenesulfonamide;
21) N-{3-[2-(1-cyclopropylpiperidin-4-yl)-5-(pyridin-4-yl)-1,3-thiazol-4-yl]-2-fluorophenyl}-2,5-difluorobenzenesulfonamide;
22) N-{3-[5-(2-aminopyridin-4-yl)-2-(1-cyclopropylpiperidin-4-yl)-1,3-thiazol-4-yl]-2-fluorophenyl}-2,5-difluorobenzenesulfonamide;
23) N-{4-[4-(3-{[(2,5-difluorophenyl)sulfonyl]amino}-2-fluorophenyl)-2-(1-methylpiperidin-4-yl)-1,3-thiazol-5-yl]pyridin-2-yl}acetamide;
24) N-{3-[5-(2-aminopyridin-4-yl)-2-(tetrahydro-2H-pyran-4-yl)-1,3-thiazol-4-yl]-2-fluorophenyl}-2,5-difluorobenzenesulfonamide;
25) 2,5-difluoro-N-(2-fluoro-3-{5-[2-(methylamino)pyridin-4-yl]-2-(tetrahydro-2H-pyran-4-yl)-1,3-thiazol-4-yl}phenyl)benzenesulfonamide;
26) 2,5-difluoro-N-{2-fluoro-3-[2-(1-methylpiperidin-4-yl)-5-(2-methylpyridin-4-yl)-1,3-thiazol-4-yl]phenyl}benzenesulfonamide;
27) 2,5-difluoro-N-{2-fluoro-3-[5-(2-fluoropyridin-4-yl)-2-(1-methylpiperidin-4-yl)-1,3-thiazol-4-yl]phenyl}benzenesulfonamide;
28) 2,5-difluoro-N-{2-fluoro-3-[5-(2-methylpyridin-4-yl)-2-(tetrahydro-2H-pyran-4-yl)-1,3-thiazol-4-yl]phenyl}benzenesulfonamide;
29) N-{4-[4-(3-{[(2,5-difluorophenyl)sulfonyl]amino}-2-fluorophenyl)-2-(1-methylpiperidin-4-yl)-1,3-thiazol-5-yl]pyridin-2-yl}-2-methylpropanamide;
30) N-{4-[2-(1-cyclopropylpiperidin-4-yl)-4-(3-{[(2,5-difluorophenyl)sulfonyl]amino}-2-fluorophenyl)-1,3-thiazol-5-yl]pyridin-2-yl}acetamide;
31) N-{3-[2-(1-cyclopropylpiperidin-4-yl)-5-(2-methylpyridin-4-yl)-1,3-thiazol-4-yl]-2-fluorophenyl}-2,5-difluorobenzenesulfonamide;
32) N-{3-[2-(1-cyclopropylpiperidin-4-yl)-5-(2-fluoropyridin-4-yl)-1,3-thiazol-4-yl]-2-fluorophenyl}-2,5-difluorobenzenesulfonamide;
33) N-[4-(3-{[(2,5-difluorophenyl)sulfonyl]amino}-2,6-difluorophenyl)-5-(pyridin-4-yl)-1,3-thiazol-2-yl]acetamide;
34) 2,5-difluoro-N-{2-fluoro-3-[5-(3-fluoropyridin-4-yl)-2-(tetrahydro-2H-pyran-4-yl)-1,3-thiazol-4-yl]phenyl}benzenesulfonamide;

35) N-{4-[4-(3-{[(2,5-difluorophenyl)sulfonyl]amino}-2-fluorophenyl)-2-(tetrahydro-2H-pyran-4-yl)-1,3-thiazol-5-yl]pyridin-2-yl}acetamide;
36) N-[2-({4-[4-(3-{[(2,5-difluorophenyl)sulfonyl]amino}-2-fluorophenyl)-2-(tetrahydro-2H-pyran-4-yl)-1,3-thiazol-5-yl]pyridin-2-yl}amino)ethyl]acetamide;
37) N-(3-{2-(1-cyclopropylpiperidin-4-yl)-5-[2-(methylamino)pyridin-4-yl]-1,3-thiazol-4-yl}-2-fluorophenyl)-2,5-difluorobenzenesulfonamide;
38) 2,5-difluoro-N-(2-fluoro-3-{5-[2-(methylamino)pyridin-4-yl]-2-(1-methylpiperidin-4-yl)-1,3-thiazol-4-yl}phenyl)benzenesulfonamide;
39) N-{3-[5-(2-aminopyridin-4-yl)-2-(1-methylpiperidin-4-yl)-1,3-thiazol-4-yl]-2-fluorophenyl}-2,5-difluorobenzenesulfonamide;
40) N-{3-[5-(2-{[2-(dimethylamino)ethyl]amino}pyridin-4-yl)-2-(tetrahydro-2H-pyran-4-yl)-1,3-thiazol-4-yl]-2-fluorophenyl}-2,5-difluorobenzenesulfonamide;
41) methyl [(2S)-1-({4-[4-(3-{[(2,5-difluorophenyl)sulfonyl]amino}-2-fluorophenyl)-2-(tetrahydro-2H-pyran-4-yl)-1,3-thiazol-5-yl]pyridin-2-yl}amino)propan-2-yl]carbamate;
42) N-{4-[2-tert-butyl-4-(3-{[(2,5-difluorophenyl)sulfonyl]amino}-2-fluorophenyl)-1,3-thiazol-5-yl]pyridin-2-yl}acetamide;
43) N-{3-[2-tert-butyl-5-(pyridin-4-yl)-1,3-thiazol-4-yl]-2-fluorophenyl}-2,5-difluorobenzenesulfonamide;
44) N-{4-[4-(3-{[(2,5-difluorophenyl)sulfonyl]amino}-2-fluorophenyl)-2-(piperidin-4-yl)-1,3-thiazol-5-yl]pyridin-2-yl}acetamide;
45) methyl [(2S)-1-({4-[4-(3-{[(2,5-difluorophenyl)sulfonyl]amino}-2-fluorophenyl)-2-(1-methylpiperidin-4-yl)-1,3-thiazol-5-yl]pyridin-2-yl}amino)propan-2-yl]carbamate;
46) 2,5-difluoro-N-{2-fluoro-3-[5-(3-fluoropyridin-4-yl)-2-(1-methylpiperidin-4-yl)-1,3-thiazol-4-yl]phenyl}benzenesulfonamide;
47) N-{4-[4-(3-{[(2,5-difluorophenyl)sulfonyl]amino}-2-fluorophenyl)-2-(1-ethylpiperidin-4-yl)-1,3-thiazol-5-yl]pyridin-2-yl}acetamide;
48) methyl [(2S)-1-({4-[2-(1-cyclopropylpiperidin-4-yl)-4-(3-{[(2,5-difluorophenyl)sulfonyl]amino}-2-fluorophenyl)-1,3-thiazol-5-yl]pyridin-2-yl}amino)propan-2-yl]carbamate;
49) N-{3-[2-(1-cyclopropylpiperidin-4-yl)-5-(3-fluoropyridin-4-yl)-1,3-thiazol-4-yl]-2-fluorophenyl}-2,5-difluorobenzenesulfonamide;
50) N-{3-[5-(2-aminopyridin-4-yl)-2-tert-butyl-1,3-thiazol-4-yl]-2-fluorophenyl}-2,5-difluorobenzenesulfonamide;
51) N-(3-{2-tert-butyl-5-[2-(methylamino)pyridin-4-yl]-1,3-thiazol-4-yl}-2-fluorophenyl)-2,5-difluorobenzenesulfonamide and
52) methyl [(2S)-1-({4-[2-tert-butyl-4-(3-{[(2,5-difluorophenyl)sulfonyl]amino}-2-fluorophenyl)-1,3-thiazol-5-yl]pyridin-2-yl}amino)propan-2-yl]carbamate.

The present invention also provides a process for the preparation of a compound of formula (I) as defined above, by using the reaction routes and synthetic schemes described below, employing the techniques available in the art and starting materials readily available. The preparation of certain embodiments of the present invention is described in the examples that follow, but those of ordinary skill in the art will recognize that the preparations described may be readily adapted to prepare other embodiments of the present invention. For example, the synthesis of non-exemplified compounds according to the invention may be performed by modifications apparent to those skilled in the art, for instance by appropriately protecting interfering groups, by changing to other suitable reagents known in the art, or by making routine modifications of reaction conditions. Alternatively, other reactions referred to herein or known in the art will be recognized as having adaptability for preparing other compounds of the invention.

A compound of formula (I) can be prepared according to the general synthetic processes described hereafter in methods A, B, C, D, E and F.

All those with ordinary skills in the art will appreciate that any transformation performed according to said methods may require standard modifications such as, for instance, protection of interfering groups, change to other suitable reagents known in the art, or make routine modifications of reaction conditions.

In a general synthetic process, a compound of formula (I)A, (I)B, (I)U1 or (I)V1 is prepared according to method A shown below.

Method A

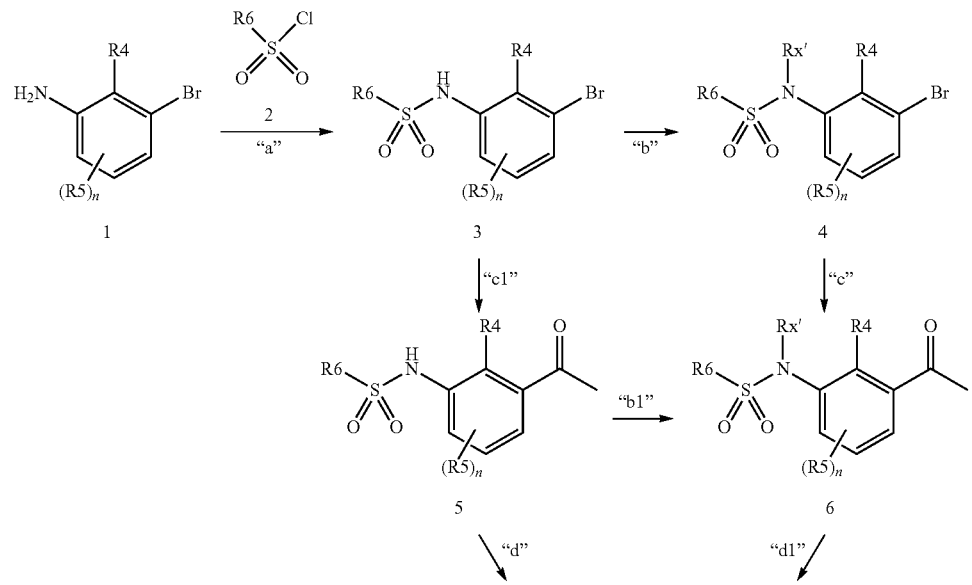

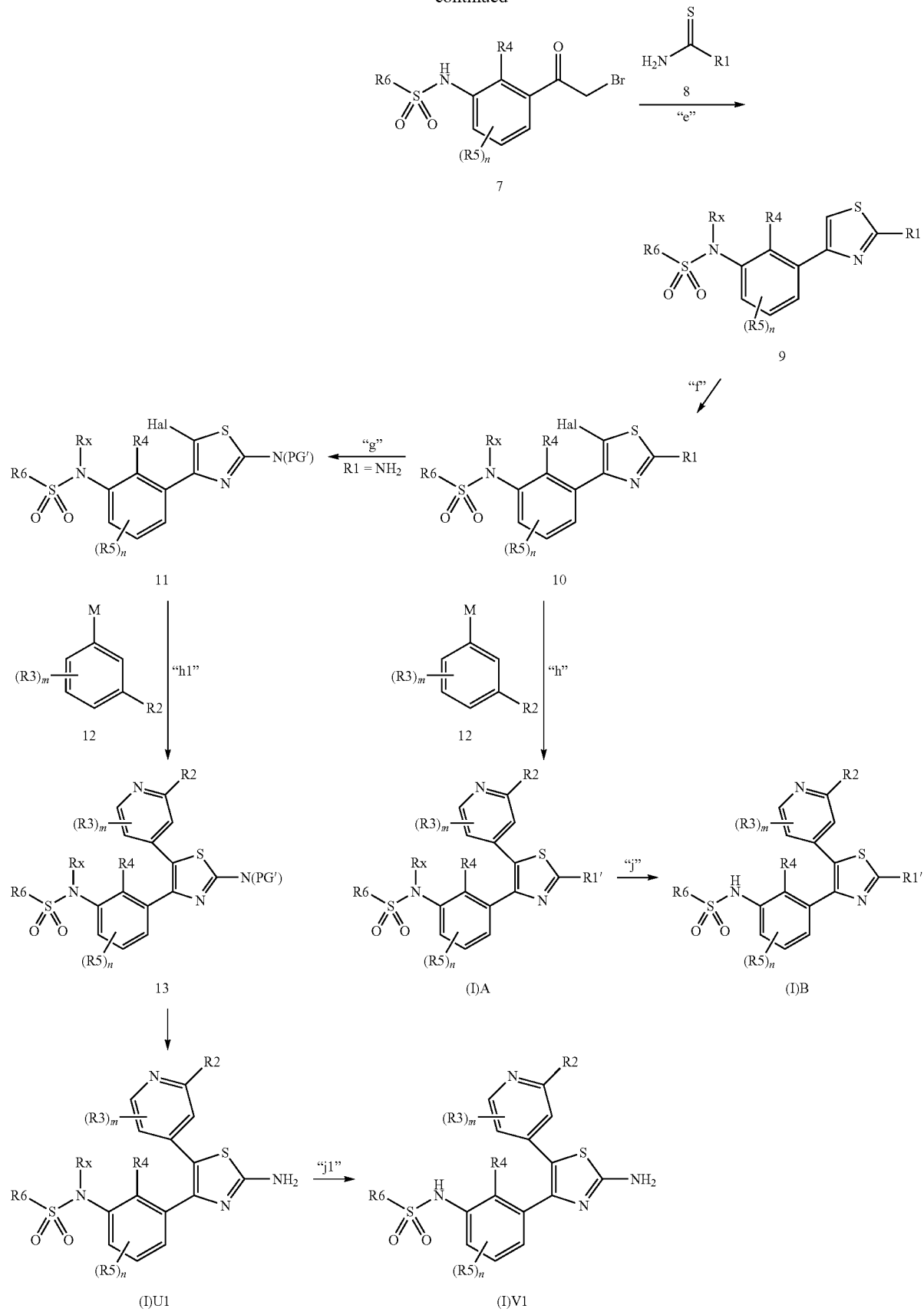
-continued

In the above scheme m, n, R2, R3, R4, R5, R6, R7, R8 and Rx are as defined above, Rx' is as Rx except hydrogen, R1' is as R1 except $NH_2$, PG' is a protecting group such as acetyl, benzoyl or dimethylaminoimino group, Hal is a halogen such as iodine or bromine and M is Li, $B(OH)_2$, $B(OAlk)_2$, $Sn(Alk)_3$, $Al(Alk)_2$, ZnHal, MgHal or $ZrCp_2Hal$, wherein Alk stands for an alkyl group and Cp stands for cyclopentadienide.

In a general synthetic process for the preparation of a compound of formula (I)A, (I)B, (I)A1 and (I)B1, which is described in method A, in step "a" a compound of formula 1 is reacted with a compound of formula 2 to yield a sulfonamide of formula 3. In step "b", optionally a group is introduced on the sulfonamido moiety, giving a compound of formula 4. In step "c" a methylketone of formula 6 is prepared in a two-step procedure involving a Heck-type reaction followed by acidic hydrolysis. In step "c1" a methylketone of formula 5 is prepared from a compound of formula 3 in a two-step procedure involving a Heck-type reaction followed by acidic hydrolysis. In step "b1", optionally a group is introduced on the sulfonamido moiety of a compound of formula 5, giving a compound of formula 6. In step "d" and "d1" a ketone of formula 5 or 6 respectively is transformed in the corresponding α-bromo ketone of formula 7, through a suitable bromination method. In step "e" generation of the thiazole system is accomplished by condensation with a thiourea or thioamide derivative of formula 8 to yield a compound of formula 9. In step "f" the thiazole ring is halogenated to yield a compound of formula 10. In step "g", a compound of formula 10 wherein R1 is $NH_2$ is protected on the amino group giving rise to a compound of formula 11. In step "h" a compound of formula 10, wherein R1 is different from $NH_2$, is submitted to a cross-coupling reaction suitable for the formation of carbon-carbon bonds, to give a compound of formula (I)A; in step "h1" a compound of formula 11 is submitted to the cross-coupling reaction said above, to give a compound of formula 13. Said reactions, which are well known in the art, imply coupling with a suitable organometallic reagent of general formula 12, such as, for instance, an organoboron, organotin, organozinc, organoaluminum or organozirconium compound and the like. In step "i" a compound of formula 13 is reacted with a suitable hydrolyzing agent to give a compound of formula (I)U1. In step "j" a compound of formula (I)A wherein Rx is as defined above except hydrogen is transformed into the corresponding compound of formula (I)B. In step "j1" a compound of formula (I)U1 wherein Rx is as defined above except hydrogen is transformed into the corresponding compound of formula (I)V1.

According to step "a" of method A, a compound of formula 1 is reacted with a sulfonyl chloride of formula 2 in the presence of a suitable base, such as, for instance, pyridine, N-methylmorpholine, diisopropylethylamine (DIPEA), triethylamine (TEA), in the appropriate solvent such as pyridine, dichloromethane (DCM) or THF, at a temperature ranging from about 0° C. to reflux and for a time varying from about 1 to 8 h.

According to step "b" of method A, a compound of formula 3 is optionally reacted with a suitable reactant such as tert-butoxycarbonyl anhydride, p-methoxybenzyl chloride, an alkoxyalkyl chloride, such as methoxymethyl chloride, an acyl chloride, such as acetyl chloride, an alkoxycarbonyl chloride, such as ethyl chloroformate, or the like, optionally in the presence of a suitable base such as dimethylaminopyridine, TEA, DIPEA, in the appropriate solvent such as DCM, acetonitrile, pyridine or THF, at a temperature ranging from 0° C. to r.t. and for a time varying from 1 to about 6 h.

According to step "b1" of method A, the optional transformation of a compound of formula 5 in a compound of formula 6 is accomplished as described under step "b" of method A.

According to step "c" of method A, a compound of formula 4 is reacted with a vinyl n-alkyl, preferably vinyl n-butylether, in the presence of a base such as TEA, a phosphine ligand such as 1,3-bis(diphenylphosphino)propane (DPPP) and in the presence of a suitable catalyst such as palladium acetate, in the appropriate solvent such as ethylenglycol, at a temperature ranging from 80 to 150° C. in a closed bottle under nitrogen atmosphere and for a time ranging from 1 to about 12 h. The intermediate thus prepared is hydrolyzed in acidic conditions, for example with aqueous hydrochloric acid (HCl), in the appropriate solvent such as dioxane or THF at room temperature and for a time ranging from 1 to about 6 h to form a compound of formula 6.

According to step "c1" of method A, transformation of a compound of formula 3 in a compound of formula 5 is accomplished as described under step "c" of method A.

According to step "d" of method A, a compound of formula 5 is reacted with a suitable brominating agent such as pyridinium bromide perbromide or tetrabutyl ammonium perbromide, in the appropriate solvent such as THF or DCM, at a temperature ranging from 60 to 100° C. in a microwave apparatus or in the classical thermal conditions and for a time ranging from 15 min to 3 h. Alternatively bromination of a compound of formula 5 is achieved in a two-step procedure involving first the reaction of compounds 5 with trimethylsilyl trifluoromethansulfonate in the presence of a base such as TEA or DIPEA, in the appropriate solvent such as DCM or THF, at a temperature ranging from −10 to 0° C. and for a time ranging from 10 to 30 min. The resulting trimethylsilyl enolether is then treated with N-bromosuccinimide, in the appropriate solvent such as DCM or THF, at a temperature ranging from −10 to 0° C. and for a time ranging from 30 min to 1 h.

According to step "d1" of method A, transformation of a compound of formula 6 in a compound of formula 7 is accomplished as described under step "d" of method A.

According to step "e" of method A, a compound of formula 7 is reacted with a thiourea or thioamide derivative of formula 8, in the appropriate solvent such as ethanol or methanol (MeOH), at a temperature ranging from 60° C. to reflux, in a microwave apparatus or in the classical thermal conditions and for a time ranging from 15 min to 3 h.

According to step "f" of method A, a compound of formula 9 is reacted with a suitable brominating agent such as N-bromosuccinimide in the appropriate solvent such as DCM or THF, or $Br_2$ in the appropriate solvent such as acetic acid, optionally in the presence of KOAc, at room temperature and for a time ranging from 1 to about 6 h.

According to step "g" of method A, a compound of formula 10 wherein R1 is $NH_2$ is reacted with a suitable protecting agent. Preferred is the reaction with dimethylformamide dimethyl acetal in the appropriate solvent such as dimethylformamide (DMF) at room temperature and for a time ranging from 1 to 16 h.

According to step "h" of method A, a compound of formula 10 wherein R1 is different from $NH_2$ is cross-coupled to a suitable organometallic compound of general formula 12, such as, for instance, an organoboron compound (Suzuki reaction), an organotin compound (Stille reaction), an organozinc, organoaluminum or organozirconium compound (Negishi reaction), and the like to yield a compound of formula (I)A. Said reactions are well known among those with ordinary skills in the art. Preferred reaction is the Suzuki reaction where an appropriate boronate derivative is used in the presence of a palladium-based catalyst, such as, for instance, palladium dichloride diphenylphosphinoferrocene complex with DCM, and a suitable base, such as $Cs_2CO_3$, $Na_2CO_3$, $K_2CO_3$, $Rb_2CO_3$, NaOH, CsF, and the like. Said reactions can be carried out in a solvent such as DMF, dimethylsulfoxide, water, dimethoxyethane (DME), 1,4-dioxane, THF or the like, and mixture thereof, at a temperature ranging from 100 to 120° C., in a microwave apparatus or under classical thermal conditions, for a time ranging from 1 to 16 h.

According to step "h1" of method A, transformation of a compound of formula 11 in a compound of formula 13 is accomplished as described under step "h" of method A.

According to step "i" of method A, a compound of formula 13 is reacted with a suitable hydrolyzing agent, depending on the nature of the protecting group PG', to form a compound of formula (I)U1. For instance when such a protecting group is represented by a dimethylaminoimino group, deprotection is achieved using ammonia 7N in MeOH, ethylendiamine in ethanol, lithium hydrate or sodium hydrate in mixtures water/THF or MeOH or ethanol, at a temperature ranging from room temperature to reflux and for a time ranging from 8 to 96 h.

According to step "j" of method A, the compound of formula (I)A, wherein Rx is Rx', is transformed into a compound of formula (I)B, using conditions depending on the nature of such group Rx'. For instance, when such a group is represented by a methoxymethyl, a benzyl, a tert-butoxycarbonyl group or the like, removal can be accomplished using strong acids like trifluoroacetic acid (TFA) or HCl. Said reaction can be carried out optionally in the presence of a suitable cosolvent such as water, THF or 1,4-dioxane, at a temperature ranging from room temperature to 90° C. and for a time ranging from 1 h to about 8 h. When such a group is represented for instance by an acetyl, an ethoxycarbonyl group or the like, removal can be accomplished using a base such as TEA or DIPEA in MeOH or ethanol, or using an aqueous solution of an inorganic base such as sodium or potassium carbonate, sodium or potassium hydroxide or the like. Said reactions can be carried out at temperatures ranging from 0° C. to reflux and for a time ranging from 30 min to about 48 h.

According to step "j1" of method A, the compound of formula (I)U1 is transformed into a compound of formula (I)V1, as described under step "j" above.

A compound of formula (I), prepared according to method A described above, may be further transformed into another compound of formula (I) following procedures well known to those skilled in the art.

For instance, when R1 is represented by a $NH_2$ group (compound of formula (I)U1), said compound can further be transformed into another compound of formula (I)C, (I)D, (I)E, (I)F, (I)G, (I)H, (I)I, (I)J, (I)K, (I)L, (I)M, (I)N, (I)O, (I)P, (I)U or (I)V according to method B shown below.

Method B

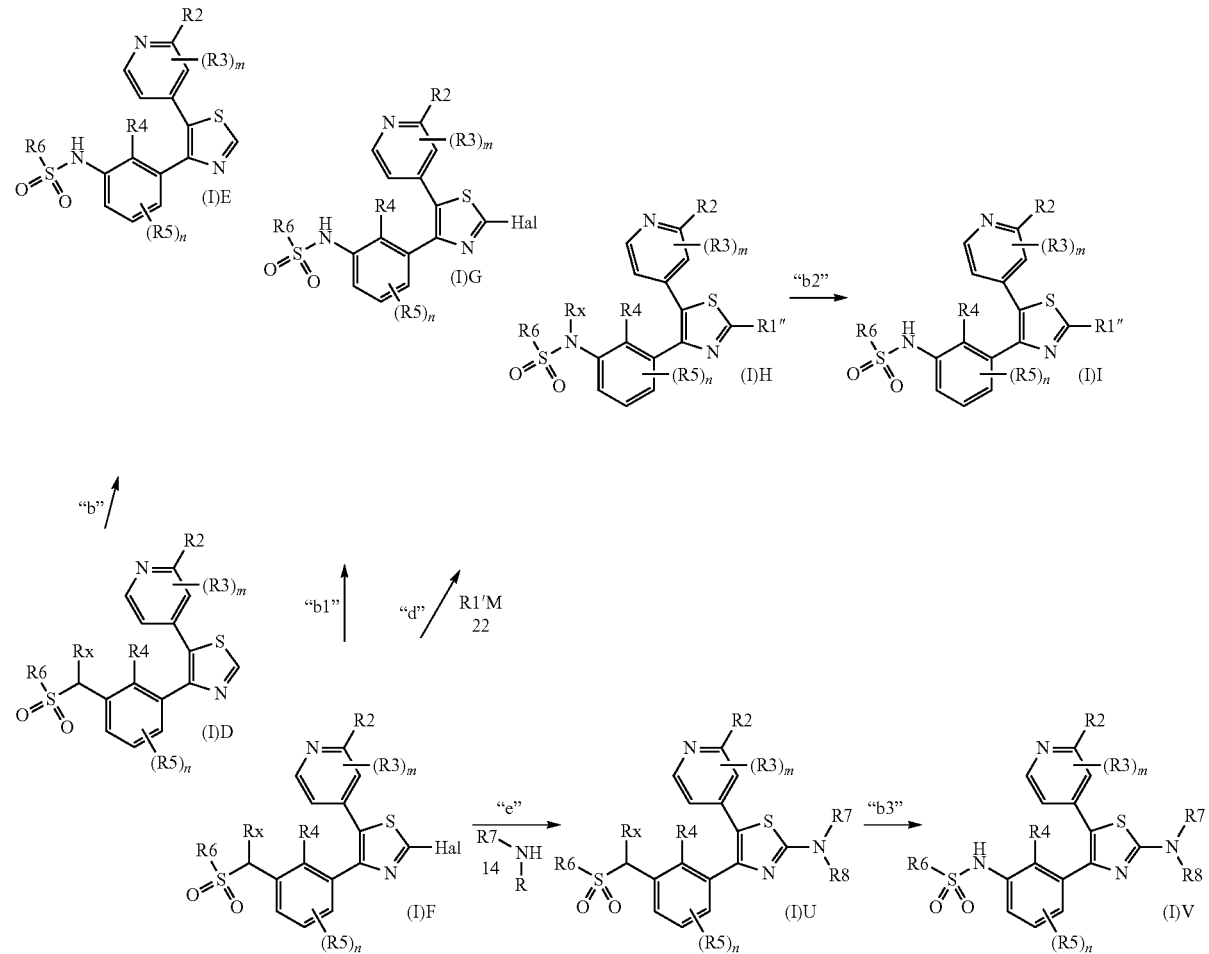

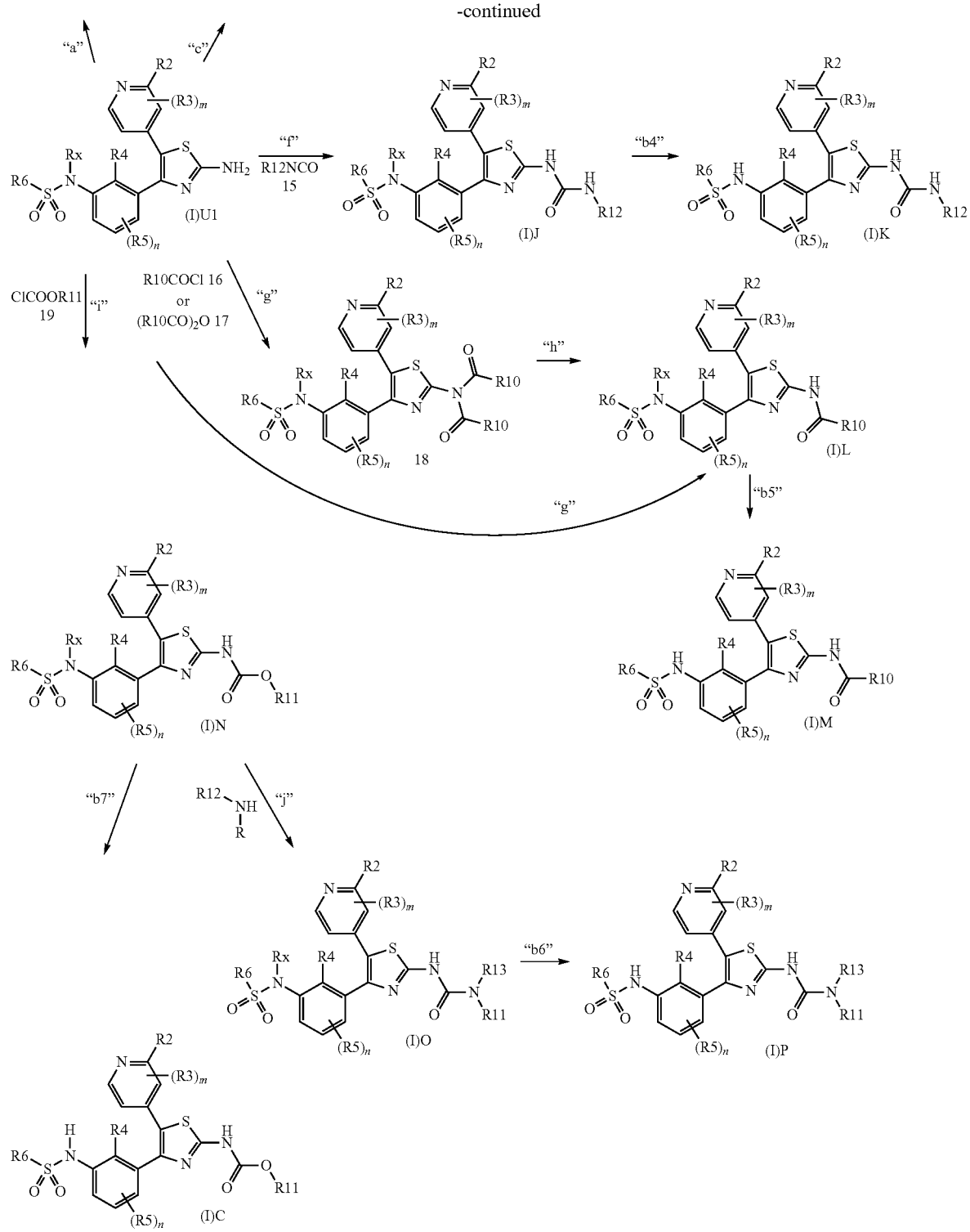

In the above scheme m, n, R2, R3, R4, R5, R6, R7, R8, R10, R11, R12, R13, Rx and Hal are as described above and R1″ is an optionally substituted ($C_2$-$C_8$) alkenyl, ($C_3$-$C_8$) cycloalkenyl, heterocyclyl, aryl or heteroaryl.

In a synthetic process for the preparation of compounds of formula (I)C, (I)D, (I)E, (I)F, (I)G, (I)H, (I)I, (I)J, (I)K, (I)L, (I)M, (I)N, (I)O, (I)P, (I)U or (I)V which is described in method B, in step "a" a compound of formula (I)U1 prepared as described in method A, is submitted to a Sandmeyer-type reaction followed by reduction of the intermediate diazonium salt, to yield a compound of general formula (I)D. In step "b", the compound of formula (I)D wherein Rx is as defined above except hydrogen, is converted into the corresponding compound of formula (I)E. In step "c" a compound of formula (I)U1 is submitted to a Sandmeyer-type reaction followed by reaction with a suitable halogenating agent to yield a haloderivative of formula (I)F. In step "b1", the compound of formula (I)F wherein Rx is as defined above except hydrogen, is converted into the corresponding compound of formula (I)G. In step "d" a compound of formula (I)F is transformed into a compound of formula (I)H exploiting any of the cross-coupling reactions suitable for the formation of carbon-carbon bonds. Said reactions, which are well known in the art, imply coupling with a suitable organometallic reagent of formula 22, such as, for instance, an organoboron, organotin, organozinc, organoaluminum or organozirconium compound and the like. In step "b2", a compound of formula (I)H wherein Rx is as defined above except hydrogen is converted into the corresponding compound of formula (I)I. In step "e" a compound of formula (I)F is converted into a compound of formula (I)U by reaction with an amine of formula 14. In step "b3", a compound of formula (I)U wherein Rx is as defined above except hydrogen is converted into the corresponding compound of formula (I)V. In step "f" a compound of formula (I)U1 is condensed with an isocyanate of formula 15 to yield a urea derivative of formula (I)J. In step "b4" a compound of formula (I)J wherein Rx is as defined above except hydrogen is converted into the corresponding compound of formula (I)K. In step "g" a compound of formula (I)U1 is condensed with a compound of formula 16 or 17 to yield an imido derivative of formula 18 or directly a compound of formula (I)L. The latter can be otherwise obtained in step "h" from a compound of formula 18 by selective hydrolysis of one of the acyl group, which can be achieved under basic conditions. In step "b5", a compound of formula (I)L wherein Rx is as defined above except hydrogen is converted into the corresponding compound of formula (I)M. In step "i" a compound of formula (I)U1 is reacted with a suitable chloroformate of formula 19 to yield a carbamate derivative of formula (I)N. In step "j" the latter is converted in an urea derivative of formula (I)O by reaction with an amine of formula 20. In step "b6", a compound of formula (I)O wherein Rx is as defined above except hydrogen is converted into the corresponding compound of formula (I)P. In step "b7", a compound of formula (I)N wherein Rx is as defined above except hydrogen is converted into the corresponding compound of formula (I)C.

According to step "a" of method B, the synthesis of a compound of formula (I)D from a compound of formula (I)U1 is accomplished preparing a diazonium salt, which can be done using sodium nitrite in water or aqueous solvents, in the presence of a mineral acid, such as HCl, sulphuric acid and the like, following reduction of said salt, which can be done using an alcohol such as ethanol, or a suitable reducing agent such as hypophosphorous acid. Alternatively the diazonium salt can be obtained using isoamyl nitrite in a suitable solvent such as DCM, DME, THF and the like at a temperature ranging from 0° C. to reflux and for a time ranging from 30 min to about 24 h.

According to step "b" of method B, the conversion of a compound of formula (I)D into the corresponding compound of formula (I)E is accomplished as described under step "j" of method A.

According to step "c" of method B, the transformation of a compound of formula (I)U1 into a compound of formula (I)F is accomplished by means of a Sandmeyer protocol. This is accomplished preparing a diazonium salt, which can be done using sodium nitrite in water or aqueous solvents, in the presence of a mineral acid, such as HCl, sulphuric acid and the like, following treatment with a halide salt. Preferred is the bromination, and accordingly the preferred halide salt is CuBr. Alternatively, iodination can be carried out, which is achieved using KI, NaI, CsI, CuI optionally in the presence of iodine. Alternatively the diazonium salt can be obtained using isoamyl nitrite or tert-butyl nitrite in a suitable solvent such as acetonitrile, DCM, DME, THF and the like at a temperature ranging from 0° C. to reflux and for a time ranging from 30 min to about 3 days. According to step "b1" of method B, the conversion of a compound of formula (I)F into the corresponding compound of formula (I)G is accomplished as described under step "j" of method A.

According to step "d" of method B, a compound of formula (I)F is cross-coupled to a suitable organometallic compound of general formula 22, such as, for instance, an organoboron compound (Suzuki reaction), an organotin compound (Stille reaction), an organozinc, organoaluminum or organozirconium compound (Negishi reaction), and the like. Said reactions are well known among those with ordinary skills in the art. Preferred reaction is the Suzuki reaction where an appropriate aryl or heteroaryl boronate is used in the presence of a palladium-based catalyst, such as, for instance, palladium-tetrakis(triphenylphosphine)(Pd(PPh$_3$)$_4$), and a suitable base, such as Cs$_2$CO$_3$, Na$_2$CO$_3$, K$_2$CO$_3$, Rb$_2$CO$_3$, NaOH, CsF, and the like. Said reactions can be carried out in a solvent such as DMF, dimethylsulfoxide, water, DME, 1,4-dioxane, THF or the like, and mixture thereof, at a temperature ranging from 20° C. to reflux and for a time ranging from 30 min to about 24 h. According to step "b2" of method B, the conversion of a compound of formula (I)H into the corresponding compound of formula (I)I is accomplished as described under step "j" of method A.

According to step "e" of method B, the reaction of a compound of formula (I)F with a compound of formula 14 can be accomplished in the appropriate solvent such as dimethylacetamide, DMF, acetonitrile or the like optionally in the presence of a suitable base such as TEA or DIPEA. The reaction can be carried out in a microwave apparatus or in the classical thermal conditions, at a temperature ranging from 80 to 120° C. and for a time ranging from 1 h to 2 days. According to step "b3" of method B, the conversion of a compound of formula (I)U into the corresponding compound of formula (I)V is accomplished as described under step "j" of method A.

According to step "f" of method B, the reaction of a compound of formula (I)U1 with a compound of formula 15 can be accomplished in the appropriate solvent, such as 1,4-dioxane, THF, DME at a temperature ranging from room temperature to reflux and for a time ranging from 5 h to 2 days. According to step "b4" of method B, the conversion of a compound of formula (I)J into the corresponding compound of formula (I)K is accomplished as described under step "j" of method A.

According to step "g" of method B, the reaction of a compound of formula (I)U1 with a compound of formula 16 or 17, can be accomplished in the presence of a suitable base, such as TEA or DIPEA or pyridine, in the appropriate solvent such as DCM, THF, 1,4-dioxane or acetonitrile at room temperature and for a time ranging from 1 to about 8 h.

According to step "h" of method B, the conversion of a compound of formula 18 into a compound of formula (I)L is accomplished by selective hydrolysis using basic hydrolytic conditions, such as TEA in MeOH or diluted aqueous solution of NaOH or LiOH in the appropriate solvent such as ethanol, MeOH or THF at room temperature and for a time ranging from 1 to about 6 h. According to step "b5" of method B, the conversion of a compound of formula (I)L into the corresponding compound of formula (I)M is accomplished as described under step "j" of method A.

According to step "i" of method B, the conversion of a compound of formula (I)U1 into a compound of formula (I)N is achieved by reaction with a chloroformate of formula 19 in the appropriate solvent such as THF, DMF, DCM, chloroform, acetonitrile, toluene or mixtures thereof, at a temperature ranging from about −10° C. to reflux and for a time varying from about 30 min to about 96 h. The reaction is normally carried out in the presence of an opportune proton scavenger such as TEA, DIPEA or pyridine.

According to step "b7" of method B, the conversion of a compound of formula (I)N into the corresponding compound of formula (I)C is accomplished as described under step "j" of method A.

According to step "j" of method B, a compound of formula (I)O is obtained from a compound of formula (I)N by reaction with an appropriate amine of formula 20. Said reaction is typically carried out in the appropriate solvent such as dimethylsulfoxide, THF, DMF, N,N-dimethylacetamide, acetonitrile, toluene or mixture thereof, optionally in the presence of a further base such as TEA, DIPEA, diazabicycloundecene or an organometallic reagent such as a Grignard reagent or trimethyl aluminium, at a temperature ranging from about −10° C. to reflux and for a time varying from about 30 min to about 96 h. According to step "b6" of method B, the conversion of a compound of formula (I)O into the corresponding compound of formula (I)P is accomplished as described under step "j" of method A.

In another general synthetic process, described in method C shown below, the synthesis of a compound of formula (I) wherein R1 is a heterocyclyl group is described; in particular, a compound of formula (I)H1 is prepared and further elaborated into a compound of formula (I)Q, (I)R, (I)R1 or (I)R2.

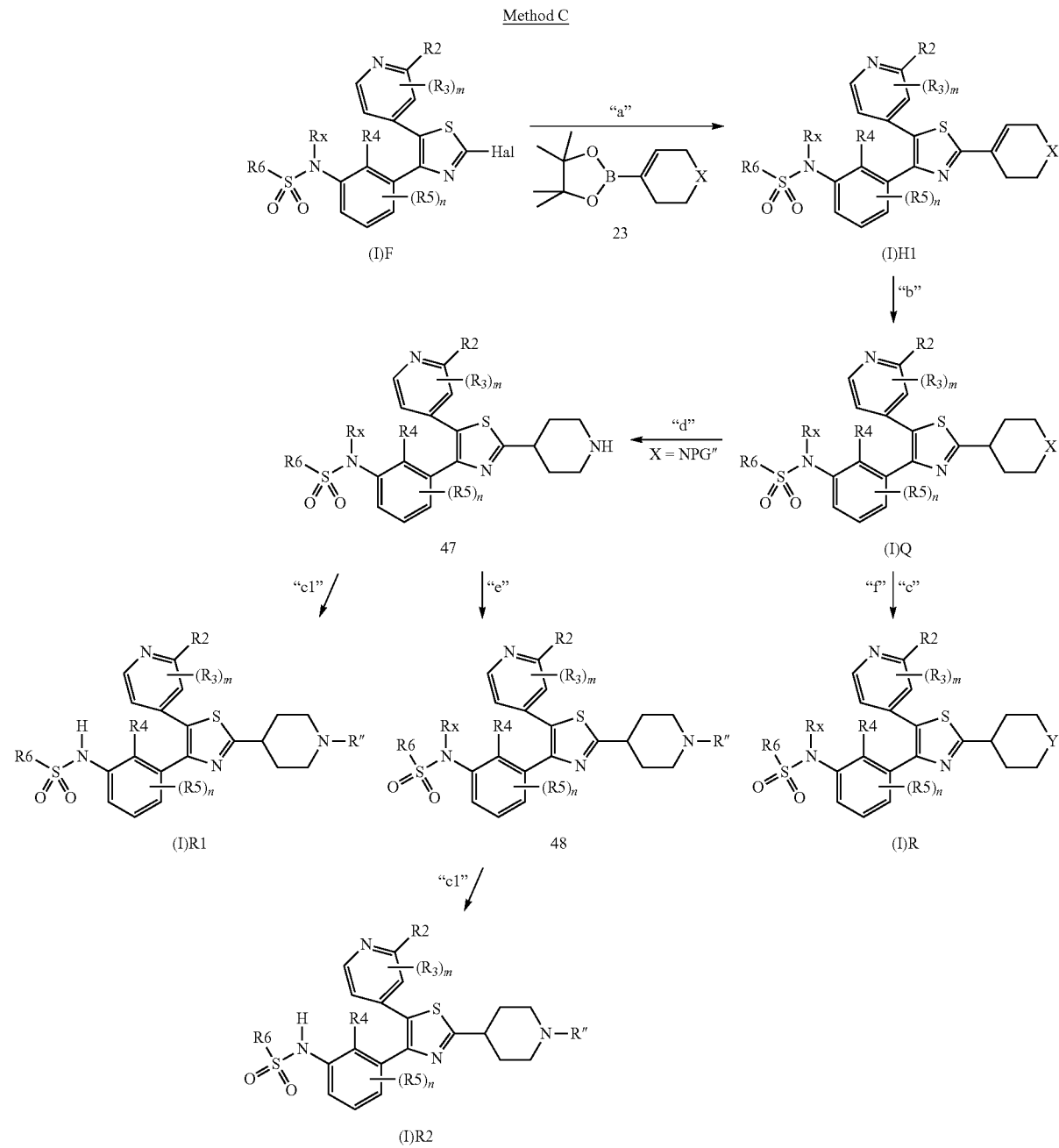

In the above scheme m, n, R2, R3, R4, R5, R6, Rx and Hal are as defined above; R2" is as R2 or NR18COR22, wherein R18 and R22 are as defined above.

X is S, O, NH or NR', wherein R' is a straight or branched ($C_1$-$C_8$) alkyl, ($C_3$-$C_8$) cycloalkyl, heterocyclyl, aryl, heteroaryl or a PG" group, wherein PG" is a suitable nitrogen protecting group, such as, for instance, tert-butoxy carbonyl, benzyl or benzyloxycarbonyl;

R" is a straight or branched ($C_1$-$C_8$) alkyl or ($C_3$-$C_8$)cycloalkyl;

Y is S, O, NH or a NR'" group, wherein R'" is a straight or branched ($C_1$-$C_8$) alkyl, ($C_3$-$C_8$) cycloalkyl, heterocyclyl, aryl or heteroaryl.

In a synthetic process for the preparation of a compound of formula (I)H1, (I)Q, (I)R, (I)R1 and (I)R2 which is described in method C, in step "a" a compound of formula (I)F is reacted with a compound of formula 23 according to a Suzuki protocol, to yield a compound of formula (I)H1. In step "b" a compound of formula (I)H1 is submitted to catalytic hydrogenation to yield a compound of formula (I)Q. In step "c", when X is S, O, NH or NR', a compound of formula (I)R is obtained. In step "d", when X is a NPG" group, a compound of formula 47 is obtained by mild selective removal of the PG" group. In step "e" a compound of formula 47 is submitted to reductive amination, to afford a compound of formula 48. In step "c1" or "c2" a compound of formula (I)R1 or (I)R2 is respectively obtained.

According to step "a" of method C, a heterocycloalkenyl derivative of formula 23 is coupled to a compound of formula (I)F according to a Suzuki reaction protocol. Said reaction can be carried out in the presence of a suitable base, such as cesium carbonate or potassium carbonate or phosphate and in the presence of a catalyst such as palladium dichloride diphenylphosphinoferrocene complex with DCM using mixtures of DME/water or 1,4-dioxane/water, as the solvents system. The reaction is accomplished in the appropriate solvent, such as mixtures DME/water or 1,4-dioxane/water, in a microwave apparatus or in the classical thermal conditions, at a temperature ranging from 90 to 120° C. and for a time ranging from 1 h to about 16 h.

According to step "b" of method C, the reduction of a compound of formula (I)H1 to give a compound of formula (I)Q is accomplished using any of the methods well known in the art for the reduction of a carbon-carbon double bond, for instance with ammonium formate in the presence of a catalyst such as palladium on charcoal 10% or palladium carbonate on charcoal 10% in a suitable solvent such as MeOH or ethanol at reflux and for a time ranging from 4 h to about 16 h. Alternatively the reduction can be carried out through hydrogenation in a Parr apparatus at a pressure ranging from 20 to 50 psi in the presence of a catalyst such as palladium on charcoal 5 or 10% at room temperature for a time ranging from 2 to about 6 h.

According to step "c" of method C, the conversion of a compound of formula (I)Q into the corresponding compound formula (I)R is accomplished as described under step "j" of method A.

According to step "d" of method C, the selective removal of the PG" group from a compound of formula (I)Q to afford a compound of formula 47 can be accomplished using acidic or reductive conditions. For instance, the reaction is carried out using strong acids, such as TFA, optionally in the presence of a suitable co-solvent, such as DCM, at temperatures ranging from 20° C. to reflux and for a time ranging from 30 min to about 48 h. Alternatively, when PG" is a benzyl or a benzyloxy group, said reaction is carried out using reductive conditions, such as $H_2$ in the presence of a suitable hydrogenation catalyst. The hydrogenation catalyst is usually a metal, most often palladium, which can be used as such or supported on carbon, in a suitable solvent such as, for instance, THF, 1,4-dioxane, DMF, MeOH, ethyl acetate, or a mixture thereof.

According to step "c1" of method C, the conversion of a compound of formula 47 into the corresponding compound of formula (I)R1 is accomplished as described under step "j" of method A.

According to step "e" of method C, the reductive amination of a compound of formula 47 to yield a compound of formula 48 is accomplished by reaction with the suitable carbonyl derivative, such as an aldehyde, a ketone or their corresponding acetal derivatives. The reaction is carried out in the presence of a suitable reducing agent, such as sodium cyanoborohydride or sodium triacethoxyborohydride, in the appropriate solvent, such as MeOH or a mixture acetic acid-MeOH, at a temperature ranging from room temperature to reflux and for a time ranging from 1 to about 24 h.

According to step "c2" of method C, the conversion of a compound of formula 48 into the corresponding compound of formula (I)R2 is accomplished as described under step "j" of method A.

In another general synthetic process, a compound of general formula (I)S or (I)T is prepared according to method D shown below.

Method D

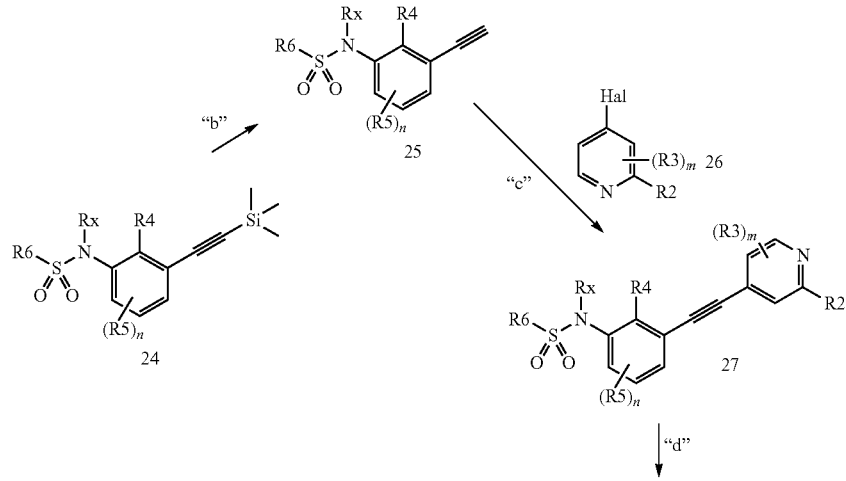

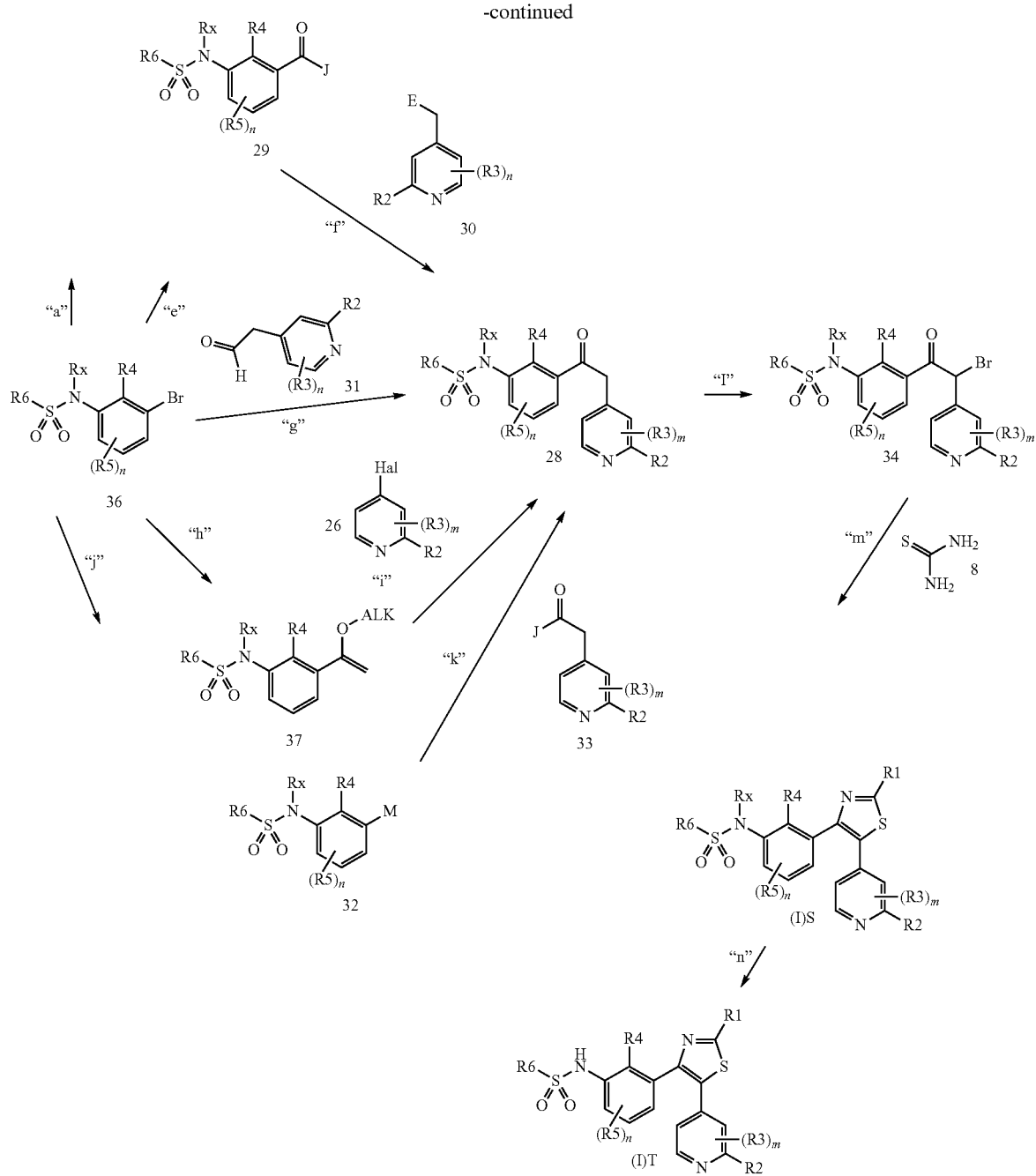

In the above scheme m, n, R1, R2, R3, R4, R5, R6, Rx and Hal are as described above; J is a halogen, such as chloride, or bromide, an O-alkyl group or a —N(CH₃)O-alkyl group, where alkyl is as defined above; E is hydrogen or an alkoxycarbonyl group;

In a synthetic process for the preparation of a compound of formula (I)S and (I)T, which is described in method D, in step "a" a compound of formula 36, which, when Rx is hydrogen corresponds to a compound of formula 3 or when Rx is Rx' corresponds to a compound of formula 4 described in scheme A, is subjected to a Sonogashira type reaction with trimethylsilylacetylene to form an intermediate of formula 24. In step "b" desilylation of the latter yields another intermediate of formula 25, that, after a second Sonogashira type coupling with a compound of formula 26 in step "c", yields an acetylene derivative of formula 27. Hydration of the latter is carried out in step "d" to form a key ketone intermediate of formula 28. Alternatively, in step "e" a compound of formula 36 is transformed in a compound of formula 29 by metallation, for instance with isopropyl magnesium chloride or butyl lithium and quenching with a suitable reagent of formula Hal-CO-J. Alternatively, quenching with CO₂ followed by carboxylic acid activation or a palladium-catalyzed carboxylation may yield the same compound of formula 29. In step "f" the latter is reacted with a compound of formula 30, which first is usually transformed in the corresponding metal anion, to give the key intermediate of formula 28. Alternatively, in step "g" a compound of formula 36 is directly transformed in a compound of formula 28 by a palladium-catalyzed cross-coupling with a suitable aldehyde of formula 31. Alternatively in step "h" a compound of formula 36 is transformed in a compound of formula 37, which in step "i" is reacted in a Heck-type reaction with a suitable compound of formula 26 to yield the key intermediate 28. Alternatively in step "j" a compound of formula 36 is transformed in an organometal derivative of formula 32, such as, for instance, an organolithium, organoboron or organomagnesium compound, which in turn in step "k" is reacted with a suitable electrophile of formula 33, to form a compound of formula 28. Such a transformation can be carried out following multiple methodologies depending on the nature of M and J as any expert in the art can readily appreciate. In step "l" halogenation of intermediate 28 yields a compound of formula 34, which, in step "m" is reacted with a suitable thiourea or thioamide derivative of formula 8 to yield a thiazole compound of formula (I)S. In step "n" the latter is converted into the corresponding compound of formula (I)T.

According to step "a" of method D, a compound of formula 36 is reacted with trimethylsilylacetylene in the presence of a suitable palladium catalyst such as $PdCl_2(PPh_3)_2$, $Pd(PPh_3)_4$, and the like, and of a suitable copper catalyst, such as CuI. Said reaction is carried out in the presence of a suitable base, such as TEA, diethylamine, diisopropylamine and the like, optionally in the presence of a phosphine ligand, such as triphenylphosphine. The reaction is normally carried out at temperatures ranging from −20° C. to reflux and for a time ranging from 30 min to about 48 h. According to step "b" of method D, the trimethylsilyl group is removed using a base such as KOH, NaOH, $K_2CO_3$, in a solvent such as MeOH, ethanol or the like or using a suitable fluoride salt, such as KF, n-$Bu_4$NF in solvents such as THF, DME, DMF or the like. According to step "c" of method D, a compound of formula 25 is transformed into a compound of formula 27 by reaction with a suitable aromatic halide of formula 26 following the conditions described under step "a" of method D. According to step "d" of method D, the hydration of the alkyne of formula 27 to give a compound of formula 28 is accomplished using, for instance acetic acid, TFA, trifluoromethansulfonic acid, sulfuric acid, $Hg(OTf)_2$, $HgSO_4$, $NaHSO_3$, and the like in a suitable aqueous solvent such as acetonitrile, 1,4-dioxane, acetone, ethanol or the like at a temperature ranging from 0° C. to reflux and for a time ranging from 1 h to 72 h.

According to step "e" of method D, the transformation of a compound of formula 36 in a compound of formula 29 can be accomplished in a number of ways. One such way involves metallation with a suitable organometallic compound such as, for instance, butyl lithium or isopropyl magnesium chloride, followed by quenching with a reagent of formula Hal-CO-J. Such reactions are normally carried out in an inert atmosphere using a suitable solvent such as, for instance, THF, 1,4-dioxane, DME or the like, at a temperature ranging from −80° C. to room temperature. Alternatively, quenching can be accomplished with dry ice, and the resulting carboxylic acid can be activated to form a compound of formula 29 following any of the methods well-known in the art. According to step "f" of method D, a compound of formula 30 is reacted with a strong base such as sodium hexamethyldisilazane (NaHMDS), lithium hexamethyldisilazane (LiHMDS), lithium diisopropylamide (LDA), a Grignard reagent and the like, following condensation with a compound of formula 29. Said reaction is typically performed using a variety of solvents such as toluene, THF, 1,4-dioxane, DME, or the like at a temperature ranging from 0° C. to reflux and for a time ranging from 30 min to about 24 h.

According to step "g" of method D, the transformation of a compound of formula 36 in a compound of formula 28 can be accomplished by reaction with a suitable aldehyde of formula 31. Such a reaction is normally carried out in the presence of suitable catalyst, such as $Pd(dba)_2$ or $Pd(OAc)_2$, and base, such as, for instance pyrrolidine, optionally in the presence of an additional ligand, such as DPPP and of molecular sieves. Said reaction is normally carried out in solvents such as, for instance, DMF at a temperature ranging from 80° C. to reflux, for a time varying from 1 h to 10 h. According to step "h" of method D, the transformation of a compound of formula 36 in a compound of formula 37 can be accomplished by reaction with vinyl n-alkylether, preferably vinyl n-butylether, in the presence of a base such as TEA, a phosphine ligand such as DPPP and in the presence of a suitable catalyst such as palladium acetate, in the appropriate solvent such as ethylenglycol, at a temperature ranging from 80 to 120° C. in a closed bottle under nitrogen atmosphere and for a time ranging from 1 to about 6 h.

According to step "i" of method D, the transformation of a compound of formula 37 in a compound of formula 28 can be accomplished using a Mizoroki-Heck protocol, where the olefin derivative 37 is reacted with an aryl halide of formula 26 in the presence of a palladium-based catalyst, such as, for instance, $Pd(PPh_3)_4$, and a suitable base, such as TEA and the like. Such a reaction is normally carried out in solvents such as DMF, THF, 1,4-dioxane, DME, or the like at a temperature ranging from 0° C. to reflux and for a time ranging from 30 min to about 24 h.

According to step "j" of method D, a compound of formula 36 is transformed in an organometallic derivative of formula 32, such as an organolithium, organoboron, an organomagnesium, or the like. Such a compound can be obtained in a variety of ways depending on the nature of the organometallic itself. For instance, organolithium compounds can be obtained reacting a compound of formula 36 with butyllithium or tert-butyllithium. Organoboron compounds can be obtained reacting a compound of formula 36 with a suitable boron compound, such as bis(pinacolato)diboron, pinacolborane, or the like in the presence of a suitable palladium catalyst such as palladium acetate, $PdCl_2$(dppf) [(1,1-Bis(diphenylphosphino)ferrocene]dichloropalladium(II)] and of a suitable base, such as KOAc, TEA and the like, in solvents such as DMF, dimethylsulfoxide, DME, 1,4-dioxane, THF or the like, at a temperature ranging from 20° C. to reflux and for a time ranging from 30 min to about 24 h. Organomagnesium compounds can be obtained reacting a compound of formula 36 with a suitable magnesium derivative, such as isopropyl magnesium chloride, or metallic magnesium in solvents such as DME, 1,4-dioxane, THF or the like, at a temperature ranging from −78° C. to reflux and for a time ranging from 30 min to about 24 h.

According to step "k" of method D, a compound of formula 32 is transformed in a compound of formula 28 by coupling with a suitable reagent of formula 33. The conditions for such a coupling depend on the nature of the organometallic compound 32 and of the reagent of formula 33. For instance, when the compound of formula 32 is an organoboron compound, coupling can be achieved with a compound of formula 33. Such a reaction is normally performed in the presence of a palladium-based catalyst, such as, for instance, $PdCl_2$ or $Pd(OAc)_2$, and a suitable base, such as $K_3PO_4$, $Cs_2CO_3$, $K_2CO_3$, $Rb_2CO_3$, NaOH, CsF, or the like, in a solvent like DME, 1,4-dioxane, THF or the like, at a temperature ranging from 20° C. to reflux and for a time ranging from 30 min to about 24 h. When 32 is an organomagnesium compound the coupling can be conveniently achieved with an ester or Weinreb amide of formula 33. Such reactions are normally performed in a solvent like DME, 1,4-dioxane, THF or the like, at a temperature ranging from −20° C. to reflux and for a time ranging from 30 min to about 24 h.

According to step "l" of method D, a compound of formula 28 is reacted with a suitable brominating agent such as $Br_2$, N-bromosuccinimide, pyridinium bromide perbromide or tetrabutyl ammonium perbromide, in the appropriate solvent such as THF or DCM, at a temperature ranging from 60 to 100° C. in a microwave apparatus or in the classical thermal conditions and for a time ranging from 15 min to 3 h. Alternatively bromination of a compound of formula 28 is achieved in a two-step procedure involving first the reaction of a compound of formula 28 with trimethylsilyl trifluoromethansulfonate in the presence of a base such as TEA or DIPEA, in the appropriate solvent such as DCM or THF, at a temperature ranging from −10 to 0° C. and for a time ranging from 10 to 30 min. The resulting trimethylsilyl enolether is then treated with N-bromosuccinimide, in the appropriate solvent such as DCM or THF, at a temperature ranging from −10 to 0° C. and for a time ranging from 30 min to 1 h.

According to step "m" of method D, a compound of formula 34 is reacted with a compound of formula 8 in the appropriate solvent such as ethanol or MeOH, at a temperature ranging from 60° C. to reflux, in a microwaves apparatus or under the classical thermal conditions, for a time ranging from 15 min to 3 h. According to step "n" of method D the conversion of a compound of formula (I)S into the corresponding compound of formula (I)T is accomplished as described under step "j" of method A.

In another general synthetic process, a compound of general formula (I)T is prepared according to method E shown below.

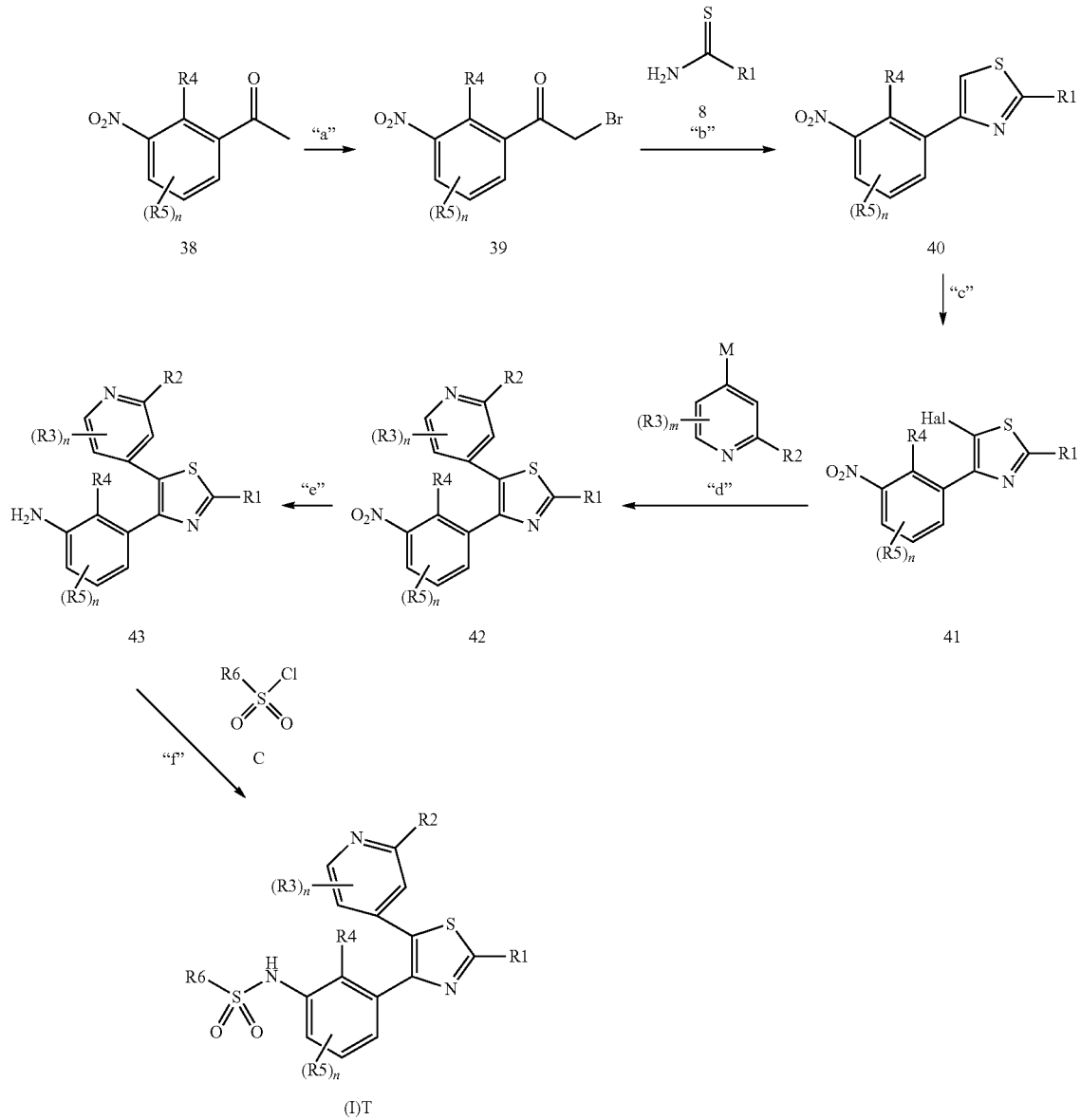

In the above scheme, m, n, R1, R2, R3, R4, R5, R6, M and Hal are as described above.

In a synthetic process for the preparation of a compound of formula (I)T, which is described in method E, in step "a" a compound of formula 38 is transformed in the corresponding α-bromo ketone of formula 39, through a suitable bromination method. In step "b", generation of the thiazole system is accomplished by condensation with a thiourea or thioamide derivative of formula 8 to yield a compound of formula 40. In step "c" the thiazole ring is halogenated to yield a compound of formula 41. In step "d" a compound of formula 41, is submitted to a cross-coupling reaction suitable for the formation of carbon-carbon bonds, to give a compound of formula 42. Said reactions, which are well known in the art, imply coupling with a suitable organometallic reagent of general formula 12, such as, for instance, an organoboron, organotin, organozinc, organoaluminum or organozirconium compound and the like. In step "e" a compound of formula 42 is treated with a suitable reducing agent to yield an amino-derivative of formula 43, which, in step "f" is reacted with a compound of formula 2 to yield a compound of formula (I)T.

According to step "a" of method E, the synthesis of a compound of general formula 39 from a compound of general formula 38 is accomplished as described under step "d" of method A.

According to step "b" of method E, the synthesis of a thiazole derivative of general formula 40 from a compound of general formula 39 is accomplished as described under step "e" of method A.

According to step "c" of method E, the halogenation of a thiazole derivative of general formula 40 to yield a compound of general formula 41 is accomplished as described under step "f" of method A.

According to step "d" of method E, the cross-coupling reaction between a derivative of general formula 41 and an organometallic compound of general formula 12 to yield a compound of general formula 42 is accomplished as described under step "h" of method A.

According to step "e" of method E, the nitro group of a compound of formula 42 is reduced to amino group to yield a compound of formula 43. The reaction may be carried out in a variety of methods and operative conditions, which are widely known in the art for reducing a nitro to an amino group. Preferably, this reaction is carried out in a suitable solvent such as, for instance, water, MeOH, THF, 1,4-dioxane, DMF, ethyl acetate, or a mixture thereof, in the presence of a suitable reducing agent, such as, for instance, hydrogen and a hydrogenation catalyst, or by treatment with cyclohexene or cyclohexadiene and a hydrogenation catalyst, or by treatment with tin (II) chloride, or by treatment with zinc or zinc(II) chloride and aqueous HCl or acetic acid or ammonium chloride, at a temperature ranging from 0° C. to reflux and for a time varying from about 1 h to about 96 h. The hydrogenation catalyst is usually a metal, most often palladium, which can be used as such or supported on carbon.

According to step "f" of method E, the synthesis of a compound of general formula (I)T from a compound of general formula 43 is accomplished as described under step "a" of method A.

A compound of formula (I) prepared according to method A, method B, method C, method D and method E above may be further transformed into another compound of formula (I) following procedures well known to those skilled in the art.

For instance, when R2 is represented by a hydrogen (compound of formula (I)W) or when R2 is a halogen (compound of formula (I)Y), said compounds can be further transformed into other compounds of formula (I)X, (I)Z, (I)Z1 and (I)Z2. In addition, a compound of formula (I)Y can be further transformed into another compound of formula (I)AB and (I)AC according to method F.

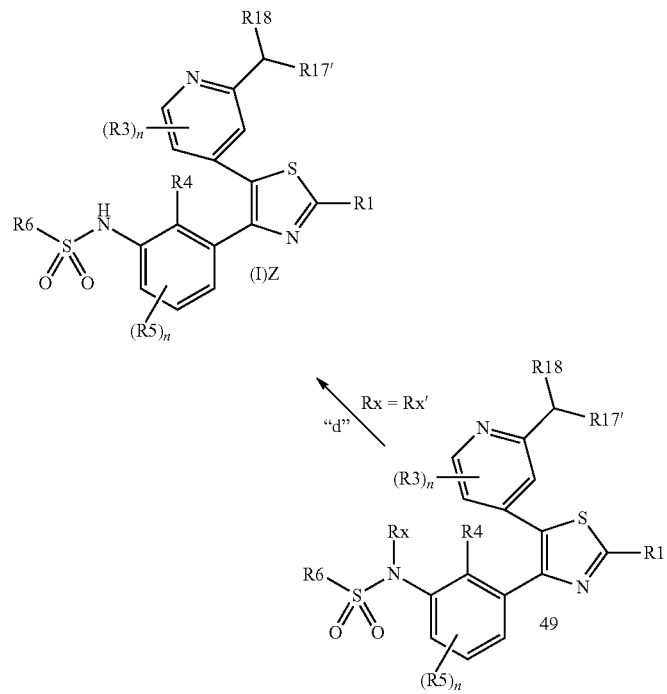

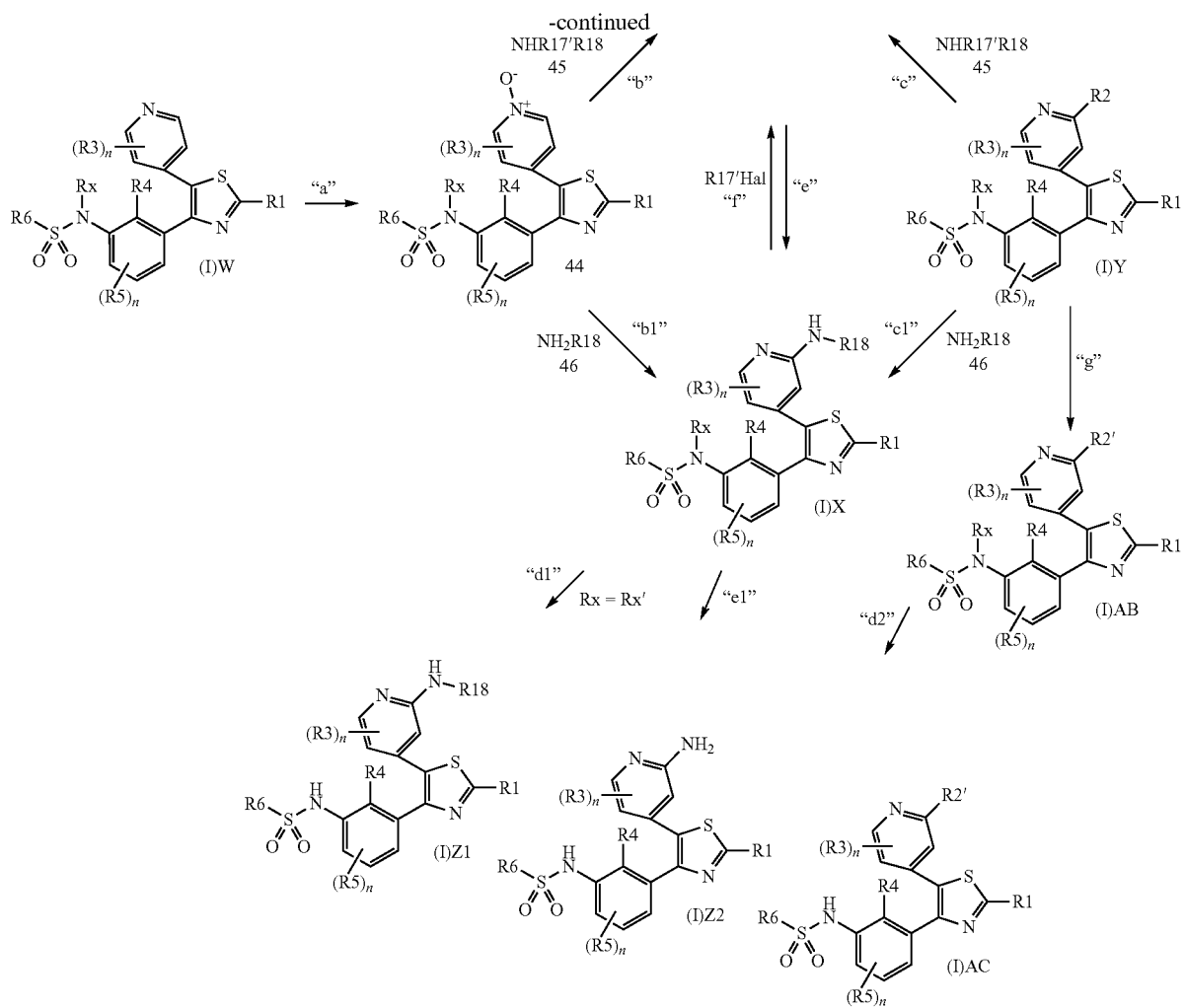

In the above scheme m, n, R1, R3, R4, R5, R6, R17, R18, Rx and Hal are as described above; R2' is an alkyl group; R17' is as R17 or COR22, wherein R22 is as defined above.

In a synthetic process for the preparation of a compound of formula (I)X, (I)Z, (I)Z1, (I)Z2, (I)AB and (I)AC, which is described in method F, in step "a" the pyridine nitrogen of a compound of formula (I)W is oxidized to form a N-oxide derivative of formula 44. In step "b" and "b1" the reaction of the latter with a suitable electrophilic species such as tosyl anhydride in the presence of or followed by treatment with a suitable nucleophile, such as a compound of general formula NHR17'R18 (45) or a primary amine of general formula NH$_2$R18 (46), yields a compound of formula 49 or (I)X respectively. In step "d" and "d1", the latter compounds, wherein Rx is as defined above except hydrogen, are converted into the corresponding compound of formula (I)Z or (I)Z1 respectively. Optionally in step "e", a compound of formula 49 wherein R17' is represented by a tert-butyl group, a benzyl group, a tert-butoxycarbonyl group or the like, is treated with an acid or under reductive conditions to remove said group yielding a compound of formula (I)X. Analogously, in step "e1" a compound of formula (I)X wherein R18 is represented by a tert-butyl group, a benzyl group, a tert-butoxycarbonyl group or the like, is treated with an acid or under reductive conditions to remove said group yielding a compound of formula (I)Z2. In step "f" a compound of formula (I)X is optionally treated with an electrophile of general formula R17'Hal to form a compound of formula 49. In steps "c" and "c1", compounds of general formula 49 and (I)X, respectively, can be obtained from a compound of general formula (I)Y by a palladium-catalyzed cross-coupling reaction with a suitable compound of general formula NHR17'R18 (45) or NH$_2$R18 (46), respectively.

In step "g" a compound of formula (I)Y is transformed into a compound of general formula (I)AB by a palladium-catalyzed cross-coupling reaction with a suitable organometallic derivative such as an organoaluminum compound; in step "d2" the latter, wherein Rx is as defined above except hydrogen, is converted into the corresponding compound of formula (I)AC.

According to step "a" of method F, the oxidation of the pyridine nitrogen can be carried out using oxidizing agents well-known to those skilled in the art, such as, for instance, hydrogen peroxide in a solvent such as acetic acid or m-chloroperbenzoic acid in solvents such as DCM, acetone, THF or the like at temperatures ranging from 0° C. to reflux and for a time ranging from 30 min to about 48 h.

According to step "b" of method F, the transformation of a compound of formula 44 into a compound of formula 49 is accomplished by activating the pyridine N-oxide and reacting it with a compound of general formula NHR17'R18 (45).

Activation is normally carried out using a suitable electrophilic reagent, such as oxalyl chloride, trifluoromethanesulfonyl chloride, tosyl chloride, benzoyl chloride, acetic anhydride, tosyl anhydride, PyBroP (bromo-tris-pyrrolidino-phosphonium hexafluorophosphate), BroP (bromo-tris-(dimethylamino)-phosphonium-hexafluorophosphate), PyBOP (benzotriazole-1-yl-oxy-tris-pyrrolidino-phosphonium hexafluorophosphate), BOP (benzotriazole-1-yl-oxy-tris-(dimethylamino)-phosphonium-hexafluorophosphate) and the like, in a solvent such as DCM, THF, dichloroethane, ethyl acetate, acetonitrile, toluene, trifluoromethylbenzene and the like, in the presence of a base, such as TEA, DIPEA, 2,6-lutidine and the like. Preferred is the use of PyBroP and DIPEA in DCM. The reaction is normally carried out in the presence of the secondary amine, and may be carried out at temperatures ranging from 20° C. to reflux and for a time ranging from 30 min to about 48 h.

According to step "b1" of method F, the conversion of a compound of formula 44 into a compound of general formula (I)X is accomplished as described under step "b" of method F but using a a suitable primary amine of general formula 46.

According to step "c" method F, a compound of formula (I)Y is cross-coupled to a suitable amine, amide or carbamoyl compound of general formula 45 (Buchwald-Hartwig reaction). Said reaction is well known among those with ordinary skills in the art. It is carried out in using a palladium-based catalyst, such as, for instance, palladium chloride, palladium acetate, $Pd(dba)_2$, $Pd_2(dba)_3$ or the like, in the presence of a suitable base, such as sodium t-butoxide, $Cs_2CO_3$, $Na_2CO_3$, $K_2CO_3$, $K_3PO_4$, LiHMDS and the like, optionally in the presence of a phosphine-based ligand, such as $P(o-tol)_3$, $P(t-Bu)_3$, DPPP, DPPF, BINAP (2,2'-bis(diphenylphosphino)-1,1'-binaphthyl), Xantphos (4,5-bis(diphenylphosphino)-9,9-dimethylxanthene) or monophosphinobiphenyl ligands. Said reactions can be carried out in a solvent such as DMF, dimethylsulfoxide, water, DME, 1,4-dioxane, THF or the like, and mixture thereof, at a temperature ranging from 20° C. to reflux and for a time ranging from 30 min to about 24 h.

According to step "c1" of method F, the conversion of a compound of formula (I)Y into a compound of general formula (I)X is accomplished as described under step "c" of method F but using a a suitable amine, amide or carbamoyl compound of general formula 46.

According to step "d" of method F, the conversion of a compound of formula 49 into the corresponding compound of formula (I)Z is accomplished as described under step "j" of method A.

According to step "d1" of method F, the conversion of a compound of formula (I)X into the corresponding compound of formula (I)Z1 is accomplished as described under step "j" of method A.

According to step "e" of method F, a compound of formula 49 wherein R17' is represented by a group such as tert-butyl, benzyl, tert-butoxycarbonyl or the like, such a R17' group may be removed to yield a compound of general formula (I)X. The reaction is normally carried out using strong acids, such as TFA, optionally in the presence of suitable co-solvent, such as DCM or water, at temperatures ranging from 20° C. to reflux and for a time ranging from 30 min to about 48 h. Alternatively, said reaction is carried out using reductive conditions, such as $H_2$ in the presence of a suitable hydrogenation catalyst. The hydrogenation catalyst is usually a metal, most often palladium, which can be used as such or supported on carbon, in a suitable solvent such as, for instance, THF, 1,4-dioxane, DMF, MeOH, ethyl acetate, or a mixture thereof.

According to step "e1" of method F, the conversion of a compound of formula (I)X into a compound of formula (I)Z2 is accomplished as described under step "e" of method F.

According to step "f" of method F, a compound of formula (I)X may be converted into another compound of formula 49 by reaction with a suitable electrophile of general formula R17'Hal. It is clear to the skilled person that this reaction can be accomplished in a variety of ways and operative conditions, which are widely known in the art for the preparation of amines, carboxamides or carbamates. Such reactions may be performed in a suitable solvent such as, for instance, DCM, chloroform, THF, diethyl ether, 1,4-dioxane, acetonitrile, toluene, or DMF, in the presence of a suitable base such as TEA, DIPEA, DBU and the like at a temperature ranging from about −10° C. to reflux and for a suitable time, for instance from about 30 min to about 96 h.

According to step "g" of method F, a compound of formula (I)Y can be converted into a compound of formula (I)AB wherein R2' is an alkyl group. The reaction is normally carried out by means of an organometallic reagent such as R2'MgBr, R2'ZnCl, R2'$_2$CuMgBr or R2'$_3$Al and the like, in the presence of a coordinating agent such as $Fe(acac)_3$, $NiBr_2$, CuBr, $ZnBr_2$, $Ni(acac)_2$ and the like, in a solvent such as THF or N-methylpirrolidone and the like, at a temperature ranging from 0° C. to reflux. Alternatively, the coupling of the organometallic reagent with the substrate can be mediated by a palladium catalyst such as $Pd(PPh_3)_4$ and the like, in a solvent such as dioxane or toluene at a temperature ranging from room temperature to reflux. Preferred is the reaction with R2'$_3$Al and $Pd(PPh_3)_4$ in dioxane. According to step "d2" of method F, the conversion of a compound of formula (I)AB into the corresponding compound of formula (I)AC is accomplished as described under step "j" of method A.

When preparing the compounds of formula (I) according to any variant of the process, which are all to be intended as within the scope of the invention, optional functional groups within the starting materials, the reagents or the intermediates thereof, and which could give rise to unwanted side reactions, need to be properly protected according to conventional techniques.

The starting materials of the process object of the present invention, comprehensive of any possible variant, as well as any reactant thereof, are known compounds and if not commercially available per se may be prepared according to well-known methods.

PHARMACOLOGY

Assays
In Vitro Cell Proliferation Assay

Exponentially growing human melanoma cells A375 (with a mutated B-Raf) and human melanoma cells Mewo (with wild-type B-Raf) were seeded and incubated at 37° C. in a humidified 5% $CO_2$ atmosphere. After 24 h, scalar doses of the compound were added to the medium and cells incubated for 72 h. At the end of treatment, cells were washed and counted. Cell number was determined by a cellular adenosine triphosphate monitoring system. Cell proliferation was compared to control cells and the concentration inhibiting cell growth by 50% was calculated.

p-MAPK (T202/Y204) ArrayScan Assay

A375 human melanoma cells, having a mutated B-Raf, were seeded in 384-well poly-lysine coated plates (Matrix) at a density of 1000 cells/well with appropriate medium supplemented with 10% FCS and incubated for 16-24 h. Cells were treated for 1.5 or 2 h with increasing doses of compounds (starting dose 10 µM, dilution factor 2.5). At the end of the treatment cells were fixed with p-formaldehyde 3.7% for 15-30 min, then washed twice with D-PBS (80 μL/well) and permeabilized with D-PBS containing 0.1% Triton X-100 and 1% BSA (Sigma-Aldrich) for 15 min at room temperature (staining solution). Anti-phospho-MAPK (T202/Y204) monoclonal antibody E10 (Cell Signaling, cat. #9106) diluted 1:100 was added in staining solution and incubated for 1 h at 37° C. After removal of the primary antibody solution, the anti-mouse Cy™ 2-conjugated (Green) secondary antibody (Amersham) diluted 1:500 in staining solution containing 2 μg/mL DAPI was added. The plate was incubated for 1 h at 37° C., washed twice and then read with Cellomics' Array-Scan VTI (4 fields/well, CytoNucTrans algorithm).

The parameter "MEAN_RingAvgIntenCh2", which measures the mean cytoplasmatic fluorescence intensity associated to p-MAPK staining, is reported as the final result.

B-Raf mutations, that constitutively activate the kinase, have been identified in the majority of melanoma and a large fraction of colorectal and papillary thyroid carcinoma. The growth of cells with activated B-Raf strictly depends on B-Raf activity. Given the above assays, the compounds of formula (I) result to posses a remarkable activity in inhibiting cell proliferation, with $IC_{50}$ values lower than 0.2 μM, more potent on the cell line with mutated B-Raf (A375) than on the cell line with wild-type B-Raf (Mewo), as reported in the following table.

In the same table the data obtained with compounds of formula (I) in the ArrayScan assay are also reported and demonstrate the ability of the compounds of formula (I) to inhibit the signal transduction pathway controlled by B-Raf activation in A375 cell line with mutated B-Raf. The $IC_{50}$ values are always lower than 0.2 μM and are in agreement with the $IC_{50}$ values obtained in the proliferation assay on the same cell line, confirming that the antiproliferative activity of the compounds is due to the inhibition of B-Raf activity.

TABLE 1

Proliferation and Array Scan data

| Cmpd. N° | Name | Proliferation A375 $IC_{50}$ (μM) | Mewo $IC_{50}$ (μM) | Array Scan A375 $IC_{50}$ (μM) |
|---|---|---|---|---|
| 19 | 2,5-difluoro-N-{2-fluoro-3-[2-(1-methylpiperidin-4-yl)-5-(pyridin-4-yl)-1,3-thiazol-4-yl]phenyl}benzenesulfonamide | 0.040 | >10 | 0.002 |
| 14 | N-{3-[2-(4,4-difluoropiperidin-1-yl)-5-(pyridin-4-yl)-1,3-thiazol-4-yl]-2,4-difluorophenyl}-2,5-difluorobenzenesulfonamide | 0.066 | >10 | 0.004 |
| 3 | N-{3-[2-(diethylamino)-5-(pyridin-4-yl)-1,3-thiazol-4-yl]-2,4-difluorophenyl}-2,5-difluorobenzenesulfonamide | 0.166 | >10 | 0.001 |
| 18 | N-{3-[2-(4,4-difluoropiperidin-1-yl)-5-(pyridin-4-yl)-1,3-thiazol-4-yl]-2-fluorophenyl}-2,5-difluorobenzenesulfonamide | 0.127 | >10 | 0.002 |
| 20 | 2,5-difluoro-N-{2-fluoro-3-[5-(pyridin-4-yl)-2-(tetrahydro-2H-pyran-4-yl)-1,3-thiazol-4-yl]phenyl}benzenesulfonamide | 0.078 | >10 | 0.002 |
| 22 | N-{3-[5-(2-aminopyridin-4-yl)-2-(1-cyclopropylpiperidin-4-yl)-1,3-thiazol-4-yl]-2-fluorophenyl}-2,5-difluorobenzenesulfonamide | 0.027 | >10 | |
| 24 | N-{3-[5-(2-aminopyridin-4-yl)-2-(tetrahydro-2H-pyran-4-yl)-1,3-thiazol-4-yl]-2-fluorophenyl}-2,5-difluorobenzenesulfonamide | 0.015 | >10 | |
| 25 | 2,5-difluoro-N-(2-fluoro-3-{5-[2-(methylamino)pyridin-4-yl]-2-(tetrahydro-2H-pyran-4-yl)-1,3-thiazol-4-yl}phenyl)benzenesulfonamide | 0.032 | >10 | |
| 30 | N-{4-[2-(1-cyclopropylpiperidin-4-yl)-4-(3-{[(2,5-difluorophenyl)sulfonyl]amino}-2-fluorophenyl)-1,3-thiazol-5-yl]pyridin-2-yl}acetamide | 0.003 | >10 | |
| 21 | N-{3-[2-(1-cyclopropylpiperidin-4-yl)-5-(pyridin-4-yl)-1,3-thiazol-4-yl]-2-fluorophenyl}-2,5-difluorobenzenesulfonamide | 0.023 | >10 | |
| 23 | N-{4-[4-(3-{[(2,5-difluorophenyl)sulfonyl]amino}-2-fluorophenyl)-2-(1-methylpiperidin-4-yl)-1,3-thiazol-5-yl]pyridin-2-yl}acetamide | 0.006 | >10 | |
| 42 | N-{4-[2-tert-butyl-4-(3-{[(2,5-difluorophenyl)sulfonyl]amino}-2-fluorophenyl)-1,3-thiazol-5-yl]pyridin-2-yl}acetamide | 0.0006 | >10 | |
| 38 | 2,5-difluoro-N-(2-fluoro-3-{5-[2-(methylamino)pyridin-4-yl]-2-(1-methylpiperidin-4-yl)-1,3-thiazol-4-yl}phenyl)benzenesulfonamide | 0.047 | >10 | |
| 41 | methyl [(2S)-1-({4-[4-(3-{[(2,5-difluorophenyl)sulfonyl]amino}-2-fluorophenyl)-2-(tetrahydro-2H-pyran-4-yl)- | 0.008 | >10 | |

TABLE 1-continued

Proliferation and Array Scan data

| | | Proliferation | | Array Scan |
|---|---|---|---|---|
| Cmpd. N° | Name | A375 IC$_{50}$ (μM) | Mewo IC$_{50}$ (μM) | A375 IC$_{50}$ (μM) |
| | 1,3-thiazol-5-yl]pyridin-2-yl}amino)propan-2-yl]carbamate | | | |
| 43 | N-{3-[2-tert-butyl-5-(pyridin-4-yl)-1,3-thiazol-4-yl]-2-fluorophenyl}-2,5-difluorobenzenesulfonamide | 0.012 | >10 | |
| 44 | N-{4-[4-(3-{[(2,5-difluorophenyl)sulfonyl]amino}-2-fluorophenyl)-2-(piperidin-4-yl)-1,3-thiazol-5-yl]pyridin-2-yl}acetamide | 0.040 | >10 | |
| 34 | 2,5-difluoro-N-{2-fluoro-3-[5-(3-fluoropyridin-4-yl)-2-(tetrahydro-2H-pyran-4-yl)-1,3-thiazol-4-yl]phenyl}benzenesulfonamide | 0.039 | >10 | |
| 36 | N-[2-({4-[4-(3-{[(2,5-difluorophenyl)sulfonyl]amino}-2-fluorophenyl)-2-(tetrahydro-2H-pyran-4-yl)-1,3-thiazol-5-yl]pyridin-2-yl}amino)ethyl]acetamide | 0.069 | >10 | |
| 37 | N-(3-{2-(1-cyclopropylpiperidin-4-yl)-5-[2-(methylamino)pyridin-4-yl]-1,3-thiazol-4-yl}-2-fluorophenyl)-2,5-difluorobenzenesulfonamide | 0.092 | >10 | |
| 39 | N-{3-[5-(2-aminopyridin-4-yl)-2-(1-methylpiperidin-4-yl)-1,3-thiazol-4-yl]-2-fluorophenyl}-2,5-difluorobenzenesulfonamide | 0.027 | >10 | |
| 35 | N-{4-[4-(3-{[(2,5-difluorophenyl)sulfonyl]amino}-2-fluorophenyl)-2-(tetrahydro-2H-pyran-4-yl)-1,3-thiazol-5-yl]pyridin-2-yl}acetamide | 0.0006 | >10 | |

Antitumor Efficacy on a Xenograft Model of Human Melanoma

Balb Nu/Nu male mice, from Harlan (Italy), were maintained in cages with paper filter cover, food and bedding sterilized and water acidified. $3 \times 10^6$ A375 human melanoma cells (from the American Type Culture Collection) were injected subcutaneously. Compounds were administered by oral route in a volume of 10 mL/kg for 10 consecutive days. Tumor growth and body weight were measured every 3 days. Tumor growth was assessed by caliper. Tumor masses were calculated as follows: Tumor weight (mg)=length (mm) ·width$^2$ (mm$^2$)/2·d (mg/mm$^3$) assuming density d=1 mg/mm$^3$ for tumor tissue. Tumor growth inhibition (TGI) was determined according to the equation % TGI=100−(mean tumor weight of treated group/mean tumor weight of control group)×100. Toxicity was evaluated on the basis of body weight reduction.

Based on the above assay, a selection of compounds of the present invention showed a TGI higher than 90% without body weight reduction.

Bioavailability

In addition to in vitro methods, in vivo methods, such as pharmacokinetic studies, can be performed in a range of animals. A compound of formula (I) of the present invention can be administered to animals, for instance mouse or rat, at different dosages, and by different route of administration, preferably per os. Blood samples can be collected at serial time points and the samples assayed for the presence of said compound of formula (I).

A compound of formula (I) of the present invention, formulated in 0.5% Methocel®, was administered orally to mice (10 to 100 mg/Kg) in pharmacokinetic studies and its concentration was monitored in blood by HPLC/MS analysis at 15 and 30 min, 1, 6 and 24 h post-dosing. All blood samples were taken from saphenous vein.

Oral bioavailability (Fos) was calculated as percent ratio of average oral AUC value of compound to average IV AUC value of compound following compound dose normalization.

Based on the above assay, a selection of compounds of the present invention showed an oral bioavailability higher than 20%.

From all of the above, the novel compounds of formula (I) of the invention appear to be particularly advantageous in the therapy of diseases caused by deregulated protein kinase activity such as cancer.

The compounds of the present invention can be administered either as single agents or, alternatively, in combination with known anticancer treatments such as radiation therapy or chemotherapy regimen in combination with, for example, antihormonal agents such as antiestrogens, antiandrogens and aromatase inhibitors, topoisomerase I inhibitors, topoisomerase II inhibitors, agents that target microtubules, platin-based agents, alkylating agents, DNA damaging or intercalating agents, antineoplastic antimetabolites, other kinase inhibitors, other anti-angiogenic agents, inhibitors of kinesins, therapeutic monoclonal antibodies, inhibitors of mTOR, histone deacetylase inhibitors, farnesyl transferase inhibitors, and inhibitors of hypoxic response.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, and conditions of the patient and administration route.

For example, a suitable dosage adopted for oral administration of a compound of formula (I) may range from about 10 mg to about 2 g per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form.

For example, the solid oral forms may contain, together with the active compound, diluents, e.g., lactose, dextrose, saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions.

As an example the syrups may contain, as a carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

EXPERIMENTAL SECTION

For a reference to any specific compound of formula (I) of the invention, optionally in the form of a pharmaceutically acceptable salt, see the experimental section and claims.

Referring to the examples that follow, compounds of the present invention were synthesized using the methods described herein, or other methods, which are well known in the art.

The short forms and abbreviations used herein have the following meaning:

g (grams)
mg (milligrams)
mL (milliliters)
μL (microliters)
mM (millimolar)
mmol (millimoles)
μM (micromolar)
$R_t$ (retention time)
h (hours)
MHz (Mega-Hertz)
mm (millimeters)
Hz (Hertz)
M (molar)
min (minutes)
mol (moles)
TLC (thin layer chromatography)
r.t. (room temperature)
TEA (triethylamine)
DMAP (dimethylaminopyridine)
DME (dimethoxyethane)
TFA (trifluoroacetic acid)
DMF (N,N-dimethylformamide)
DIPEA (N,N-diisopropyl-N-ethylamine)
DCM (dichloromethane)
THF (tetrahydrofuran)
Hex (hexane)
MeOH (methanol)
DMSO (dimethylsulfoxide)
DPPP (1,3-bis(diphenylphosphino)propane)
acac (acetylacetonate)
Dppf (1,1'-bis(diphenylphosphino)ferrocene)
ESI=electrospray ionization
RP-HPLC (reverse phase high performance liquid chromatography)

With the aim at better illustrating the present invention, without posing any limitation to it, the following examples are now given.

As used herein the symbols and conventions used in the processes, schemes and examples are consistent with those used in the contemporary scientific literature, for example, the *Journal of the American Chemical Society* or the *Journal of Biological Chemistry*.

Unless otherwise noted, all materials were obtained from commercial suppliers, of the best grade and used without further purification. Anhydrous solvent such as DMF, THF, DCM and toluene were obtained from the Aldrich Chemical Company. All reactions involving air- or moisture-sensitive compounds were performed under nitrogen or argon atmosphere.

General Purification and Analytical Methods

Flash Chromatography was performed on silica gel (Merck grade 9395, 60A).

HPLC was performed on Waters X Terra RP 18 (4.6×50 mm, 3.5 μm) column using a Waters 2790 HPLC system equipped with a 996 Waters PDA detector and Micromass mod. ZQ single quadrupole mass spectrometer, equipped with an electrospray (ESI) ion source. Mobile phase A was ammonium acetate 5 mM buffer (pH 5.5 with acetic acid-acetonitrile 95:5), and Mobile phase B was water-acetonitrile (5:95). Gradient from 10 to 90% B in 8 min, hold 90% B 2 min. UV detection at 220 nm and 254 nm. Flow rate 1 mL/min. Injection volume 10 μL. Full scan, mass range from 100 to 800 amu. Capillary voltage was 2.5 KV; source temperature was 120° C.; cone was 10 V. Retention times (HPLC $R_t$.) are given in minutes (min) at 220 nm or at 254 nm. Mass are given as m/z ratio.

When necessary, compounds were purified by preparative HPLC on a Waters Symmetry C18 (19×50 mm, 5 μm) column or on a Waters X Terra RP 18 (30×150 mm, 5 μm) column using a Waters preparative HPLC 600 equipped with a 996 Waters PDA detector and a Micromass mod. ZMD single quadrupole mass spectrometer, electron spray ionization, positive mode. Mobile phase A was water-0.01% TFA, and mobile phase B was acetonitrile. Gradient from 10 to 90% B in 8 min, hold 90% B 2 min. Flow rate 20 mL/min. In alternative, mobile phase A was water-0.1% $NH_3$, and mobile phase B was acetonitrile. Gradient from 10 to 100% B in 8 min, hold 100% B 2 min. Flow rate 20 mL/min. $^1$H-NMR spectra were recorded at a constant temperature of 28° C. on a Varian INOVA 400 spectrometer operating at 400.50 MHz and equipped with a 5 mm z-axis PFG Indirect Detection Probe ($^1$H{$^{15}$N—$^{31}$P}).

Chemical shifts were referenced with respect to the residual solvent signals (DMSO-$d_6$: 2.50 ppm for $^1$H, where not otherwise specified). Data are reported as follows: chemical shift (δ), multiplicity (s=singlet, d=doublet, t=triplet, q=quartet, br. s=broad singlet, td=triplet of doublets, dd=doublet of doublets, ddd=doublet of doublets of doublets, m=multiplet, spt=septet), coupling constants (J, Hz), and number of protons.

As formerly reported (M. Colombo, F. R. Sirtori, V. Rizzo, Rapid Commun Mass Spectrom 2004, 18(4), 511-517), ESI (+) high-resolution mass spectra (HRMS) were obtained on a Q-T of Ultima (Waters, Manchester, UK) mass spectrometer directly connected with an Agilent 1100 micro-HPLC system (Palo Alto, US).

Preparation of N-(3-acetyl-2-fluorophenyl)-2,5-difluoro-N-(methoxymethyl)benzenesulfonamide, cmpd. of formula 6 [n=1; R4=F; R5=H; R6=2,5-difluorophenyl; Rx'=methoxymethyl] (Preparation 1, Method A)

N-(3-bromo-2-fluorophenyl)-2,5-difluorobenzenesulfonamide, cmpd. of formula 3 [n=1; R4=F; R5=H; R6=2,5-difluorophenyl]

Method A, Step a

3-Bromo-2-fluoroaniline (10 g, 52.63 mmol) was dissolved in DCM (100 mL) under nitrogen atmosphere. Dry pyridine was added (6 mL, 73.68 mmol), followed by 2,5-difluorobenzenesulfonyl chloride (7.08 mL, 52.63 mmol) and the mixture was stirred at r.t. for 2 h. It was then diluted with DCM and washed with aqueous 0.5 N HCl (3×80 mL) and brine. The organic layer was dried over $Na_2SO_4$ and evaporated to dryness. The solid was taken up with diethyl ether and stirred for 30 min. It was then filtered and dried at 40° C. under reduced pressure to give 17.8 g of N-(3-bromo-2-fluoro-phenyl)-2,5-difluoro-benzenesulfonamide as a pale yellow solid (92%).

HPLC: $R_t$: 6.28 min $^1$H NMR (401 MHz, DMSO-$d_6$) δ ppm 10.86 (s, 1H), 7.50-7.73 (m, 4H), 7.23-7.31 (m, 1H), 7.12 (dt, J=1.3, 8.1 Hz, 1H)

N-(3-bromo-2-fluorophenyl)-2,5-difluoro-N-(methoxymethyl)benzenesulfonamide, cmpd. of formula 4 [n=1; R4=F; R5=H; R6=2,5-difluorophenyl; Rx'=methoxymethyl]

Method A, Step b

To a solution of N-(3-bromo-2-fluoro-phenyl)-2,5-difluoro-benzenesulfonamide (17.8 g, 48.61 mmol) in anhydrous DCM (160 mL) at 0° C., DIPEA (12.5 mL, 73 mmol) was added followed by methoxymethyl chloride (5.7 mL, 73 mmol). The reaction mixture was stirred at 0° C. for 10 min and then allowed to warm to r.t. After 2 h a saturated solution of ammonium chloride was added and the mixture was stirred at r.t. for 10 min. It was then diluted with DCM and washed with water and brine, dried over $Na_2SO_4$ and evaporated to dryness. The residue was treated with Hex and stirred for 30 min. The solid was filtered and dried to give 18.52 g (93%) of the title compound as a white powder.

HPLC: $R_t$: 6.88 min $^1$H NMR (401 MHz, DMSO-$d_6$) δ ppm 7.78 (ddd, J=1.7, 6.4, 8.1 Hz, 1H), 7.67-7.73 (m, 1H), 7.61 (dt, J=4.3, 9.6, 1H), 7.49-7.55 (m, 1H), 7.28-7.34 (m, 1H), 7.17-7.23 (m, 1H), 5.06 (s, 2H), 3.35 (s, 3H)

HRMS (ESI) calcd for $C_{14}H_{11}BrF_3NO_3SNa$ [M+Na]+ 431.9487. found 431.9487.

N-(3-acetyl-2-fluorophenyl)-2,5-difluoro-N-(methoxymethyl)benzenesulfonamide, cmpd. of formula 6 [n=1; R4=F; R5=H; R6=2,5-difluorophenyl; Rx'=methoxymethyl]

Method A, Step c

To a solution of 6.15 g (15 mmol) of N-(3-bromo-2-fluorophenyl)-2,5-difluoro-N-(methoxymethyl)benzenesulfonamide in 35 mL of ethylenglycol in a flask equipped with a rubber septum, through which nitrogen is fluxed by a needle, 37.5 mg (0.15 mmol) of palladium acetate, 129 mg (0.30 mmol) of DPPP, 5.4 mL (37.5 mmol) of TEA and 5.9 mL (45 mmol) of n-butylvinylether were added consecutively. The mixture was heated at 120° C. under stirring for 6 h and then diluted with DCM and washed with brine. The organic layer was dried over $Na_2SO_4$ and evaporated, giving N-[3-(1-butoxyethenyl)-2-fluorophenyl]-2,5-difluoro-N-(methoxymethyl)benzenesulfonamide as a brown oil. The latter, without any further purification, was dissolved in 65 mL of 1,4-dioxane and 11 mL of 1N HCl were added to the resulting solution. After 1 h under stirring at r.t. the reaction was complete. The solvent was then removed, the residue re-dissolved with DCM and washed with aqueous $NaHCO_3$. The organic layer was dried over anhydrous $Na_2SO_4$ and evaporated. After trituration with diethylether 4.82 g (86%) of the title compound were collected by filtration.

HPLC: $R_t$: 6.28 min $^1$H NMR (401 MHz, DMSO-$d_6$) δ ppm 7.81-7.89 (m, 1H), 7.47-7.73 (m, 5H), 7.36 (t, J=7.8 Hz, 1H), 5.05-5.10 (m, 2H), 3.35-3.38 (m, 3H), 2.48-2.49 (m, 3H)

HRMS (ESI) calcd for $C_{16}H_{14}F_3NO_4SNa$ [M+Na]+ 396.0488. found 396.0488.

Preparation of 3-{[(2,5-Difluorophenyl)sulfonyl](methoxymethyl)amino}-2-fluoro-N-methoxy-N-methylbenzamide, cmpd. of formula 29 [n=1; R4=F; R5=H; Rx=methoxymethyl; R6=2,5-difluorophenyl; J=NMe(OMe)] (Preparation 2, Method D)

3-{[(2,5-Difluorophenyl)sulfonyl](methoxymethyl)amino}-2-fluorobenzoic acid

N-(3-bromo-2-fluorophenyl)-2,5-difluoro-N-(methoxymethyl)benzenesulfonamide (prepared as described in Preparation 1, 10.92 g, 26.62 mmol) was dissolved in anhydrous THF (53 mL) and cooled to 0° C. A solution of isopropylmagnesium chloride (2 N in THF) (13.3 mL, 26.62 mmol, 1 eq) was added dropwise. At the end of the addition the reaction mixture was allowed to warm to r.t. and stirred for 2 h. The yellow solution was then cooled back to 0° C. and gaseous carbonic anhydride (generated from solid carbonic anhydride and dried through concentrated sulfuric acid) was bubbled through the solution for 20 min. A 0.5 N HCl solution (50 mL) was then added and the mixture was extracted with diisopropyl ether (3×130 mL). The desired product was then extracted from the organic phase with a 1 N sodium hydroxide solution (3×100 mL). Under vigorous stirring 2 N HCl (150 mL) was then added. The precipitate was collected by filtration, washed with water and Hex and dried in the oven, giving 9.07 g (91%) of the title compound as a white solid.

HPLC: $R_t$: 3.67 min $^1$H NMR (600 MHz, DMSO-$d_6$) δ ppm 7.88 (t, J=6.7 Hz, 1H), 7.71-7.64 (m, 1H), 7.61 (dt, J=4.1, 9.4 Hz, 1H), 7.53-7.44 (m, 2H), 7.32 (t, J=7.9 Hz, 1H), 5.06 (s, 2H).

HRMS (ESI) calcd for $C_{15}H_{12}NO_5F_3SNa$ [M+Na]$^+$ 398.0280. found 398.0280.

3-{[(2,5-Difluorophenyl)sulfonyl](methoxymethyl)amino}-2-fluoro-N-methoxy-N-methylbenzamide, cmpd. of formula 29 [n=1; R4=F; R5=H; Rx=methoxymethyl; R6=2,5-difluorophenyl; J=NMe(OMe)]

3-{[(2,5-difluorophenyl)sulfonyl](methoxymethyl)amino}-2-fluorobenzoic acid (8.86 g, 23.61 mmol) was dissolved in DCM (73 mL) under nitrogen atmosphere. Dry DMF (14 mL) was added, followed by N-methoxy-N-methyl amine hydrochloride (3.72 g, 38.13 mmol, 1.6 eq), N-methylmorpholine (4.1 mL, 37.3 mmol, 1.6 eq) and DMAP (293 mg, 2.4 mmol, 0.1 eq). The reaction mixture was then cooled to 0° C. and EDC hydrochloride (5.38 g, 28.06 mmol, 1.2 eq) was added portionwise. The mixture was allowed to warm to r.t. and stirred for 4 h. It was then cooled to 0° C. and a cold 1 N HCl solution (100 mL) was added. The mixture was extracted with diisopropylether and the organic phase was washed with saturated aqueous NaHCO$_3$ and brine, dried over Na$_2$SO$_4$ and evaporated to dryness. The crude product was purified by flash chromatography on silica gel (DCM/MeOH 98:2) to give 8.97 g (91%) of the title compound as an amorphous colourless solid.

HPLC: $R_t$: 5.25 min $^1$H NMR (600 MHz, DMSO-$d_6$) δ ppm 7.70-7.64 (m, 1H), 7.61 (dt, J=3.9, 9.4 Hz, 1H), 7.54-7.44 (m, 2H), 7.42 (t, J=7.2 Hz, 1H), 7.31 (t, J=7.9 Hz, 1H), 5.07 (s, 2H), 3.36 (s, 3H), 3.29 (s, 3H), 3.21 (br.s., 1H).

HRMS (ESI) calcd for $C_{17}H_{18}N_2O_5F_3S$ [M+H]$^+$ 419.0883. found 419.0893.

Preparation of tert-butyl-4-carbamothioylpiperidine-1-carboxylate, cmpd. of formula 8 [R1=1-tert-butoxycarbonyl-piperidin-4-yl] (Preparation 3, Methods A, D and E)

tert-Butyl 4-carbamoylpiperidine-1-carboxylate

To a solution of piperidine-4-carboxamide (2 g, 15.6 mmol) in acetonitrile (30 mL), tert-butyldicarbonate (4.4 g, 20.2 mmol, 1.3 eq) and DMAP (190 mg, 1.56 mmol, 0.1 eq) were added and the mixture was stirred at r.t. overnight. It was then concentrated under reduced pressure, taken up with DCM and washed with saturated aqueous NaHCO$_3$, saturated aqueous NH$_4$Cl, brine and water. The organic phase was dried over Na$_2$SO$_4$ and evaporated to dryness. The residue was triturated with diethyl ether and the white solid was filtered and dried to give 2.65 g (74%) of the title product.

HPLC: $R_t$: 4.23 min $^1$H NMR (401 MHz, DMSO-$d_6$) δ ppm 7.24 (br. s., 1H), 6.75 (br. s., 1H), 4.06-3.73 (m, 2H), 2.71 (br. s., 2H), 2.23 (tt, J=3.8, 11.5 Hz, 1H), 1.66 (dd, J=2.7, 13.2 Hz, 2H), 1.44-1.26 (m, 2H), 1.36 (s, 9H).

tert-Butyl-4-carbamothioylpiperidine-1-carboxylate, cmpd. of formula 8 [R1=1-tert-butoxycarbonyl-piperidin-4-yl]

To a solution of tert-butyl-4-carbamoylpiperidine-1-carboxylate (2.65 g, 11.62 mmol) in a DME/DCM 2:1 mixture (78 mL), Lawesson reagent (2.35 g, 5.81 mmol, 0.5 eq) was added and the mixture was stirred at r.t. overnight. The solvent was removed and the residue was taken up with ethyl acetate and washed with saturated aqueous K$_2$CO$_3$. The organic layer was separated, dried over Na$_2$SO$_4$ and concentrated to dryness. The residue was triturated with diethyl ether and dried to give 2.65 g (92%) of the title compound as a white solid.

HPLC: $R_t$: 5.06 min $^1$H NMR (401 MHz, DMSO-$d_6$) δ ppm 9.39 (br. s., 1H), 9.09 (br. s., 1H), 4.00 (d, J=12.6 Hz, 2H), 2.77-2.61 (m, 3H), 1.71-1.51 (m, 4H), 1.39 (br. s., 9H)

Preparation of benzyl-4-carbamothioylpiperidine-1-carboxylate, cmpd. of formula 8 [R1=1-benzyloxycarbonyl-piperidin-4-yl] (Preparation 4, Methods A, D and E)

Benzyl-4-carbamoylpiperidine-1-carboxylate

To a solution of piperidine-4-carboxamide (5 g, 39 mmol) and benzylchloroformate (5.54 mL, 39 mmol) in a mixture of water (30 mL) and acetone (40 mL), NaOH 1N (39 mL, 39 mmol) was added dropwise, while maintaining the pH between 6 and 8. The mixture was stirred at r.t. for 3 h; then acetone was evaporated and the resulting precipitate filtered and dried at 70° C. under reduced pressure, giving 7.75 g of benzyl-4-carbamoylpiperidine-1-carboxylate (76%).

HPLC: $R_t$: 4.54 min $^1$H NMR (600 MHz, DMSO-$d_6$) δ ppm 7.41-7.29 (m, 5H), 7.25 (br. s., 1H), 6.76 (br. s., 1H), 5.07 (s, 2H), 4.06-3.81 (m, J=13.2 Hz, 2H), 2.92-2.72 (m, 2H), 2.27 (tt, J=3.7, 11.5 Hz, 1H), 1.75-1.64 (m, 2H), 1.40 (dq, J=4.3, 12.4 Hz, 2H)

HRMS (ESI) [M+H]+ calcd for $C_{14}H_{18}O_3N_2$ 263.1390. found 263.1390.

Benzyl-4-carbamothioylpiperidine-1-carboxylate, cmpd. of formula 8 [R1=1-benzyloxycarbonyl-piperidin-4-yl]

Benzyl-4-carbamoylpiperidine-1-carboxylate (7.5 g, 38.6 mmol) was dissolved in THF (160 mL) and Lawesson's reagent (6.9 g, 17.1 mmol) was added. After 4 h the solvent was evaporated and the residue purified by flash-chromatography on silica gel (DCM-MeOH 95/5) affording 1.8 g (23%) of the title compound, crystallized from MeOH.

HPLC: $R_t$: 5.28 min $^1$H NMR (600 MHz, DMSO-$d_6$) δ ppm 9.40 (br. s., 1H), 9.11 (br. s., 1H), 7.42-7.24 (m, 5H), 5.07 (s, 2H), 4.07 (d, J=13.2 Hz, 2H), 2.90-2.73 (m, 2H), 2.69 (tt, J=3.8, 11.6 Hz, 1H), 1.70-1.64 (m, 2H), 1.64-1.55 (m, 2H)

HRMS (ESI) [M+H]+ calcd for $C_{14}H_{18}O_2N_2S$ 279.1162. found 279.1163.

Preparation of 1-methylpiperidine-4-carbothioamide, cmpd. of formula 8 [R1=1-methyl-piperidin-4-yl] (Preparation 5, Methods A, D and E)

To a suspension of tert-butyl-4-carbamothioylpiperidine-1-carboxylate (prepared as described in Preparation 3, 2.65 g, 10.86 mmol) in dry dioxane (40 mL) a 4 M solution of HCl in dioxane was added (16 mL, 64 mmol, 5.9 eq) and the mixture was stirred at r.t. After 1 h a further addition of HCl (10 mL) was made and stirring was continued for 2 more h. The solvent was evaporated to dryness and the residue was taken up with toluene and evaporated to dryness two times.

The residue was dissolved in MeOH (64 mL) and aqueous formaldehyde (2 mL, 26.86 mmol, 2.5 eq) was added, followed by acetic acid (2.24 mL, 39.17 mmol, 3.6 eq) and sodium cyanoborohydride (2.08 g, 28.24 mmol, 2.6 eq) and the mixture was stirred at r.t. for 2 h. The solvent was then concentrated under reduced pressure and the residue was taken up with ethyl acetate, washed with aqueous saturated $NaHCO_3$ and brine, dried over $Na_2SO_4$ and evaporated to dryness to give 2.2 g of the title compound as white solid.

$^1$H NMR (401 MHz, DMSO-$d_6$) δ ppm 9.35 (br. s., 1H), 9.08 (br. s., 1H), 3.44-3.19 (m, 2H), 2.86 (br. s., 2H), 2.44 (t, J=10.2 Hz, 1H), 2.21 (br. s., 3H), 1.82-1.73 (m, 2H), 1.63 (d, J=11.9 Hz, 2H)

HRMS (ESI) calcd for $C_7H_{15}N_2S$ [M+H]$^+$ 159.0951. found 159.0944.

Preparation of tetrahydro-2H-pyran-4-carbothioamide, cmpd. of formula 8 [R1=tetrahydropyran-4-yl] (Preparation 6, Methods A, D and E)

Tetrahydro-2H-pyran-4-carboxamide

A mixture of methyl tetrahydro-2H-pyran-4-carboxylate (7 g, 48.6 mmol) and 30% aqueous ammonia (20 mL) was stirred in a closed bottle at r.t. for 18 h. The ammonia excess was removed under reduced pressure and the residue was crystallized from ethanol affording 5.6 g (89%) of tetrahydro-2H-pyran-4-carboxamide.

$^1$H NMR (401 MHz, DMSO-$d_6$) δ ppm 7.21 (br. s., 1H), 6.73 (br. s., 1H), 3.90-3.80 (m, 2H), 3.30-3.23 (m, 2H), 2.36-2.24 (m, 1H), 1.66-1.47 (m, 4H)

Tetrahydro-2H-pyran-4-carbothioamide, cmpd. of formula 8 [R1=tetrahydropyran-4-yl]

Tetrahydro-2H-pyran-4-carboxamide (2 g, 15.5 mmol) was suspended in dry THF (20 mL) and Lawesson's reagent (3.13 g, 7.75 mmol) was added. After refluxing for 4 h the mixture was poured into a saturated $NaHCO_3$ aqueous solution (200 mL) and then extracted with diethylether (4×100 mL). The organic layer was dried over $Na_2SO_4$ and evaporated to dryness, affording 1.2 g (54%) of the title compound.

HPLC: $R_t$: min 2.79

$^1$H NMR (401 MHz, DMSO-$d_6$) δ ppm 9.37 (br. s., 1H), 9.08 (br. s., 1H), 3.87 (dd, J=4.0, 11.0 Hz, 2H), 3.37-3.23 (m, 2H), 2.78-2.67 (m, 1H), 1.75 (dq, J=4.5, 12.5 Hz, 2H), 1.63-1.52 (m, 2H)

HRMS (ESI) calcd for $C_{16}H_{11}NOS$ [M+H]$^+$ 146.0634. found 146.0634.

Preparation of 1-cyclopropylpiperidine-4-carbothioamide, cmpd. of formula 8 [R1=1-cyclopropyl-piperidin-4-yl] (Preparation 7, Methods A, D and E)

To a solution of piperidine-4-carboxamide (1 g, 7.8 mmol) in MeOH (80 mL) 1-ethoxy-1-trimethylsilyloxycyclopropane (2.35 mL, 11.7 mmol, 1.5 eq) was added, followed by acetic acid (1.34 mL, 23.4 mmol, 3 eq) and sodium cyanoborohydride (923 mg, 12.48 mmol, 1.6 eq) and the mixture was stirred at 60° C. overnight. The solvent was then concentrated under reduced pressure and the residue was purified by flash chromatography on silica gel (DCM/MeOH/$NH_3$ 7 N in MeOH 90:9:1) affording 1.6 g of 1-cyclopropylpiperidine-4-carboxamide.

1-cyclopropylpiperidine-4-carboxamide was suspended in dry THF (20 mL) and Lawesson's reagent (2.7 g, 6.67 mmol) was added. After refluxing for 6 h the solvent was concentrated under reduced pressure. The residue was dissolved in a ethyl acetate/MeOH mixture and washed with saturated aqueous $NaHCO_3$. The aqueous phase was back-extracted with ethyl acetate and evaporated to dryness. The crude product was treated with ethanol and filtered. The white solid was dried under high vacuum affording 2.7 g of the title compound.

$^1$H NMR (600 MHz, DMSO-$d_6$) δ ppm 9.32 (br. s., 1H), 9.04 (br. s., 1H), 2.95 (br. s., 2H), 2.54-2.43 (m, 1H), 2.20-2.04 (m, 2H), 1.75-1.38 (m, 5H), 0.39 (br. s., 2H), 0.27 (br. s., 2H)

HRMS (ESI) calcd for $C_9H_{17}N_2S$ [M+H]$^+$ 185.1107. found 185.1104.

Preparation of tert-butyl-methylcarbamate, cmpd. of formula 45 [R17'=tert-butoxycarbonyl; R18=methyl] (Preparation 8, Method F)

Methylamine 2M in THF (15 mL, 33 mmol) and TEA (4.35 mL) were added to dry DCM (25 mL), cooled to −20° C. under stirring. A solution of di-tert-butyl-dicarbonate (7.2 g, 33 mmol) in DCM (25 mL) was dropped into the reaction mixture, while maintaining the temperature between −20 and −10° C. The temperature was then made to rise to r.t. overnight. The mixture was then washed with brine and the organic layer dried over $Na_2SO_4$ and evaporated to dryness, giving 2.83 g (66%) of the title compound as a colorless oil.

$^1$H NMR (600 MHz, DMSO-d$_6$) δ ppm 6.63 (br. s., 1H), 2.49 (br. s., 3H), 1.37 (s, 9H)

Example 1

Synthesis of N-{2,4-difluoro-3-[2-(4-methylpiperazin-1-yl)-5-(pyridin-4-yl)-1,3-thiazol-4-yl]phenyl}-2,5-difluorobenzenesulfonamide, cmpd. of formula (I)A (cmpd. 8) [m, n=1; R2, R3, Rx=H; R4=F; R5=4-F; R6=2,5-difluorophenyl; R1'=4-methylpiperazin-1-yl]

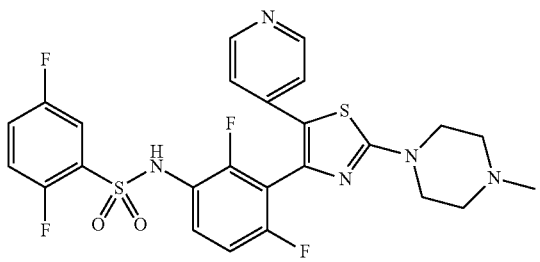 [SMILES: CN1CCN(c2nc(-c3c(F)ccc(NS(=O)(=O)c4cc(F)ccc4F)c3F)c(-c3ccncc3)s2)CC1]

N-[3-(2-Bromo-acetyl)-2,4-difluoro-phenyl]-2,5-difluoro-benzenesulfonamide, cmpd. of formula 7 [n=1; Rx=H; R4=F; R5=4-F; R6=2,5-difluorophenyl]

Method A, Step d

N-(3-Acetyl-2,4-difluoro-phenyl)-2,5-difluoro-benzenesulfonamide (7.6 g, 21.88 mmol) prepared as described in WO2010/10154, was dissolved in acetic acid (30 mL). A solution of 1.12 mL (26.25 mmol) of bromine in 2 mL of acetic acid was then added in three portions. 48% Aqueous hydrobromic acid (0.248 mL, 2.19 mmol) dissolved in 1 mL of acetic acid was then added and the mixture was stirred at r.t. for 21 h. Aqueous 5% NaHCO$_3$ was added dropwise (50 mL) and the mixture was extracted with methyl tert-butylether (2×30 mL). Combined organic layers were dried over Na$_2$SO$_4$ and evaporated to dryness. The crude was recrystallized from a mixture of ethyl acetate/toluene/cyclohexane giving 5.79 g (61%) of the title compound as a light brown solid.

HPLC: R$_t$: 6.10 min
$^1$H-NMR (401 MHz, DMSO-d$_6$) δ ppm 10.75 (br. s., 1H), 7.68-7.39 (m, 4H), 7.29-7.17 (m, 1H), 4.34 (s, 2H).

N-{2,4-Difluoro-3-[2-(4-methyl-piperazin-1-yl)-thiazol-4-yl]-phenyl}-2,5-difluoro-benzenesulfonamide, cmpd. of formula 9 [n=1; Rx=H; R4=F; R5=4-F; R6=2,5-difluorophenyl; R1=4-methylpiperazin-1-yl]

Method A, Step e 50 mg (0.31 mmol) of 4-methylpiperazine-1-carbothioamide (prepared as described in Heterocycles, 1989, 29, 1601) were dissolved in 15 mL of ethanol and 134 mg (0.31 mmol) of N-[3-(bromoacetyl)-2,4-difluorophenyl]-2,5-difluorobenzenesulfonamide were added to the resulting solution. The mixture was stirred at 60° C. for 20 min in a microwave oven. The solvent was then evaporated and the residue triturated with diisopropyl ether, giving 140 mg (97%) of the title compound.

HPLC: R$_t$: 5.51 min
$^1$H NMR (401 MHz, DMSO-d$_6$) δ ppm 10.50 (s, 1H), 7.60-7.66 (m, 1H), 7.53-7.60 (m, 1H), 7.46-7.53 (m, 1H), 7.27 (td, J=5.7, 8.7 Hz, 1H), 7.15 (td, J=1.5, 9.2 Hz, 1H), 7.11 (s, 1H), 2.80 (br. s., 3H)
HRMS (ESI) calcd for C$_{20}$H$_{19}$F$_4$N$_{14}$O$_2$S$_2$ [M+H]+ 487.0880. found 487.0857.

Analogously the following intermediate was obtained:

N-[3-(2-amino-1,3-thiazol-4-yl)-2,4-difluorophenyl]-2,5difluorobenzenesulfonamide, cmpd. of formula 9 [n=1; Rx=H; R1=NH$_2$; R4=F; R5=4-F; R6=2,5-difluorophenyl]

HPLC: R$_t$: 5.50 min
$^1$H NMR (401 MHz, DMSO-d$_6$) δ ppm 10.60 (s, 1H), 7.46-7.65 (m, 3H), 7.24 (td, J=5.7, 8.8 Hz, 1H), 7.11 (td, J=1.6, 9.3 Hz, 1H), 7.07 (br. s., 2H), 6.69 (s, 7H)
HRMS (ESI) calcd for C$_{15}$H$_{10}$F$_4$N$_3$O$_2$S$_2$ [M+H]$^+$ 404.0145. found 404.0142.

N-{3-[5-Bromo-2-(4-methyl-piperazin-1-yl)-thiazol-4-yl]-2,4-difluoro-phenyl}-2,5-difluoro-benzenesulfonamide, cmpd. of formula 10 [n=1; Rx=H; R4=F; R5=4-F; R6=2,5-difluorophenyl; R1=4-methylpiperazin-1-yl; Hal=Br]

Method A, Step f 150 mg (0.31 mmol) of N-{2,4-Difluoro-3-[2-(4-methylpiperazin-1-yl)-thiazol-4-yl]-phenyl}-2,5-difluoro-benzenesulfonamide were suspended in 15 mL of dry DCM and 103 mg (0.62 mmol) of N-bromosuccinimide were added. The reaction was maintained at r.t. for 1 h then diluted with the same solvent and washed with aqueous NaHCO$_3$. The organic layer was dried over Na$_2$SO$_4$ and evaporated. The residue was triturated with petroleum ether and filtered, to afford 128 mg (73%) of N-{3-[5-bromo-2-(4-methylpiperazin-1-yl)-1,3-thiazol-4-yl]-2,4-difluorophenyl}-2,5-difluorobenzenesulfonamide.

HPLC: R$_t$: 6.33 min
HRMS (ESI) calcd for C$_{20}$H$_{18}$BrF$_4$N$_4$O$_2$S$_2$ [M+H]+ 564.9985. found 564.9982.

Analogously the following intermediate was obtained:

N-[3-(2-amino-5-bromo-1,3-thiazol-4-yl)-2,4-difluorophenyl]-2,5-difluorobenzenesulfonamide, cmpd. of formula 10 [n=1; Rx=H; R1=NH$_2$; R4=F; R5=4-F; R6=2,5-difluorophenyl; Hal=Br]

HPLC: R$_t$: 5.91 min
$^1$H NMR (401 MHz, DMSO-d$_6$) δ ppm 10.67 (s, 1H), 7.43-7.65 (m, 3H), 7.36-7.42 (m, 1H), 7.35 (br. s., 2H), 7.17 (td, J=1.5, 8.9 Hz, 1H).
HRMS (ESI) calcd for C$_{15}$H$_9$BrF$_4$N$_{13}$O$_2$S$_2$ [M+H]+ 481.9250. found 481.9232.

N-{2,4-difluoro-3-[2-(4-methylpiperazin-1-yl)-5-(pyridin-4-yl)-1,3-thiazol-4-yl]phenyl}-2,5-difluorobenzenesulfonamide, cmpd. of formula (I)A (cmpd. 8) [m, n=1; R2, R3, Rx=H; R4=F; R5=4-F; R6=2,5-difluorophenyl; R1'=4-methylpiperazin-1-yl]

Method A, Step h 100 mg (0.18 mmol) of N-{3-[5-Bromo-2-(4-methyl-piperazin-1-yl)-thiazol-4-yl]-2,4-difluoro-phenyl}-2,5-difluoro-benzenesulfonamide were dissolved in 9 mL of DME and 1 mL of water. 170 mg (0.54 mmol) of $Cs_2CO_3$, 116 mg (0.35 mmol) of 4-pyridyl-boropinacolate and 42 mg (0.05 mmol) of $PdCl_2(dppf)_2 \cdot CH_2Cl_2$ were added to the mixture, that was submitted to microwave irradiation at 110° C. for 1 h. The crude was filtered through a celite pad and the filtrate evaporated. The residue was taken up with DCM and washed with $NH_4OH$ 15%. The organic layer was dried over $Na_2SO_4$ and evaporated. The product was finally purified by flash chromatography on a silica gel precoated column, eluted with DCM-MeOH 95/5, affording 30 mg (30%) of the title compound.

HPLC: $R_t$: 5.44 min $^1$H NMR (401 MHz, DMSO-$d_6$) δ ppm 8.38-8.44 (m, 2H), 7.53-7.62 (m, 1H), 7.38-7.52 (m, 3H), 7.19 (td, J=1.4, 8.8 Hz, 1H), 6.79-6.96 (m, 2H), 3.64 (br. s., 4H), 3.15 (br. s., 4H), 2.73 (br. s., 3H)

HRMS (ESI) calcd for $C_{25}H_{21}F_4N_{15}O_2S_2$ [M+H]+ 523.0516. found 523.0508.

Analogously the following compounds were obtained:

N-{2,4-difluoro-3-[2-(methylamino)-5-(pyridin-4-yl)-1,3-thiazol-4-yl]phenyl}-2,5-difluorobenzenesulfonamide, cmpd. of formula (I)A (cmpd. 2) [m, n=1; R2, R3, Rx=H; R4=F; R5=4-F; R6=2,5-difluorophenyl; R1'=methylamino]

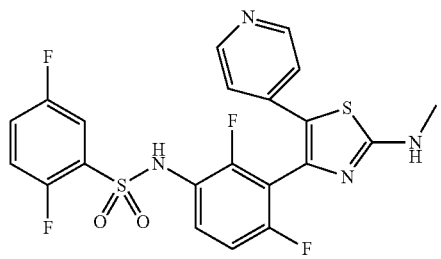 [SMILES: CNc1nc(-c2c(F)ccc(NS(=O)(=O)c3cc(F)ccc3F)c2F)c(-c2ccncc2)s1]

HPLC: $R_t$: 5.55 min $^1$H NMR (401 MHz, DMSO-$d_6$) δ ppm 10.67 (br. s., 1H), 8.29-8.44 (m, 2H), 8.14 (q, J=4.8 Hz, 1H), 7.52-7.61 (m, 1H), 7.38-7.52 (m, 3H), 7.19 (td, J=1.5, 8.8 Hz, 1H), 6.83-6.91 (m, 2H), 2.85 (d, J=4.8 Hz, 3H)

HRMS (ESI) calcd for $C_{21}H_{14}F_4N_4O_2S_2$ [M+H]+ 495.0567. found 495.0548.

N-{3-[2-amino-5-(pyridin-4-yl)-1,3-thiazol-4-yl]-2,4-difluorophenyl}-2,5-difluorobenzenesulfonamide, cmpd. of formula (I)U1 (cmpd. 1) [m, n=1; R2, R3, Rx=H; R4=F; R5=4-F; R6=2,5-difluorophenyl]

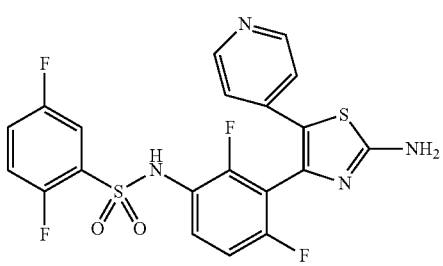 [SMILES: Nc1nc(-c2c(F)ccc(NS(=O)(=O)c3cc(F)ccc3F)c2F)c(-c2ccncc2)s1]

HPLC: $R_t$: 5.15 min $^1$H NMR (401 MHz, DMSO-$d_6$) δ ppm 10.67 (br. s., 1H), 8.33 (d, J=5.7 Hz, 2H), 7.59-7.51 (m, 3H), 7.50-7.35 (m, 3H), 7.20-7.11 (m, 1H), 6.82 (d, J=5.9 Hz, 2H)

HRMS (ESI) calcd for $C_{20}H_{12}F_4N_4O_2S_2$ [M+H]+ 481.0411. found 481.0394.

Example 2

Synthesis of N-[4-(3-{[(2,5-difluorophenyl)sulfonyl]amino}-2,6-difluorophenyl)-5-(pyridin-4-yl)-1,3-thiazol-2-yl]acetamide, cmpd. of formula (I)M (cmpd. 33) [m, n=1; R2, R3=H; R4=F; R5=4-F; R6=2,5-difluorophenyl; R10=methyl]

Method B, Steps g and b5

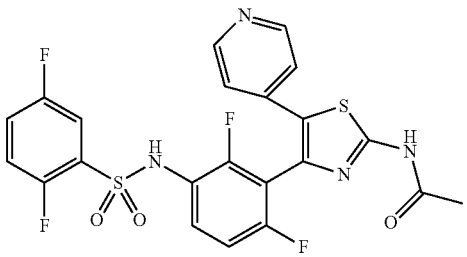 [SMILES: CC(=O)Nc1nc(-c2c(F)ccc(NS(=O)(=O)c3cc(F)ccc3F)c2F)c(-c2ccncc2)s1]

50 mg (0.104 mmol) of N-{3-[2-amino-5-(pyridin-4-yl)-1,3-thiazol-4-yl]-2,4-difluorophenyl}-2,5-difluorobenzenesulfonamide were dissolved in 5 mL of acetic anhydride and the solution was stirred at r.t. for 3 days. The mixture was poured into a saturated aqueous solution of $NaHCO_3$ and extracted several times with DCM. The organic layer was dried over $Na_2SO_4$ and evaporated. The crude was dissolved in 5 mL of MeOH and 2 mL of TEA were added. The solution was stirred for 3 days at r.t. The solvent was then removed, the residue taken up with DCM and washed with water. The organic layer was dried over $Na_2SO_4$ and evaporated, to yield 30 mg (58%) of the title compound, triturated with diisopropylether-petroleum ether.

HPLC: $R_t$: 5.23 min $^1$H NMR (401 MHz, DMSO-$d_6$) δ ppm 12.48 (s, 1H), 8.40-8.48 (m, 2H), 7.30-7.62 (m, 4H), 7.12 (br. s., 1H), 7.02-7.07 (m, 2H), 2.19 (s, 3H)

HRMS (ESI) calcd for $C_{22}H_{14}F_4N_4O_3S_2$ [M+H]+ 523.0516. found 523.0497.

Example 3

Synthesis of 2,5-difluoro-N-{2-fluoro-3-[2-(1-methylpiperidin-4-yl)-5-(pyridin-4-yl)-1,3-thiazol-4-yl]phenyl}benzenesulfonamide, cmpd. of formula (I)R2 (cmpd. 19) [m, n=1; R2, R3, R5=H; R4=F, R6=2,5-difluorophenyl; R"=methyl]

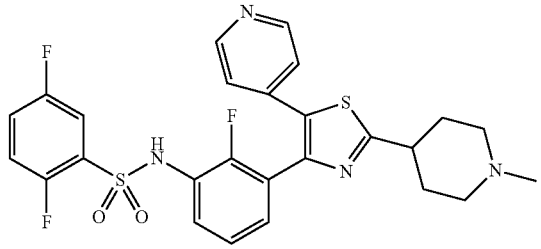 [SMILES: CN1CCC(c2nc(-c3cccc(NS(=O)(=O)c4cc(F)ccc4F)c3F)c(-c3ccncc3)s2)CC1]

N-[3-(bromoacetyl)-2-fluorophenyl]-2,5-difluoro-N-(methoxymethyl)benzenesulfonamide, cmpd. of formula 7 [n=1; R5=H; R4=F; R6=2,5-difluorophenyl; Rx=methoxymethyl]

Method A, Step d1
Conditions 1

100 mg (0.27 mmol) of N-(3-acetyl-2-fluorophenyl)-2,5-difluoro-N-(methoxymethyl)benzenesulfonamide were dissolved in 10 mL of dry THF and 100 mg (0.3 mmol) of pyridinium bromide perbromide were added. The resulting solution was heated in a microwave apparatus at 80° C. for 15 min. The solvent was then evaporated, the residue taken up with DCM and washed with 0.5 N HCl. The organic layer was then dried over $Na_2SO_4$ and evaporated to give the title compound as an oil.

Conditions 2

100 mg (0.27 mmol) of N-(3-acetyl-2-fluorophenyl)-2,5-difluoro-N-(methoxymethyl)benzenesulfonamide were dissolved in 4 mL of dry DCM under nitrogen atmosphere. The solution was cooled to 0° C. and 94 µL (0.65 mmol) of TEA and 106 µL (0.54 mmol) of trimethylsilyl-trifluoromethansulfonate were added. The solution was stirred 15 min at the same temperature and then diluted with DCM and washed rapidly with brine. The organic layer was dried over $Na_2SO_4$ and evaporated giving 2,5-difluoro-N-(2-fluoro-3-{1-[(trimethylsilyl)oxy]ethenyl}phenyl)-N-(methoxymethyl)benzenesulfonamide as a clear oil. The latter was re-dissolved in 4 mL of dry DCM under nitrogen atmosphere and 58 mg (0.32 mmol) of N-bromosuccinimide were added at 0° C. After 30 min the reaction was complete. The mixture was diluted with DCM and washed with aqueous $NaHCO_3$. The organic layer was dried over $Na_2SO_4$ and evaporated to give the title compound, which was used without any further purification.

HPLC: $R_t$: 6.77 min.
HPLC/MS (ESI): 469-471 $[M+NH_4]^+$

N-[3-(2-amino-1,3-thiazol-4-yl)-2-fluorophenyl]-2,5-difluoro-N-(methoxymethyl)benzenesulfonamide, cmpd. of formula 9 [n=1; R1=$NH_2$; R4=F; R5=H; R6=2,5-difluorophenyl; Rx=methoxymethyl]

Method A, Step e 21 mg (0.27 mmol) of thiourea were added to a solution of 122 mg (0.27 mmol) of N-[3-(bromoacetyl)-2-fluorophenyl]-2,5-difluoro-N-(methoxymethyl)benzenesulfonamide in 5 mL of ethanol. The mixture was heated at 60° C. for 20 min in a microwave apparatus. The solvent was then removed, the residue taken up with DCM and washed with water. The organic layer was separated, dried over $Na_2SO_4$ and evaporated. The crude was purified by flash chromatography eluted with DCM-$CH_3OH$ 95/5, giving 92 mg (80%) of the title compound.

HPLC: $R_t$: 6.26 min.
$^1$H NMR (401 MHz, DMSO-$d_6$) δ ppm 7.97 (td, J=1.8, 7.5 Hz, 1H), 7.57-7.76 (m, 2H), 7.40-7.54 (m, 1H), 7.21-7.30 (m, 1H), 7.13-7.19 (m, 1H), 7.11 (s, 2H), 6.82 (d, J=2.6 Hz, 1H), 5.09 (s, 2H), 3.37 (s, 3H).
HRMS (ESI) calcd for $C_{17}H_{15}F_3N_3O_3S_2$ $[M+H]^+$ 430.0505. found 430.0493.

N-[3-(2-amino-5-bromo-1,3-thiazol-4-yl)-2-fluorophenyl]-2,5-difluoro-N-(methoxymethyl)benzenesulfonamide, cmpd. of formula 10 [n=1; R1=$NH_2$; R4=F; R5=H; R6=2,5-difluorophenyl; Rx=methoxymethyl; Hal=Br]

Method A, Step f 1.26 g (2.94 mmol) of N-[3-(2-amino-1,3-thiazol-4-yl)-2-fluorophenyl]-2,5-difluoro-N-(methoxymethyl)-benzenesulfonamide were dissolved in 30 ml of dry DCM and 523 mg (2.94 mmol) of N-bromosuccinimide were added. The resulting solution was stirred at r.t. for 30 min. The mixture was diluted with the same solvent and washed with aqueous $NaHCO_3$. The organic layer was dried over $Na_2SO_4$ and evaporated. The residue was triturated with diisopropyl ether and filtered to afford 1.4 g (93%) of the title compound.

HPLC: $R_t$: 6.52 min.
$^1$H NMR (401 MHz, DMSO-$d_6$) δ ppm 7.57-7.71 (m, 2H), 7.44-7.55 (m, 2H), 7.31-7.42 (m, 2H), 7.24-7.32 (m, 1H), 4.96-5.21 (m, 2H), 3.36-3.39 (m, 3H).

N-[3-(5-bromo-2-{[(E)-(dimethylamino)methylidene]amino}-1,3-thiazol-4-yl)-2-fluorophenyl]-2,5-difluoro-N-(methoxymethyl)benzenesulfonamide, cmpd. of formula 11 [n=1; R4=F; R5=H; R6=2,5-difluorophenyl; Rx=methoxymethyl; PG'=dimethylaminomethylen; Hal=Br]

Method A, Step g 1.4 g (2.75 mmol) of N-[3-(2-amino-5-bromo-1,3-thiazol-4-yl)-2-fluorophenyl]-2,5-difluoro-N-(methoxymethyl)benzenesulfonamide were dissolved in 30 mL of dry DMF and 448 µL (2.75 mmol) of dimethylformamide dimethylacetale were added to the mixture. The reaction was stirred at r.t. overnight and then the solvent was removed under reduced pressure. The residue was taken up with DCM and washed with brine. The organic layer was then dried over $Na_2SO_4$ and evaporated. The crude was finally purified by flash chromatography eluted with cyclohexane ethanol 9/1, affording 0.8 g (52%) of the title compound.

HPLC: $R_t$: 7.18 min.
$^1$H NMR (401 MHz, DMSO-$d_6$) δ ppm 8.25 (s, 1H), 7.72-7.57 (m, 2H), 7.57-7.52 (m, 1H), 7.52-7.45 (m, 1H), 7.45-7.37 (m, 1H), 7.34-7.28 (m, 1H), 5.09 (s, 2H), 3.38 (s, 3H), 3.11 (s, 3H), 2.97 (s, 3H).
HRMS (ESI) calcd for $C_{20}H_{19}BrF_3N_{14}O_3S_2$ $[M+H]^+$ 563.0029. found 563.0049.

Analogously, but starting from the suitable aminothiazole derivatives, the following compounds were obtained:

N-[3-(5-bromo-2-{[(E)-(dimethylamino)methylidene]amino}-1,3-thiazol-4-yl)-2,4-difluorophenyl]-2,5-difluoro-N-(methoxymethyl)benzenesulfonamide, cmpd. of formula 11 [n=1; R4=F; R5=4-F; R6=2,5-difluorophenyl; Rx=methoxymethyl; PG'=dimethylaminomethylen; Hal=Br]

HPLC: $R_t$: 7.00 min.
$^1$H NMR (401 MHz, DMSO-$d_6$) δ ppm 8.25 (s, 1H), 7.57-7.71 (m, 2H), 7.45-7.56 (m, 2H), 7.25-7.34 (m, 1H), 5.07 (s, 2H), 3.37 (s, 3H), 3.11 (s, 3H), 2.97 (s, 3H).
HRMS (ESI) calcd for $C_{20}H_{18}BrF_4N_4O_3S_2$ $[M+H]^+$ 580.9935. found 580.9921.

N-[3-(5-bromo-2-{[(E)-(dimethylamino)methylidene]amino}-1,3-thiazol-4-yl)-2,4-difluorophenyl]-2,5-difluorobenzenesulfonamide, cmpd. of formula 11 [n=1; R4=F; R5=4-F; R6=2,5-difluorophenyl; Rx=H; PG'=dimethylaminomethylen; Hal=Br]

HPLC: $R_t$: 6.47 min.
$^1$H NMR (401 MHz, DMSO-$d_6$) δ ppm 10.70 (s, 1H), 8.24 (s, 1H), 7.65-7.59 (m, 1H), 7.59-7.52 (m, 1H), 7.51-7.46 (m, 1H), 7.42 (dt, J=5.9, 8.9 Hz, 1H), 7.24-7.17 (m, 1H), 3.11 (s, 3H), 2.97 (s, 3H)

HRMS (ESI) calcd for $C_{18}H_{14}BrF_4N_4O_2S_2$ [M+H]$^+$ 536.9672. found 536.9646.

N-{3-[2-{[(E)-(dimethylamino)methylidene]amino}-5-(pyridin-4-yl)-1,3-thiazol-4-yl]-2-fluorophenyl}-2,5-difluoro-N-(methoxymethyl)benzenesulfonamide, cmpd. of formula 13 [m, n=1; R2, R3, R5=H; R4=F; R6=2,5-difluorophenyl; Rx=methoxymethyl; PG'=dimethylaminomethylen]

Method A, Step h1

To a solution of 342 mg (0.61 mmol) of N-[3-(5-bromo-2-{[(E)-(dimethylamino)methylidene]amino}-1,3-thiazol-4-yl)-2-fluorophenyl]-2,5-difluoro-N-(methoxymethyl)benzenesulfonamide in a mixture of 12 mL of DME and 2 mL of water, 596 mg (1.83 mmol) of $Cs_2CO_3$, 160 mg (0.2 mmol) of $PdCl_2(dppf)_2 \cdot CH_2Cl_2$ and 244 mg (1.22 mmol) of 4-pyridylboropinacolate were added consecutively. The mixture was heated in a microwave oven at 110° C. for 1 h and then filtered through a celite pad. The filtrate was evaporated under reduced pressure, the crude taken up with DCM and washed with brine. The organic layer was separated, dried over $Na_2SO_4$ and the solvent removed. The product was purified by flash-chromatography eluted by DCM-MeOH 98/2 giving 240 mg (70%) of the title compound.

HPLC: $R_t$: 6.30 min.

$^1$H NMR (401 MHz, DMSO-$d_6$) δ ppm 8.39 (s, 1H), 8.40-8.37 (m, 2H), 7.68-7.59 (m, 1H), 7.59-7.52 (m, 2H), 7.50-7.45 (m, 1H), 7.38-7.25 (m, 2H), 7.03-6.90 (m, 2H), 4.98 (s, 2H), 3.27 (s, 3H), 3.14 (s, 3H), 3.01 (s, 3H).

HRMS (ESI) calcd for $C_{25}H_{23}F_3N_5O_3S_2$ [M+H]$^+$ 562.1189. found 562.1183.

Analogously, but starting from the suitable bromothiazole derivative, the following compound was obtained:

N-{3-[2-{[(E)-(dimethylamino)methylidene]amino}-5-(pyridin-4-yl)-1,3-thiazol-4-yl]-2,4-difluorophenyl}-2,5-difluoro-N-(methoxymethyl)benzenesulfonamide, cmpd. of formula 13 [m, n=1; R2, R3, =H; R4=F; R5=4-F; R6=2,5-difluorophenyl; Rx=methoxymethyl; PG'=dimethylaminomethylen]

HPLC: $R_t$: 6.20 min.

$^1$H NMR (401 MHz, DMSO-$d_6$) δ ppm 8.40-8.44 (m, 2H), 8.38 (s, 1H), 7.58-7.68 (m, 1H), 7.42-7.58 (m, 4H), 7.22-7.30 (m, 1H), 6.93-6.99 (m, 2H), 5.01-5.04 (m, 2H), 5.03 (s, 2H), 3.14 (s, 3H), 3.01 (s, 3H).

HRMS (ESI) calcd for $C_{25}H_{22}F_4N_5O_3S_2$ [M+H]$^+$ 580.1095. found 580.1072.

N-{3-[2-amino-5-(pyridin-4-yl)-1,3-thiazol-4-yl]-2-fluorophenyl}-2,5-difluoro-N-(methoxymethyl)benzenesulfonamide, cmpd. of formula (I)U1 [m, n=1; R2, R3, R5=H; R4=F; R6=2,5-difluorophenyl; Rx=methoxymethyl]

Method A, Step i 550 mg (0.98 mmol) of N-{3-[2-{[(E)-(dimethylamino)methylidene]amino}-5-(pyridin-4-yl)-1,3-thiazol-4-yl]-2-fluorophenyl}-2,5-difluoro-N-(methoxymethyl)benzenesulfonamide were suspended in 15 mL of ethanol and 460 μL (6.86 mmol) of ethylenediamine were added. The mixture was maintained at reflux giving a clear solution. After 8 h the solvent was removed under reduced pressure and the residue was re-dissolved in DCM and washed with brine. The organic phase was dried over $Na_2SO_4$ and the solvent evaporated. The crude was triturated with diethyl ether, giving, after filtration, 450 mg (90%) of the title compound.

HPLC: $R_t$: 5.68 min.

$^1$H NMR (401 MHz, DMSO-$d_6$) δ ppm 8.15-8.35 (m, 2H), 7.58-7.66 (m, 1H), 7.42-7.57 (m, 5H), 7.24-7.36 (m, 2H), 6.84-6.91 (m, 2H), 4.99 (s, 2H), 3.27 (s, 3H).

HRMS (ESI) calcd for $C_{22}H_{18}F_3N_4O_3S_2$ [M+H]$^+$ 507.0767. found 507.0769.

Analogously, but starting from the suitable imino derivative, the following compound was obtained:

N-{3-[2-amino-5-(pyridin-4-yl)-1,3-thiazol-4-yl]-2,4-difluorophenyl}-2,5-difluoro-N-(methoxymethyl)benzenesulfonamide, cmpd. of formula (I)U1 [m, n=1; R2, R3, =H; R4=F; R5=4-F; R6=2,5-difluorophenyl; Rx=methoxymethyl]

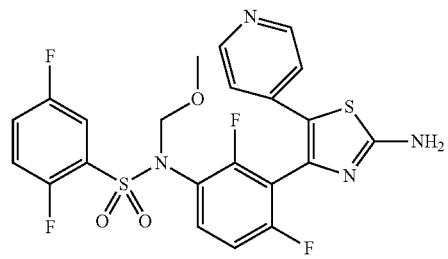

HPLC: $R_t$: 5.62 min.

$^1$H NMR (401 MHz, DMSO-$d_6$) δ ppm 8.34-8.38 (m, 2H), 7.59-7.67 (m, 2H), 7.49-7.59 (m, 5H), 7.41-7.49 (m, 1H), 7.20-7.27 (m, 1H), 6.85-6.90 (m, 2H), 5.02 (s, 2H)

HRMS (ESI) calcd for $C_{22}H_{17}F_4N_4O_3S_2$ [M+H]$^+$ 525.0673. found 525.0659.

N-{3-[2-bromo-5-(pyridin-4-yl)-1,3-thiazol-4-yl]-2-fluorophenyl}-2,5-difluoro-N-(methoxymethyl)benzenesulfonamide, cmpd. of formula (I)F [m, n=1; R2, R3, R5=H; R4=F; R6=2,5-difluorophenyl; Rx=methoxymethyl; Hal=Br]

Method B, Step c

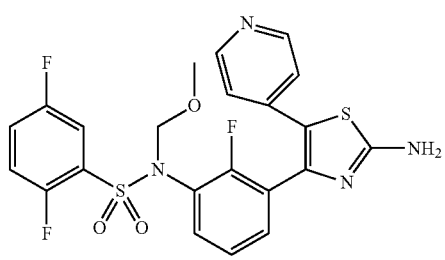 [SMILES: COCN(c1cccc(-c2nc(N)sc2-c2ccncc2)c1F)S(=O)(=O)c1cc(F)ccc1F]

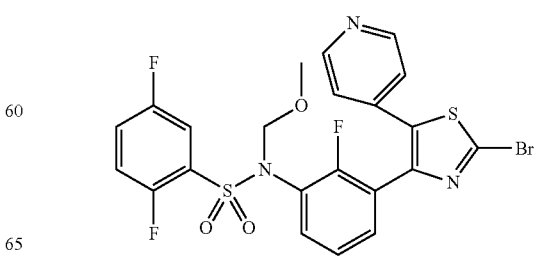

450 mg (0.89 mmol) of N-{3-[2-amino-5-(pyridin-4-yl)-1,3-thiazol-4-yl]-2-fluorophenyl}-2,5-difluoro-N-(methoxymethyl)benzenesulfonamide were suspended in 45 mL of dry acetonitrile and 298 mg (1.34 mmol) of CuBr$_2$ and 2 mL (16.8 mmol) of tert-butyl nitrite were added. The mixture was stirred at 85° C. for 8 h. After this time the reaction was filtered through a celite pad and the filtrate evaporated. The residue was taken up with DCM and washed with aqueous NaHCO$_3$. The organic layer was separated, dried over Na$_2$SO$_4$ and evaporated. The crude was purified by flash-chromatography, eluted with DCM-MeOH 98/2, affording 350 mg (69%) of the title compound.

HPLC: R$_t$: 7.14 min.

$^1$H NMR (401 MHz, DMSO-d$_6$) δ ppm 8.52 (d, J=5.2 Hz, 2H), 7.57-7.70 (m, 2H), 7.42-7.57 (m, 2H), 7.25-7.42 (m, 2H), 7.14 (d, J=6.0 Hz, 2H), 4.97 (s, 2H), 3.23 (s, 3H)

HRMS (ESI) calcd for C$_{22}$H$_{16}$BrF$_3$N$_3$O$_3$S$_2$ [M+H]$^+$ 569.9763. found 569.9789.

Analogously, but starting from the corresponding aminothiazole derivative, the following compound was obtained:

N-{3-[2-bromo-5-(pyridin-4-yl)-1,3-thiazol-4-yl]-2,4-difluorophenyl}-2,5-difluoro-N-(methoxymethyl)benzenesulfonamide, cmpd. of formula (I)F [m, n=1; R2, R3, =H; R4=F; R5=4-F; R6=2,5-difluorophenyl; Rx=methoxymethyl; Hal=Br]

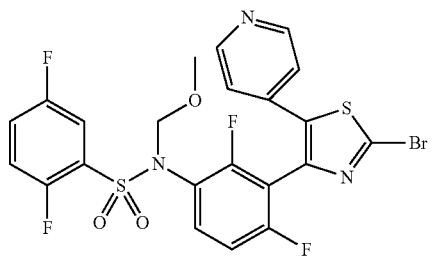 [SMILES: COCN(c1ccc(F)c(-c2nc(Br)sc2-c2ccncc2)c1F)S(=O)(=O)c1cc(F)ccc1F]

HPLC: R$_t$: 6.95 min.

$^1$H NMR (401 MHz, DMSO-d$_6$) δ ppm 8.53-8.59 (m, 2H), 7.60-7.68 (m, 1H), 7.45-7.59 (m, 3H), 7.26-7.34 (m, 1H), 7.12-7.18 (m, 2H), 5.01 (s, 2H), 3.27 (s, 3H)

HRMS (ESI) calcd for C$_{22}$H$_{15}$BrF$_4$N$_{13}$O$_3$S$_2$ [M+H]$^+$ 587.9669. found 587.9645.

tert-butyl-4-[4-(3-{[(2,5-difluorophenyl)sulfonyl](methoxymethyl)amino}-2-fluorophenyl)-5-(pyridin-4-yl)-1,3-thiazol-2-yl]-3,6-dihydropyridine-1(2H)-carboxylate, cmpd. of formula (I)H1 [m, n=1; R2, R3, R5=H; R4=F; R6=2,5-difluorophenyl; Rx=methoxymethyl; X=NCOOt-Bu]

Method C, Step a

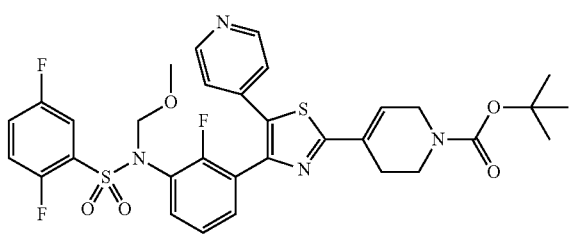 [SMILES: COCN(c1cccc(-c2nc(C3=CCN(C(=O)OC(C)(C)C)CC3)sc2-c2ccncc2)c1F)S(=O)(=O)c1cc(F)ccc1F]

200 mg (0.35 mmol) of N-{3-[2-bromo-5-(pyridin-4-yl)-1,3-thiazol-4-yl]-2-fluorophenyl}-2,5-difluoro-N-(methoxymethyl)benzenesulfonamide were dissolved in a mixture of 7.8 mL of DME and 1.2 mL of water. 344 mg (1.05 mmol) of Cs$_2$CO$_3$, 216 mg (0.70 mmol) of 4-(4,4,5,5-tetramethyl-[1,3,2]dioxaborolan-2-yl)-3,6-dihydro-2H-pyridine-1-carboxylic acid tert-butyl ester and 96 mg (0.12 mmol) of PdCl$_2$(dppf)$_2$.CH$_2$Cl$_2$ were added and the resulting mixture heated in a microwave oven at 100° C. for an h. The reaction was filtered through a celite pad and the filtrate evaporated. The residue was then taken up with DCM and washed with brine. The organic layer was dried over Na$_2$SO$_4$ and evaporated. The crude was finally purified by flash chromatography, eluted with cyclohexane-ethylacetate-ethanol 4/1/0.5, giving, after trituration with diethylether and filtration, 225 mg (85%) of the title compound.

HPLC: R$_t$: 7.91 min.

$^1$H NMR (401 MHz, DMSO-d$_6$) δ ppm 8.28-8.65 (m, 2H), 7.49-7.73 (m, 4H), 7.46 (ddd, J=3.2, 5.1, 7.9 Hz, 1H), 7.24-7.40 (m, 2H), 7.03-7.19 (m, 2H), 4.97 (s, 2H), 3.96-4.08 (m, J=12.8 Hz, 2H), 3.21-3.24 (m, 3H), 2.92 (br. s., 2H), 2.08 (dd, J=3.4, 14.1 Hz, 2H), 1.60 (qd, J=4.3, 12.1 Hz, 2H), 1.41 (s, 9H)

HRMS (ESI) calcd for C$_{32}$H$_{32}$F$_3$N$_4$O$_5$S$_{22}$ [M+H]$^+$ 673.1761. found 673.1771.

Analogously, but employing the suitable boropinacolate derivative, the following compound was obtained:

N-{3-[2-(3,6-dihydro-2H-pyran-4-yl)-5-(pyridin-4-yl)-1,3-thiazol-4-yl]-2-fluorophenyl}-2,5-difluoro-N-(methoxymethyl)benzenesulfonamide, cmpd. of formula (I)H1 [m, n=1; R2, R3, R5=H; R4=F; R6=2,5-difluorophenyl; Rx=methoxymethyl; X=O]

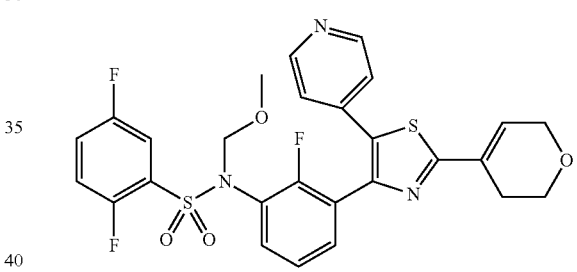

HPLC: R$_t$: 6.12 min.

$^1$H NMR (401 MHz, DMSO-d$_6$) δ ppm 8.49 (d, J=6.1 Hz, 2H), 7.57-7.69 (m, 2H), 7.50-7.57 (m, 1H), 7.42-7.49 (m, 1H), 7.28-7.41 (m, 2H), 7.07-7.17 (m, 2H), 6.79 (s, 1H), 4.98 (s, 2H), 4.29 (d, J=2.8 Hz, 2H), 3.79-3.87 (m, 2H), 3.24 (s, 3H), 2.57 (br. s., 2H), 2.02-2.10 (m, 1H)

HRMS (ESI) calcd for C$_{27}$H$_{23}$F$_3$N$_3$O$_4$S$_2$ [M+H]$^+$ 574.1077. found 574.1086.

tert-butyl-4-[4-(3-{[(2,5-difluorophenyl)sulfonyl](methoxymethyl)amino}-2-fluorophenyl)-5-(pyridin-4-yl)-1,3-thiazol-2-yl]piperidine-1-carboxylate, cmpd. of formula (I)Q [m, n=1; R2, R3, R5=H; R4=F; R6=2,5-difluorophenyl; Rx=methoxymethyl; X=NCOOt-Bu]

Method C, Step b

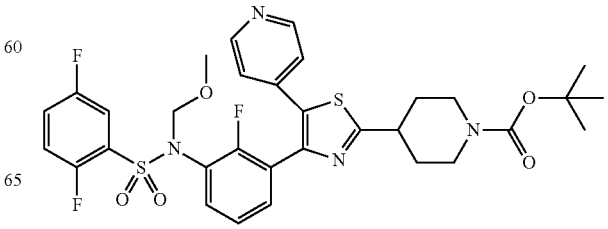

220 mg (0.33 mmol) of tert-butyl 4-[4-(3-{[(2,5-difluorophenyl)sulfonyl](methoxymethyl)amino}-2-fluorophenyl)-5-(pyridin-4-yl)-1,3-thiazol-2-yl]-3,6-dihydropyridine-1(2H)-carboxylate were suspended in 30 mL of MeOH and 880 mg (14 mmol) of ammonium formate and 50 mg of Pd—C 10% were added. The reaction was stirred under reflux for 2 days. After this time the mixture was filtered through a celite pad and the filtrate evaporated. The crude was taken up with DCM and washed with brine. The organic layer was dried over $Na_2SO_4$ and evaporated. The crude was then triturated with diethylether-petroleum ether and collected by filtration affording 200 mg (91%) of the title compound.

HPLC: $R_t$: 7.72 min.

$^1$H NMR (401 MHz, DMSO-$d_6$) δ ppm 8.28-8.65 (m, 2H), 7.49-7.73 (m, 4H), 7.46 (ddd, J=3.2, 5.1, 7.9 Hz, 1H), 7.24-7.40 (m, 2H), 7.03-7.19 (m, 2H), 4.97 (s, 2H), 3.96-4.08 (m, J=12.8 Hz, 2H), 3.21-3.24 (m, 3H), 2.92 (br. s., 2H), 2.08 (dd, J=3.4, 14.1 Hz, 2H), 1.60 (qd, J=4.3, 12.1 Hz, 2H), 1.41 (s, 9H)

HRMS (ESI) calcd for $C_{32}H_{34}F_3N_4O_5S_2$ [M+H]$^+$ 675.1917. found 675.1938.

Analogously, the following compound was obtained, from the suitable unsaturated derivative:

2,5-difluoro-N-{2-fluoro-3-[5-(pyridin-4-yl)-2-(tetrahydro-2H-pyran-4-yl)-1,3-thiazol-4-yl]phenyl}-N-(methoxymethyl)benzenesulfonamide, cmpd. of formula (I)Q [m, n=1; R2, R3, R5=H; R4=F; R6=2,5-difluorophenyl; Rx=methoxymethyl; X=O]

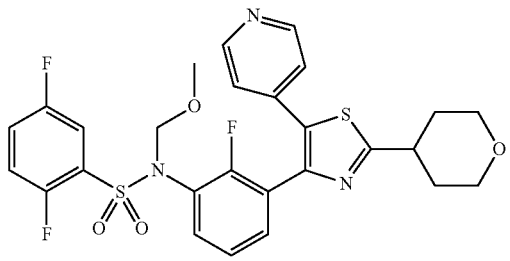 [SMILES: COCN(c1cccc(-c2nc(C3CCOCC3)sc2-c2ccncc2)c1F)S(=O)(=O)c1cc(F)ccc1F]

HPLC: $R_t$: 5.83 min.

$^1$H NMR (401 MHz, DMSO-$d_6$) δ ppm 8.46-8.50 (m, J=4.9 Hz, 2H), 7.41-7.67 (m, 4H), 7.28-7.38 (m, 2H), 7.07-7.17 (m, 3H), 4.97 (s, 2H), 3.91-3.99 (m, 1H), 3.44-3.52 (m, 1H), 1.98-2.06 (m, 2H), 1.70-1.84 (m, 2H)

HRMS (ESI) calcd for $C_{27}H_{25}F_3N_3O_4S_2$ [M+H]$^+$ 576.1233. found 576.1252.

2,5-difluoro-N-{2-fluoro-3-[2-(piperidin-4-yl)-5-(pyridin-4-yl)-1,3-thiazol-4-yl]phenyl}-N-(methoxymethyl)benzenesulfonamide, cmpd. of formula 47 [m, n=1; R2", R3, R5=H; R4=F; R6=2,5-difluorophenyl; Rx=methoxymethyl], corresponding to a compound of formula (I), wherein m, n=1; R1=4-piperidinyl; R2, R3, R5=H; R4=F; R6=2,5-difluorophenyl; Rx=methoxymethyl Method C, Step d

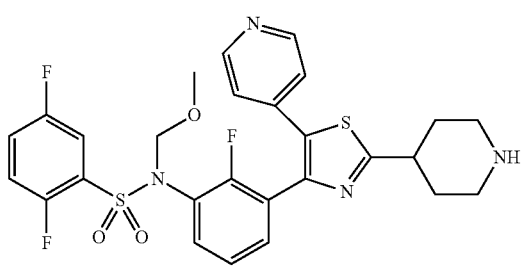 [SMILES: COCN(c1cccc(-c2nc(C3CCNCC3)sc2-c2ccncc2)c1F)S(=O)(=O)c1cc(F)ccc1F]

200 mg (0.3 mmol) of tert-butyl-4-[4-(3-{[(2,5-difluorophenyl)sulfonyl](methoxymethyl)amino}-2-fluorophenyl)-5-(pyridin-4-yl)-1,3-thiazol-2-yl]piperidine-1-carboxylate were dissolved in 20 mL of dry DCM and 2 mL of TFA were added. After 3 h at r.t. the solvent was removed at 30° C. The residue was taken up with DCM, washed with NH$_4$OH 15% and extracted several times with a mixture DCM-MeOH 9/1. The organic layer was separated, dried over $Na_2SO_4$ and evaporated. The residue was triturated with diethyl ether, affording, after filtration, 155 mg (91%) of the title compound.

HPLC: $R_t$: 4.82 min.

$^1$H NMR (401 MHz, DMSO-$d_6$) δ ppm 8.48 (d, J=6.1 Hz, 2H), 7.42-7.69 (m, 5H), 7.27-7.39 (m, 2H), 7.04-7.15 (m, 2H), 4.97 (s, 2H), 3.23 (s, 3H), 3.15 (tt, J=3.6, 11.6 Hz, 1H), 2.96-3.08 (m, J=8.9 Hz, 2H), 2.60-2.69 (m, 2H), 1.97-2.06 (m, J=11.1 Hz, 2H), 1.63 (qd, J=3.8, 12.1 Hz, 2H)

HRMS (ESI) calcd for $C_{27}H_{26}F_3N_4O_3S_2$ [M+H]$^+$ 575.1393. found 575.1418.

2,5-difluoro-N-{2-fluoro-3-[2-(1-methylpiperidin-4-yl)-5-(pyridin-4-yl)-1,3-thiazol-4-yl]phenyl}-N-(methoxymethyl)benzenesulfonamide, cmpd. of formula 48 [m, n=1; R2", R3, R5=H; R4=F; R6=2,5-difluorophenyl; Rx=methoxymethyl; R"'=methyl], corresponding to a compound of formula (I), wherein m, n=1; R1=1-methyl-4-piperidinyl; R2, R3, R5=H; R4=F; R6=2,5-difluorophenyl; Rx=methoxymethyl Method C, Step e

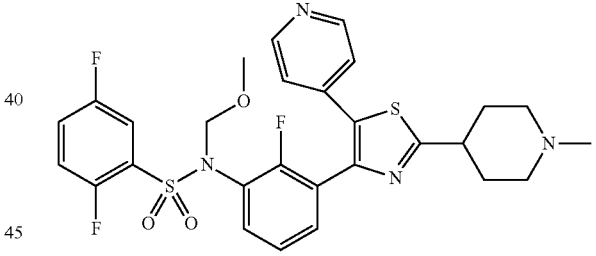

150 mg (0.26 mmol) of 2,5-difluoro-N-{2-fluoro-3-[2-(piperidin-4-yl)-5-(pyridin-4-yl)-1,3-thiazol-4-yl]phenyl}-N-(methoxymethyl)benzenesulfonamide were dissolved in 15 mL of MeOH and 45 μL (0.78 mmol) of glacial acetic acid, 26 mg (0.52 mmol) of NaBH$_3$CN and 20 μL (0.39 mmol) of 37% formaldehyde were added. The resulting solution was stirred at r.t. for 2 h and then the solvent evaporated. The residue was taken up with DCM, washed with NH$_4$OH 15% and extracted several times with a mixture of DCM-MeOH 9/1. The organic layer was dried over $Na_2SO_4$ and evaporated, giving 145 mg (94%) of the title compound.

HPLC: $R_t$: 4.91 min $^1$H NMR (401 MHz, DMSO-$d_6$) δ ppm 8.48 (d, J=6.0 Hz, 2H), 7.41-7.71 (m, 5H), 7.27-7.39 (m, 2H), 6.97-7.18 (m, 2H), 4.97 (s, 2H), 3.23 (s, 3H), 3.01 (tt, J=3.6, 11.5 Hz, 1H), 2.73-2.91 (m, J=11.5 Hz, 2H), 2.20 (s, 3H), 1.90-2.12 (m, 4H), 1.60-1.87 (m, 2H)

HRMS (ESI) calcd for $C_{28}H_{28}F_3N_4O_3S_2$ [M+H]$^+$ 589.1549. found 589.1551.

2,5-difluoro-N-{2-fluoro-3-[2-(1-methylpiperidin-4-yl)-5-(pyridin-4-yl)-1,3-thiazol-4-yl]phenyl}benzenesulfonamide, cmpd. of formula (I)R2 (cmpd. 19) [m, n=1; R2, R3, R5=H; R4=F; R6=2,5-difluorophenyl; R"=methyl]

Method C, Step c2

A solution of 140 mg (0.24 mmol) of 2,5-difluoro-N-{2-fluoro-3-[2-(1-methylpiperidin-4-yl)-5-(pyridin-4-yl)-1,3-thiazol-4-yl]phenyl}-N-(methoxymethyl)benzenesulfonamide in 9 mL of TFA and 1 mL of water was heated under stirring at 80° C. for 1.5 h. The solvent was then evaporated, the residue re-dissolved in DCM, washed with NH$_4$OH 15% and extracted several times with a mixture of DCM-MeOH 9/1. The organic layer was dried over Na$_2$SO$_4$ and evaporated. The product was finally purified by preparative RP-HPLC eluted with NH$_4$OH 0.05%-CH$_3$CN 95/5, affording, after trituration with diethylether-diisopropylether, 70 mg (54%) of the title compound.

HPLC: R$_t$: 4.57 min $^1$H NMR (401 MHz, DMSO-d$_6$) δ ppm 8.46 (d, J=5.9 Hz, 2H), 7.35-7.43 (m, 2H), 7.21-7.34 (m, 2H), 7.07-7.16 (m, 2H), 7.00 (t, J=7.9 Hz, 1H), 6.80-6.95 (m, 1H), 2.97-3.17 (m, 4H), 2.42 (s, 4H), 2.10-2.21 (m, 2H), 1.68-1.96 (m, 2H)

HRMS (ESI) calcd for C$_{26}$H$_{23}$F$_3$N$_4$O$_2$S$_2$ [M+H]+ 545.1287. found 545.1298.

Analogously, but starting from the suitable sulfonamide protected derivative, the following compound was obtained:

2,5-difluoro-N-{2-fluoro-3-[5-(pyridin-4-yl)-2-(tetrahydro-2H-pyran-4-yl)-1,3-thiazol-4-yl]phenyl}benzenesulfonamide, cmpd. of formula (I)R (cmpd. 20) [m, n=1; R2, R3, R5=H; R4=F; R6=2,5-difluorophenyl]

Method C, Step c

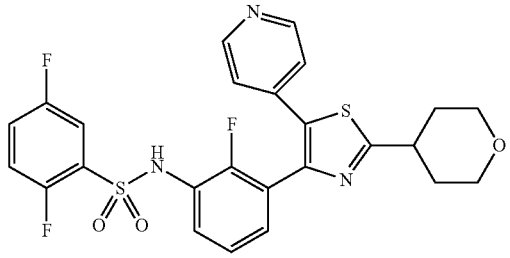 [SMILES: O=S(=O)(Nc1cccc(-c2nc(C3CCOCC3)sc2-c2ccncc2)c1F)c1cc(F)ccc1F]

HPLC: R$_t$: 5.38 min $^1$H NMR (401 MHz, DMSO-d$_6$) δ ppm 10.66 (br. s., 1H), 8.46 (d, J=6.0 Hz, 2H), 7.51-7.61 (m, 1H), 7.27-7.49 (m, 4H), 7.17-7.26 (m, 1H), 7.07 (d, J=6.1 Hz, 2H), 3.94 (dt, J=2.3, 9.4 Hz, 2H), 3.47 (td, J=1.9, 11.6 Hz, 2H), 1.94-2.05 (m, J=1.9, 12.8 Hz, 2H), 1.76 (qd, J=4.2, 12.2 Hz, 2H)

HRMS (ESI) calcd for C$_{25}$H$_{20}$F$_3$N$_3$O$_3$S$_2$ [M+H]+ 532.0971. found 532.0991.

Example 4

N-{3-[2-bromo-5-(pyridin-4-yl)-1,3-thiazol-4-yl]-2-fluorophenyl}-2,5-difluorobenzenesulfonamide, cmpd. of formula (I)G [m, n=1; R2, R3, R5=H; R4=F; R6=2,5-difluorophenyl; Hal=Br]

Method B, Step b

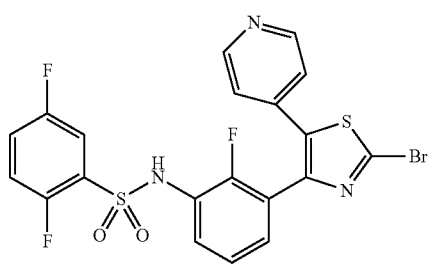 [SMILES: O=S(=O)(Nc1cccc(-c2nc(Br)sc2-c2ccncc2)c1F)c1cc(F)ccc1F]

N-{3-[2-bromo-5-(pyridin-4-yl)-1,3-thiazol-4-yl]-2,4-difluorophenyl}-2,5-difluoro-N-(methoxymethyl)benzenesulfonamide (prepared as described in Example 3, 174 mg, 0.305 mmol) was dissolved in 6 mL of TFA. Water (0.5 mL) was added and the mixture was stirred at 80° C. for 6 h. The solvent was concentrated under reduced pressure and the residue was taken up with DCM and washed with saturated aqueous NaHCO$_3$ and brine. The organic phase was dried over Na$_2$SO$_4$ and evaporated to dryness. The crude product was treated with petroleum ether, filtered and dried under high vacuum affording 130 mg (80%) of the title compound as white solid.

HPLC: R$_t$: 5.81 min $^1$H NMR (401 MHz, DMSO-d$_6$) δ ppm 10.71 (s, 1H), 8.53 (d, J=4.8 Hz, 2H), 7.32-7.72 (m, 5H), 7.26 (q, J=7.7 Hz, 1H), 7.11-7.19 (m, 2H)

HRMS (ESI) calcd for C$_{20}$H$_{11}$BrF$_3$N$_3$O$_2$S$_2$ [M+H]+ 525.9501. found 525.9508.

Example 5

Synthesis of N-{3-[2-(4,4-difluoropiperidin-1-yl)-5-(pyridin-4-yl)-1,3-thiazol-4-yl]-2-fluorophenyl}-2,5-difluorobenzenesulfonamide, cmpd. of formula (I)U (cmpd. 18) [m, n=1; R2, R3, R5, Rx=H; R4=F; R6=2,5-difluorophenyl; R7-R8=—(CH$_2$CH$_2$)$_2$CF$_2$]

Method B, Step e

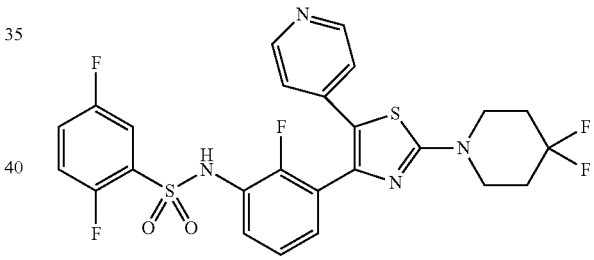

mg (0.09 mmol) of N-{3-[2-bromo-5-(pyridin-4-yl)-1,3-thiazol-4-yl]-2-fluorophenyl}-2,5-difluorobenzenesulfonamide were dissolved in 3 mL of dimethylacetamide and 100 µL (1.39 mmol) of TEA and 100 mg (0.6 mmol) of 4,4-difluoropiperidine hydrochloride were added to the mixture. The solution was heated in a microwave oven at 120° C. for 3 h. After that time the solvent was removed under reduced pressure, the residue was taken up with DCM and washed with aqueous NaHCO$_3$. The organic phase was dried over Na$_2$SO$_4$ and evaporated. The crude was then purified by preparative RP-HPLC, eluted with NH$_4$OH 0.05%-CH$_3$CN 95/5, affording 30 mg (59%) of the title compound.

HPLC: R$_t$: 6.1 min $^1$H NMR (401 MHz, DMSO-d$_6$) δ ppm 10.66 (br. s., 1H), 8.35 (d, J=5.7 Hz, 2H), 7.55 (br. s., 1H), 7.39-7.49 (m, 2H), 7.32-7.37 (m, 1H), 7.10-7.30 (m, 2H), 6.73-6.96 (m, 2H), 3.59-3.73 (m, 4H), 2.03-2.19 (m, 4H)

HRMS (ESI) calcd for C$_{25}$H$_{19}$F$_5$N$_4$O$_2$S$_2$ [M+H]+ 567.0943. found 567.0963.

Analogously, but employing the proper commercial amino derivatives, the following compounds were obtained:

N-{3-[2-(1,4-dioxa-8-azaspiro[4.5]dec-8-yl)-5-(pyridin-4-yl)-1,3-thiazol-4-yl]-2-fluorophenyl}-2,5-difluorobenzenesulfonamide, cmpd. of formula (I)U (cmpd. 17) [m, n=1; R2, R3, R5, Rx=H; R4=F; R6=2,5-difluorophenyl; R7-R8=—(CH$_2$CH$_2$)$_2$C(OCH$_2$CH$_2$O)]

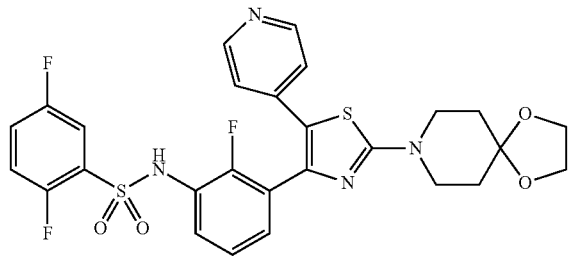 [SMILES: O=S(=O)(Nc1cccc(-c2nc(N3CCC4(CC3)OCCO4)sc2-c2ccncc2)c1F)c1cc(F)ccc1F]

HPLC: R$_t$: 5.76 min $^1$H NMR (401 MHz, DMSO-d$_6$) δ ppm 10.66 (br. s., 1H), 8.18-8.40 (m, 2H), 7.52-7.61 (m, 1H), 7.40-7.48 (m, 2H), 7.36 (td, J=1.8, 7.6 Hz, 1H), 7.25-7.31 (m, 1H), 7.17-7.24 (m, 1H), 6.83-6.90 (m, 2H), 3.93 (s, 4H), 3.54-3.60 (m, 4H), 1.70-1.78 (m, 4H)

HRMS (ESI) calcd for C$_{27}$H$_{23}$F$_3$N$_4$O$_4$S$_2$ [M+H]+ 589.1186. found 589.1193.

N-{3-[2-(diethylamino)-5-(pyridin-4-yl)-1,3-thiazol-4-yl]-2-fluorophenyl}-2,5-difluorobenzenesulfonamide, cmpd. of formula (I)U (cmpd. 16) [m, n=1; R2, R3, R5, Rx=H; R4=F; R6=2,5-difluorophenyl; R7, R8=ethyl]

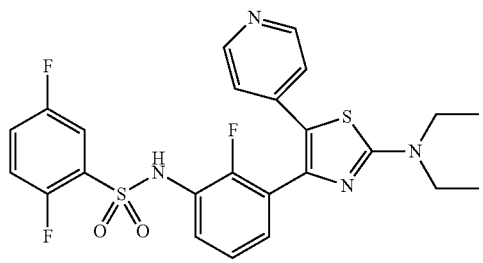 [SMILES: CCN(CC)c1nc(-c2cccc(NS(=O)(=O)c3cc(F)ccc3F)c2F)c(-c2ccncc2)s1]

HPLC: R$_t$: 6.17 min $^1$H NMR (401 MHz, DMSO-d$_6$) δ ppm 10.66 (br. s., 1H), 8.31 (d, J=6.1 Hz, 2H), 7.51-7.59 (m, 1H), 7.40-7.48 (m, 1H), 7.32-7.39 (m, J=1.8 Hz, 1H), 7.26-7.31 (m, 1H), 7.27 (d, J=5.6 Hz, 1H), 7.16-7.25 (m, 1H), 6.82-6.87 (m, 2H), 3.47 (q, J=7.0 Hz, 4H), 1.14-1.23 (m, 6H)

HRMS (ESI) calcd for C$_{24}$H$_{21}$F$_3$N$_4$O$_2$S$_2$ [M+H]+ 519.1131. found 519.1134.

Example 6

Synthesis of N-{3-[2-(cyclohexylamino)-5-(pyridin-4-yl)-1,3-thiazol-4-yl]-2,4-difluorophenyl}-2,5-difluorobenzenesulfonamide, cmpd. of formula (I)V [m, n=1; R2, R3, R7=H; R4=F; R5=4-F; R6=2,5-difluorophenyl; R8=cyclohexyl]

Method B, Steps e and b3

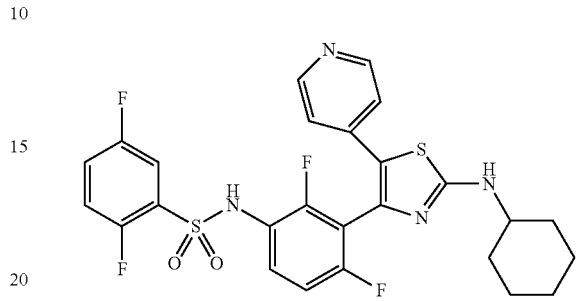

N-{3-[2-bromo-5-(pyridin-4-yl)-1,3-thiazol-4-yl]-2,4-difluorophenyl}-2,5-difluoro-N-(methoxymethyl)benzenesulfonamide (prepared as described in Example 3, 50 mg, 0.09 mmol) was dissolved in 3 mL of dimethylacetamide and 74 μL (0.85 mmol) of cyclohexylamine were added. The mixture was stirred at 110° C. for 16 h. The solvent was evaporated under reduced pressure and the residue was taken up with DCM and washed with brine. The organic layer was dried over Na$_2$SO$_4$ and evaporated, giving N-{3-[2-(cyclohexylamino)-5-(pyridin-4-yl)-1,3-thiazol-4-yl]-2,4-difluorophenyl}-2,5-difluoro-N-(methoxymethyl)benzenesulfonamide. The latter, without any further purification, was treated with 4 mL of TFA and 1 mL of water and stirred at 75° C. for 8 h. The solvent was then removed, the residue taken up with DCM and washed with aqueous NaHCO$_3$. The organic layer was dried over Na$_2$SO$_4$ and evaporated. The crude was purified by flash chromatography eluted with cyclohexane-ethanol 9/1, affording 20 mg (42%) of the title compound.

HPLC: R$_t$: 7.08 min $^1$H NMR (401 MHz, DMSO-d$_6$) δ ppm 10.67 (br. s., 1H), 8.33 (d, J=5.6 Hz, 2H), 8.12 (d, J=7.6 Hz, 1H), 7.54 (td, J=4.1, 8.1 Hz, 1H), 7.37-7.48 (m, 3H), 7.17 (t, J=9.1 Hz, 1H), 6.77-6.83 (m, 2H), 3.40-3.52 (m, J=7.8 Hz, 1H), 1.84-1.97 (m, J=3.1, 9.6 Hz, 2H), 1.65-1.78 (m, J=4.6 Hz, 2H), 1.48-1.60 (m, J=3.3 Hz, 1H), 1.09-1.37 (m, J=11.8 Hz, 6H)

HRMS (ESI) calcd for C$_{26}$H$_{22}$F$_4$N$_4$O$_2$S$_2$ [M+H]+ 563.1193. found 563.1194.

Analogously the following compounds were obtained:

N-(2,4-difluoro-3-{2-[(2-methoxyethyl)amino]-5-(pyridin-4-yl)-1,3-thiazol-4-yl}phenyl)-2,5-difluorobenzenesulfonamide, cmpd. of formula (I)V (cmpd. 5) [m, n=1; R2, R3, R7=H; R4=F; R5=4-F; R6=2,5-difluorophenyl; R8=2-methoxyethyl]

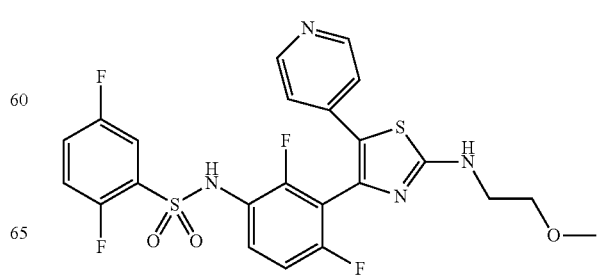

HPLC: R$_t$: 6.01 min $^1$H NMR (401 MHz, DMSO-d$_6$) δ ppm 10.67 (br. s., 1H), 8.34 (d, J=5.9 Hz, 2H), 8.18-8.28 (m, 1H), 7.51-7.61 (m, 1H), 7.36-7.51 (m, 3H), 7.17 (t, J=8.7 Hz, 1H), 6.82 (d, J=6.1 Hz, 2H), 3.45-3.51 (m, 2H), 3.39-3.44 (m, 2H), 3.27 (s, 3H)

HRMS (ESI) calcd for C$_{23}$H$_{18}$F$_4$N$_4$O$_3$S$_2$ [M+H]+ 539.0829. found 539.0845.

N-(2,4-difluoro-3-{5-(pyridin-4-yl)-2-[(pyridin-3-ylmethyl)amino]-1,3-thiazol-4-yl}phenyl)-2,5-difluorobenzenesulfonamide, cmpd. of formula (I)V [m, n=1; R2, R3, R7=H; R4=F; R5=4-F; R6=2,5-difluorophenyl; R8=3-pyridylmethyl]

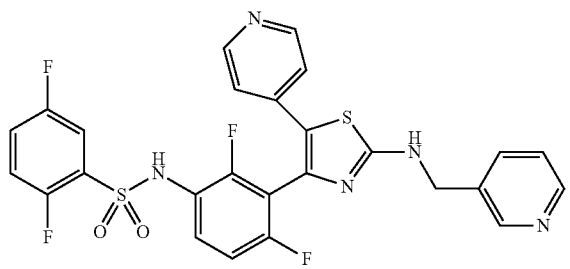 [SMILES: O=S(=O)(Nc1ccc(F)c(-c2nc(NCc3cccnc3)sc2-c2ccncc2)c1F)c1cc(F)ccc1F]

HPLC: R$_t$: 6.11 min $^1$H NMR (401 MHz, DMSO-d$_6$) δ ppm 8.66 (t, J=5.7 Hz, 1H), 8.57 (d, J=1.6 Hz, 1H), 8.50 (d, J=1.3 Hz, 1H), 8.35 (d, J=6.1 Hz, 2H), 7.70-7.85 (m, 1H), 7.50-7.57 (m, J=6.5 Hz, 1H), 7.32-7.48 (m, 4H), 7.16 (t, J=9.9 Hz, 1H), 6.79-6.86 (m, 2H), 4.48-4.54 (m, 2H)

HRMS (ESI) calcd for C$_{26}$H$_{17}$F$_4$N$_5$O$_2$S$_2$ [M+H]+ 572.0833. found 572.0829.

N-(2,4-difluoro-3-{2-[(2-methylpropyl)amino]-5-(pyridin-4-yl)-1,3-thiazol-4-yl}phenyl)-2,5-difluorobenzenesulfonamide cmpd. of formula (I)V (cmpd. 4) [m, n=1; R2, R3, R7=H; R4=F; R5=4-F; R6=2,5-difluorophenyl; R8=isobutyl]

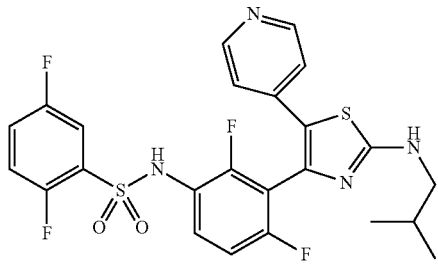 [SMILES: CC(C)CNc1nc(-c2c(F)ccc(NS(=O)(=O)c3cc(F)ccc3F)c2F)c(-c2ccncc2)s1]

HPLC: R$_t$: 6.75 min $^1$H NMR (401 MHz, DMSO-d$_6$) δ ppm 10.67 (br. s., 1H), 8.33 (d, J=6.1 Hz, 2H), 8.20 (t, J=5.6 Hz, 1H), 7.33-7.60 (m, 5H), 7.15 (br. s., 1H), 6.78-6.85 (m, 2H), 3.05 (dd, J=5.9, 6.7 Hz, 2H), 1.80-1.94 (m, 1H), 0.87-0.94 (m, 6H)

HRMS (ESI) calcd for C$_{24}$H$_{20}$F$_4$N$_4$O$_2$S$_2$ [M+H]+ 537.1037. found 537.1043.

N-(3-{2-[cyclohexyl(methyl)amino]-5-(pyridin-4-yl)-1,3-thiazol-4-yl}-2,4-difluorophenyl)-2,5-difluorobenzenesulfonamide, cmpd. of formula (I)V (cmpd. 7) [m, n=1; R2, R3=H; R4=F; R5=4-F; R6=2,5-difluorophenyl; R7=methyl; R8=cyclohexyl]

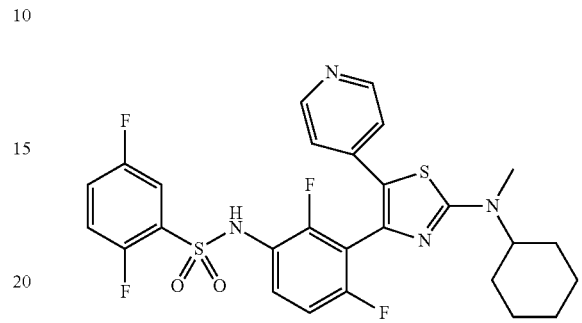

HPLC: R$_t$: 7.64 min $^1$H NMR (401 MHz, DMSO-d$_6$) δ ppm 10.68 (br. s., 1H), 8.34 (d, J=6.0 Hz, 2H), 7.35-7.61 (m, 4H), 7.11-7.20 (m, 1H), 6.79-6.87 (m, 2H), 3.70-3.84 (m, 1H), 2.95 (s, 3H), 1.77 (br. s., 4H), 1.57 (br. s., 3H), 1.35 (br. s., 2H), 1.06-1.23 (m, 1H)

HRMS (ESI) calcd for C$_{27}$H$_{24}$F$_4$N$_4$O$_2$S$_2$ [M+H]+ 577.135. found 577.1358.

N-{2,4-difluoro-3-[2-(4-oxopiperidin-1-yl)-5-(pyridin-4-yl)-1,3-thiazol-4-yl]phenyl}-2,5-difluorobenzenesulfonamide cmpd. of formula (I)V (cmpd. 12) [m, n=1; R2, R3, R4=F; R5=4-F; R6=2,5-difluorophenyl; R7-R8=—(CH$_2$CH$_2$)$_2$CO]

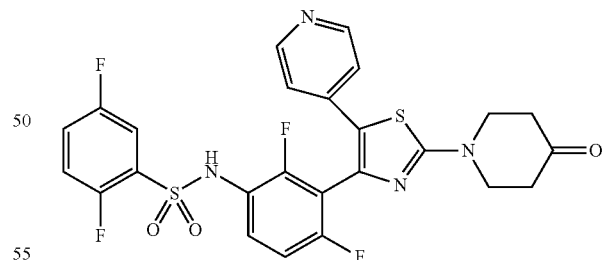

HPLC: R$_t$: 6.14 min $^1$H NMR (401 MHz, DMSO-d$_6$) δ ppm 8.25-8.44 (m, 2H), 7.49 (s, 4H), 7.05 (t, J=7.6 Hz, 1H), 6.91 (d, J=6.2 Hz, 2H), 3.84 (t, J=6.3 Hz, 4H), 2.56 (t, J=6.3 Hz, 4H)

HRMS (ESI) calcd for C$_{25}$H$_{18}$F$_4$N$_4$O$_3$S$_2$ [M+H]+ 563.0829. found 563.083.

N-{3-[2-(diethylamino)-5-(pyridin-4-yl)-1,3-thiazol-4-yl]-2,4-difluorophenyl}-2,5-difluorobenzenesulfonamide, cmpd. of formula (I)V (cmpd. 3) [m, n=1; R2, R3=H; R4=F; R5=4-F; R6=2,5-difluorophenyl; R7, R8=ethyl]

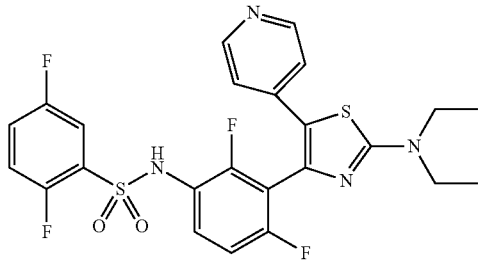 [SMILES: CCN(CC)c1nc(-c2c(F)ccc(NS(=O)(=O)c3cc(F)ccc3F)c2F)c(-c2ccncc2)s1]

HPLC: R$_t$: 6.99 min
$^1$H NMR (401 MHz, DMSO-d$_6$) δ ppm 10.67 (br. s., 1H), 8.35 (d, J=5.6 Hz, 2H), 7.36-7.61 (m, 4H), 7.18 (s, 1H), 6.80-6.87 (m, 2H), 3.47 (q, J=7.2 Hz, 4H), 1.18 (t, J=7.0 Hz, 6H)
HRMS (ESI) calcd for C$_{24}$H$_{20}$F$_4$N$_4$O$_2$S$_2$ [M+H]+ 537.1037. found 537.1025.

N-(3-{2-[4-(dimethylamino)piperidin-1-yl]-5-(pyridin-4-yl)-1,3-thiazol-4-yl}-2,4-difluorophenyl)-2,5-difluorobenzenesulfonamide trifluoroacetate, cmpd. of formula (I)V (cmpd. 10) [m, n=1; R2, R3=H; R4=F; R5=4-F; R6=2,5-difluorophenyl; R7-R8=—(CH$_2$CH$_2$)$_2$CHN(Me)$_2$)]

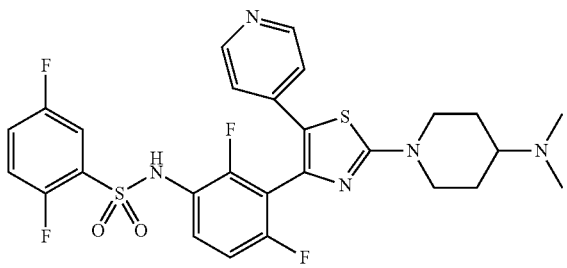 [SMILES: CN(C)C1CCN(c2nc(-c3c(F)ccc(NS(=O)(=O)c4cc(F)ccc4F)c3F)c(-c3ccncc3)s2)CC1]

HPLC: R$_t$: 4.88 min
$^1$H NMR (401 MHz, DMSO-d$_6$) δ ppm 10.67 (br. s., 1H), 9.60 (br. s., 1H), 8.35-8.44 (m, 2H), 7.53-7.62 (m, 1H), 7.37-7.50 (m, 3H), 7.16-7.23 (m, 1H), 6.85-6.89 (m, 2H), 4.04 (d, J=13.7 Hz, 2H), 3.38-3.47 (m, 1H), 3.15 (t, J=11.7 Hz, 3H), 2.78 (s, 6H), 2.07-2.14 (m, 2H), 1.62-1.78 (m, 2H)
HRMS (ESI) calcd for C$_{27}$H$_{25}$F$_4$N$_5$O$_2$S$_2$·C$_2$HF$_3$O$_2$ [M+H]+ 592.1459. found 592.1483.

N-{2,4-difluoro-3-[2-(piperidin-1-yl)-5-(pyridin-4-yl)-1,3-thiazol-4-yl]phenyl}-2,5-difluorobenzenesulfonamide, cmpd. of formula (I)V (cmpd. 9) [m, n=1; R2, R3=H; R4=F; R5=4-F; R6=2,5-difluorophenyl; R7-R8=—(CH$_2$CH$_2$)$_2$CH$_2$]

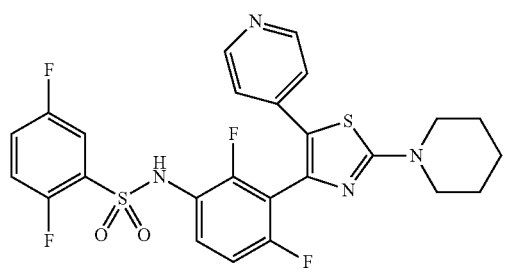 [SMILES: O=S(=O)(Nc1ccc(F)c(-c2nc(N3CCCCC3)sc2-c2ccncc2)c1F)c1cc(F)ccc1F]

HPLC: R$_t$: 6.84 min
$^1$H NMR (401 MHz, DMSO-d$_6$) δ ppm 10.67 (br. s., 1H), 8.33-8.45 (m, 2H), 7.52-7.61 (m, 1H), 7.38-7.50 (m, 3H), 7.18 (t, J=8.4 Hz, 1H), 6.81-6.91 (m, 2H), 3.46 (br. s., 4H), 1.61 (br. s., 6H)
HRMS (ESI) calcd for C$_{25}$H$_{20}$F$_4$N$_4$O$_2$S$_2$ [M+H]+ 549.1037. found 549.1046.

N-{2,4-difluoro-3-[2-(morpholin-4-yl)-5-(pyridin-4-yl)-1,3-thiazol-4-yl]phenyl}-2,5-difluorobenzenesulfonamide, cmpd. of formula (I)V (cmpd. 15) [m, n=1; R2, R3=H; R4=F; R5=4-F; R6=2,5-difluorophenyl; R7-R8=—(CH$_2$CH$_2$)$_2$O]

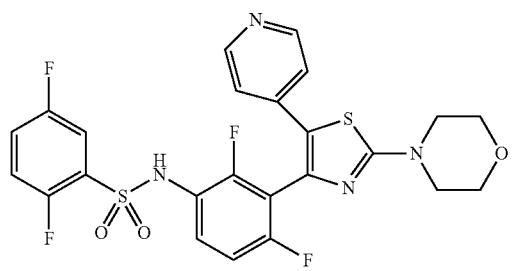 [SMILES: O=S(=O)(Nc1ccc(F)c(-c2nc(N3CCOCC3)sc2-c2ccncc2)c1F)c1cc(F)ccc1F]

HPLC: R$_t$: 5.95 min
$^1$H NMR (401 MHz, DMSO-d$_6$) δ ppm 10.67 (br. s., 1H), 8.34-8.47 (m, 2H), 7.51-7.63 (m, 1H), 7.33-7.51 (m, 3H), 7.18 (t, J=8.2 Hz, 1H), 6.78-7.00 (m, 2H), 3.66-3.79 (m, 4H), 3.39-3.49 (m, 4H)
HRMS (ESI) calcd for C$_{24}$H$_{18}$F$_4$N$_4$O$_3$S$_2$ [M+H]+ 551.0829. found 551.0855.

1-[4-(3-{[(2,5-difluorophenyl)sulfonyl]amino}-2,6-difluorophenyl)-5-(pyridin-4-yl)-1,3-thiazol-2-yl]piperidine-4-carboxamide, cmpd. of formula (I)V [m, n=1; R2, R3=H; R4=F; R5=4-F; R6=2,5-difluorophenyl; R7-R8=—(CH$_2$CH$_2$)$_2$CHCONH$_2$]

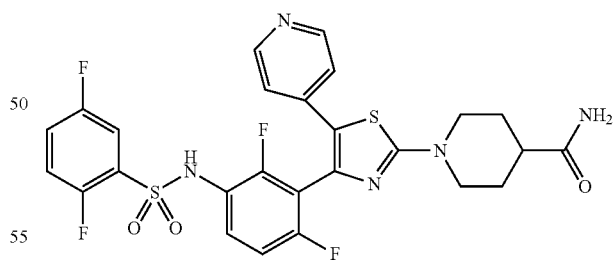

HPLC: R$_t$: 5.25 min
$^1$H NMR (401 MHz, DMSO-d$_6$) δ ppm 10.67 (br. s., 1H), 8.32-8.41 (m, 1H), 7.52-7.63 (m, J=7.8 Hz, 1H), 7.37-7.51 (m, 3H), 7.32 (s, 1H), 7.18 (t, J=8.2 Hz, 1H), 6.84-6.87 (m, J=1.5 Hz, 2H), 6.82 (br. s., 1H), 3.89 (d, J=12.6 Hz, 2H), 3.03-3.19 (m, 2H), 1.82 (d, J=10.1 Hz, 2H), 1.49-1.69 (m, 2H)
HRMS (ESI) calcd for C$_{26}$H$_{21}$F$_4$N$_5$O$_3$S$_2$ [M+H]+ 592.1095. found 592.11.

N-{2,4-difluoro-3-[2-(4-hydroxypiperidin-1-yl)-5-(pyridin-4-yl)-1,3-thiazol-4-yl]phenyl}-2,5-difluorobenzenesulfonamide, cmpd. of formula (I)V (cmpd. 13) [m, n=1; R2, R3=H; R4=F; R5=4-F; R6=2,5-difluorophenyl; R7-R8=—(CH₂CH₂)₂CHOH]

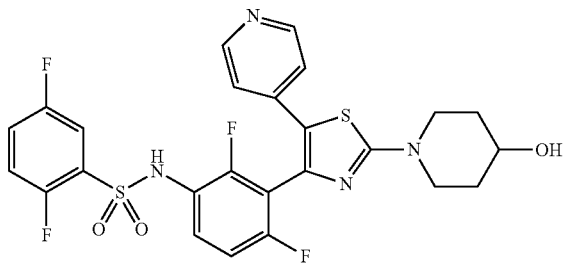 [SMILES: O=S(=O)(Nc1ccc(F)c(-c2nc(N3CCC(O)CC3)sc2-c2ccncc2)c1F)c1cc(F)ccc1F]

HPLC: R$_t$: 5.5 min
$^1$H NMR (401 MHz, DMSO-d$_6$) δ ppm 10.67 (br. s., 1H), 8.36 (d, J=6.1 Hz, 2H), 7.50-7.59 (m, 1H), 7.36-7.50 (m, 5H), 7.17 (t, J=8.5 Hz, 1H), 6.78-6.88 (m, 2H), 4.82 (d, J=4.2 Hz, 1H), 3.66-3.85 (m, 3H), 1.77-1.91 (m, J=4.3, 8.5 Hz, 1H), 1.39-1.56 (m, 2H)
HRMS (ESI) calcd for C$_{25}$H$_{20}$F$_4$N$_4$O$_3$S$_2$ [M+H]+ 565.0986. found 565.0993.

N-{3-[2-(4,4-difluoropiperidin-1-yl)-5-(pyridin-4-yl)-1,3-thiazol-4-yl]-2,4-difluorophenyl}-2,5-difluorobenzenesulfonamide, cmpd. of formula (I)V (cmpd. 14) [m, n=1; R2, R3=H; R4=F; R5=4-F; R6=2,5-difluorophenyl; R7-R8=—(CH₂CH₂)₂CF₂]

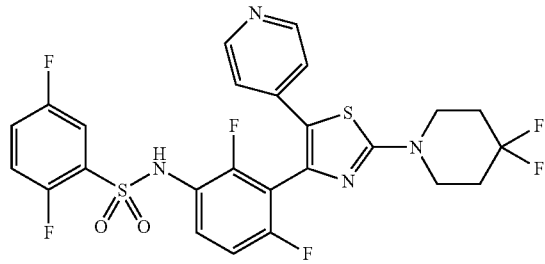 [SMILES: O=S(=O)(Nc1ccc(F)c(-c2nc(N3CCC(F)(F)CC3)sc2-c2ccncc2)c1F)c1cc(F)ccc1F]

HPLC: R$_t$: 6.64 min
$^1$H NMR (401 MHz, DMSO-d$_6$) δ ppm 10.67 (br. s., 1H), 8.39 (d, J=6.1 Hz, 2H), 7.50-7.61 (m, 1H), 7.34-7.50 (m, 3H), 7.18 (t, J=8.5 Hz, 1H), 6.84-6.95 (m, 2H), 3.54-3.69 (m, 4H), 2.00-2.22 (m, 4H)
HRMS (ESI) calcd for C$_{25}$H$_{18}$F$_6$N$_4$O$_2$S$_2$ [M+H]+ 585.0848. found 585.0858.

N-{2,4-difluoro-3-[2-{[2-(morpholin-4-yl)ethyl]amino}-5-(pyridin-4-yl)-1,3-thiazol-4-yl]phenyl}-2,5-difluorobenzenesulfonamide, cmpd. of formula (I)V [m, n=1; R2, R3, R7=H; R4=F; R5=4-F; R6=2,5-difluorophenyl; R8=2-(morpholin-4-yl)ethyl]

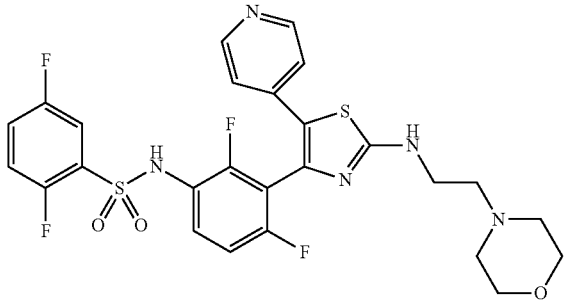 [SMILES: O=S(=O)(Nc1ccc(F)c(-c2nc(NCCN3CCOCC3)sc2-c2ccncc2)c1F)c1cc(F)ccc1F]

HPLC: R$_t$: 5.2 min
$^1$H NMR (401 MHz, DMSO-d$_6$) δ ppm 10.70 (s, 1H), 8.28-8.38 (m, 2H), 8.10 (t, J=5.4 Hz, 1H), 7.50-7.59 (m, 1H), 7.35-7.50 (m, 3H), 7.10-7.20 (m, 1H), 6.76-6.86 (m, 2H), 3.50-3.60 (m, 4H), 3.37 (br. s., 2H)
HRMS (ESI) calcd for C$_{26}$H$_{23}$F$_4$N$_5$O$_3$S$_2$ [M+H]+ 594.1251. found 594.127.

N-(2,4-difluoro-3-{2-[(1-methylpiperidin-4-yl)amino]-5-(pyridin-4-yl)-1,3-thiazol-4-yl}phenyl)-2,5-difluorobenzenesulfonamide, cmpd. of formula (I)V [m, n=1; R2, R3, R7=H; R4=F; R5=4-F; R6=2,5-difluorophenyl; R8=1-methylpiperidin-4-yl]

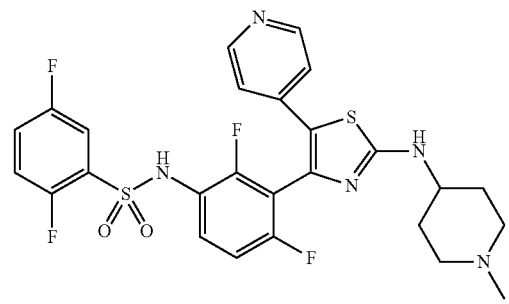 [SMILES: CN1CCC(Nc2nc(-c3c(F)ccc(NS(=O)(=O)c4cc(F)ccc4F)c3F)c(-c3ccncc3)s2)CC1]

HPLC: R$_t$: 4.65 min
$^1$H NMR (401 MHz, DMSO-d$_6$) δ ppm 8.28-8.41 (m, 2H), 8.18 (d, J=7.1 Hz, 1H), 7.22-7.49 (m, 4H), 6.91-7.00 (m, 1H), 6.85-6.91 (m, 2H), 3.70 (br. s., 1H), 2.01-2.13 (m, 2H), 1.54-1.66 (m, 2H)
HRMS (ESI) calcd for C26H23F4N5O2S2 [M+H]+ 578.1302. found 578.1301.

Example 7

Synthesis of N-(3-{2-[(ethylcarbamoyl)amino]-5-(pyridin-4-yl)-1,3-thiazol-4-yl}-2,4-difluorophenyl)-2,5-difluorobenzenesulfonamide, cmpd. of formula (I)K [m, n=1; R2, R3=H; R4=F; R5=4-F; R6=2,5-difluorophenyl; R12=ethyl]

Method B, Steps f and b4

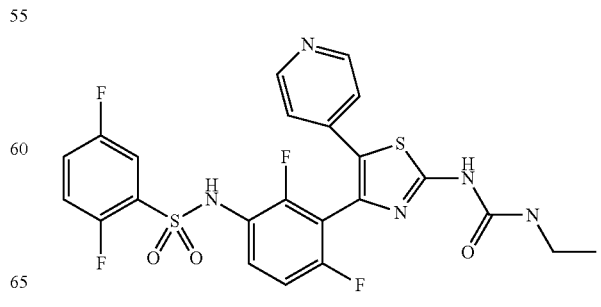

N-{3-[2-amino-5-(pyridin-4-yl)-1,3-thiazol-4-yl]-2,4-difluorophenyl}-2,5-difluoro-N-(methoxymethyl)benzenesulfonamide (prepared as described in Example 3, 50 mg, 0.1 mmol) was dissolved in 2 mL of dry 1,4-dioxane and a total amount of 320 μL (4 mmol) of ethylisocyanate were added portionwise until the reaction was complete. The solution was heated at 80° C. under stirring for 18 h. The solvent was then removed and the residue taken up with DCM and washed with water. The organic phase was dried over $Na_2SO_4$ and evaporated to dryness, giving N-(3-{2-[(ethylcarbamoyl)amino]-5-(pyridin-4-yl)-1,3-thiazol-4-yl}-2,4-difluorophenyl)-2,5-difluoro-N-(methoxymethyl)benzenesulfonamide. The latter, without any further purification, was dissolved in 9 mL of TFA and 1 mL of water and the resulting mixture was maintained at 60° C. under stirring for 8 h. The solvent was evaporated and the residue taken up with DCM and washed with aqueous $NaHCO_3$. The organic layer was then dried over $Na_2SO_4$ and evaporated again. The product was purified by flash chromatography on a silica gel precoated column eluted with DCM-MeOH 95/5, affording, after trituration with diethylether-diisopropyl ether, 17 mg (31%) of the title compound.

HPLC: $R_t$: 5.59 min $^1$H NMR (401 MHz, DMSO-$d_6$) δ ppm 10.82 (s, 1H), 10.68 (br. s., 1H), 8.42 (d, J=5.4 Hz, 2H), 7.56 (d, J=11.4 Hz, 1H), 7.36-7.51 (m, 4H), 7.17 (t, J=8.6 Hz, 1H), 6.93-7.02 (m, 2H), 6.59 (br. s., 1H), 3.11-3.23 (m, 2H), 1.05-1.11 (m, 3H)

HRMS (ESI) calcd for $C_{23}H_{17}F_4N_5O_3S_2$ [M+H]+ 552.0782. found 552.078.

Example 8

Synthesis of N-[4-(3-{[(2,5-difluorophenyl)sulfonyl]amino}-2,6-difluorophenyl)-5-(pyridin-4-yl)-1,3-thiazol-2-yl]cyclohexanecarboxamide, cmpd. of formula (I)M [m, n=1; R2, R3=H; R4=F; R5=4-F; R6=2,5-difluorophenyl; R10=cyclohexyl]

Method B, Steps g, h and b5

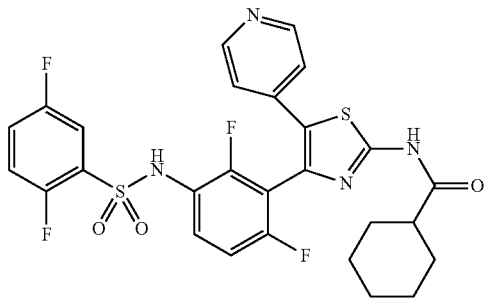 [SMILES: O=C(Nc1nc(-c2c(F)ccc(NS(=O)(=O)c3cc(F)ccc3F)c2F)c(-c2ccncc2)s1)C1CCCCC1]

50 mg (0.39 mmol) of cyclohexanecarboxylic acid were dissolved in 3 mL of dry DCM and 56 μL (0.39 mmol) of TEA were added to the mixture. A solution of 33 μL of oxalyl chloride in 2 mL of DCM was then added dropwise at r.t. After 3 h the solvent was removed under reduced pressure, toluene was added several times and re-evaporated again. The residue was dissolved in 2 mL of dry DCM and dropped into a solution of 50 mg (0.095 mmol) of N-{3-[2-amino-5-(pyridin-4-yl)-1,3-thiazol-4-yl]-2,4-difluorophenyl}-2,5-difluoro-N-(methoxymethyl)benzenesulfonamide in 3 mL of the same solvent containing 56 μL of TEA. The reaction was maintained at r.t. overnight under stirring. The solution was then diluted with DCM and washed with aqueous $NaHCO_3$. The organic layer was dried over $Na_2SO_4$ and evaporated, to give N-(cyclohexylcarbonyl)-N-[4-(3-{[(2,5-difluorophenyl)sulfonyl]-(methoxymethyl)amino}-2,6-difluorophenyl)-5-(pyridin-4-yl)-1,3-thiazol-2-yl]cyclohexanecarboxamide as an oil. The latter was taken up with 5 mL of MeOH and 1 mL of TEA was added to the resulting solution. The reaction was maintained at r. t. overnight. The solvent was then evaporated, the residue re-dissolved with DCM and washed with brine. The organic phase was dried over $Na_2SO_4$ and evaporated again, to afford N-[4-(3-{[(2,5-difluorophenyl)sulfonyl](methoxymethyl)-amino}-2,6-difluorophenyl)-5-(pyridin-4-yl)-1,3-thiazol-2-yl]cyclohexanecarboxamide. The latter was finally dissolved with 9 mL of TFA and 1 mL of water and heated at 75° C. for 6 h. The solvent was removed under reduced pressure, the residue re-dissolved with DCM and washed with aqueous $NaHCO_3$. The organic layer was dried over $Na_2SO_4$ and evaporated. The crude was finally purified by flash chromatography on a silica gel precoated column, eluted with DCM-MeOH 98/2, yielding 35 mg (63% overall) of the title compound.

HPLC: $R_t$: 6.75 min $^1$H NMR (401 MHz, DMSO-$d_6$) δ ppm 12.43 (s, 1H), 10.69 (br. s., 1H), 8.45 (d, J=6.0 Hz, 2H), 7.55 (br. s., 2H), 7.34-7.49 (m, 4H), 7.17 (br. s., 1H), 7.00-7.05 (m, 2H)

HRMS (ESI) calcd for $C_{27}H_{22}F_4N_4O_3S_2$ [M+H]+ 591.1142. found 591.1124.

Analogously the following compounds were obtained:

N-[4-(3-{[(2,5-difluorophenyl)sulfonyl]amino}-2,6-difluorophenyl)-5-(pyridin-4-yl)-1,3-thiazol-2-yl]-2-methylpropanamide, cmpd. of formula (I)M [m, n=1; R2, R3=H; R4=F; R5=4-F; R6=2,5-difluorophenyl; R10=isopropyl]

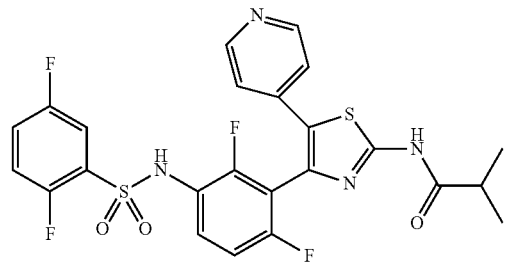 [SMILES: CC(C)C(=O)Nc1nc(-c2c(F)ccc(NS(=O)(=O)c3cc(F)ccc3F)c2F)c(-c2ccncc2)s1]

HPLC: $R_t$: 6.11 min $^1$H NMR (401 MHz, DMSO-$d_6$) δ ppm 12.48 (s, 1H), 10.69 (d, J=0.5 Hz, 1H), 8.43-8.47 (m, 2H), 7.51-7.60 (m, 1H), 7.36-7.52 (m, 4H), 7.18 (br. s., 1H), 7.00-7.06 (m, 2H), 2.76 (quin, J=6.8 Hz, 1H), 1.15 (d, J=6.8 Hz, 6H)

HRMS (ESI) calcd for $C_{24}H_{18}F_4N_4O_3S_2$ [M+H]+ 551.0829. found 551.0809.

N-[4-(3-{[(2,5-difluorophenyl)sulfonyl]amino}-2,6-difluorophenyl)-5-(pyridin-4-yl)-1,3-thiazol-2-yl]benzamide, cmpd. of formula (I)M [m, n=1; R2, R3=H; R4=F; R5=4-F; R6=2,5-difluorophenyl; R10=phenyl]

Method B, Steps g and b5

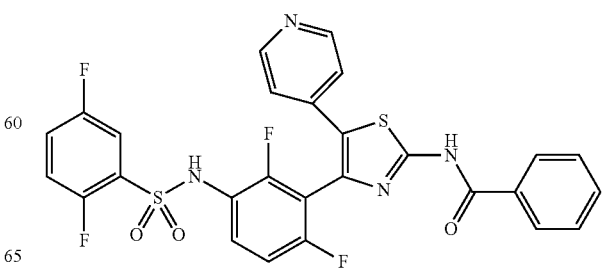

HPLC: R$_t$: 6.46 min
$^1$H NMR (401 MHz, DMSO-d$_6$) δ ppm 13.07 (s, 1H), 10.72 (s, 1H), 8.44-8.50 (m, 2H), 8.07-8.19 (m, 2H), 7.63-7.73 (m, 1H), 7.54-7.62 (m, 3H), 7.40-7.50 (m, 4H), 7.18-7.26 (m, 1H), 7.01-7.12 (m, 2H)
HRMS (ESI) calcd for C27H16F4N4O3S2 [M+H]+ 585.0673. found 585.0679.

Example 9

Synthesis of N-{3-[5-(2-chloropyridin-4-yl)-2-(tetrahydro-2H-pyran-4-yl)-1,3-thiazol-4-yl]-2-fluorophenyl}-2,5-difluorobenzenesulfonamide, cmpd. of formula (I)T [m, n=1; R1=tetrahydropyran-4-yl; R2=Cl; R3, R5=H; R4=F; R6=2,5-difluorophenyl]

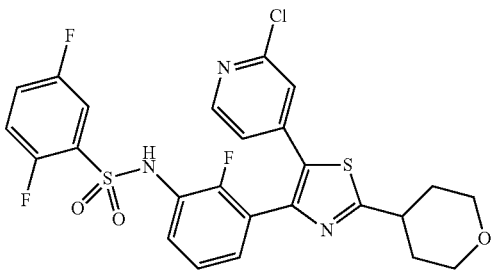 [SMILES: O=S(=O)(Nc1cccc(-c2nc(C3CCOCC3)sc2-c2ccnc(Cl)c2)c1F)c1cc(F)ccc1F]

2,5-difluoro-N-{2-fluoro-3-[(2-chloropyridin-4-yl)acetyl]phenyl}-N-(methoxymethyl)benzenesulfonamide, cmpd. of formula 28 [m, n=1; R2=Cl; R3, R5=H; R4=F; Rx=methoxymethyl; R6=2,5-difluorophenyl]

Method D, Step f
Dry diisopropylamine (1.2 mL, 8.604 mmol, 1.2 eq) was dissolved in dry THF (16 mL) under argon atmosphere and cooled to −78° C. Buthyllithium 2.5 M in hexanes (3.44 mL, 8.604 mmol, 1.2 eq) was then added, followed, after 5 min, by a solution of 2-Cl-4-methylpyridine (0.628 mL, 7.17 mmol, 1 eq) in THF (10 mL). The mixture was stirred at −78° C. for 1 h, then a solution of 3-{[(2,5-difluorophenyl)-sulfonyl] (methoxymethyl)amino}-2-fluoro-N-methoxy-N-methyl-benzamide (prepared as described in Preparation 2, 3.0 g, 7.17 mmol, 1 eq) in THF (20 mL) was added dropwise. After 10 min at −78° C. the deep yellow mixture was warmed to 0° C. and stirred for 1 h. It was then quenched with saturated aqueous ammonium chloride and extracted with ethyl acetate. The organic layer was washed with brine, dried over Na$_2$SO$_4$ and concentrated under reduced pressure. The crude product was purified by flash chromatography on silica gel (Hex/ethyl acetate 1:1) to give 2.37 g (68%) of the title compound as a yellow oil.
HPLC: R$_t$: 6.04 min
$^1$H NMR (600 MHz, DMSO-d$_6$) δ ppm 8.35 (d, J=5.1 Hz, 1H), 7.97-7.93 (m, 1H), 7.73-7.66 (m, 1H), 7.65-7.56 (m, 2H), 7.52 (ddd, J=3.3, 5.0, 7.8 Hz, 1H), 7.42 (s, 1H), 7.40 (t, J=7.9 Hz, 1H), 7.29 (dd, J=5.1, 1.1, 1H), 5.09 (s, 2H), 4.39 (s, 2H), 3.37 (s, 3H).
HRMS (ESI) calcd for C$_{21}$H$_{17}$N$_2$O$_4$F$_3$SCl [M+H]+ 485.0544. found 485.0539.
Operating in an analogous way but using the appropriate pyridine derivative the following intermediates were also obtained:

2,5-difluoro-N-{2-fluoro-3-[(2-fluoropyridin-4-yl)acetyl]phenyl}-N-(methoxymethyl)benzenesulfonamide, cmpd. of formula 28 [m, n=1; R2=F; R3, R5=H; R4=F; Rx=methoxymethyl; R6=2,5-difluorophenyl]

HPLC: R$_t$: 5.97 min
$^1$H NMR (600 MHz, DMSO-d$_6$) δ ppm 8.18 (d, J=5.1 Hz, 1H), 7.95 (t, J=6.5 Hz, 1H), 7.71-7.65 (m, 1H), 7.64-7.55 (m, 2H), 7.54-7.49 (m, 1H), 7.40 (t, J=7.9 Hz, 1H), 7.22 (d, J=5.1 Hz, 1H), 7.07 (s, 1H), 5.09 (s, 2H), 4.42 (s, 2H), 3.37 (s, 3H).
HRMS (ESI) calcd for C$_{21}$H$_{17}$N$_2$O$_4$F$_4$S [M+H]$^+$ 469.0840. found 469.0828.

2,5-difluoro-N-{2-fluoro-3-[(pyridin-4-yl)acetyl]phenyl}-N-(methoxymethyl)benzenesulfonamide, cmpd. of formula 28 [m, n=1; R2, R$_3$, R5=H; R4=F; Rx=methoxymethyl; R6=2,5-difluorophenyl]

HPLC: R$_t$: 5.31 min
HRMS (ESI) calcd for C$_{21}$H$_{18}$N$_{12}$O$_4$F$_3$S [M+H]$^+$ 451.0934. found 451.0922.

tert-butyl-{4-[2-(3-{[(2,5-difluorophenyl)sulfonyl] (methoxymethyl)amino}-2-fluorophenyl)-2-oxoethyl]pyridin-2-yl}carbamate, cmpd. of formula 28 [m, n=1; R2=tert-butoxycarbonylamino; R3, R5=H; R4=F; Rx=methoxymethyl; R6=2,5-difluorophenyl]

HPLC: R$_t$: 6.49 min
$^1$H NMR (600 MHz, DMSO-d$_6$) δ ppm 9.67 (s, 1H), 8.15 (d, J=4.9 Hz, 1H), 7.93 (t, J=6.9 Hz, 1H), 7.70-7.65 (m, 2H), 7.61-7.54 (m, 2H), 7.53-7.46 (m, 1H), 7.38 (t, J=7.8 Hz, 1H), 6.84 (d, J=4.8 Hz, 1H), 5.08 (s, 2H), 4.27 (s, 2H), 3.31 (s, 3H), 1.46 (s, 9H)
HRMS (ESI) calcd for C$_{26}$H$_{27}$N$_3$O$_6$F$_3$S [M+H]$^+$ 566.1567. found 566.1579.

N-{3-[5-(2-chloropyridin-4-yl)-2-(tetrahydro-2H-pyran-4-yl)-1,3-thiazol-4-yl]-2-fluorophenyl}-2,5-difluoro-N-(methoxymethyl)benzenesulfonamide, cmpd. of formula (I)S [m, n=1; R1=tetrahydropyran-4-yl; R2=Cl; R3, R5=H; R4=F; Rx=methoxymethyl; R6=2,5-difluorophenyl]

Method D, Steps l and m

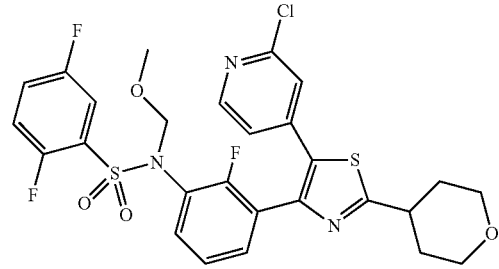 [SMILES: COCN(c1cccc(-c2nc(C3CCOCC3)sc2-c2ccnc(Cl)c2)c1F)S(=O)(=O)c1cc(F)ccc1F]

2,5-Difluoro-N-{2-fluoro-3-[(2-chloropyridin-4-yl)acetyl]phenyl}-N-(methoxymethyl)benzenesulfonamide (937 mg, 1.932 mmol) was dissolved in dry DMF (17 mL) under argon atmosphere. Pyridinium bromide perbromide (556 mg, 1.739 mmol, 0.9 eq) was added and the mixture was stirred at r.t. After 50 min tetrahydro-2H-pyran-4-carbothioamide (prepared as described in Preparation 5, 305 mg, 2.1 mmol, 1.09 eq) was added and the reaction mixture was heated to 60° C. and stirred for 2 h. The mixture was concentrated under reduced pressure and taken up with ethyl acetate and was washed with saturated aqueous NaHCO$_3$. The aqueous phase was back extracted with ethyl acetate. The combined organic layers were washed with water and brine, dried over Na$_2$SO$_4$ and concentrated under reduced pressure. The crude product was purified by flash chromatography on silica gel (DCM/MeOH 98:2) to give 996 mg (72%) of the title product as oil.

HPLC: R$_t$: 7.14 min
$^1$H NMR (600 MHz, DMSO-d$_6$) δ ppm 8.33 (dd, J=0.5, 5.1 Hz, 1H), 7.68-7.60 (m, 2H), 7.55 (dt, J=3.9, 9.4 Hz, 1H), 7.47-7.44 (m, 1H), 7.35-7.32 (m, 2H), 7.24 (dd, J=0.6, 1.6 Hz, 1H), 7.16 (dd, J=1.6, 5.1 Hz, 1H), 4.98 (s, 2H), 3.98-3.93 (m, 2H), 3.52-3.46 (m, 2H), 3.39-3.31 (m, 1H), 3.24 (s, 3H), 2.06-2.01 (m, J=2.9, 13.7 Hz, 2H), 1.82-1.74 (m, 2H)

HRMS (ESI) calcd for C$_{27}$H$_{24}$N$_3$O$_4$F$_3$S$_2$Cl [M+H]$^+$ 610.0844. found 610.0860.

Operating in an analogous way but using the suitable thioamide the following intermediates were also obtained:

N-{3-[5-(2-chloropyridin-4-yl)-2-(1-cyclopropylpiperidin-4-yl)-1,3-thiazol-4-yl]-2-fluorophenyl}-2,5-difluoro-N-(methoxymethyl)benzenesulfonamide, cmpd. of formula (I)S [m, n=1; R1=1-cyclopropylpiperidin-4-yl; R2=Cl; R3, R5=H; R4=F; Rx=methoxymethyl; R6=2,5-difluorophenyl]

Method D, Steps l and m

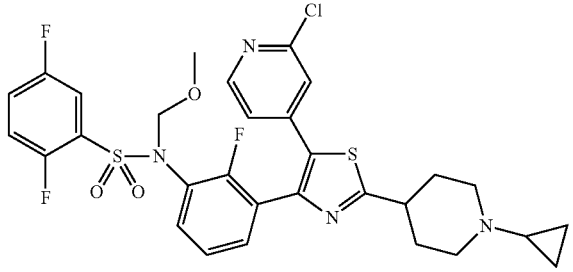 [SMILES: COCN(c1cccc(-c2nc(C3CCN(C4CC4)CC3)sc2-c2ccnc(Cl)c2)c1F)S(=O)(=O)c1cc(F)ccc1F]

HPLC: R$_t$: 7.74 min
$^1$H NMR (600 MHz, DMSO-d$_6$) δ ppm 8.32 (d, J=5.2 Hz, 1H), 7.70-7.60 (m, 2H), 7.56 (dt, J=4.0, 9.3 Hz, 1H), 7.46 (ddd, J=3.2, 5.1, 7.8 Hz, 1H), 7.37-7.27 (m, 2H), 7.26-7.20 (m, 1H), 7.15 (dd, J=1.4, 5.3 Hz, 1H), 4.98 (s, 2H), 3.24 (s, 3H), 3.14-2.94 (m, 3H), 2.32 (t, J=11.1 Hz, 2H), 2.06 (d, J=11.9 Hz, 2H), 1.73-1.56 (m, 3H), 0.50-0.35 (m, J=5.0 Hz, 2H), 0.31 (br. s., 2H).

HRMS (ESI) calcd for C$_{30}$H$_{29}$N$_4$O$_3$F$_3$S$_2$Cl [M+H]$^+$ 649.1316. found 649.1313.

N-{3-[2-tert-butyl-5-(2-chloropyridin-4-yl)-1,3-thiazol-4-yl]-2-fluorophenyl}-2,5-difluoro-N-(methoxymethyl)benzenesulfonamide, cmpd. of formula (I)S [m, n=1; R1=tert-butyl; R2=Cl; R3, R5=H; R4=F; Rx=methoxymethyl; R6=2,5-difluorophenyl]

Method D, Steps l and m

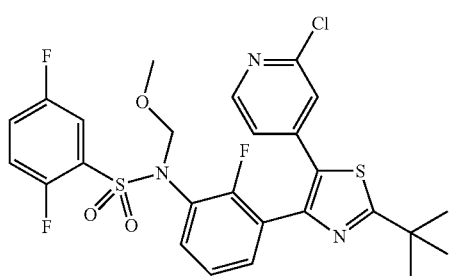 [SMILES: COCN(c1cccc(-c2nc(C(C)(C)C)sc2-c2ccnc(Cl)c2)c1F)S(=O)(=O)c1cc(F)ccc1F]

HPLC: R$_t$: 7.29 min
$^1$H NMR (600 MHz, DMSO-d$_6$) δ ppm 8.32 (d, J=5.1 Hz, 1H), 7.67-7.61 (m, 2H), 7.55 (dt, J=4.0, 9.4 Hz, 1H), 7.48-7.43 (m, 1H), 7.36-7.30 (m, 2H), 7.25 (d, J=0.9 Hz, 1H), 7.16 (dd, J=1.6, 5.2 Hz, 1H), 4.98 (s, 2H), 3.24 (s, 3H), 1.47-1.43 (m, 9H)

HRMS (ESI) calcd for C$_{26}$H$_{24}$N$_3$O$_3$F$_3$S$_2$Cl [M+H]$^+$ 582.0894. found 582.0913.

Benzyl-4-[5-(2-chloropyridin-4-yl)-4-(3-{[(2,5-difluorophenyl)sulfonyl](methoxymethyl)amino}-2-fluorophenyl)-1,3-thiazol-2-yl]piperidine-1-carboxylate, cmpd. of formula (I)S [m, n=1; R1=1-benzyloxycarbonyl-piperidin-4-yl; R2=Cl; R3, R5=H; R4=F; Rx=methoxymethyl; R6=2,5-difluorophenyl]

Method D, Steps l and m

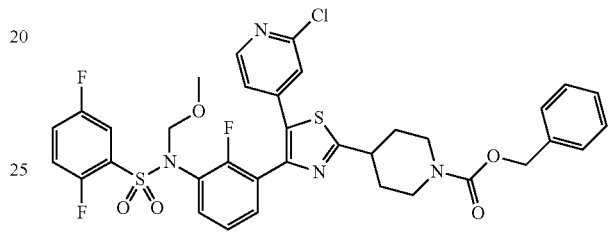

HPLC: R$_t$: 7.93 min
$^1$H NMR (600 MHz, DMSO-d$_6$) δ ppm 8.32 (d, J=5.1 Hz, 1H), 7.68-7.59 (m, 2H), 7.55 (dt, J=4.1, 9.4 Hz, 1H), 7.48-7.42 (m, 1H), 7.40-7.35 (m, 4H), 7.35-7.30 (m, 3H), 7.24 (d, J=0.9 Hz, 1H), 7.15 (dd, J=1.6, 5.2 Hz, 1H), 5.10 (s, 2H), 4.98 (s, 2H), 4.15-3.98 (m, 2H), 3.38-3.33 (m, 1H), 3.24 (s, 3H), 3.09-2.93 (br. s., 2H), 2.15-2.09 (m, 2H), 1.65 (dq, J=4.2, 12.2 Hz, 2H).

HRMS (ESI) calcd for C$_{35}$H$_{31}$N$_4$O$_5$F$_3$S$_2$Cl [M+H]$^+$ 743.1371. found 743.1379.

N-{3-[5-(2-chloropyridin-4-yl)-2-(tetrahydro-2H-pyran-4-yl)-1,3-thiazol-4-yl]-2-fluorophenyl}-2,5-difluorobenzenesulfonamide, cmpd. of formula (I)T [m, n=1; R1=tetrahydropyran-4-yl; R2=Cl; R3, R5=H; R4=F; R6=2,5-difluorophenyl]

Method D, Step n

N-{3-[5-(2-chloropyridin-4-yl)-2-(tetrahydro-2H-pyran-4-yl)-1,3-thiazol-4-yl]-2-fluorophenyl}-2,5-difluoro-N-(methoxymethyl)benzenesulfonamide (50 mg, 0.082 mmol) was dissolved in TFA/water 9:1 (1 mL) and stirred at 60° C. for 5 h. The mixture was evaporated to dryness, taken up with DCM and washed with saturated aqueous NaHCO$_3$ and brine, dried over Na$_2$SO$_4$ and concentrated under reduced pressure. The crude product was purified by flash chromatography on silica gel (toluene/ethyl acetate 6:4) to give 38 mg (82%) of product, which was triturated with diethylether/ethyl acetate, filtered and dried under high vacuum. 34 mg of the title compound were obtained as white solid.

HPLC: R$_t$: 6.94 min
$^1$H NMR (600 MHz, DMSO-d$_6$) δ ppm 10.69 (s, 1H), 8.29 (d, J=5.1 Hz, 1H), 7.63-7.52 (m, 1H), 7.50-7.44 (m, 1H), 7.44-7.39 (m, 1H), 7.39-7.32 (m, 2H), 7.29-7.23 (m, 1H), 7.22 (d, J=0.9 Hz, 1H), 7.08 (dd, J=1.6, 5.2 Hz, 1H), 3.97-3.91 (m, 2H), 3.48 (dt, J=1.9, 11.6 Hz, 2H), 3.39-3.34 (m, 1H), 2.05-1.94 (m, 2H), 1.84-1.57 (m, 2H)

HRMS (ESI) calcd for C$_{25}$H$_{20}$N$_3$O$_3$F$_3$S$_2$Cl [M+H]$^+$ 566.0581. found 566.0588.

Operating in an analogous way but using the appropriate starting material and thioamide the following compounds were also obtained:

2,5-Difluoro-N-{2-fluoro-3-[5-(2-fluoropyridin-4-yl)-2-(1-methylpiperidin-4-yl)-1,3-thiazol-4-yl]phenyl}benzenesulfonamide, cmpd. of formula (I)T (cmpd. 27) [m, n=1; R1=1-methyl-piperidin-4-yl; R2=F; R3, R5=H; R4=F; R6=2,5-difluorophenyl]

Method D, Step n

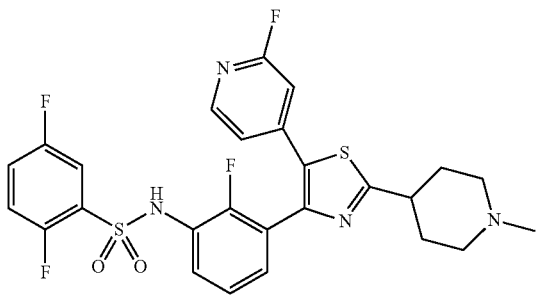 [SMILES: CN1CCC(c2nc(-c3cccc(NS(=O)(=O)c4cc(F)ccc4F)c3F)c(-c3ccnc(F)c3)s2)CC1]

HPLC: R$_t$: 4.19 min
$^1$H NMR (600 MHz, DMSO-d$_6$) δ ppm 8.14 (d, J=5.3 Hz, 1H), 7.45-7.35 (m, 2H), 7.35-7.24 (m, 2H), 7.15-6.96 (m, 3H), 6.89 (s, 1H), 3.41-3.36 (m, 1H), 3.23-3.09 (m, 2H), 2.60-2.40 (m, 3H), 2.18 (d, J=12.6 Hz, 2H), 1.93-1.77 (m, 2H).
HRMS (ESI) calcd for C$_{26}$H$_{23}$N$_4$O$_2$F$_4$S$_2$ [M+H]$^+$ 563.1193. found 563.1202.

N-{3-[2-tert-butyl-5-(pyridin-4-yl)-1,3-thiazol-4-yl]-2-fluorophenyl}-2,5-difluorobenzenesulfonamide, cmpd. of formula (I)T (cmpd. 43) [m, n=1; R1=tert-butyl; R2, R3, R5=H; R4=F; R6=2,5-difluorophenyl]

Method D, Step n

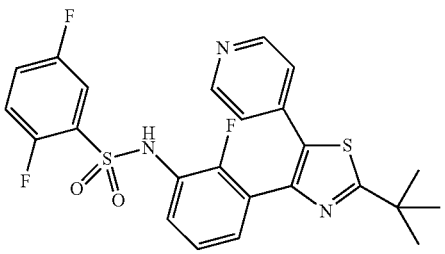 [SMILES: CC(C)(C)c1nc(-c2cccc(NS(=O)(=O)c3cc(F)ccc3F)c2F)c(-c2ccncc2)s1]

HPLC: R$_t$: 7.16 min
$^1$H NMR (600 MHz, DMSO-d$_6$) δ ppm 10.65 (br. s., 1H), 8.49-8.40 (m, 2H), 7.63-7.52 (m, 1H), 7.51-7.43 (m, 1H), 7.44-7.37 (m, 1H), 7.37-7.30 (m, 2H), 7.27-7.18 (m, 1H), 7.12-6.90 (m, 2H), 1.43 (s, 9H)
HRMS (ESI) calcd for C$_{24}$H$_{21}$N$_3$O$_2$F$_3$S$_2$ [M+H]$^+$ 504.1022. found 504.1031.

N-{3-[2-(1-cyclopropylpiperidin-4-yl)-5-(pyridin-4-yl)-1,3-thiazol-4-yl]-2-fluorophenyl}-2,5-difluorobenzenesulfonamide, cmpd. of formula (I)T (cmpd. 21) [m, n=1; R1=1-cyclopropyl-piperidin-4-yl; R2, R3, R5=H; R4=F; R6=2,5-difluorophenyl]

Method D, Step n

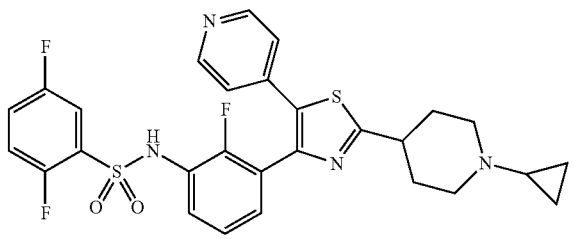 [SMILES: O=S(=O)(Nc1cccc(-c2nc(C3CCN(C4CC4)CC3)sc2-c2ccncc2)c1F)c1cc(F)ccc1F]

HPLC: R$_t$: 4.70 min
$^1$H NMR (600 MHz, DMSO-d$_6$) δ ppm 10.53 (br. s., 1H), 8.47-8.44 (m, 2H), 7.57-7.51 (m, 1H), 7.46-7.43 (m, 1H), 7.40 (ddd, J=3.2, 5.1, 7.8 Hz, 1H), 7.36-7.32 (m, 1H), 7.28 (m, 1H), 7.22-7.18 (m, 1H), 7.08-7.05 (m, 2H), 3.12-2.98 (m, 3H), 2.35-2.42 (m, 2H), 2.06 (d, J=9.9 Hz, 2H), 1.73 (m, 1H), 1.71-1.64 (m, 2H), 0.45 (d, J=4.8 Hz, 2H), 0.35 (br. s., 2H)
HRMS (ESI) calcd for C$_{28}$H$_{26}$N$_4$O$_2$F$_3$S$_2$ [M+H]$^+$ 571.1444. found 571.1463.

Example 10

N-{3-[5-(2-aminopyridin-4-yl)-2-(1-cyclopropylpiperidin-4-yl)-1,3-thiazol-4-yl]-2-fluorophenyl}-2,5-difluorobenzenesulfonamide, cmpd. of formula (I)T (cmpd. 22) [m, n=1; R1=1-cyclopropyl-piperidin-4-yl; R2=NH$_2$; R3, R5=H; R4=F; R6=2,5-difluorophenyl]

Method D, Steps l, m, n

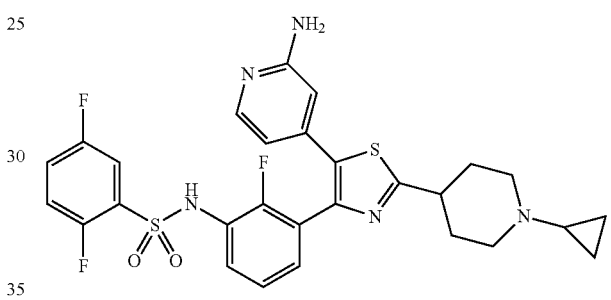

Tert-butyl-{4-[2-(3-{[(2,5-difluorophenyl)sulfonyl](methoxymethyl)amino}-2-fluorophenyl)-2-oxoethyl]pyridin-2-yl}carbamate (prepared as described in Example 9, 374 mg, 0.662 mmol) was dissolved in dry DMF (5 mL) under argon atmosphere. Pyridinium bromide perbromide (190 mg, 0.596 mmol, 0.9 eq) was added and the reaction mixture was stirred at r.t. for 50 min. 1-Cyclopropylpiperidine-4-carbothioamide (146 mg, 0.794 mmol, 1.2 eq) was then added and the mixture was heated to 70° C. After 1 h the reaction was allowed to cool to r.t. overnight. The solvent was concentrated under reduced pressure. The residue was taken up with ethyl acetate and washed with saturated aqueous NaHCO$_3$ and brine. The organic phase was dried over Na$_2$SO$_4$ and evaporated to dryness. The crude product was purified by flash chromatography on silica gel (DCM/MeOH 98:2) to give 290 mg (60%) of tert-butyl {4-[2-(1-cyclopropylpiperidin-4-yl)-4-(3-{[(2,5-difluorophenyl)sulfonyl](methoxymethyl)amino}-2-fluorophenyl)-1,3-thiazol-5-yl]pyridin-2-yl}carbamate as amorphous solid.

HPLC/MS (ESI): 730 [M+H]$^+$, 728 [M−H]$^−$

This intermediate was dissolved in a 9:1 TFA/H$_2$O mixture (4 mL) and stirred at 70° C. for 2 h. The mixture was then concentrated under reduced pressure, taken up with DCM and washed with saturated aqueous NaHCO$_3$ and brine. The organic phase was dried over Na$_2$SO$_4$ and evaporated to dryness. The crude product was purified by flash chromatography on silica gel (DCM/EtOH 95:5) and treated with a i-propylether/ethyl acetate mixture, filtered and dried under high vacuum to give 70 mg (30%) of the title compound as light orange solid.

HPLC: R$_t$: 5.49 min $^1$H NMR (600 MHz, DMSO-d$_6$) δ ppm 10.99-10.01 (br. s, 1H), 7.70 (d, J=5.3 Hz, 1H), 7.57-7.51 (m, 1H), 7.48-7.40 (m, 2H), 7.31 (m, 1H), 7.21 (br. s., 1H), 7.18-7.11 (m, 1H), 6.33 (s, 1H), 6.01 (s, 2H), 5.98 (d, J=5.3 Hz, 1H), 3.09-2.95 (m, 3H), 2.40-2.28 (m, 2H), 2.10-1.98 (m, 2H), 1.75-1.54 (m, 3H), 0.50-0.41 (m, 2H), 0.37-0.29 (m, 2H)

HRMS (ESI) calcd for C$_{28}$H$_{27}$N$_5$O$_2$F$_3$S$_2$ [M+H]$^+$ 586.1553. found 586.1556.

Example 11

Synthesis of N-{4-[2-(1-cyclopropylpiperidin-4-yl)-4-(3-{[(2,5-difluorophenyl)sulfonyl]amino}-2-fluorophenyl)-1,3-thiazol-5-yl]pyridin-2-yl}acetamide, cmpd. of formula (I)T (cmpd. 30) [m, n=1; R1=1-cyclopropyl-piperidin-4-yl; R2=acetylamino; R3, R5=H; R4=F; R6=2,5-difluorophenyl]

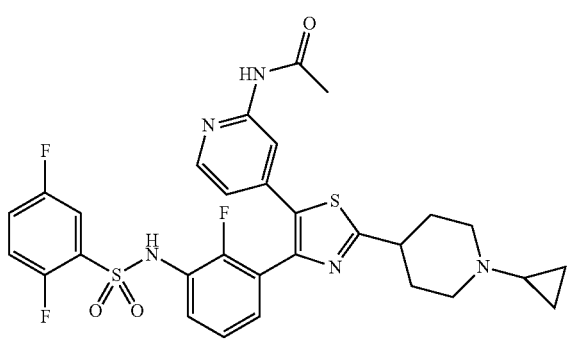 [SMILES: CC(=O)Nc1cc(-c2sc(C3CCN(C4CC4)CC3)nc2-c2cccc(NS(=O)(=O)c3cc(F)ccc3F)c2F)ccn1]

To a solution of N-{3-[5-(2-aminopyridin-4-yl)-2-(1-cyclopropylpiperidin-4-yl)-1,3-thiazol-4-yl]-2-fluorophenyl}-2,5-difluorobenzenesulfonamide (prepared as described in Example 10, 66 mg, 0.113 mmol) in dry DCM (1 mL), TEA (0.063 mL, 0.452 mmol, 4 eq) and acetylchloride (0.024 mL, 0.338 mmol, 3 eq) were added and the mixture was stirred at r.t. for 16 h. It was then diluted with DCM and washed with saturated aqueous NaHCO$_3$ and brine. The organic phase was dried over Na$_2$SO$_4$ and evaporated to dryness to give a 1:1 mixture of diacetylated and triacetylated products.

To a solution of this mixture in MeOH (2 mL) 1N sodium hydroxide (1 mL) was added and the solution was stirred at r.t. for 1 h. The solvent was evaporated under reduced pressure and the residue was taken up with ethyl acetate and washed with saturated aqueous NaHCO$_3$ and brine. The organic phase was dried over Na$_2$SO$_4$ and evaporated to dryness. The crude product was purified by flash chromatography on silica gel (DCM/EtOH 95:5) to give 47 mg (66%) of the title compound as white solid.

HPLC: R$_t$: 5.57 min $^1$H NMR (600 MHz, DMSO-d$_6$) δ ppm 10.54 (s, 1H), 8.12 (d, J=5.3 Hz, 1H), 8.04 (s, 1H), 7.53 (t, J=8.3 Hz, 1H), 7.47-7.37 (m, 2H), 7.33-7.23 (m, 2H), 7.21-7.12 (m, 1H), 6.62 (dd, J=1.6, 5.3 Hz, 1H), 3.14-2.96 (m, 3H), 2.38 (dd, J=1.8, 3.7 Hz, 2H), 2.12-2.01 (m, 2H), 2.06 (s, 3H), 1.79-1.56 (m, 3H), 0.45 (d, J=4.8 Hz, 2H), 0.35 (br. s., 2H)

HRMS (ESI) calcd for C$_{30}$H$_{29}$N$_5$O$_3$F$_3$S$_2$ [M+H]$^+$ 628.1659. found 628.1659.

Example 12

Synthesis of N-{3-[5-(2-aminopyridin-4-yl)-2-(tetrahydro-2H-pyran-4-yl)-1,3-thiazol-4-yl]-2-fluorophenyl}-2,5-difluorobenzenesulfonamide, cmpd. of formula (I)Z2 (cmpd. 24) [m, n=1; R1=tetrahydropyran-4-yl; R3, R5=H; R4=F; R6=2,5-difluorophenyl]

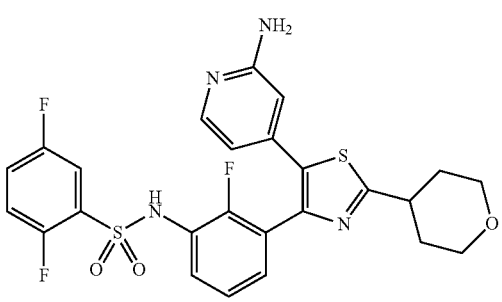 [SMILES: Nc1cc(-c2sc(C3CCOCC3)nc2-c2cccc(NS(=O)(=O)c3cc(F)ccc3F)c2F)ccn1]

Tert-butyl-{4-[4-(3-{[(2,5-difluorophenyl)sulfonyl](methoxymethyl)amino}-2-fluorophenyl)-2-(tetrahydro-2H-pyran-4-yl)-1,3-thiazol-5-yl]pyridin-2-yl}carbamate, cmpd. of formula (I)X [m, n=1; R1=tetrahydropyran-4-yl; R3, R5=H; R4=F; R6=2,5-difluorophenyl; R18=tert-butoxycarbonyl]

Method F, Step c1

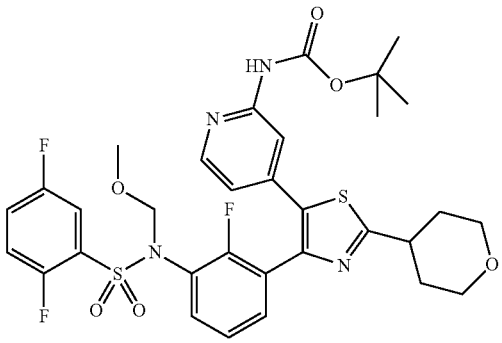 [SMILES: COCN(c1cccc(-c2nc(C3CCOCC3)sc2-c2ccnc(NC(=O)OC(C)(C)C)c2)c1F)S(=O)(=O)c1cc(F)ccc1F]

In a microwave tube N-{3-[5-(2-chloropyridin-4-yl)-2-(tetrahydro-2H-pyran-4-yl)-1,3-thiazol-4-yl]-2-fluorophenyl}-2,5-difluoro-N-(methoxymethyl)benzenesulfonamide (prepared as described in Example 9, 200 mg, 0.328 mmol, 1 eq) was dissolved in anhydrous THF (3 mL) and the solution was degassed by bubbling argon for 5 min. Tert-butyl carbamate (152 mg, 1.311 mmol, 4 eq) was then added, followed by cesium carbonate (212 mg, 0.656 mmol, 2 eq), palladium acetate (8 mg, 0.033 mmol, 0.1 eq) and Xantphos (40 mg, 0.66 mmol, 0.2 eq) and the mixture was irradiated in the microwave oven at 120° C. for 30 min. The mixture was filtered on a celite pad and the celite was washed with ethyl acetate. The filtrate was washed with saturated aqueous NaHCO$_3$ and brine, dried over Na$_2$SO$_4$ and evaporated to dryness. The crude product was purified by flash chromatography on silica gel (ethyl acetate/Hex 6:4) to give 160 mg of the title compound as a pale yellow solid.

HPLC: $R_t$: 7.57 min $^1$H NMR (600 MHz, DMSO-$d_6$) δ ppm 9.83 (s, 1H), 8.08 (d, J=5.1 Hz, 1H), 7.76 (s, 1H), 7.65-7.56 (m, 2H), 7.56-7.50 (m, 1H), 7.48-7.42 (m, 1H), 7.36-7.25 (m, 2H), 6.60 (dd, J=1.6, 5.2 Hz, 1H), 3.95 (td, J=1.9, 9.6 Hz, 2H), 3.48 (dt, J=1.8, 11.6 Hz, 2H), 3.36-3.32 (m, 1H), 3.23 (s, 3H), 2.11-1.99 (m, 2H), 1.82-1.73 (m, 2H), 1.44 (s, 9H)

HRMS (ESI) calcd for $C_{32}H_{34}N_4O_6F_3S_2$ [M+H]$^+$ 691.1867. found 691.1866.

Operating in an analogous way but using the proper starting material the following intermediate was also obtained:

Benzyl-4-[5-{2-[(tert-butoxycarbonyl)amino]pyridin-4-yl}-4-(3-{[(2,5-difluorophenyl)sulfonyl](methoxymethyl)amino}-2-fluorophenyl)-1,3-thiazol-2-yl]piperidine-1-carboxylate, cmpd. of formula (I)X [m, n=1; R1=1-benzyloxycarbonyl-piperidin-4-yl; R3, R5=H; R4=F; R6=2,5-difluorophenyl; R18=tert-butoxycarbonyl]

Method F, Step c1

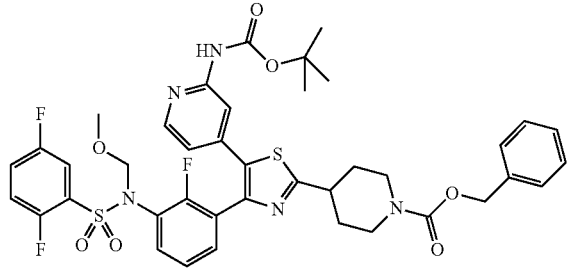 [SMILES: COCN(c1cccc(-c2nc(C3CCN(C(=O)OCc4ccccc4)CC3)sc2-c2ccnc(NC(=O)OC(C)(C)C)c2)c1F)S(=O)(=O)c1cc(F)ccc1F]

HPLC: $R_t$: 8.22 min $^1$H NMR (600 MHz, DMSO-$d_6$) δ ppm 9.83 (s, 1H), 8.08 (d, J=5.5 Hz, 1H), 7.76 (s, 1H), 6.60 (dd, J=1.6, 5.2 Hz, 1H), 5.10 (s, 2H), 4.96 (s, 2H), 4.16-4.07 (m, J=13.4 Hz, 2H), 3.25-3.22 (m, 3H), 3.02 (br. s., 2H), 2.11 (d, J=11.0 Hz, 2H), 1.71-1.61 (m, 2H), 1.44 (s, 9H)

HRMS (ESI) [M+H]+ calcd for $C_{40}H_{40}O_7N_5S_2F_3$ 824.2394. found 824.2386.

N-{3-[5-(2-aminopyridin-4-yl)-2-(tetrahydro-2H-pyran-4-yl)-1,3-thiazol-4-yl]-2-fluorophenyl}-2,5-difluorobenzenesulfonamide, cmpd. of formula (I)Z2 (cmpd. 24) [m, n=1; R1=tetrahydropyran-4-yl; R3, R5=H; R4=F; R6=2,5-difluorophenyl]

Method F, Step e1

Tert-butyl-{4-[4-(3-{[(2,5-difluorophenyl)sulfonyl](methoxymethyl)amino}-2-fluorophenyl)-2-(tetrahydro-2H-pyran-4-yl)-1,3-thiazol-5-yl]pyridin-2-yl}carbamate (58 mg, 0.084 mmol) was dissolved in a 9:1 TFA/water mixture and stirred at 70° C. for 1 h. The mixture was evaporated to dryness, taken up with DCM and washed with saturated aqueous NaHCO$_3$ and brine, dried over Na$_2$SO$_4$ and concentrated under reduced pressure. The crude product was purified by flash chromatography on silica gel (pure ethyl acetate) to give 32 mg (70%) of product, which was triturated with diethyl ether, filtered and dried under high vacuum. 30 mg of the title compound were obtained as white solid.

HPLC: $R_t$: 5.86 min $^1$H NMR (600 MHz, DMSO-$d_6$) δ ppm 10.69 (br. s., 1H), 7.70 (d, J=5.3 Hz, 1H), 7.61-7.52 (m, J=4.8, 7.7 Hz, 1H), 7.51-7.42 (m, 2H), 7.33 (t, J=7.0 Hz, 1H), 7.30-7.23 (m, 1H), 7.22-7.15 (m, 1H), 6.34 (s, 1H), 6.04 (br. s., 2H), 5.98 (d, J=5.1 Hz, 1H), 3.99-3.78 (m, 2H), 3.46 (dt, J=1.8, 11.6 Hz, 2H), 3.34-3.26 (m, 1H), 2.05-1.86 (m, 2H), 1.80-1.65 (m, 2H)

HRMS (ESI) calcd for $C_{25}H_{22}N_4O_3F_3S_2$ [M+H]$^+$ 547.1080. found 547.1092.

Operating in an analogous way but using the suitable starting material the following compounds were obtained:

N-{3-[5-(2-aminopyridin-4-yl)-2-(piperidin-4-yl)-1,3-thiazol-4-yl]-2-fluorophenyl}-2,5-difluorobenzenesulfonamide cmpd. of formula (I)Z2 [m, n=1; R1=piperidin-4-yl; R3, R5=H; R4=F; R6=2,5-difluorophenyl]

Method F, Step e1

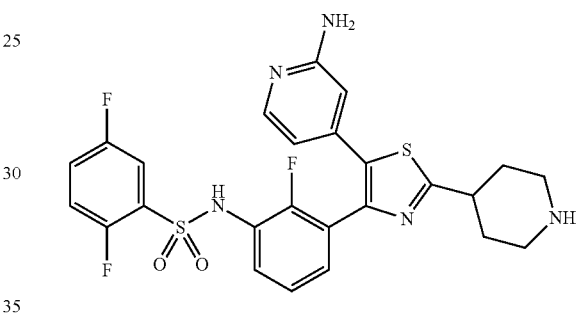

HPLC: $R_t$: 4.46 min $^1$H NMR (600 MHz, DMSO-$d_6$) (selected signals) δ ppm 8.47 (s, 1H), 7.73 (d, J=5.3 Hz, 1H), 7.43 (br. s., 1H), 7.40-7.24 (m, 2H), 7.21 (br. s., 1H), 6.36 (s, 1H), 6.13 (br. s., 1H), 5.99 (s, 2H), 2.27-2.19 (m, 2H), 1.98-1.86 (m, 2H)

HRMS (ESI) [M+H]$^+$ calcd for $C_{25}H_{22}O_2N_5S_2F_3$ 546.1240. found 546.1251.

Example 13

Synthesis of N-{3-[5-(2-aminopyridin-4-yl)-2-(1-methylpiperidin-4-yl)-1,3-thiazol-4-yl]-2-fluorophenyl}-2,5-difluorobenzenesulfonamide, cmpd. of formula (I)R2 (cmpd. 39) [m, n=1; R2=NH$_2$; R3, R5=H; R4=F; R6=2,5-difluorophenyl; R"=methyl]

Method C, Steps d, e and c2

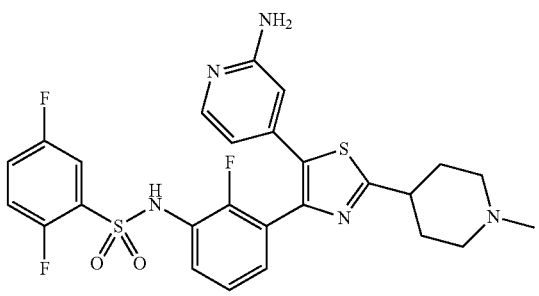 [SMILES: CN1CCC(c2nc(-c3cccc(NS(=O)(=O)c4cc(F)ccc4F)c3F)c(-c3ccnc(N)c3)s2)CC1]

Benzyl-4-[5-{2-[(tert-butoxycarbonyl)amino]pyridin-4-yl}-4-(3-{[(2,5-difluorophenyl)sulfonyl]-(methoxymethyl)amino}-2-fluorophenyl)-1,3-thiazol-2-yl]piperidine-1-carboxylate (prepared as described in Example 10, 110 mg, 0.13 mmol) was dissolved in absolute ethanol (10 mL) under nitrogen atmosphere. Ammonium formate (440 mg, 7 mmol) and palladium on charcoal 5% (150 mg portionwise) were then added. The mixture was refluxed for 2 days, then filtered on a celite pad and evaporated to dryness. The residue was taken up with DCM and washed with water. The organic layer was dried over $Na_2SO_4$ and evaporated, affording 75 mg (84%) of tert-butyl-{4-[4-(3-{[(2,5-difluorophenyl)sulfonyl]-(methoxymethyl)amino}-2-fluorophenyl)-2-(piperidin-4-yl)-1,3-thiazol-5-yl]pyridin-2-yl}carbamate.

HPLC/MS (ESI): 690 [M+H]$^+$, 688 [M−H]$^-$

This intermediate (75 mg, 0.11 mmol) was dissolved in a mixture of MeOH (9 mL) and glacial acetic acid (28 μL, 0.48 mmol). 37% aqueous formaldehyde (12 μL, 0.24 mmol) and sodium cyanoborohydride (16 mg, 0.32 mmol) were added. The solution was stirred at r.t. for 1 h and then the solvent removed under reduced pressure. The residue was taken up with DCM and washed with diluted aqueous ammonia. The organic layer was finally dried over $Na_2SO_4$ and evaporated to dryness. The crude was purified by flash chromatography on silica gel (cyclohexane-ethylacetate-ethanol 4/2/1 for eluting impurities, then DCM-MeOH—NH$_4$OH 20/5/0.5 for eluting product) giving 55 mg (71%) of tert-butyl-{4-[4-(3-{[(2,5-difluorophenyl)sulfonyl]methoxymethyl)amino}-2-fluorophenyl)-2-(1-methylpiperidin-4-yl)-1,3-thiazol-5-yl]pyridin-2-yl}carbamate.

HPLC/MS (ESI): 704 [M+H]$^+$, 702 [M−H]$^-$

The latter intermediate (55 mg, 0.08 mmol) was dissolved in a mixture TFA-H$_2$O 9/1 (10 mL) and stirred at 70° C. for 2 h. The solvent was removed and the residue taken up with DCM and washed with a NaHCO$_3$ saturated aqueous solution. The organic layer was dried over $Na_2SO_4$ and evaporated. The product was then purified by flash chromatography on silica gel (DCM-NH$_3$ 7N in MeOH for eluting impurities, then DCM-MeOH—NH$_4$OH 30% 20-5-0.5 for eluting product) and triturated with diethylether to afford 30 mg (67%) of the title compound.

HPLC: R$_t$: 3.65 min $^1$H NMR (401 MHz, DMSO-d$_6$) δ ppm 7.72 (d, J=5.2 Hz, 1H), 7.47-7.37 (m, 2H), 7.38-7.29 (m, 1H), 7.25 (dt, J=1.8, 7.9 Hz, 1H), 7.04-6.96 (m, 1H), 6.92 (br. s., 1H), 6.35 (d, J=0.9 Hz, 1H), 6.07 (dd, J=1.3, 5.2 Hz, 1H), 5.98 (s, 2H), 3.18-2.91 (m, 4H), 2.43 (br. s., 5H), 2.18-2.10 (m, J=12.5 Hz, 2H), 1.89-1.76 (m, 2H)

HRMS (ESI) [M+H]+ calcd for $C_{26}H_{24}O_2N_5S_2F_3$ 560.1396. found 560.1403.

Example 14

Synthesis of 2,5-difluoro-N-(2-fluoro-3-{5-[2-(methylamino)pyridin-4-yl]-2-(tetrahydro-2H-pyran-4-yl)-1,3-thiazol-4-yl}phenyl)benzenesulfonamide, cmpd. of formula (I)Z (cmpd. 25) [m, n=1; R1=tetrahydropyran-4-yl; R3, R5, R18=H; R4=F; R6=2,5-difluorophenyl; R17=methyl]

Method F, Steps f and d

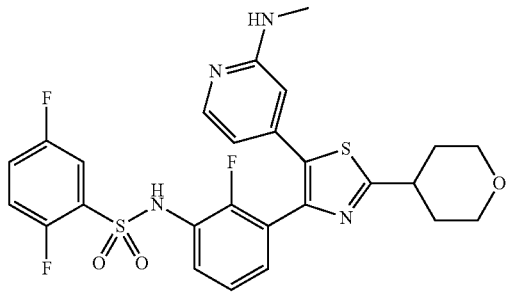 [SMILES: CNc1cc(-c2sc(C3CCOCC3)nc2-c2cccc(NS(=O)(=O)c3cc(F)ccc3F)c2F)ccn1]

Tert-butyl-{4-[4-(3-{[(2,5-difluorophenyl)sulfonyl](methoxymethyl)amino}-2-fluorophenyl)-2-(tetrahydro-2H-pyran-4-yl)-1,3-thiazol-5-yl]pyridin-2-yl}carbamate (prepared as described in Example 12, 97 mg, 0.140 mmol) was dissolved in dry THF (1.5 mL) under Ar atmosphere. The solution was cooled to 0° C. and methyl iodide (0.02 mL, 0.321 mmol, 2.3 eq) was added, followed by sodium hydride (60% in mineral oil) (20 mg, 0.353 mmol, 2.5 eq) and the mixture was stirred at r.t. overnight. The mixture was then diluted with water and ethyl acetate. The two phases were separated and the aqueous phase was extracted with ethyl acetate three times. The combined organic layers were washed with brine, dried over Na$_2$SO$_4$ and evaporated to dryness. The residue was treated with of a 9:1 TFA/water mixture (2 mL) and stirred at 70° C. for 1 h. The mixture was evaporated to dryness, taken up with DCM and washed with saturated aqueous NaHCO$_3$ and brine, dried over Na$_2$SO$_4$ and concentrated under reduced pressure. The crude product was purified by flash chromatography on silica gel (ethyl acetate/Hex 3:1) to give 59 mg of product, which was triturated with diethyl ether, filtered and dried under high vacuum. 36 mg (46%) of the title compound were obtained as white solid.

HPLC: R$_t$: 6.24 min $^1$H NMR (600 MHz, DMSO-d$_6$) δ ppm 10.68 (br. s., 1H), 7.80 (d, J=5.3 Hz, 1H), 7.56 (t, J=8.6 Hz, 1H), 7.52-7.40 (m, 2H), 7.36-7.31 (m, 1H), 7.30-7.23 (m, J=6.0 Hz, 1H), 7.22-7.16 (m, 1H), 6.54 (br. s., 1H), 6.24 (s, 1H), 6.03 (d, J=4.4 Hz, 1H), 3.96-3.89 (m, 2H), 3.46 (dt, J=1.9, 11.6 Hz, 2H), 3.32-3.26 (m, 1H), 2.66 (d, J=4.8 Hz, 3H), 2.04-1.94 (m, 2H), 1.79-1.68 (m, 2H)

HRMS (ESI) calcd for $C_{26}H_{24}N_4O_3F_3S_2$ [M+H]$^+$ 561.1237. found 561.1223.

Operating in an analogous way but using the suitable starting material the following compound was also obtained:

N-(3-{2-(1-cyclopropylpiperidin-4-yl)-5-[2-(methylamino)pyridin-4-yl]-1,3-thiazol-4-yl}-2-fluorophenyl)-2,5-difluorobenzenesulfonamide, cmpd. of formula (I)Z (cmpd. 37) [m, n=1; R1=1-cyclopropylpiperidin-4-yl; R3, R5, R18=H; R4=F; R6=2,5-difluorophenyl; R17=methyl]

Method F, Steps f and d

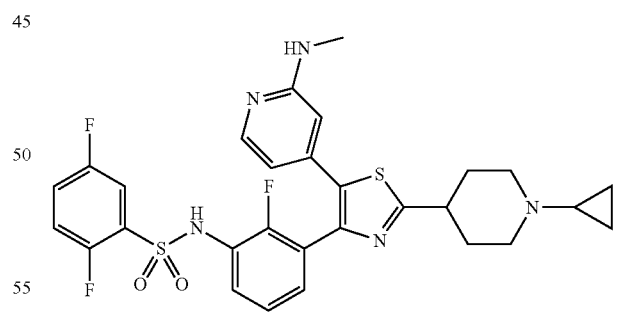

HPLC: R$_t$: 5.94 min $^1$H NMR (600 MHz, DMSO-d$_6$) δ ppm 10.56 (br. s., 1H), 7.80 (d, J=5.5 Hz, 1H), 7.58-7.51 (m, 1H), 7.47-7.39 (m, 2H), 7.35-7.29 (m, 1H), 7.26-7.18 (m, 1H), 7.18-7.09 (m, 1H), 6.52 (q, J=4.6 Hz, 1H), 6.23 (s, 1H), 6.04 (d, J=5.3 Hz, 1H), 3.03 (m, 3H), 2.66 (d, J=4.6 Hz, 3H), 2.38-2.30 (m, 2H), 2.09-2.01 (m, 2H), 1.76-1.60 (m, 3H), 0.49-0.42 (br. d, J=4.8 Hz, 2H), 0.34 (br. s., 2H)

HRMS (ESI) calcd for $C_{29}H_{29}N_5O_2F_3S_2$ [M+H]$^+$ 600.1709. found 600.1710.

Example 15

N-{4-[4-(3-{[(2,5-difluorophenyl)sulfonyl]amino}-2-fluorophenyl)-2-(tetrahydro-2H-pyran-4-yl)-1,3-thiazol-5-yl]pyridin-2-yl}acetamide, cmpd. of formula (I)Z1 (cmpd. 35) [m, n=1; R1=tetrahydropyran-4-yl; R3, R5=H; R4=F; R6=2,5-difluorophenyl; R18=acetyl]

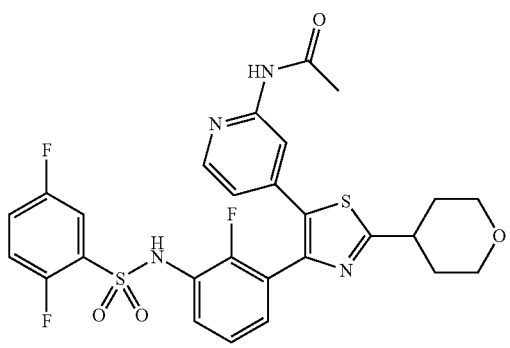 [SMILES: CC(=O)Nc1cc(-c2sc(C3CCOCC3)nc2-c2cccc(NS(=O)(=O)c3cc(F)ccc3F)c2F)ccn1]

N-{4-[4-(3-{[(2,5-difluorophenyl)sulfonyl](methoxymethyl)amino}-2-fluorophenyl)-2-(tetrahydro-2H-pyran-4-yl)-1,3-thiazol-5-yl]pyridin-2-yl}acetamide cmpd. of formula (I)X [m, n=1; R1=tetrahydropyran-4-yl; R3, R5=H; R4=F; R6=2,5-difluorophenyl; R18=acetyl; Rx=methoxymethyl]

Method F, Step c1

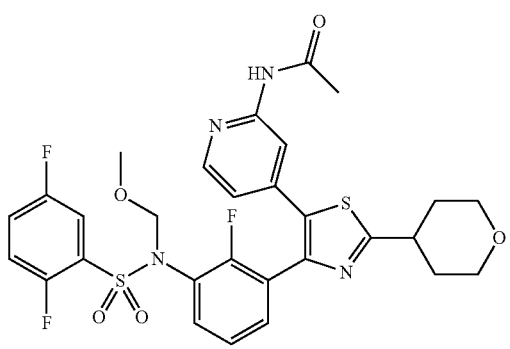 [SMILES: COCN(c1cccc(-c2nc(C3CCOCC3)sc2-c2ccnc(NC(C)=O)c2)c1F)S(=O)(=O)c1cc(F)ccc1F]

N-{3-[5-(2-chloropyridin-4-yl)-2-(tetrahydro-2H-pyran-4-yl)-1,3-thiazol-4-yl]-2-fluorophenyl}-2,5-difluoro-N-(methoxymethyl)benzenesulfonamide (prepared as described in Example 9, 100 mg, 0.164 mmol) was dissolved in dry THF (2 mL) and the solution was degassed by bubbling Ar for 5 min. Acetamide (20 mg, 0.339 mmol, 2.1 eq) was then added, followed by cesium carbonate (107 mg, 0.328 mmol, 2 eq), palladium acetate (2 mg, 0.008 mmol, 0.05 eq) and Xantphos (10 mg, 0.016 mmol, 0.1 eq) and the mixture was irradiated in the microwave oven at 100° C. for 30 min. The mixture was filtered on a celite pad and the celite was washed with ethyl acetate. The filtrate was washed with saturated aqueous NaHCO₃, water and brine, dried over Na₂SO₄ and evaporated to dryness. The crude product was purified by flash chromatography on silica gel (DCM/EtOH 98:2) to obtain 50 mg of the title compound.

MS (ESI) [M+H]⁺ 633, [M–H]⁻ 631

Operating in an analogous way but using the suitable starting material the following intermediates were also obtained:

N-{4-[2-(1-cyclopropyl piperidin-4-yl)-4-(3-{[(2,5-difluorophenyl)sulfonyl](methoxymethyl)amino}-2-fluorophenyl)-1,3-thiazol-5-yl]pyridin-2-yl}acetamide cmpd. of formula (I)X [m, n=1; R1=1-cyclopropyl-piperidin-4-yl; R3, R5=H; R4=F; R6=2,5-difluorophenyl; R18=acetyl; Rx=methoxymethyl]

Method F, Step c1

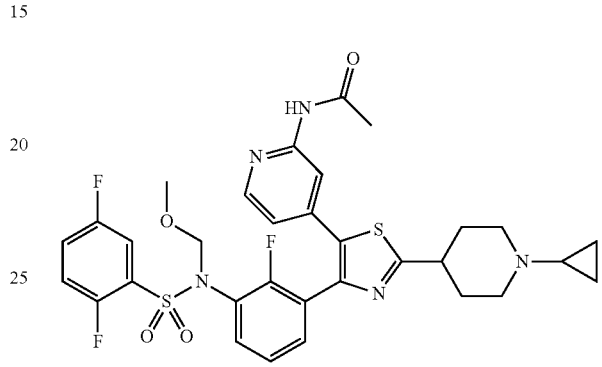

HPLC: $R_t$: 5.01 min

¹H NMR (600 MHz, DMSO-$d_6$) δ ppm 10.52 (s, 1H), 8.16 (d, J=5.4 Hz, 1H), 8.01 (s, 1H), 7.67-7.50 (m, 3H), 7.46-7.40 (m, 1H), 7.33-7.22 (m, 2H), 6.73 (dd, J=1.3, 5.1 Hz, 1H), 4.95 (s, 2H), 3.23 (s, 3H), 3.11-2.95 (m, 3H), 2.40-2.26 (m, 2H), 2.12-2.06 (m, J=1.7, 4.3 Hz, 2H), 2.04 (s, 3H), 1.76-1.55 (m, 3H), 0.49-0.38 (m, J=4.8 Hz, 2H), 0.31 (br. s., 2H)

HRMS (ESI) calcd for $C_{32}H_{33}N_5O_4F_3S_2$ [M+H]⁺ 672.1921. found 672.1926.

N-{4-[2-tert-butyl-4-(3-{[(2,5-difluorophenyl)sulfonyl](methoxymethyl)amino}-2-fluorophenyl)-1,3-thiazol-5-yl]pyridin-2-yl}acetamide, cmpd. of formula (I)X [m, n=1; R1=tert-butyl; R3, R5=H; R4=F; R6=2,5-difluorophenyl; R18=acetyl; Rx=methoxymethyl]

Method F, Step c1

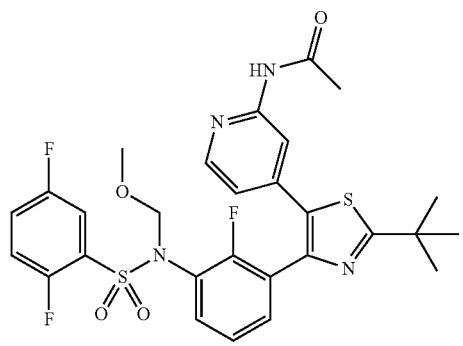 [SMILES: COCN(c1cccc(-c2nc(C(C)(C)C)sc2-c2ccnc(NC(C)=O)c2)c1F)S(=O)(=O)c1cc(F)ccc1F]

HPLC: R$_t$: 7.23 min
MS (ESI) [M+H]$^+$ 605, [M–H]$^-$ 603

Benzyl-4-{5-[2-(acetylamino)pyridin-4-yl]-4-(3-{[(2,5-difluorophenyl)sulfonyl](methoxymethyl)amino}-2-fluorophenyl)-1,3-thiazol-2-yl}piperidine-1-carboxylate, cmpd. of formula (I)X [m, n=1; R1=1-benzyloxycarbonyl-piperidin-4-yl; R3, R5=H; R4=F; R6=2,5-difluorophenyl; R18=acetyl; Rx=methoxymethyl]

Method F, Step c1

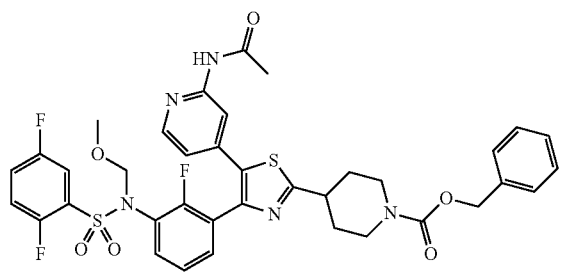 [SMILES: COCN(c1cccc(-c2nc(C3CCN(C(=O)OCc4ccccc4)CC3)sc2-c2ccnc(NC(C)=O)c2)c1F)S(=O)(=O)c1cc(F)ccc1F]

HPLC: R$_t$: 7.23 min
$^1$H NMR (401 MHz, DMSO-d$_6$) δ ppm 10.52 (s, 1H), 8.17 (dd, J=0.7, 5.2 Hz, 1H), 8.02 (s, 1H), 7.66-7.48 (m, 3H), 7.46-7.41 (m, 1H), 7.39-7.35 (m, 3H), 7.34-7.26 (m, 3H), 6.73 (dd, J=1.6, 5.2 Hz, 1H), 5.10 (s, 2H), 4.96 (s, 2H), 4.10 (td, J=3.9, 13.7 Hz, 1H), 3.23 (s, 3H), 3.05 (br. s., 2H), 2.11 (d, J=10.5 Hz, 2H), 2.04 (s, 3H), 1.76-1.56 (m, 2H)
HRMS (ESI) [M+H]+ calcd for C$_{37}$H$_{34}$O$_6$N$_5$S$_2$F$_3$ 766.1976. found 766.1995.

N-{4-[4-(3-{[(2,5-difluorophenyl)sulfonyl]amino}-2-fluorophenyl)-2-(tetrahydro-2H-pyran-4-yl)-1,3-thiazol-5-yl]pyridin-2-yl}acetamide, cmpd. of formula (I)Z1 (cmpd. 35) [m, n=1; R1=tetrahydropyran-4-yl; R3, R5=H; R4=F; R6=2,5-difluorophenyl; R18=acetyl]

Method F, Step d1

Crude N-{4-[2-(tetrahydropyran-4-yl)-4-(3-{[(2,5-difluorophenyl)sulfonyl](methoxymethyl)amino}-2-fluorophenyl)-1,3-thiazol-5-yl]pyridin-2-yl}acetamide (50 mg) was treated with of a 9:1 TFA/water mixture (1 mL) and stirred at 70° C. for 1.5 h. The mixture was evaporated to dryness, taken up with DCM and washed with saturated aqueous NaHCO$_3$ and brine, dried over Na$_2$SO$_4$ and concentrated under reduced pressure. The crude product was purified by flash chromatography on silica gel (DCM/MeOH 95:5) to give 35 mg of product, which was triturated with ethyl ether filtered and dried under high vacuum. 28 mg (60%) of the title compound were obtained as an off-white solid.
HPLC: R$_t$: 5.84 min
$^1$H NMR (600 MHz, DMSO-d$_6$) δ ppm 10.63 (s, 1H), 10.54 (s, 1H), 8.12 (d, J=5.3 Hz, 1H), 8.04 (s, 1H), 7.59-7.51 (m, 1H), 7.47-7.42 (m, 1H), 7.42-7.38 (m, 1H), 7.37-7.28 (m, 2H), 7.25-7.17 (m, 1H), 6.62 (dd, J=1.6, 5.3 Hz, 1H), 3.93 (td, J=2.2, 9.4 Hz, 2H), 3.47 (dt, J=2.2, 11.6 Hz, 2H), 3.39-3.31 (m, 1H), 2.07 (s, 3H), 2.03-1.97 (m, 2H), 1.81-1.69 (m, 2H)
HRMS (ESI) calcd for C$_{27}$H$_{24}$N$_{14}$O$_4$F$_3$S$_2$ [M+H]$^+$ 589.1186. found 589.1187.
Operating in an analogous way but using the suitable starting material the following compounds were also obtained:

N-{4-[2-(1-cyclopropylpiperidin-4-yl)-4-(3-{[(2,5-difluorophenyl)sulfonyl]amino}-2-fluorophenyl)-1,3-thiazol-5-yl]pyridin-2-yl}acetamide, cmpd. of formula (I)Z1 (cmpd. 30) [m, n=1; R1=1-cyclopropyl-piperidin-4-yl; R3, R5=H; R4=F; R6=2,5-difluorophenyl; R18=acetyl]

Method F, Step d1

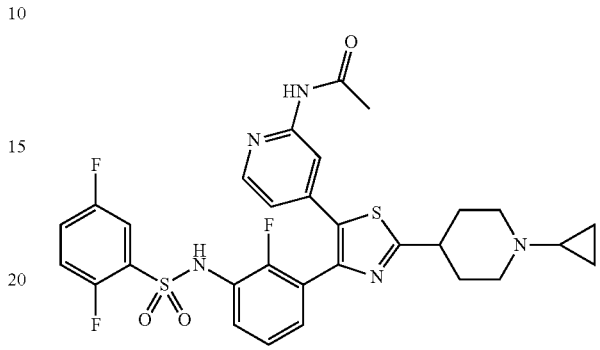

HPLC: R$_t$: 5.57 min
$^1$H NMR (600 MHz, DMSO-d$_6$) δ ppm 10.54 (s, 1H), 8.12 (d, J=5.3 Hz, 1H), 8.04 (s, 1H), 7.53 (t, J=8.3 Hz, 1H), 7.47-7.37 (m, 2H), 7.33-7.23 (m, 2H), 7.21-7.12 (m, 1H), 6.62 (dd, J=1.6, 5.3 Hz, 1H), 3.14-2.96 (m, 3H), 2.38 (dd, J=1.8, 3.7 Hz, 2H), 2.12-2.01 (m, 2H), 2.06 (s, 3H), 1.79-1.56 (m, 3H), 0.45 (d, J=4.8 Hz, 2H), 0.35 (br. s., 2H)
HRMS (ESI) calcd for C$_{30}$H$_{29}$N$_5$O$_3$F$_3$S$_2$ [M+H]$^+$ 628.1659. found 628.1659.

N-{4-[2-tert-butyl-4-(3-{[(2,5-difluorophenyl)sulfonyl]amino}-2-fluorophenyl)-1,3-thiazol-5-yl]pyridin-2-yl}acetamide, cmpd. of formula (I)Z1 (cmpd. 42) [m, n=1; R1=tert-butyl; R3, R5=H; R4=F; R6=2,5-difluorophenyl; R18=acetyl]

Method F, Step d1

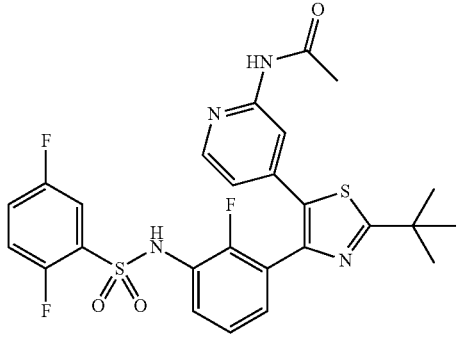 [SMILES: CC(=O)Nc1cc(-c2sc(C(C)(C)C)nc2-c2cccc(NS(=O)(=O)c3cc(F)ccc3F)c2F)ccn1]

HPLC: R$_t$: 6.11 min
$^1$H NMR (600 MHz, DMSO-d$_6$) δ ppm 10.63 (s, 1H), 10.54 (s, 1H), 8.12 (d, J=5.3 Hz, 1H), 8.05 (s, 1H), 7.59-7.51 (ddd, J=4.2, 4.2, 8.4 Hz, 1H), 7.45 (dt, J=3.9, 9.1 Hz, 1H), 7.43-7.38 (m, 1H), 7.37-7.29 (m, 2H), 7.25-7.16 (m, 1H), 6.61 (dd, J=1.6, 5.3 Hz, 1H), 2.07 (s, 3H), 1.43 (s, 9H)
HRMS (ESI) calcd for C$_{26}$H$_{24}$N$_4$O$_3$F$_3$S$_2$[M+H]$^+$ 561.1237. found 561.1257.

N-{4-[4-(3-{[(2,5-difluorophenyl)sulfonyl]amino}-2-fluorophenyl)-2-(piperidin-4-yl)-1,3-thiazol-5-yl]pyridin-2-yl}acetamide; cmpd. of formula (I)Z1 (cmpd. 44) [m, n=1; R1=piperidin-4yl; R3, R5=H; R4=F; R6=2,5-difluorophenyl; R18=acetyl]

Method F, Step d1

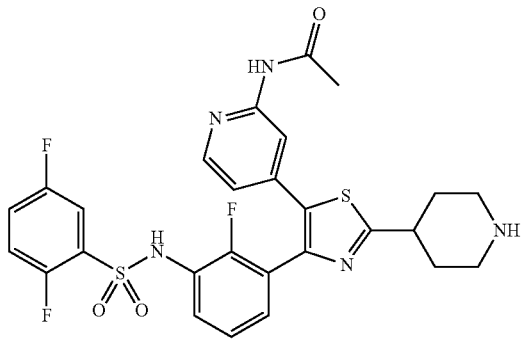 [SMILES: CC(=O)Nc1cc(-c2sc(C3CCNCC3)nc2-c2cccc(NS(=O)(=O)c3cc(F)ccc3F)c2F)ccn1]

HPLC: R$_t$: 4.70 min
$^1$H NMR (401 MHz, DMSO-d$_6$)(selected signals) δ ppm 10.56 (s, 1H), 8.12 (d, J=4.8 Hz, 1H), 7.43-7.17 (m, 4H), 6.92 (br. s., 1H), 6.72-6.67 (m, 1H), 3.04 (dt, J=2.9, 12.5 Hz, 1H), 2.30-2.19 (m, J=2.8, 14.2 Hz, 2H), 2.07 (s, 3H), 1.99-1.85 (m, 2H)
HRMS (ESI) [M+H]$^+$ calcd for C$_{27}$H$_{24}$O$_3$N$_5$S$_2$F$_3$ 588.1346. found 588.1349.

Example 16

Synthesis of N-{4-[4-(3-{[(2,5-difluorophenyl)sulfonyl]amino}-2-fluorophenyl)-2-(1-methylpiperidin-4-yl)-1,3-thiazol-5-yl]pyridin-2-yl}acetamide, cmpd. of formula (I)Z1 (cmpd. 23) [m, n=1; R1=1-methyl-piperidin-4-yl; R3, R5=H; R4=F; R6=2,5-difluorophenyl; R18=acetyl]

Method F (analogously to Method C, Step e)

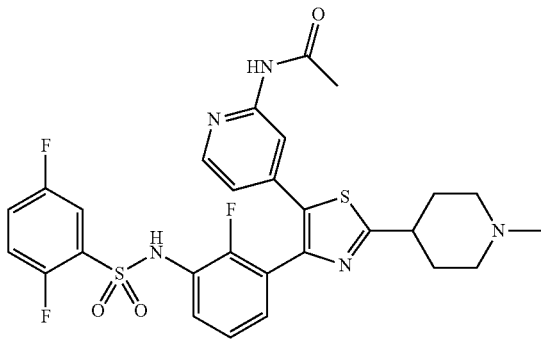 [SMILES: CC(=O)Nc1cc(-c2sc(C3CCN(C)CC3)nc2-c2cccc(NS(=O)(=O)c3cc(F)ccc3F)c2F)ccn1]

N-{4-[4-(3-{[(2,5-difluorophenyl)sulfonyl](methoxymethyl)amino}-2-fluorophenyl)-2-(piperidin-4-yl)-1,3-thiazol-5-yl]pyridin-2-yl}acetamide (prepared as described in Example 15, 50 mg, 0.085 mmol) was dissolved in MeOH (5 mL) and glacial acetic acid (15 μL, 0.26 mmol). 37% aqueous formaldehyde (6.5 μL, 0.13 mmol) and sodium cyanoborohydride (8.5 mg, 0.17 mmol) were then added to the mixture, which was stirred at r.t. for 1 h. The solvent was removed under reduced pressure and the residue partitioned between ethyl acetate and aqueous NaHCO$_3$. The organic phase was dried over Na$_2$SO$_4$ and evaporated to dryness. The product was purified by flash chromatography on silica gel (DCM-MeOH 4/1) giving 30 mg (59%) of the title compound, after trituration with petroleum ether.

HPLC: R$_t$: 3.72 min
$^1$H NMR (600 MHz, DMSO-d$_6$)(selected signals) δ ppm 10.55 (s, 1H), 8.11 (d, J=5.3 Hz, 1H), 8.09 (s, 1H), 7.44-7.36 (m, J=5.3 Hz, 2H), 7.35-7.28 (m, 1H), 7.26 (t, J=7.5 Hz, 1H), 7.02 (br. s., 2H), 6.66 (dd, J=1.4, 5.2 Hz, 1H), 3.18-2.97 (m, 3H), 2.44 (br. s., 3H), 2.20-2.12 (m, J=14.1 Hz, 2H), 2.07 (s, 3H), 1.91-1.78 (m, 2H)
HRMS (ESI) [M+H]+ calcd for C$_{28}$H$_{26}$O$_3$N$_5$S$_2$F$_3$ 602.1502. found 602.1503.

Example 17

Synthesis of 2,5-difluoro-N-(2-fluoro-3-{5-[2-(methylamino)pyridin-4-yl]-2-(1-methylpiperidin-4-yl)-1,3-thiazol-4-yl}phenyl)benzenesulfonamide, cmpd. of formula (I)Z (cmpd. 38) [m, n=1; R1=1-methyl-piperidin-4-yl; R3, R5, R17=H; R4=F; R6=2,5-difluorophenyl; R18=methyl]

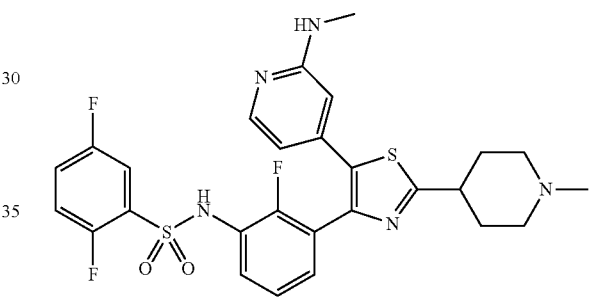

Benzyl-4-[5-{2-[(tert-butoxycarbonyl)(methyl)amino]pyridin-4-yl}-4-(3-{[(2,5-difluorophenyl)sulfonyl](methoxymethyl)amino}-2-fluorophenyl)-1,3-thiazol-2-yl]piperidine-1-carboxylate, cmpd. of formula 49 [m, n=1; R1=1-benzyloxycarbonyl-piperidin-4-yl; R3, R5=H; R4=F; R6=2,5-difluorophenyl; R17'=tert-butoxycarbonyl; R18=methyl; Rx=methoxymethyl]

Method F, Step c

Benzyl-4-[5-(2-chloropyridin-4-yl)-4-(3-{[(2,5-difluorophenyl)sulfonyl](methoxymethyl)amino}-2-fluorophenyl)-1,3-thiazol-2-yl]piperidine-1-carboxylate (prepared as described in example 9, 100 mg, 0.14 mmol) was dissolved in dry THF (6 mL) and Cs$_2$CO$_3$ (90 mg, 0.28 mmol), Xantphos (17 mg, 0.03 mmol) tert-butyl methylcarbamate (prepared as described in Preparation 8, 74 mg, 0.56 mmol) and Pd(AcO)$_2$ (12 mg, 0.03 mmol) were added consecutively. The mixture was submitted to microwave irradiation in a closed vial at 120° C. for 2 h for three times. The suspension was then filtered through a celite pad and the solvent evaporated under reduced pressure. The suspension was then filtered through a celite pad and the solvent evaporated under reduced pressure. The crude was then purified by flash chromatography (cyclohexane-ethylacetate-ethanol 4/0.5/0.5) giving 73 mg (62%) of benzyl-4-[5-{2-[(tert-butoxycarbonyl)(methyl)amino]pyridin-4-yl}-4-(3-{[(2,5-difluorophenyl)sulfonyl](methoxymethyl)amino}-2-fluorophenyl)-1,3-thiazol-2-yl]piperidine-1-carboxylate.

HPLC: R$_t$: 7.66 min $^1$H NMR (600 MHz, DMSO-d$_6$) δ ppm 8.24 (d, J=5.3 Hz, 1H), 7.65-7.57 (m, 2H), 7.53 (dt, J=3.9, 9.4 Hz, 1H), 7.43 (ddd, J=3.1, 5.0, 7.6 Hz, 1H), 7.39-7.35 (m, 3H), 7.34-7.29 (m, 2H), 6.75 (dd, J=1.6, 5.2 Hz, 1H), 5.10 (s, 2H), 4.96 (s, 2H), 4.17-4.06 (m, J=7.9 Hz, 2H), 3.28-3.27 (m, 3H), 3.24-3.19 (m, 3H), 3.02 (br. s., 2H), 2.12 (d, J=4.6 Hz, 1H), 1.71-1.62 (m, 2H), 1.41 (s, 9H)

HRMS (ESI) [M+H]+ calcd for C$_{41}$H$_{42}$O$_7$N$_5$S$_2$F$_3$ 838.2551. found 838.2573.

tert-butyl {4-[4-(3-{[(2,5-difluorophenyl)sulfonyl](methoxymethyl)amino}-2-fluorophenyl)-2-(piperidin-4-yl)-1,3-thiazol-5-yl]pyridin-2-yl}methylcarbamate, cmpd. of formula 47 [m, n=1; R2"=N-methyl-N-tert-butoxycarbonyl amine; R3, R5=H; R4=F; R6=2,5-difluorophenyl; Rx=methoxymethyl]

Method C, Step d

Benzyl-4-[5-{2-[(tert-butoxycarbonyl)(methyl)amino]pyridin-4-yl}-4-(3-{[(2,5-difluorophenyl)sulfonyl](methoxymethyl)amino}-2-fluorophenyl)-1,3-thiazol-2-yl]piperidine-1-carboxylate (177 mg, 0.21 mmol) was dissolved in absolute ethanol (7 mL) under nitrogen atmosphere. Ammonium formate (53 mg, 0.84 mmol) and palladium on charcoal 5% (150 mg portionwise) were then added. The mixture was refluxed for 2 days, then filtered on a celite pad and evaporated to dryness. The residue was taken up with DCM and washed with water. The organic layer was dried over Na$_2$SO$_4$ and evaporated. The crude was then purified by flash chromatography on silica gel (DCM-MeOH for eluting the impurities, then DCM-MeOH—NH$_4$OH 30% 20-5-0.5 for eluting the product) affording 65 mg (44%) of the title compound.

HPLC: R$_t$: 5.60 min $^1$H NMR (500 MHz, DMSO-d$_6$) δ ppm 8.24 (d, J=5.2 Hz, 1H), 7.70-7.52 (m, 5H), 7.44 (br. s., 1H), 6.76 (d, J=5.2 Hz, 1H), 4.96 (s, 2H)

HRMS (ESI) [M+H]+ calcd for C$_{33}$H$_{36}$O$_5$N$_5$S$_2$F$_3$ 704.2183. found 704.2191.

Tert-butyl {4-[4-(3-{[(2,5-difluorophenyl)sulfonyl](methoxymethyl)amino}-2-fluorophenyl)-2-(1-methylpiperidin-4-yl)-1,3-thiazol-5-yl]pyridin-2-yl}methylcarbamate, cmpd. of formula 48 [m, n=1; R"=methyl; R2"=N-methyl-N-tert-butoxycarbonyl amine; R3, R5=H; R4=F; R6=2,5-difluorophenyl; Rx=methoxymethyl]

Method C, Step e

Tert-butyl-{4-[4-(3-{[(2,5-difluorophenyl)sulfonyl](methoxymethyl)amino}-2-fluorophenyl)-2-(piperidin-4-yl)-1,3-thiazol-5-yl]pyridin-2-yl}methylcarbamate (65 mg, 0.09 mmol) was dissolved in MeOH (5 mL) and glacial acetic acid (15 µL, 0.26 mmol). 37% aqueous formaldehyde (6.5 µL, 0.13 mmol) and sodium cyanoborohydride (8.5 mg, 0.17 mmol) were then added to the mixture, that was stirred at r.t. for 1 h. The solvent was removed under reduced pressure and the residue partitioned between ethyl acetate and 15% aqueous ammonia. The organic phase was dried over Na$_2$SO$_4$ and evaporated to dryness, to give 34 mg of tert-butyl-{4-[4-(3-{[(2,5-difluorophenyl)sulfonyl](methoxymethyl)amino}-2-fluorophenyl)-2-(1-methylpiperidin-4-yl)-1,3-thiazol-5-yl]pyridin-2-yl}methylcarbamate that were employed for the next step without any further purification.

HPLC/MS (ESI): 718 [M+H]+, 716 [M-H]-

2,5-difluoro-N-(2-fluoro-3-{5-[2-(methylamino)pyridin-4-yl]-2-(1-methylpiperidin-4-yl)-1,3-thiazol-4-yl}phenyl)benzenesulfonamide, cmpd. of formula (I)Z (cmpd. 38) [m, n=1; R1=1-methyl-piperidin-4-yl; R3, R5, R17=H; R4=F; R6=2,5-difluorophenyl; R18=methyl]

Method F, Step d

Tert-butyl-{4-[4-(3-{[(2,5-difluorophenyl)sulfonyl](methoxymethyl)amino}-2-fluorophenyl)-2-(1-methylpiperidin-4-yl)-1,3-thiazol-5-yl]pyridin-2-yl}methylcarbamate (34 mg, 0.05 mmol) was dissolved in a mixture TFA-H$_2$O 9/1 (5 mL) and stirred at 70° C. for 2 h. The solvent was removed under reduced pressure and the residue partitioned between DCM and 15% aqueous NH$_4$OH. The aqueous phase was further extracted twice with ethyl acetate and the solvent evaporated to dryness. The crude was purified by RP-HPLC (mobile phase A: 0.05% NH$_3$ in water/acetonitrile (95:5), mobile phase B: acetonitrile/H$_2$O (95:5); gradient from 0 to 60% B in 15 min then ramp to 100% B in 0.1 min) affording 15 mg (37%) of the title compound, as trifluoroacetate salt.

HPLC: R$_t$: 3.85 min $^1$H NMR (600 MHz, DMSO-d$_6$) δ ppm 10.70 (br. s., 1H), 9.46 (br. s., 1H), 7.83 (d, J=6.0 Hz, 1H), 7.64-7.54 (m, 1H), 7.52-7.41 (m, 2H), 7.39-7.30 (m, 1H), 7.27-7.21 (m, 1H), 6.65-6.39 (m, 1H), 6.27 (br. s., 1H), 3.56 (br. s., 2H), 3.14-3.04 (m, 2H), 2.82 (d, J=3.5 Hz, 2H), 2.78 (br. s., 2H), 2.35-2.28 (m, J=14.3 Hz, 2H), 1.99-1.86 (m, 2H)

HRMS (ESI) [M+H]+ calcd for C$_{27}$H$_{26}$O$_2$N$_5$S$_2$F$_3$ 574.1553. found 574.1564.

Operating in an analogous way but using the suitable aldehyde in the reductive amination step, the following compound was also obtained:

N-(3-{2-(1-ethylpiperidin-4-yl)-5-[2-(methylamino)pyridin-4-yl]-1,3-thiazol-4-yl}-2-fluorophenyl)-2,5-difluorobenzenesulfonamide, cmpd. of formula (I)Z [m, n=1; R1=1-ethyl-piperidin-4-yl; R3, R5, R17=H; R4=F; R6=2,5-difluorophenyl; R18=methyl]

Method F, Step d

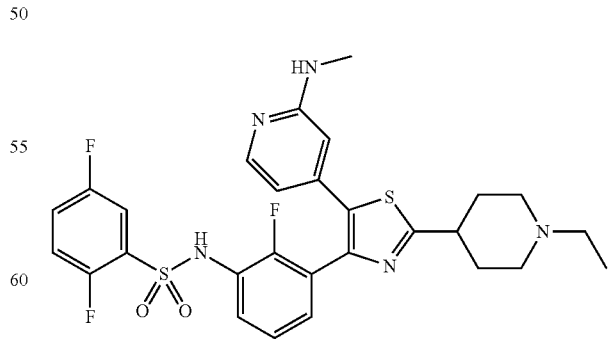

HPLC: R$_t$: 4.90 min $^1$H NMR (600 MHz, DMSO-d$_6$) δ ppm 10.70 (br. s., 1H), 9.19 (br. s., 1H), 7.82 (d, J=5.9 Hz, 1H), 7.58 (t, J=8.4 Hz, 1H), 7.52-7.41 (m, 3H), 7.37-7.29 (m, 2H), 7.27-7.20 (m, 1H), 6.48 (br. s., 1H), 6.24 (br. s., 1H), 3.64-3.56 (m, J=12.3 Hz, 2H), 3.19-3.12 (m, 2H), 3.09-3.00 (m, 2H), 2.76 (br. s., 3H), 2.33 (d, J=13.6 Hz, 2H), 2.00-1.86 (m, 2H), 1.27-1.22 (m, 3H)

HRMS (ESI) [M+H]+ calcd for $C_{28}H_{28}O_2N_5S_2F_3$ 588.1709. found 588.1729.

Example 18

Synthesis of N-{3-[2-(1-cyclopropylpiperidin-4-yl)-5-(2-methylpyridin-4-yl)-1,3-thiazol-4-yl]-2-fluorophenyl}-2,5-difluorobenzenesulfonamide, cmpd. of formula (I)AC (cmpd. 31) [m, n=1; R1=1-cyclopropyl-piperidin-4-yl; R3, R5=H; R4=F; R6=2,5-difluorophenyl; R2'=methyl]

Method F, Steps g and d2

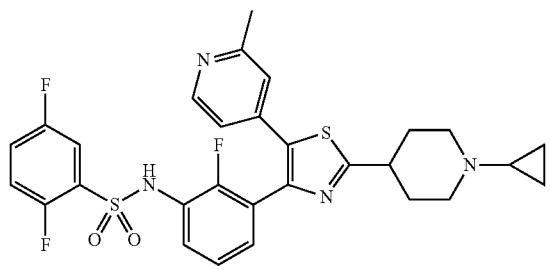 [SMILES: Cc1cc(-c2sc(C3CCN(C4CC4)CC3)nc2-c2cccc(NS(=O)(=O)c3cc(F)ccc3F)c2F)ccn1]

N-{3-[5-(2-chloropyridin-4-yl)-2-(1-cyclopropylpiperidin-4-yl)-1,3-thiazol-4-yl]-2-fluorophenyl}-2,5-difluoro-N-(methoxymethyl)benzenesulfonamide (prepared as described in Example 9, 100 mg, 0.154 mmol) was dissolved in dry dioxane (1 mL). Argon was bubbled through the solution for 5 min and a 2M AlMe₃ solution in Hex (0.154 mL, 0.308 mmol, 2 eq) was added, followed by Pd(PPh₃)₄ (4 mg, 0.004 mmol, 0.02 eq). The mixture was heated to 105° C. in a sealed tube for 2 h. It was then diluted with ethyl acetate and saturated aqueous NaHCO₃. The two phases were separated and the aqueous phase was extracted three times with ethyl acetate. The combined organic layers were washed with brine, dried over Na₂SO₄ and concentrated under reduced pressure. Crude N-{3-[2-(1-cyclopropylpiperidin-4-yl)-5-(2-methylpyridin-4-yl)-1,3-thiazol-4-yl]-2-fluorophenyl}-2,5-difluoro-N-(methoxymethyl)benzenesulfonamide was treated with a 9:1 TFA/water mixture at 70° C. for 1.5 h. The mixture was evaporated to dryness, taken up with DCM and washed with saturated aqueous NaHCO₃ and brine, dried over Na₂SO₄ and concentrated under reduced pressure. The crude product was purified by flash chromatography on silica gel (DCM/MeOH 95:5) to give 72 mg (80%) of the title compound as pale yellow solid.

HPLC: R,: 6.00 min

¹H NMR (600 MHz, DMSO-d₆) δ ppm 10.56 (br. s., 1H), 8.29 (d, J=5.3 Hz, 1H), 7.51-7.59 (m, 1H), 7.44 (dt, J=4.0, 9.2 Hz, 1H), 7.40-7.36 (m, 1H), 7.33 (dt, J=1.5, 7.7 Hz, 1H), 7.27 (m, 1H), 7.22-7.15 (m, 1H), 7.02 (s, 1H), 6.79 (dd, J=1.4, 5.3 Hz, 1H), 3.07-3.00 (m, 3H), 2.38 (s, 3H), 2.42-2.33 (m, 2H), 2.06 (d, J=12.6 Hz, 2H), 1.76-1.60 (m, 3H), 0.45 (br. d, J=4.6 Hz, 2H), 0.35 (br. s, 2H)

HRMS (ESI) calcd for $C_{29}H_{28}N_{14}O_2F_3S_2$ [M+H]+ 585.1601. found 585.1599.

Operating in an analogous way but using the appropriate starting material the following compounds were obtained:

2,5-difluoro-N-{2-fluoro-3-[5-(2-methylpyridin-4-yl)-2-(tetrahydro-2H-pyran-4-yl)-1,3-thiazol-4-yl]phenyl}benzenesulfonamide, cmpd. of formula (I)AC (cmpd. 28) [m, n=1; R1=tetrahydropyran-4-yl; R3, R5=H; R4=F; R6=2,5-difluorophenyl; R2'=methyl]

Method F, Steps g and d2

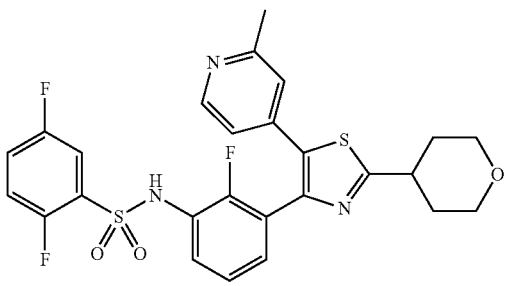 [SMILES: Cc1cc(-c2sc(C3CCOCC3)nc2-c2cccc(NS(=O)(=O)c3cc(F)ccc3F)c2F)ccn1]

HPLC: R,: 6.23 min

¹H NMR (600 MHz, DMSO-d₆) (selected signals) δ ppm 10.67 (s, 1H), 8.29 (d, J=5.2 Hz, 1H), 7.63-7.53 (m, 1H), 7.46 (dt, J=3.9, 9.2 Hz, 1H), 7.43-7.38 (m, 1H), 7.37-7.29 (m, 2H), 7.25-7.17 (m, 1H), 7.03 (s, 1H), 6.79 (dd, J=1.2, 5.2 Hz, 1H), 3.93 (td, J=2.1, 9.6 Hz, 2H), 3.53-3.42 (m, 2H), 2.39 (s, 3H), 2.01 (m, 2H), 1.81-1.63 (m, 2H)

HRMS (ESI) calcd for $C_{26}H_{23}N_3O_3F_3S_2$ [M+H]+ 546.1128. found 546.1127.

2,5-difluoro-N-{2-fluoro-3-[5-(2-methylpyridin-4-yl)-2-(piperidin-4-yl)-1,3-thiazol-4-yl]phenyl}benzenesulfonamide, cmpd. of formula (I)AC [m, n=1; R1=piperidin-4-yl; R3, R5=H; R4=F; R6=2,5-difluorophenyl; R2'=methyl]

Method F, Steps g and d2

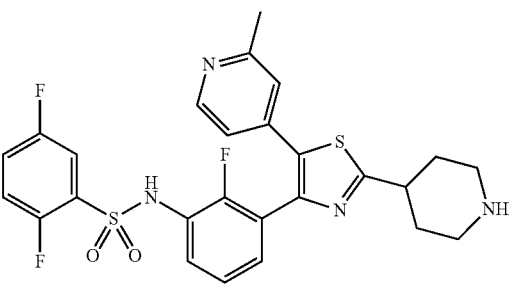 [SMILES: Cc1cc(-c2sc(C3CCNCC3)nc2-c2cccc(NS(=O)(=O)c3cc(F)ccc3F)c2F)ccn1]

HPLC: R,: 4.79 min

¹H NMR (600 MHz, DMSO-d₆) δ ppm 8.33 (d, J=5.3 Hz, 1H), 7.42-7.35 (m, 1H), 7.30-7.14 (m, 3H), 7.08 (br. s, 1H), 6.91 (d, J=5.3 Hz, 1H), 6.88-6.78 (m, 1H), 6.60 (br. s., 1H), 3.49-3.27 (m, 3H), 3.02 (dt, J=2.4, 12.4 Hz, 2H), 2.37 (s, 3H), 2.23 (dd, J=2.4, 14.0 Hz, 2H), 1.96-1.83 (m, 2H)

HRMS (ESI) calcd for $C_{26}H_{24}N_4O_2F_3S_2$ [M+H]+ 545.1288. found 545.1304.

Example 19

Synthesis of 2,5-difluoro-N-{2-fluoro-3-[2-(1-methylpiperidin-4-yl)-5-(2-methylpyridin-4-yl)-1,3-thiazol-4-yl]phenyl}benzenesulfonamide, cmpd. of formula (I)AC (cmpd. 26) [m, n=1; R1=1-methylpiperidin-4-yl; R3, R5=H; R4=F; R6=2,5-difluorophenyl; R2'=methyl]

Method F (analogously to Method C, Step e)

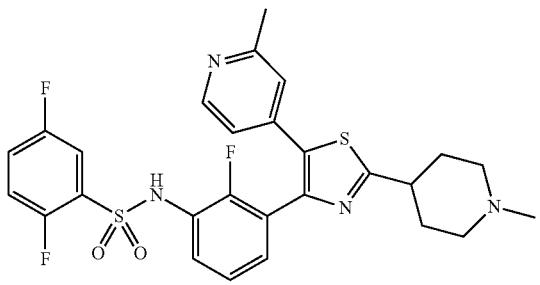 [SMILES: Cc1cc(-c2sc(C3CCN(C)CC3)nc2-c2cccc(NS(=O)(=O)c3cc(F)ccc3F)c2F)ccn1]

2,5-difluoro-N-{2-fluoro-3-[5-(2-methylpyridin-4-yl)-2-(piperidin-4-yl)-1,3-thiazol-4-yl]phenyl}benzenesulfonamide (obtained as described in Example 18, 100 mg, 0.184 mmol) was dissolved in MeOH (2 mL). Aqueous formaldehyde (37%, 0.021 mL, 0.276 mmol, 1.5 eq) was added, followed by acetic acid (0.032 mL, 0.552 mmol, 3 eq) and sodium cyanoborohydride (22 g, 0.294 mmol, 1.6 eq) and the mixture was stirred at r.t. for 1 h. The mixture was then diluted with ethyl acetate, washed with aqueous saturated NaHCO$_3$ and brine, dried over Na$_2$SO$_4$ and evaporated to dryness. The crude product was purified by flash chromatography on silica gel (DCM/MeOH/NH$_3$ 7N in MeOH 90:9:1), treated with diethyl ether, filtered and dried under high vacuum to give 68 mg (66%) of the title compound as pale yellow solid.

HPLC: R$_t$: 4.87 min $^1$H NMR (401 MHz, DMSO-d$_6$) δ ppm 8.29 (d, J=5.1 Hz, 1H), 7.41-7.37 (m, 1H), 7.37-7.33 (m, 1H), 7.29 (dt, J=4.0, 8.9 Hz, 1H), 7.27-7.21 (m, 1H), 7.06 (br. s, 1H), 6.97 (t, J=7.4 Hz, 1H), 6.86 (dd, J=1.1, 5.1 Hz, 1H), 6.86-6.82 (m, 1H), 3.13-3.06 (m, 1H), 3.06-2.98 (m, 1H), 2.44-2.27 (m, 5H), 2.15-2.10 (m, 2H), 1.87-1.76 (m, 2H)

HRMS (ESI) calcd for C$_{27}$H$_{26}$N$_4$O$_2$F$_3$S$_2$ [M+H]$^+$ 559.1444. found 559.1464.

Operating in an analogous way but using the suitable aldehyde, the following compound was also obtained:

2,5-difluoro-N-{2-fluoro-3-[2-(1-ethylpiperidin-4-yl)-5-(2-methylpyridin-4-yl)-1,3-thiazol-4-yl]phenyl}benzenesulfonamide, cmpd. of formula (I)AC [m, n=1; R1=1-ethyl-piperidin-4-yl; R3, R5=H; R4=F; R6=2,5-difluorophenyl; R2'=methyl]

Method F (analogously to Method C, Step e)

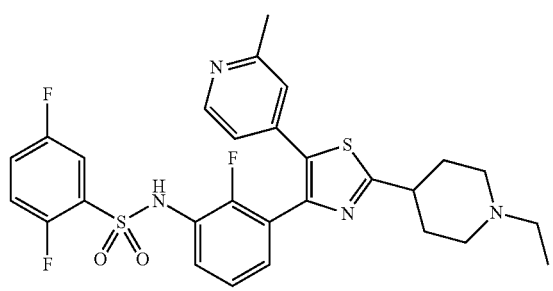 [SMILES: CCN1CCC(c2nc(-c3cccc(NS(=O)(=O)c4cc(F)ccc4F)c3F)c(-c3ccnc(C)c3)s2)CC1]

HPLC: R$_t$: 5.00 min $^1$H NMR (401 MHz, DMSO-d$_6$) δ ppm 8.30 (d, J=5.3 Hz, 1H), 7.45-7.36 (m, 2H), 7.36-7.30 (m, 2H), 7.27 (m, 1H), 7.05 (br. s, 1H), 7.04-6.89 (m, 2H), 6.85 (br. d, J=5.3 Hz, 1H), 2.87-2.54 (m, 3H), 2.42-2.28 (m, 5H), 2.27-2.10 (m, 2H), 2.09-2.09 (m, 2H), 1.92-1.73 (m, 2H), 1.13 (t, J=7.1 Hz, 3H)

HRMS (ESI) calcd for C$_{28}$H$_{28}$N$_4$O$_2$F$_3$S$_2$ [M+H]$^+$ 573.1601. found 573.1600.

Example 20

Synthesis of 2,5-difluoro-N-{2-fluoro-3-[5-(3-fluoropyridin-4-yl)-2-(tetrahydro-2H-pyran-4-yl)-1,3-thiazol-4-yl]phenyl}benzenesulfonamide, cmpd. of formula (I)B (cmpd. 34) [m, n=1; R2, R5=H; R3=3-F; R4=F; R6=2,5-difluorophenyl; R1'=tetrahydropyran-4-yl]

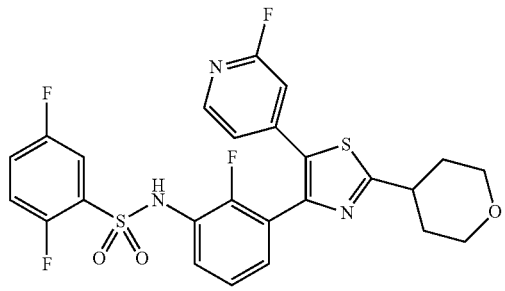 [SMILES: O=S(=O)(Nc1cccc(-c2nc(C3CCOCC3)sc2-c2ccnc(F)c2)c1F)c1cc(F)ccc1F]

2,5-difluoro-N-{2-fluoro-3-[2-(tetrahydro-2H-pyran-4-yl)-1,3-thiazol-4-yl]phenyl}-N-(methoxymethyl)benzenesulfonamide, cmpd. of formula 9 [n=1; R1=tetrahydropyran-4-yl; R4=F; R5=H; R6=2,5-difluorophenyl; Rx=methoxymethyl]

Method A, Steps d1 and e

To a solution of N-(3-acetyl-2-fluorophenyl)-2,5-difluoro-N-(methoxymethyl)benzenesulfonamide (prepared as described in Preparation 1, 2.55 g, 6.830 mmol) in dry THF (34 mL) pyridinium bromide perbromide (2.18 g, 6.83 mmol, 1 eq) was added and the mixture was refluxed for 1 h. The mixture was then concentrated under reduced pressure, taken up with ethyl acetate and washed with 0.25 M HCl, water and brine. The organic phase was dried over Na$_2$SO$_4$ and evaporated to dryness, affording 4.1 g of crude N-[3-(bromoacetyl)-2-fluorophenyl]-2,5-difluoro-N-(methoxymethyl)benzenesulfonamide.

Half of this material (3.40 mmol) was dissolved in absolute ethanol (34 mL). Tetrahydro-2H-pyran-4-carbothioamide (prepared as described in Preparation 6, 595 mg, 1.2 eq) was added and the mixture was stirred at 60° C. for 1 h. The mixture was then concentrated under reduced pressure, taken up with ethyl acetate and washed with saturated aqueous NaHCO$_3$, water and brine. The organic phase was dried over Na$_2$SO$_4$ and evaporated to dryness. The crude product was purified by flash chromatography on silica gel (Hex/ethyl acetate 6:4) to give 1.5 g (88%) of the title compound as amorphous solid.

HPLC: R$_t$: 7.07 min $^1$H NMR (600 MHz, DMSO-d$_6$) δ ppm 8.17-8.05 (m, 1H), 7.78 (d, J=2.4 Hz, 1H), 7.71-7.64 (m, 1H), 7.61 (dt, J=4.0, 9.3 Hz, 1H), 7.54-7.46 (m, 1H), 7.34-7.29 (m, 1H), 7.29-7.21 (m, 1H), 5.10 (s, 2H), 3.98-3.90 (m, J=2.1, 2.1, 9.6 Hz, 2H), 3.48 (dt, J=1.9, 11.6 Hz, 2H), 3.38 (s, 3H), 3.37-3.31 (m, 1H), 2.04-1.99 (m, J=1.8, 12.8 Hz, 2H), 1.81-1.66 (m, 2H)

HRMS (ESI) calcd for C$_{22}$H$_{22}$N$_2$O$_4$F$_3$S$_2$ [M+H]$^+$ 499.0968. found 499.0974.

Operating in an analogous way, but using the proper thioamide, the following intermediate was also obtained:

Benzyl 4-[4-(3-{[(2,5-difluorophenyl)sulfonyl]
(methoxymethyl)amino}-2-fluorophenyl)-1,3-thia-
zol-2-yl]piperidine-1-carboxylate, cmpd. of formula
9 [n=1; R1=1-benzyloxycarbonyl-piperidin-4-yl;
R4=F; R5=H; R6=2,5-difluorophenyl;
Rx=methoxymethyl]

Method A, Steps d1 and e
HPLC: $R_t$: 7.90 min
$^1$H NMR (600 MHz, DMSO-$d_6$) δ ppm 8.15-8.07 (m, 1H), 7.77 (d, J=2.4 Hz, 1H), 7.70-7.64 (m, 1H), 7.63-7.57 (m, 1H), 7.53-7.46 (m, 1H), 7.40-7.34 (m, 4H), 7.34-7.28 (m, 2H), 7.28-7.24 (m, 1H), 5.10 (s, 2H), 5.09 (s, 2H), 4.14-4.05 (m, 2H), 3.12-2.93 (m, 2H), 3.37 (s, 3H), 3.37-3.31 (m, 1H), 2.13-2.03 (m, J=11.5 Hz, 2H), 1.63 (dq, J=4.2, 12.2 Hz, 2H)
HRMS (ESI) calcd for $C_{30}H_{29}N_3O_5F_3S_2$ [M+H]$^+$ 632.1495. found 632.1501.

N-{3-[5-bromo-2-(tetrahydro-2H-pyran-4-yl)-1,3-
thiazol-4-yl]-2-fluorophenyl}-2,5-difluoro-N-(meth-
oxymethyl)benzenesulfonamide, cmpd. of formula
10 [n=1; R1=tetrahydropyran-4-yl; R4=F; R5=H;
R6=2,5-difluorophenyl; Rx=methoxymethyl;
Hal=Br]

Method A, Step f
2,5-difluoro-N-{2-fluoro-3-[2-(tetrahydro-2H-pyran-4-yl)-1,3-thiazol-4-yl]phenyl}-N-(methoxymethyl)benzene-sulfonamide (1.4 g, 2.808 mmol) was dissolved in acetic acid (28 mL), sodium acetate (461 mg, 5.616 mmol, 2 eq) was added and the mixture was stirred until complete dissolution. Bromine (0.2 mL, 3.9 mmol, 1.4 eq) was then added dropwise over 45 min and stirred at r.t. overnight. The reaction mixture was then added dropwise to a cooled 1 N solution of sodium hydroxide (300 mL) and the mixture was extracted with ethyl acetate. The organic phase was washed with 0.5 N sodium hydroxide, 5% NaHSO$_3$ and brine, dried over Na$_2$SO$_4$ and evaporated to dryness, affording 1.26 g (78%) of the title product as colourless oil.
HPLC: $R_t$: 7.24 min
$^1$H NMR (600 MHz, DMSO-$d_6$) δ ppm 7.69-7.64 (m, 1H), 7.63-7.56 (m, 2H), 7.53-7.48 (m, 1H), 7.47-7.42 (m, 1H), 7.35 (t, J=7.9, 1H), 5.10 (s, 2H), 3.95-3.85 (m, 2H), 3.44 (dt, J=1.9, 11.6 Hz, 2H), 3.38 (s, 3H), 3.31-3.23 (m, 2H), 1.98-1.92 (m, 2H), 1.75-1.65 (m, 2H)
HRMS (ESI) calcd for $C_{22}H_{21}N_2O_4F_3S_2Br$ [M+H]$^+$ 577.0073. found 577.0075.

Operating in an analogous way the following intermediate was also obtained:

Benzyl 4-[5-bromo-4-(3-{[(2,5-difluorophenyl)sul-
fonyl](methoxymethyl)amino}-2-fluorophenyl)-1,3-
thiazol-2-yl]piperidine-1-carboxylate, cmpd. of for-
mula 10 [n=1; R1=1-benzyloxycarbonyl-piperidin-4-
yl; R4=F; R5=H; R6=2,5-difluorophenyl;
Rx=methoxymethyl; Hal=Br]

Method A, Step f
HPLC: $R_t$: 8.03 min
$^1$H NMR (600 MHz, DMSO-$d_6$) δ ppm 7.67-7.62 (m, 1H), 7.62-7.55 (m, 2H), 7.53-7.47 (m, 1H), 7.47-7.42 (m, 1H), 7.40-7.33 (m, 5H), 7.33-7.29 (m, 1H), 5.09 (br. s., 2H), 5.08 (br. s., 2H), 4.10-4.04 (m, J=13.2 Hz, 2H), 3.38 (s, 3H), 3.29-3.22 (m, 1H), 3.05-2.93 (m, J=11.0 Hz, 2H), 2.05-1.99 (m, J=11.5 Hz, 2H), 1.63-1.54 (m, 2H)

HRMS (ESI) calcd for $C_{30}H_{28}N_3O_5F_3S_2Br$ [M+H]$^+$ 710.0601. found 710.0618.

2,5-difluoro-N-{2-fluoro-3-[5-(3-fluoropyridin-4-
yl)-2-(tetrahydro-2H-pyran-4-yl)-1,3-thiazol-4-yl]
phenyl}benzenesulfonamide, cmpd. of formula (I)B
(cmpd. 34) [m, n=1; R2, R5=H; R3=3-F; R4=F;
R6=2,5-difluorophenyl; R1'=tetrahydropyran-4-yl]

Method A, Steps h and j
N-{3-[5-bromo-2-(tetrahydro-2H-pyran-4-yl)-1,3-thiazol-4-yl]-2-fluorophenyl}-2,5-difluoro-N-(methoxymethyl)benzenesulfonamide (105 mg, 0.182 mmol) was dissolved in a microwave tube in a 9:1 DME/H$_2$O mixture (2.2 mL) and argon was bubbled through the solution for 5 min. Cesium carbonate (148 mg, 0.454 mmol, 2.5 eq) was added, followed by 3-F-4-pyridineboronic acid pinacol ester (82 mg, 0.368 mmol, 2 eq) and Pd(dppf)Cl$_2$.DCM (15 mg, 0.018 mmol, 0.1 eq) and the mixture was irradiated in the microwave oven at 100° c. for 30 min. An addition of Pd(dppf)Cl$_2$.DCM (15 mg, 0.018 mmol, 0.1 eq) was made and the mixture underwent a second microwave cycle. The mixture was filtered through a celite pad and the celite was washed thoroughly with ethyl acetate. The filtrate was washed with saturated aqueous NaHCO$_3$ and brine, dried over Na$_2$SO$_4$ and evaporated to dryness. The crude product was purified by flash chromatograpy on silica gel to give 76 mg of 2,5-difluoro-N-{2-fluoro-3-[5-(3-fluoropyridin-4-yl)-2-(tetrahydro-2H-pyran-4-yl)-1,3-thiazol-4-yl]phenyl}-N-(methoxymethyl) benzenesulfonamide impure of a dimeric by-product. This product was treated with a 9:1 TFA/water mixture (1 mL) and stirred at 60° C. for 1 h. The mixture was evaporated to dryness, taken up with DCM and washed with saturated aqueous NaHCO$_3$ and brine, dried over Na$_2$SO$_4$ and concentrated under reduced pressure. The crude product was purified by flash chromatography on silica gel (Hex/acetone 65:35) to give 24 mg of the title compound as an off-white solid.
HPLC: $R_t$: 6.27 min
$^1$H NMR (401 MHz, DMSO-$d_6$)(selected signals) δ ppm 10.64 (s, 1H), 8.56 (d, J=1.6 Hz, 1H), 8.33 (d, J=4.9 Hz, 1H), 7.61-7.54 (m, 1H), 7.49-7.43 (m, 1H), 7.39-7.35 (m, 1H), 7.34-7.28 (m, 2H), 7.22-7.16 (m, 2H), 4.00-3.88 (m, 2H), 3.48 (dt, J=2.0, 11.6 Hz, 2H), 2.02 (dd, J=2.0, 12.8 Hz, 2H), 1.82-1.71 (m, 2H)
HRMS (ESI) calcd for $C_{25}H_{20}N_3O_3F_4S_2$ [M+H]$^+$ 550.0877. found 550.0894.

Example 21

Synthesis of N-[2-({4-[4-(3-{[(2,5-difluorophenyl)
sulfonyl]amino}-2-fluorophenyl)-2-(tetrahydro-2H-
pyran-4-yl)-1,3-thiazol-5-yl]pyridin-2-yl}amino)
ethyl]acetamide, cmpd. of formula (I)Z1 (cmpd. 36)
[m, n=1; R1=tetrahydropyran-4-yl; R3, R5=H;
R4=F; R6=2,5-difluorophenyl; R18=2-acetylamino-
ethyl]

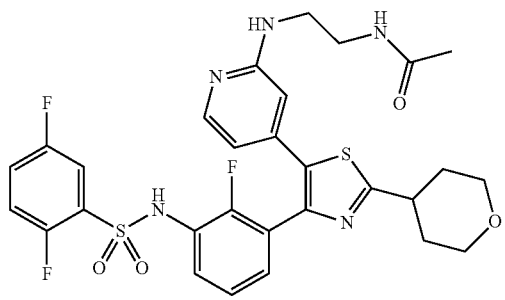 [SMILES: CC(=O)NCCNc1cc(-c2sc(C3CCOCC3)nc2-c2cccc(NS(=O)(=O)c3cc(F)ccc3F)c2F)ccn1]

2,5-difluoro-N-{2-fluoro-3-[5-(pyridin-4-yl)-2-(tetrahydro-2H-pyran-4-yl)-1,3-thiazol-4-yl]phenyl}-N-(methoxymethyl)benzenesulfonamide, cmpd. of formula (I)A [m, n=1; R2, R3, R5=H; R4=F; R6=2,5-difluorophenyl; R1'=tetrahydropyran-4-yl; Rx=methoxymethyl] (corresponding to the cmpd. of formula (I)W of Method F, wherein m, n=1; R1=tetrahydropyran-4-yl; R3, R5=H; R4=F; R6=2,5-difluorophenyl; Rx=methoxymethyl)

Method A, Step h

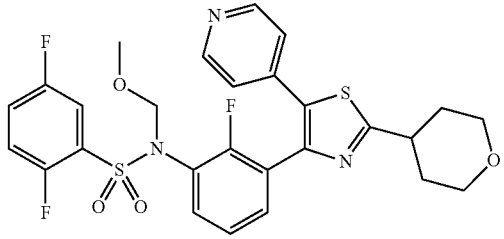 [SMILES: COCN(c1cccc(-c2nc(C3CCOCC3)sc2-c2ccncc2)c1F)S(=O)(=O)c1cc(F)ccc1F]

N-{3-[5-bromo-2-(tetrahydro-2H-pyran-4-yl)-1,3-thiazol-4-yl]-2-fluorophenyl}-2,5-difluoro-N-(methoxymethyl)benzenesulfonamide (1.26 g, 2.182 mmol) was dissolved in a 9:1 dioxane/H$_2$O mixture (22 mL) and argon was bubbled through the solution for 5 min. Cesium carbonate (1.78 mg, 5.455 mmol, 2.5 eq) was added, followed by 4-pyridineboronic acid pinacol ester (895 mg, 4.364 mmol, 2 eq) and Pd(dppf)Cl$_2$.DCM (178 mg, 0.218 mmol, 0.1 eq) and the mixture was stirred at 100° C. for 1.5 h. The mixture was filtered through a celite pad and the celite was washed thoroughly with ethyl acetate. The filtrate was concentrated under reduced pressure, taken up with ethyl acetate and washed with saturated aqueous NaHCO$_3$ and brine, dried over Na$_2$SO$_4$ and evaporated to dryness. The crude product was purified by flash chromatography on silica gel (DCM/MeOH 97:3) to give 1.09 g (87%) of the title compound as amorphous solid.

HPLC: R$_t$: 5.83 min.

$^1$H NMR (401 MHz, DMSO-d$_6$) δ ppm 8.46-8.50 (m, J=4.9 Hz, 2H), 7.41-7.67 (m, 4H), 7.28-7.38 (m, 2H), 7.07-7.17 (m, 3H), 4.97 (s, 2H), 3.91-3.99 (m, 1H), 3.44-3.52 (m, 1H), 1.98-2.06 (m, 2H), 1.70-1.84 (m, 2H)

HRMS (ESI) calcd for C$_{27}$H$_{25}$F$_3$N$_3$O$_4$S$_2$ [M+H]$^+$ 576.1233. found 576.1252.

Operating in an analogous way the following compound was also obtained:

Benzyl-4-[4-(3-{[(2,5-difluorophenyl)sulfonyl](methoxymethyl)amino}-2-fluorophenyl)-5-(pyridin-4-yl)-1,3-thiazol-2-yl]piperidine-1-carboxylate, cmpd. of formula (I)A [m, n=1; R2, R3, R5=H; R4=F; R6=2,5-difluorophenyl; R1'=1-benzyloxycarbonyl-piperidin-4-yl; Rx=methoxymethyl]

Method A, Step h

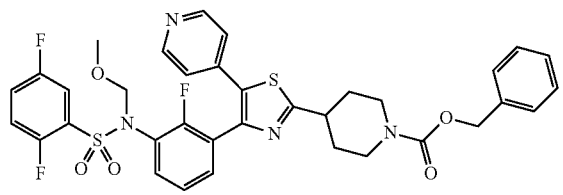 [SMILES: COCN(c1cccc(-c2nc(C3CCN(C(=O)OCc4ccccc4)CC3)sc2-c2ccncc2)c1F)S(=O)(=O)c1cc(F)ccc1F]

HPLC: R$_t$: 7.37 min.

$^1$H NMR (600 MHz, DMSO-d$_6$) δ ppm 8.54-8.43 (m, 2H), 7.65-7.56 (m, 2H), 7.52 (dt, J=4.0, 9.4 Hz, 1H), 7.47-7.42 (m, 1H), 7.40-7.35 (m, 4H), 7.35-7.28 (m, 3H), 7.14-7.03 (m, 2H), 5.09 (s, 2H), 4.96 (s, 2H), 4.16-4.01 (m, 2H), 3.35-3.29 (m, 1H), 3.23 (s, 3H), 3.03 (dd, J=7.1, 11.6 Hz, 2H), 2.13-2.07 (m, J=13.0 Hz, 2H), 1.65 (dq, J=4.2, 12.2 Hz, 2H)

HRMS (ESI) calcd for C$_{35}$H$_{31}$N$_{14}$O$_5$F$_3$S$_2$ [M+H]$^+$ 709.1761. found 709.1763.

2,5-difluoro-N-{2-fluoro-3-[5-(1-oxidopyridin-4-yl)-2-(tetrahydro-2H-pyran-4-yl)-1,3-thiazol-4-yl]phenyl}-N-(methoxymethyl)benzenesulfonamide, cmpd. of formula 44 [m, n=1; R1=tetrahydropyran-4-yl; R3, R5=H; R4=F; R6=2,5-difluorophenyl; Rx=methoxymethyl]

Method F, Step a 2,5-Difluoro-N-{2-fluoro-3-[5-(pyridin-4-yl)-2-(tetrahydro-2H-pyran-4-yl)-1,3-thiazol-4-yl]phenyl}-N-(methoxymethyl)benzenesulfonamide (500 mg, 0.869 mmol) was dissolved in DCM (9 mL) and 70% m-chloroperbenzoic acid was added (215 mg, 0.869 mmol, 1 eq). After stirring for 1 h an addition of m-chloroperbenzoic acid (215 mg, 0.869 mmol, 1 eq) was made, followed by a second addition of 190 mg after 1 more h. After 5 total h the mixture was diluted with DCM and washed with saturated aqueous NaHCO$_3$ and brine, dried over Na$_2$SO$_4$ and evaporated to dryness. The crude product was purified by flash chromatography on silica gel (DCM/MeOH 95:5) to give 420 mg (82%) of the title compound as amorphous solid.

HPLC: R$_t$: 5.40 min.

$^1$H NMR (600 MHz, DMSO-d$_6$) δ ppm 8.20-8.02 (m, 2H), 7.68-7.61 (m, 2H), 7.58-7.53 (m, 1H), 7.53-7.49 (m, 1H), 7.36-7.23 (m, 2H), 7.19-7.09 (m, 2H), 4.99 (s, 2H), 3.98-3.87 (m, 2H), 3.48 (dt, J=2.0, 11.6 Hz, 2H), 3.39-3.31 (m, 1H), 3.26 (s, 3H), 2.05-1.94 (m, 2H), 1.81-1.71 (m, 2H)

HRMS (ESI) calcd for C$_{27}$H$_{25}$N$_3$O$_5$F$_3$S$_2$ [M+H]$^+$ 592.1182. found 592.1188.

Operating in an analogous way the following intermediate was also obtained:

Benzyl 4-[4-(3-{[(2,5-difluorophenyl)sulfonyl](methoxymethyl)amino}-2-fluorophenyl)-5-(1-oxidopyridin-4-yl)-1,3-thiazol-2-yl]piperidine-1-carboxylate, cmpd. of formula 44 [m, n=1; R1=1-benzyloxycarbonyl-piperidin-4-yl; R3, R5=H; R4=F; R6=2,5-difluorophenyl; Rx=methoxymethyl]

Method F, Step a

HPLC: R$_t$: 6.52 min $^1$H NMR (600 MHz, DMSO-d$_6$) δ ppm 8.16-8.02 (m, 2H), 7.66-7.61 (m, 2H), 7.56 (dd, J=3.9, 9.4 Hz, 1H), 7.52-7.48 (m, 1H), 7.39-7.36 (m, 4H), 7.34-7.29 (m, 3H), 7.19-7.11 (m, 2H), 5.10 (s, 2H), 4.99 (s, 2H), 4.15-3.97 (m, J=13.6 Hz, 2H), 3.34-3.29 (m, 1H), 3.26 (s, 3H), 3.08-2.96 (m, 2H), 2.13-2.07 (m, 2H), 1.69-1.59 (m, J=3.6, 12.2 Hz, 2H)

HRMS (ESI) calcd for $C_{35}H_{32}N_4O_6F_3S_2$ [M+H]$^+$ 725.1710. found 725.1710.

N-[2-({4-[4-(3-{[(2,5-difluorophenyl)sulfonyl](methoxymethyl)amino}-2-fluorophenyl)-2-(tetrahydro-2H-pyran-4-yl)-1,3-thiazol-5-yl]pyridin-2-yl}amino)ethyl]acetamide, cmpd. of formula (I)X [m, n=1; R1=tetrahydropyran-4-yl; R3, R5=H; R4=F; R6=2,5-difluorophenyl; Rx=methoxymethyl; R18=2-acetylaminoethyl;]

Method F, Step b

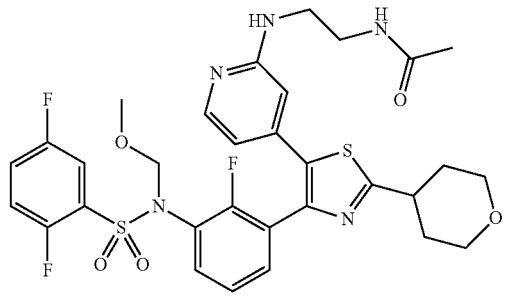 [SMILES: COCN(c1cccc(-c2nc(C3CCOCC3)sc2-c2ccnc(NCCNC(C)=O)c2)c1F)S(=O)(=O)c1cc(F)ccc1F]

2,5-Difluoro-N-{2-fluoro-3-[5-(1-oxidopyridin-4-yl)-2-(tetrahydro-2H-pyran-4-yl)-1,3-thiazol-4-yl]phenyl}-N-(methoxymethyl)benzenesulfonamide (104 mg, 0.175 mmol) was dissolved in DCM (1.5 mL). DIPEA (0.112 mL, 0.656 mmol, 3.75 eq) was added, followed by PyBroP (106 mg, 0.228 mmol, 1.3 eq) and N-acetylethylenediamine (0.021 mL, 0.219 mmol, 1.25 eq) and the mixture was stirred at r.t. overnight. Further additions of both acetylethylenediamine (0.01 mL) and PyBroP (20 mg) were made and, after 2 more h of stirring the mixture was diluted with DCM and washed with water and brine, dried over Na$_2$SO$_4$ and evaporated to dryness. The crude product was purified by flash chromatograpy on silica gel (DCM/MeOH 96:4) to give 110 mg (93%) of the title compound.

HPLC: R$_t$: 5.78 min.

$^1$H NMR (600 MHz, DMSO-d$_6$) δ ppm 7.88 (t, J=5.4 Hz, 1H), 7.80 (d, J=5.1 Hz, 1H), 7.67-7.59 (m, 1H), 7.58-7.51 (m, 2H), 7.49-7.43 (m, 1H), 7.36-7.31 (m, 1H), 7.29 (t, J=7.9 Hz, 1H), 6.63 (t, J=5.6 Hz, 1H), 6.33 (s, 1H), 6.06 (dd, J=1.4, 5.2 Hz, 1H), 4.98 (s, 2H), 3.94 (ddd, J=1.9, 1.9, 9.7 Hz, 2H), 3.47 (dt, J=2.0, 11.6 Hz, 2H), 3.42-3.35 (m, 1H), 3.32-3.28 (m, 1H), 3.26 (s, 3H), 3.24-3.19 (m, 1H), 3.18-3.09 (m, 2H), 2.01 (dd, J=2.1, 12.7 Hz, 2H), 1.78 (s, 3H), 1.30-1.21 (m, 2H)

HRMS (ESI) calcd for $C_{31}H_{33}N_5O_5F_3S_2$ [M+H]$^+$ 676.1870. found 676.1880.

N-[2-({4-[4-(3-{[(2,5-difluorophenyl)sulfonyl]amino}-2-fluorophenyl)-2-(tetrahydro-2H-pyran-4-yl)-1,3-thiazol-5-yl]pyridin-2-yl}amino)ethyl]acetamide, cmpd. of formula (I)Z1 (cmpd. 36) [m, n=1; R1=tetrahydropyran-4-yl; R3, R5=H; R4=F; R6=2,5-difluorophenyl; R18=2-acetylaminoethyl]

Method F, Step d1

N-[2-({4-[4-(3-{[(2,5-difluorophenyl)sulfonyl](methoxymethyl)amino}-2-fluorophenyl)-2-(tetrahydro-2H-pyran-4-yl)-1,3-thiazol-5-yl]pyridin-2-yl}amino)ethyl]acetamide (197 mg, 0.158 mmol) was treated with a 9:1 TFA/water mixture (2 mL) and stirred at 60° C. for 2 h. The mixture was evaporated to dryness, taken up with DCM and washed with saturated aqueous NaHCO$_3$ and brine, dried over Na$_2$SO$_4$ and concentrated under reduced pressure. The crude product was purified by flash chromatography on silica gel (DCM/MeOH 95:5) to give 55 mg of the title compound as an off-white solid.

HPLC: R$_t$: 5.47 min.

$^1$H NMR (600 MHz, DMSO-d$_6$) δ ppm 10.68 (br. s., 1H), 7.91 (t, J=5.4 Hz, 1H), 7.77 (d, J=5.5 Hz, 1H), 7.60-7.53 (m, 1H), 7.48-7.42 (m, 2H), 7.36-7.26 (m, 2H), 7.24-7.16 (m, 1H), 6.83-6.59 (m, 1H), 6.38 (br. s., 1H), 6.02 (br. s., 1H), 3.93 (td, J=2.1, 9.5 Hz, 2H), 3.46 (dt, J=1.8, 11.6 Hz, 2H), 3.32-3.27 (m, 1H), 3.26-3.21 (m, J=5.3 Hz, 2H), 3.16 (q, J=5.9 Hz, 2H), 2.03-1.96 (m, J=1.9, 12.9 Hz, 2H), 1.80 (s, 3H), 1.77-1.68 (m, 2H)

HRMS (ESI) calcd for $C_{29}H_{29}N_5O_4F_3S_2$ [M+H]$^+$ 632.1608. found 632.1625.

The following side-product was also isolated:

N-(3-{5-[2-(3-acetylimidazolidin-1-yl)pyridin-4-yl]-2-(tetrahydro-2H-pyran-4-yl)-1,3-thiazol-4-yl}-2-fluorophenyl)-2,5-difluorobenzenesulfonamide, cmpd. of formula (I)Z [m, n=1; R3, R5=H; R4=F; R6=2,5-difluorophenyl; R1=tetrahydropyran-4-yl; R17-R18=3-acetyl-imidazolidin-1-yl]

Method F, Step d1

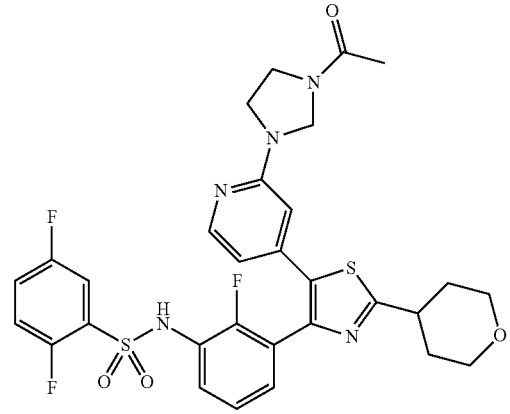 [SMILES: CC(=O)N1CCN(c2cc(-c3sc(C4CCOCC4)nc3-c3cccc(NS(=O)(=O)c4cc(F)ccc4F)c3F)ccn2)C1]

HPLC: R$_t$: 5.74 min.

$^1$H NMR (600 MHz, DMSO-d$_6$) δ ppm 10.67 (br. s., 1H), 7.99 (t, J=5.9 Hz, 1H), 7.55 (br. s., 1H), 7.45 (br. s., 1H), 7.41-7.37 (m, 1H), 7.33 (t, J=6.9 Hz, 2H), 7.23 (br. s., 1H), 6.34 (dd, J=4.9, 19.6 Hz, 1H), 6.28 (d, J=7.7 Hz, 1H), 4.78 and 4.66 (s, 2H, 2 rotamers), 3.98-3.87 (m, J=2.4, 9.0 Hz, 2H), 3.81-3.75 (m, 1H), 3.63 (t, J=6.8 Hz, 1H), 3.54-3.50 (m, 1H), 3.47 (t, J=11.0 Hz, 2H), 3.44-3.40 (m, 3H), 3.32-3.27 (m, 1H), 2.04-1.97 (m, 3H), 1.79-1.74 (m, 2H)

HRMS (ESI) calcd for $C_{30}H_{29}N_5O_4F_3S_2$ [M+H]$^+$ 644.1608. found 644.1623.

Operating in an analogous way but using the proper amine the following compounds were also obtained:

N-{3-[5-(2-{[2-(dimethylamino)ethyl]amino}pyridin-4-yl)-2-(tetrahydro-2H-pyran-4-yl)-1,3-thiazol-4-yl]-2-fluorophenyl}-2,5-difluorobenzenesulfonamide, cmpd. of formula (I)Z1 (cmpd. 40) [m, n=1; R3, R5=H; R4=F; R6=2,5-difluorophenyl; R1=tetrahydropyran-4-yl; R18=2-dimethylaminoethyl]

Method F, Step d1

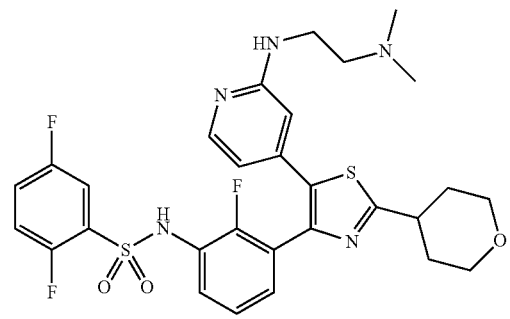 [SMILES: CN(C)CCNc1cc(-c2sc(C3CCOCC3)nc2-c2cccc(NS(=O)(=O)c3cc(F)ccc3F)c2F)ccn1]

HPLC: R$_t$: 5.33 min.

$^1$H NMR (600 MHz, DMSO-d$_6$) δ ppm 7.85 (d, J=5.3 Hz, 1H), 7.42 (ddd, J=3.3, 5.1, 8.1 Hz, 1H), 7.39-7.34 (m, 1H), 7.31 (dt, J=4.2, 9.0 Hz, 1H), 7.23 (dt, J=1.4, 7.9 Hz, 1H), 6.96 (t, J=7.9 Hz, 1H), 6.86 (br. s., 1H), 6.66 (t, J=5.2 Hz, 1H), 6.40 (s, 1H), 6.22 (dd, J=1.2, 5.2 Hz, 1H), 3.93 (td, J=2.0, 9.6 Hz, 2H), 3.47 (dt, J=1.8, 11.6 Hz, 2H), 3.41-3.25 (m, 3H), 2.86 (br. s., 2H), 2.56 (s, 6H), 2.07-1.93 (m, J=2.0, 12.8 Hz, 2H), 1.79-1.68 (m, 2H)

HRMS (ESI) calcd for C$_{29}$H$_{31}$N$_5$O$_3$F$_3$S$_2$ [M+H]$^+$ 618.1815. found 618.1822.

Methyl [(2S)-1-({4-[4-(3-{[(2,5-difluorophenyl)sulfonyl]amino}-2-fluorophenyl)-2-(tetrahydro-2H-pyran-4-yl)-1,3-thiazol-5-yl]pyridin-2-yl}amino)propan-2-yl]carbamate, cmpd. of formula (I)Z1 (cmpd. 41) [m, n=1; R1=tetrahydropyran-4-yl; R3, R5=H; R4=F; R6=2,5-difluorophenyl; R18=2-methoxycarbonyl-2-methyl aminoethyl]

Method F, Step d1

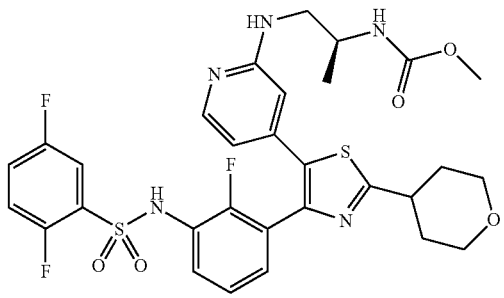 [SMILES: COC(=O)N[C@@H](C)CNc1cc(-c2sc(C3CCOCC3)nc2-c2cccc(NS(=O)(=O)c3cc(F)ccc3F)c2F)ccn1]

HPLC: R$_t$: 6.11 min.

$^1$H NMR (600 MHz, DMSO-d$_6$) δ ppm 10.66 (br. s., 1H), 7.75 (d, J=5.5 Hz, 1H), 7.60-7.54 (m, 1H), 7.51-7.42 (m, 2H), 7.33 (t, J=6.9 Hz, 1H), 7.27 (br. s., 1H), 7.22-7.16 (m, 1H), 7.01 (d, J=7.3 Hz, 1H), 6.63 (br. s., 1H), 6.40 (s, 1H), 5.96 (d, J=4.9 Hz, 1H), 3.93 (td, J=2.0, 9.5 Hz, 2H), 3.64 (td, J=6.8, 14.0 Hz, 1H), 3.50 (s, 3H), 3.47 (dt, J=1.9, 11.6 Hz, 2H), 3.34-3.26 (m, 1H), 3.21-3.15 (m, 2H), 2.00 (dd, J=1.9, 12.9 Hz, 2H), 1.80-1.65 (m, 2H), 1.03 (d, J=6.6 Hz, 3H)

HRMS (ESI) calcd for C$_{30}$H$_{31}$N$_5$O$_5$F$_3$S$_2$ [M+H]$^+$ 662.1713. found 662.1714.

The following side-product was also isolated:

2,5-difluoro-N-{2-fluoro-3-[5-{2-[(4S)-3-(methoxymethyl)-4-methyl-2-oxoimidazolidin-1-yl]pyridin-4-yl}-2-(tetrahydro-2H-pyran-4-yl)-1,3-thiazol-4-yl]phenyl}benzenesulfonamide, cmpd. of formula (I)Z [m, n=1; R1=tetrahydropyran-4-yl; R3, R5=H; R4=F; R6=2,5-difluorophenyl; R17-R18=3-methoxymethyl-4-methyl-2-oxoimidazolidin-1-yl]

Method F, Step d1

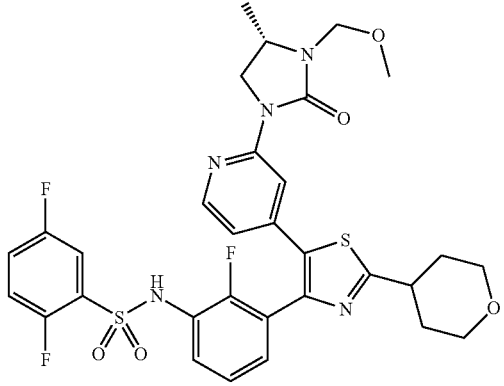 [SMILES: COCN1C(=O)N(c2cc(-c3sc(C4CCOCC4)nc3-c3cccc(NS(=O)(=O)c4cc(F)ccc4F)c3F)ccn2)C[C@@H]1C]

HPLC: R$_t$: 6.66 min.

$^1$H NMR (600 MHz, DMSO-d$_6$) δ ppm 10.67 (s, 1H), 7.98 (d, J=5.3 Hz, 1H), 7.55 (d, J=7.5 Hz, 1H), 7.46 (dt, J=3.8, 9.0 Hz, 1H), 7.42-7.38 (m, 1H), 7.37-7.29 (m, 2H), 7.26-7.14 (m, 1H), 6.33 (d, J=4.9 Hz, 1H), 6.25 (s, 1H), 4.67 (s, 2H), 4.19 (dquin, J=2.8, 6.6 Hz, 1H), 3.98-3.87 (m, 2H), 3.65 (s, 3H), 3.51-3.42 (m, 3H), 3.29-3.14 (m, 2H), 2.05-1.97 (m, J=1.9, 12.7 Hz, 2H), 1.80-1.67 (m, 2H), 1.21 (d, J=6.4 Hz, 3H)

HRMS (ESI) calcd for C$_{31}$H$_{31}$N$_5$O$_5$F$_3$S$_2$ [M+H]$^+$ 674.1713. found 674.1726.

Example 22

Synthesis of 2,5-difluoro-N-{3-[5-(pyridin-4-yl)-2-(tetrahydro-2H-pyran-4-yl)-1,3-thiazol-4-yl]phenyl}benzenesulfonamide, cmpd. of formula (I)T [m, n=1; R1=tetrahydropyran-4-yl; R2, R3, R4, R5=H; R6=2,5-difluorophenyl]

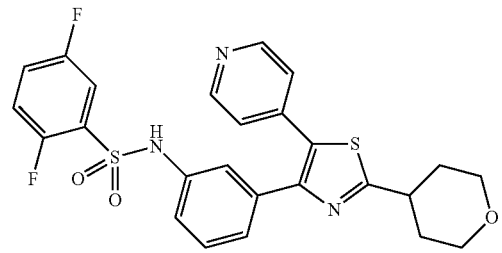 [SMILES: O=S(=O)(Nc1cccc(-c2nc(C3CCOCC3)sc2-c2ccncc2)c1)c1cc(F)ccc1F]

4-(3-nitrophenyl)-2-(tetrahydro-2H-pyran-4-yl)-1,3-thiazole, cmpd. of formula 40 [n=1; R1=tetrahydropyran-4-yl; R4, R5=H]

Method E, Step b

A mixture of 2-bromo-1-(3-nitrophenyl)ethanone (245 mg, 1 mmol) and tetrahydro-2H-pyran-4-carbothioamide (144 mg, 1 mmol) is suspended in absolute ethanol (20 mL) and heated to reflux for 2 h. The solution is then cooled and evaporated to dryness. The crude is dissolved in DCM and washed twice with a solution of saturated sodium bicarbonate and once with water. The organic layer is dried up with sodium sulfate, filtered and evaporated to dryness to yield 285 mg of the title compound (98%).

HPLC: R$_t$: 5.66 min $^1$H NMR (600 MHz, DMSO-d$_6$) δ ppm 8.75 (t, J=1.4 Hz, 1H), 8.40 (dt, J=1.4, 8.0 Hz, 1H), 8.33 (s, 1H), 8.19 (dd, J=1.4, 8.0 Hz, 1H), 7.75 (t, J=8.0 Hz, 1H), 3.95 (dt, J=1.8, 11.7 Hz, 2H), 3.50 (dt, J=1.8, 11.7 Hz, 2H), 3.40-3.33 (m, 1H), 2.06-1.99 (m, 2H), 1.84-1.71 (m, 2H).

HRMS (ESI) calcd for C$_{14}$H$_{15}$N$_2$O$_3$S [M+H]+ 291.0798. found 291.0798.

5-bromo-4-(3-nitrophenyl)-2-(tetrahydro-2H-pyran-4-yl)-1,3-thiazole, cmpd. of formula 41 [n=1; R1=tetrahydropyran-4-yl; R4, R5=H; Hal=Br]

Method E, Step c

To a solution of 4-(3-nitrophenyl)-2-(tetrahydro-2H-pyran-4-yl)-1,3-thiazole (113 mg, 0.390 mmol) in acetic acid (10.5 mL), sodium acetate (71 mg, 0.866 mmol, 2.2 eq.) was added, and the mixture stirred for 30 min. To the solution so obtained, bromine was added dropwise and the reaction followed by HPLC up to completion (total Br$_2$: 44 μL, 137 mg, 0.86 mmol, 2.2 eq). The solution was poured in 100 mL of 1M sodium hydroxide and extracted three times with ethyl acetate. The organic layer was washed with brine, dried up with sodium sulfate and evaporated to dryness to yield 5-bromo-4-(3-nitrophenyl)-2-(tetrahydro-2H-pyran-4-yl)-1,3-thiazole (141 mg, 100%)

HPLC: R$_t$: 7.29 min $^1$H NMR (600 MHz, DMSO-d$_6$) δ ppm 8.72 (t, J=2.2 Hz, 1H), 8.39 (ddd, J=1.2, 2.2, 8.0 Hz, 1H), 8.29 (ddd, J=1.2, 2.2, 8.0 Hz, 1H), 7.82 (t, J=8.0 Hz, 1H), 3.93 (dt, J=2.1, 2.1, 11.6 Hz, 2H), 3.47 (dt, J=2.1, 11.6 Hz, 2H), 2.03-1.98 (m, 2H), 1.81-1.69 (m, 2H).

HRMS (ESI) calcd for C$_{14}$H$_{14}$N$_2$O$_3$SBr [M+H]$^+$ 368.9903. found 368.9894.

4-[4-(3-nitrophenyl)-2-(tetrahydro-2H-pyran-4-yl)-1,3-thiazol-5-yl]pyridine, cmpd. of formula 42 [m, n=1; R1=tetrahydropyran-4-yl; R2, R3, R4, R5=H]

Method E, Step d 5-bromo-4-(3-nitrophenyl)-2-(tetrahydro-2H-pyran-4-yl)-1,3-thiazole (140 mg, 0.379 mmol) was dissolved into a mixture of degassed dioxane (8 mL) and water (1.6 mL). 2-(4-pyridyl)-4,4,5,5-tetramethyl-1,3,2-dioxaborolane (78 mg, 0.379 mmol, 1 eq.), cesium carbonate (370 mg, 1.137 mmol, 3 eq.) and PdCl$_2$(dppf)$_2$.CH$_2$Cl$_2$ (31 mg, 0.0379 mmol, 0.1 eq) were subsequently added to the solution. The mixture so obtained was stirred and heated to reflux under argon atmosphere for 5 h. After cooling, the suspension was filtered through a celite pad, and evaporated to dryness. The crude was re-dissolved in ethyl acetate and washed twice with brine. The organic layer was dried over sodium sulphate and evaporated to dryness. The solid material so obtained was then purified by silica gel column chromatography eluting with ethyl acetate/Hex (6/4) yielding the title compound (98 mg, 70%).

HPLC: R$_t$: 6.01 min $^1$H NMR (600 MHz, DMSO-d$_6$) δ ppm 8.65-8.51 (m, 2H), 8.29 (t, J=2.1 Hz, 1H), 8.21 (ddd, J=1.2, 2.1, 8.1 Hz, 1H), 7.82 (td, J=1.2, 8.1 Hz, 1H), 7.65 (t, J=8.1 Hz, 1H), 7.42-7.29 (m, 2H), 4.02-3.91 (m, 2H), 3.50 (dt, J=1.8, 11.6 Hz, 2H), 2.10-2.02 (m, J=2.6, 12.3 Hz, 2H), 1.85-1.73 (m, J=4.3, 13.1 Hz, 2H).

HRMS (ESI) calcd for C$_{19}$H$_{18}$O$_3$S [M+H]+ 368.1064. found 368.1062.

3-[5-(pyridin-4-yl)-2-(tetrahydro-2H-pyran-4-yl)-1,3-thiazol-4-yl]aniline, cmpd. of formula 43 [m, n=1; R1=tetrahydropyran-4-yl; R2, R3, R4, R5=H]

Method E, Step e

To a solution of 4-[4-(3-nitrophenyl)-2-(tetrahydro-2H-pyran-4-yl)-1,3-thiazol-5-yl]pyridine in absolute ethanol (5 mL) and acetic acid (1 mL), zinc (300 mg) was added. The mixture was stirred and heated to reflux for 3 h. The mixture was dried up and treated with a small amount of 1 N HCl. After stirring for 1 h, the solution was brought to pH 14 using sodium hydroxide and extracted with DCM. The organic layer was dried with sodium sulfate and evaporated to driness. The solid material so obtained was purified by silica gel column chromatography eluting with ethyl acetate/hex/ammonium hydroxyde 8/2/0.1 yielding the title compound (52 mg, 59%).

HPLC: R$_t$: 4.97 min $^1$H NMR (600 MHz, DMSO-d$_6$) δ ppm 8.70-8.30 (m, 2H), 7.34-7.18 (m, 2H), 6.96 (t, J=7.8 Hz, 1H), 6.74 (t, J=1.8 Hz, 1H), 6.58-6.50 (m, 1H), 6.48-6.31 (m, 1H), 5.13 (s, 2H), 3.95 (dt, J=2.1, 11.6 Hz, 2H), 3.48 (dt, J=2.1, 11.6 Hz, 3H), 3.33-3.26 (m, 2H), 2.02 (dd, J=1.8, 13.0 Hz, 2H), 1.82-1.71 (m, 2H).

HRMS (ESI) calcd for C$_{19}$H$_{20}$N$_3$OS [M+H]+ 338.1322. found 338.1331.

2,5-difluoro-N-{3-[5-(pyridin-4-yl)-2-(tetrahydro-2H-pyran-4-yl)-1,3-thiazol-4-yl]phenyl}benzenesulfonamide, cmpd. of formula (I)T [m, n=1; R1=tetrahydropyran-4-yl; R2, R3, R4, R5=H; R6=2,5-difluorophenyl]

Method E, Step f

3-[5-(pyridin-4-yl)-2-(tetrahydro-2H-pyran-4-yl)-1,3-thiazol-4-yl]aniline (28 mg, 0.083 mmol) was dissolved in DCM (2 mL) under nitrogen atmosphere. Dry pyridine (10 uL) was added followed by 2,5-difluorobenzenesulfonyl chloride (20 uL). The mixture was stirred at r.t. for 2 h, then diluted with DCM and washed with a saturated sodium bicarbonate solution. The organic layer was dried up with sodium sulfate and evaporated to dryness. The crude was purified by silica gel column chromatography eluting with DCM/MeOH/ammonium hydroxyde 100/2/0.2 yielding the title compound (23 mg, 53%).

HPLC: R$_t$: 6.11 min $^1$H NMR (600 MHz, DMSO-d$_6$) δ ppm 10.83 (br. s., 1H), 8.75-8.24 (m, 2H), 7.63-7.57 (m, 1H), 7.54-7.40 (m, 2H), 7.26-7.22 (m, 2H), 7.21-7.18 (m, 2H), 7.14-7.04 (m, 2H), 3.95 (td, J=2.1, 11.7 Hz, 2H), 3.49 (dt, J=2.0, 11.6 Hz, 2H), 2.06-1.96 (m, 2H), 1.82-1.67 (m, 2H)

HRMS (ESI) calcd for C$_{25}$H$_{22}$N$_3$O$_3$F$_2$S$_2$ [M+H]$^+$ 514.1065. found 514.1075.

Analogously, but employing the proper sulfonyl chloride, the following compound was obtained:

2,6-difluoro-N-{3-[5-(pyridin-4-yl)-2-(tetrahydro-2H-pyran-4-yl)-1,3-thiazol-4-yl]phenyl}benzenesulfonamide, cmpd. of formula (I)T [m, n=1; R1=tetrahydropyran-4-yl; R2, R3, R4, R5=H; R6=2,6-difluorophenyl]

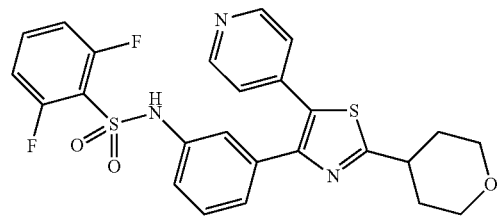 [SMILES: O=S(=O)(Nc1cccc(-c2nc(C3CCOCC3)sc2-c2ccncc2)c1)c1c(F)cccc1F]

HPLC: R$_t$: 5.89 min $^1$H NMR (600 MHz, DMSO-d$_6$) δ ppm 10.96 (s, 1H), 8.60-8.38 (m, 2H), 7.80-7.62 (m, 1H), 7.30 (s, 1H), 7.28-7.21

(m, 3H), 7.20-7.17 (m, 2H), 7.13 (dd, J=1.2, 8.2 Hz, 1H), 7.06 (d, J=7.5 Hz, 1H), 3.99-3.91 (m, J=2.0, 2.0, 9.5 Hz, 2H), 3.49 (dt, J=1.9, 11.6 Hz, 2H), 3.36-3.32 (m, 1H), 2.05-1.98 (m, J=2.0, 12.8 Hz, 2H), 1.82-1.70 (m, 2H)

HRMS (ESI) calcd for $C_{25}H_{22}N_3O_3F_2S_2$ [M+H]$^+$ 514.1065. found 514.1074.

The invention claimed is:
1. A compound of formula (I):

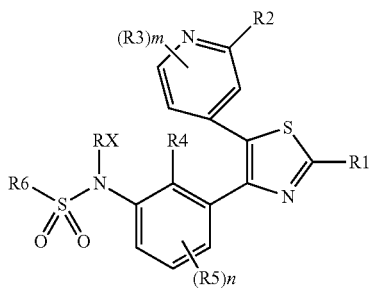

wherein:
n and m are each independently 1 or 2;
R1 is hydrogen, halogen, cyano or an optionally substituted group selected from straight or branched ($C_1$-$C_8$) alkyl, ($C_2$-$C_8$) alkenyl, ($C_2$-$C_8$) alkynyl, ($C_3$-$C_8$) cycloalkyl, ($C_3$-$C_8$) cycloalkenyl, heterocyclyl, aryl and heteroaryl; or R1 is NR7R8 or COR9
wherein:
R7 and R8 are, each independently, hydrogen or an optionally substituted group selected from straight or branched ($C_1$-$C_8$) alkyl, ($C_2$-$C_8$) alkenyl, ($C_2$-$C_8$) alkynyl, ($C_3$-$C_8$) cycloalkyl, ($C_3$-$C_8$) cycloalkenyl, heterocyclyl, aryl and heteroaryl; or, taken together with the nitrogen atom to which they are bonded, R7 and R8 may form an optionally substituted 3 to 8 membered heterocyclyl, optionally containing one additional heteroatom or heteroatomic group selected from S, O, N and NH; or
R7 is hydrogen and R8 is COR10,
wherein:
R10 is OR11, NR12R13 or an optionally substituted group selected from straight or branched ($C_1$-$C_8$) alkyl, ($C_2$-$C_8$) alkenyl, ($C_2$-$C_8$) alkynyl, ($C_3$-$C_8$) cycloalkyl, ($C_3$-$C_8$) cycloalkenyl, heterocyclyl, aryl and heteroaryl, wherein:
R11 is an optionally substituted group selected from straight or branched ($C_1$-$C_8$) alkyl, ($C_2$-$C_8$) alkenyl, ($C_2$-$C_8$) alkynyl, ($C_3$-$C_8$) cycloalkyl, heterocyclyl, aryl and heteroaryl;
R12 and R13 are, each independently, hydrogen or an optionally substituted group selected from straight or branched ($C_1$-$C_8$) alkyl, ($C_2$-$C_8$) alkenyl, ($C_2$-$C_8$) alkynyl, ($C_3$-$C_8$) cycloalkyl, heterocyclyl, aryl and heteroaryl; or, taken together with the nitrogen atom to which they are bonded, R12 and R13 may form an optionally substituted 3 to 8 membered heterocyclyl or heteroaryl, optionally containing one additional heteroatom or heteroatomic group selected from S, O, N and NH;
R9 is OR14 or NR15R16 wherein:
R14 is hydrogen or an optionally substituted group selected from straight or branched ($C_1$-$C_8$) alkyl, ($C_2$-$C_8$) alkenyl, ($C_2$-$C_8$) alkynyl, ($C_3$-$C_8$) cycloalkyl, heterocyclyl, aryl and heteroaryl;
R15 and R16 are, each independently, hydrogen or an optionally substituted group selected from straight or branched ($C_1$-$C_8$) alkyl, ($C_2$-$C_8$) alkenyl, ($C_2$-$C_8$) alkynyl, ($C_3$-$C_8$) cycloalkyl, heterocyclyl, aryl and heteroaryl; or, taken together with the nitrogen atom to which they are bonded, R15 and R16 may form an optionally substituted 3 to 8 membered heterocyclyl or heteroaryl, optionally containing one additional heteroatom or heteroatomic group selected from S, O, N and NH;
R2 is a NHCOR22 group, wherein:
R22 is OR23, NR24R25 or an optionally substituted group selected from straight or branched ($C_1$-$C_8$) alkyl, ($C_2$-$C_8$) alkenyl, ($C_2$-$C_8$) alkynyl, ($C_3$-$C_8$) cycloalkyl, ($C_3$-$C_8$) cycloalkenyl, heterocyclyl, aryl and heteroaryl, wherein:
R23 is an optionally substituted group selected from straight or branched ($C_1$-$C_8$) alkyl, ($C_2$-$C_8$) alkenyl, ($C_2$-$C_8$) alkynyl, ($C_3$-$C_8$) cycloalkyl, ($C_3$-$C_8$) cycloalkenyl, heterocyclyl, aryl and heteroaryl, and
R24 and R25 are, each independently, hydrogen or an optionally substituted group selected from straight or branched ($C_1$-$C_8$) alkyl, ($C_2$-$C_8$) alkenyl, ($C_2$-$C_8$) alkynyl, ($C_3$-$C_8$) cycloalkyl, heterocyclyl, aryl and heteroaryl; or, taken together with the nitrogen atom to which they are bonded, R24 and R25 may form an optionally substituted 3 to 8 membered heterocyclyl or heteroaryl, optionally containing one additional heteroatom or heteroatomic group selected from S, O, N and NH;
R3 is hydrogen, halogen, cyano or an optionally substituted group selected from straight or branched ($C_1$-$C_8$) alkyl, ($C_2$-$C_8$) alkenyl, ($C_2$-$C_8$) alkynyl, ($C_3$-$C_8$) cycloalkyl, ($C_3$-$C_8$) cycloalkenyl, heterocyclyl, aryl and heteroaryl; or R2 is NR17R18, CONR19R20, OR21, SR21 or $SO_2$R21,
wherein:
R17 and R18 are, independently, hydrogen or an optionally substituted group selected from straight or branched ($C_1$-$C_8$) alkyl, ($C_2$-$C_8$) alkenyl, ($C_2$-$C_8$) alkynyl, ($C_3$-$C_8$) cycloalkyl, heterocyclyl, aryl and heteroaryl; or, taken together with the nitrogen atom to which they are bonded, R17 and R18 may form an optionally substituted 3 to 8 membered heterocyclyl or heteroaryl, optionally containing one additional heteroatom or heteroatomic group selected from S, O, N and NH; or
R17 is hydrogen and R18 is COR22,
R19 and R20 are, each independently, hydrogen or an optionally substituted group selected from straight or branched ($C_1$-$C_8$) alkyl, ($C_2$-$C_8$) alkenyl, ($C_2$-$C_8$) alkynyl, ($C_3$-$C_8$) cycloalkyl, heterocyclyl, aryl and heteroaryl; or, taken together with the nitrogen atom to which they are bonded, R19 and R20 may form an optionally substituted 3 to 8 membered heterocyclyl or heteroaryl, optionally containing one additional heteroatom or heteroatomic group selected from S, O, N and NH;
R21 is hydrogen or an optionally substituted group selected from straight or branched ($C_1$-$C_8$) alkyl, ($C_2$-$C_8$) alkenyl, ($C_2$-$C_8$) alkynyl, ($C_3$-$C_8$) cycloalkyl, heterocyclyl, aryl and heteroaryl;
R4 and R5 are, each independently, hydrogen, halogen, trifluoromethyl, trichloromethyl, cyano, OR26 or an optionally substituted group selected from straight or branched (C$_1$-C$_8$) alkyl, (C$_2$-C$_8$) alkenyl, (C$_2$-C$_8$) alkynyl and (C$_3$-C$_8$) cycloalkyl, wherein:
R26 is hydrogen or an optionally substituted group selected from straight or branched (C$_1$-C$_8$) alkyl, (C$_2$-C$_8$) alkenyl, (C$_2$-C$_8$) alkynyl and (C$_3$-C$_8$) cycloalkyl;
Rx is hydrogen, an optionally substituted straight or branched (C$_1$-C$_3$) alkyl, an optionally substituted (C$_2$-C$_6$) acyl group or an optionally substituted (C$_2$-C$_6$) alkoxycarbonyl group;
R6 is a 2,5-difluoro substituted phenyl group;
or pharmaceutically acceptable salts thereof.

2. A compound of formula (I) as defined in claim 1 wherein:
R1 is NR7R8 or an optionally substituted heterocyclyl, wherein R7 and R8 are as defined in claim 1.

3. A compound of formula (I) as defined in claim 1 wherein:
R3 is hydrogen, R4 is halogen and R5 is hydrogen or halogen.

4. A compound of formula (I) as defined in claim 1, wherein:
Rx is hydrogen.

5. A compound of formula (I) or a pharmaceutically acceptable salt thereof as defined in claim 1 which is selected from the group consisting of:
N-{4-[4-(3-{[(2,5-difluorophenyl)sulfonyl]amino}-2-fluorophenyl)-2-(1-methylpiperidin-4-yl)-1,3-thiazol-5-yl]pyridin-2-yl}acetamide;
N-{4-[4-(3-{[(2,5-difluorophenyl)sulfonyl]amino}-2-fluorophenyl)-2-(1-methylpiperidin-4-yl)-1,3-thiazol-5-yl]pyridin-2-yl}-2-methylpropanamide;
N-{4-[2-(1-cyclopropylpiperidin-4-yl)-4-(3-{[(2,5-difluorophenyl)sulfonyl]amino}-2-fluorophenyl)-1,3-thiazol-5-yl]pyridin-2-yl}acetamide;
N-[4-{(3-[(2,5-difluorophenyl)sulfonyl]amino}-2,6-difluorophenyl)-5-(pyridin-4-yl)-1,3-thiazol-2-yl]acetamide;
N-{4-[4-(3-{[(2,5-difluorophenyl)sulfonyl]amino}-2-fluorophenyl)-2-(tetrahydro-2H-pyran-4-yl)-1,3-thiazol-5-yl]pyridin-2-yl}acetamide;
N-{4-[2-tert-butyl-4-(3-{[(2,5-difluorophenyl)sulfonyl]amino}-2-fluorophenyl)-1,3-thiazol-5-yl]pyridin-2-yl}acetamide;
N-{4-[4-(3-{[(2,5-difluorophenyl)sulfonyl]amino}-2-fluorophenyl)-2-(piperidin-4-yl)-1,3-thiazol-5-yl]pyridin-2-yl}acetamide; and
N-{4-[4-(3-{[(2,5-difluorophenyl)sulfonyl]amino}-2-fluorophenyl)-2-(1-ethylpiperidin-4-yl)-1,3-thiazol-5-yl]pyridin-2-yl}acetamide.

6. A pharmaceutical composition comprising a therapeutically effective amount of a compound of formula (I) or a pharmaceutically acceptable salt thereof, as defined in claim 1, and at least one pharmaceutically acceptable excipient, carrier and/or diluent.

7. A pharmaceutical composition according to claim 6, further comprising one or more chemotherapeutic agents.

8. A product or kit comprising a compound of formula (I) or a pharmaceutically acceptable salt thereof, as defined in claim 1, or pharmaceutical compositions thereof comprising a therapeutically effective amount of a compound of formula (I) or a pharmaceutically acceptable salt thereof, as defined in claim 1, and at least one pharmaceutically acceptable excipient, carrier and/or diluent and one or more chemotherapeutic agents, as a combined preparation for simultaneous, separate or sequential use in anticancer therapy.

* * * * *